United States Patent
English et al.

(10) Patent No.: US 11,555,203 B2
(45) Date of Patent: Jan. 17, 2023

(54) INSECTICIDAL PROTEINS AND METHODS FOR THEIR USE

(71) Applicant: PIONEER HI-BRED INTERNATIONAL, INC., Johnston, IA (US)

(72) Inventors: James J English, San Ramon, CA (US); Jimei Wang, Johnston, IA (US); Nasser Yalpani, Kelowna (CA)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 16/611,962

(22) PCT Filed: May 9, 2018

(86) PCT No.: PCT/US2018/031746
§ 371 (c)(1),
(2) Date: Nov. 8, 2019

(87) PCT Pub. No.: WO2018/208882
PCT Pub. Date: Nov. 15, 2018

(65) Prior Publication Data
US 2021/0079418 A1 Mar. 18, 2021

Related U.S. Application Data

(60) Provisional application No. 62/504,650, filed on May 11, 2017.

(51) Int. Cl.
*C12N 15/82* (2006.01)
*A01N 63/50* (2020.01)

(52) U.S. Cl.
CPC ......... *C12N 15/8286* (2013.01); *A01N 63/50* (2020.01)

(58) Field of Classification Search
CPC ................................................ C12N 12/8286
USPC ....................................................... 800/300
See application file for complete search history.

(56) References Cited

U.S. PATENT DOCUMENTS

| 10,006,014 B2 * | 6/2018 | Singh ............. C12Y 302/01014 |
| 2015/0139976 A1 | 5/2015 | Singh et al. |
| 2016/0201044 A1 | 7/2016 | Singh et al. |

FOREIGN PATENT DOCUMENTS

| CN | 106834318 A | 6/2017 |
| WO | 2013098858 A2 | 7/2013 |
| WO | 2016061206 A1 | 4/2016 |

OTHER PUBLICATIONS

Falcon-Perez JM et al. J Biol Chem. 274:23584-90 (Year: 1999).*
Lazar et al. Mol. Cell. Biol. 8:1247-1252 (Year: 1988).*
Guo et al. Proc. Natl. Acad. Sci. USA 101: 9205-9210 (Year: 2004).*
Unknown: "AFR32946" Feb. 14, 2014 (Feb. 14, 2014), XP55486005, URL:https://www.ebi.ac.uk/ena/data/view/AFR32946&display=text.
International Search Report and Written Opinion for International Application No. PCT/US18/31746, dated Jul. 5, 2018.
Shukla, Anoop Kumar; et al.: "Expression of an insecticidal fern protein in cotton protects against whitefly," Nature Biotechnology, Oct. 2016 (Oct. 2016), vol. 34, No. 10, pp. 1046-1054.

* cited by examiner

*Primary Examiner* — Li Zheng

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of plant species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

12 Claims, 7 Drawing Sheets

Specification includes a Sequence Listing.

| Gene | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|---|---|---|---|---|---|
| IPD121Aa | SBL | 8 | 0 | FAW | 5.8 | 0.4 | CEW | 5.7 | 1 | ECB | 7 | 0.9 | VBC | 5.7 | 1.6 |
| IPD121Ab | | 1 | 0 | | 1 | 0 | | 2.3 | 3.3 | | 4.3 | 1.2 | | 2.3 | 3.2 |
| IPD121Ac | | 8 | 0 | | 5.3 | 0.8 | | 5 | 1.1 | | 7.2 | 1 | | 4.7 | 2.1 |
| IPD121Ad | | 8 | 0 | | 3.3 | 2.2 | | 5.7 | 1 | | 6.5 | 1.2 | | 5.2 | 1.3 |
| IPD121Ae | | 8.3 | 0.5 | | 3 | 2 | | 5.2 | 2 | | 7.5 | 1.4 | | 5.5 | 1.9 |
| IPD121Af | | 7.7 | 1 | | 4 | 1.1 | | 4.7 | 2.5 | | 5.7 | 1.2 | | 5.3 | 2.2 |
| IPD121Ah | | 7.5 | 0.8 | | 5.5 | 0.5 | | 4.8 | 2.7 | | 5.3 | 0.5 | | 5.2 | 1.3 |
| IPD121Aj | | 7.5 | 0.8 | | 4.5 | 1 | | 4.7 | 2.3 | | 5 | 1.5 | | 4.3 | 1.9 |
| IPD121Ba | | 7.3 | 0.5 | | 5.5 | 0.6 | | 5.5 | 1.1 | | 6 | 0 | | 8 | 1.4 |
| IPD121Bb | | 6.8 | 1 | | 5.5 | 0.6 | | 4.8 | 2.4 | | 6 | 0 | | 6 | 0 |
| IPD121Bc | | 7.8 | 1 | | 6 | 0 | | 7.5 | 1.7 | | 6.3 | 0.5 | | 6.3 | 1.7 |
| IPD121Bd | | 7.8 | 1 | | 6.5 | 0.6 | | 4.5 | 1.3 | | 1 | 0 | | 5.8 | 0.5 |
| IPD121Be | | 1 | 0 | | 3.8 | 3.6 | | 1.5 | 1 | | 2 | 0.4 | | 1 | 0 |
| IPD121Bf | | 7.7 | 1.4 | | 3.8 | 0.8 | | 4.5 | 1 | | 5.8 | 0.4 | | 3.3 | 0.9 |
| IPD121Bg | | 7 | 1.5 | | 5.2 | 0.8 | | 3.7 | 1.9 | | 6 | 0.6 | | 1 | 1.4 |
| IPD121Bk | | 1 | 0 | | 2.2 | 2 | | 1.3 | 0.8 | | 2.8 | 3.1 | | 1 | 0 |
| IPD121Bi | | 1.5 | 0.5 | | 3.2 | 2.1 | | 1 | 0 | | 2.3 | 1.2 | | 1 | 0 |
| IPD121Bm | | 7.8 | 0.5 | | 3.2 | 2.7 | | 4 | 1.9 | | 6 | 1.1 | | 3.3 | 2.3 |
| IPD121Ca | | 7.7 | 0.5 | | 4.5 | 0.8 | | 6 | 0 | | 5.7 | 0.5 | | 6 | 0.6 |
| IPD121Cb | | 8 | 0 | | 4 | 0.9 | | 6 | 0 | | 6.3 | 1 | | 6.8 | 0.8 |
| IPD121Cc | | 6.7 | 1.2 | | 4.3 | 0.8 | | 5.7 | 0.5 | | 7.2 | 1.7 | | 6.2 | 1 |
| IPD121Cd | | 7.3 | 1 | | 2.8 | 1.5 | | 6 | 0.6 | | 6 | 0.6 | | 5 | 1.3 |
| IPD121Ce | | 7.2 | 0.8 | | 1.7 | 1.6 | | 4.7 | 1.6 | | 4.8 | 0.8 | | 2 | 1.1 |
| IPD121Cf | | 1 | 0 | | 1 | 0 | | 1 | 0 | | 2.8 | 1.9 | | 1.8 | 2 |
| IPD121Cg | | 5.2 | 3.3 | | 1 | 0 | | 2.5 | 1.4 | | 4.2 | 1.5 | | 1.5 | 0.8 |

FIG. 2A

| Gene | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|---|---|---|---|---|---|
| IPD121Ch | SBL | 3.3 | 2.9 | FAW | 1 | 0 | CEW | 2.3 | 1.8 | ECB | 3.2 | 1.2 | VBC | 1 | 0 |
| IPD121Ci | | 7.8 | 0.5 | | 6 | 0 | | 6 | 1.4 | | 5 | 1.2 | | 7.3 | 1.3 |
| IPD121Cj | | 1 | 0 | | 1.3 | 0.5 | | 1 | 0 | | 1.8 | 1.5 | | 2.8 | 1.7 |
| IPD121Ck | | 7.3 | 1 | | 5.3 | 1 | | 4.5 | 2.4 | | 5.8 | 2.1 | | 7.8 | 1.3 |
| IPD121Cl | | 7.8 | 0.5 | | 6 | 0 | | 6.5 | 1 | | 6.8 | 1.5 | | 8.5 | 0.6 |
| IPD121Cm | | 7.5 | 1 | | 6 | 0 | | 5.5 | 0.6 | | 6.8 | 1 | | 7 | 1.6 |
| IPD121Cn | | 7 | 0.8 | | 6.3 | 0.5 | | 5.3 | 1 | | 6.3 | 0.5 | | 8 | 1.4 |
| IPD121Co | | 7.8 | 0.5 | | 6 | 0 | | 5.3 | 2.9 | | 6.3 | 0.5 | | 7.8 | 1.5 |
| IPD121Cp | | 6.7 | 1 | | 5 | 1.7 | | 4.7 | 1.9 | | 5.5 | 0.5 | | 6.2 | 0.4 |
| IPD121Cq | | 7.8 | 0.4 | | 5.7 | 0.5 | | 4.8 | 1.2 | | 6.8 | 0.8 | | 6.5 | 0.5 |
| IPD121Cr | | 7 | 0.9 | | 5.8 | 0.4 | | 5.7 | 1 | | 7.2 | 1.2 | | 6 | 0 |
| IPD121Cs | | 6.8 | 0.8 | | 4.7 | 0.8 | | 4.2 | 2.3 | | 6 | 2.1 | | 6 | 0 |
| IPD121Ct | | 7 | 0.8 | | 2.8 | 0.5 | | 4.5 | 2.4 | | 5 | 1.4 | | 3.5 | 2.1 |
| IPD121Cu | | 7.8 | 1.3 | | 2.3 | 1.5 | | 3.3 | 1.7 | | 4.5 | 2.6 | | 1.8 | 1.5 |
| IPD121Cv | | 6.8 | 1 | | 3.8 | 2.6 | | 3.8 | 2.1 | | 2.5 | 0.6 | | 1 | 0 |
| IPD121Cw | | 7.8 | 0.5 | | 3.5 | 1.9 | | 6 | 2.2 | | 4.3 | 1.5 | | 2 | 1.4 |
| IPD121Cx | | 8.3 | 0.5 | | 5.8 | 2.1 | | 4.8 | 1.9 | | 7 | 1.4 | | 4 | 1.6 |
| IPD121Cy | | 7.5 | 0.6 | | 3.5 | 2.4 | | 5.5 | 0.6 | | 5.5 | 0.6 | | 2.3 | 2.5 |
| IPD121Cz | | 7.5 | 0.6 | | 3.3 | 2.2 | | 3.5 | 1.9 | | 4.5 | 1.9 | | 2.5 | 2.4 |
| IPD121Caa | | 7.8 | 0.5 | | 2.3 | 1.5 | | 1.3 | 0.5 | | 3.8 | 1.9 | | 1.8 | 1.5 |
| IPD121Cab | | 7.3 | 1 | | 3.5 | 0.6 | | 4 | 2.4 | | 5.3 | 1 | | 2.3 | 1.9 |
| IPD121Cac | | 2.3 | 1 | | 1 | 0 | | 1 | 0 | | 3 | 4 | | 1 | 1.9 |
| IPD121Cad | | 2.8 | 2.2 | | 2.5 | 1.7 | | 1.3 | 0.5 | | 1.8 | 1.5 | | 2 | 1.4 |
| IPD121Cae | | 7.3 | 1 | | 6 | 0.6 | | 4.3 | 1.4 | | 6.5 | 1.2 | | 6.3 | 0.8 |
| IPD121Cag | | 4.5 | 2.6 | | 2.3 | 1.9 | | 1.5 | 0.6 | | 4.5 | 1.7 | | 2.3 | 2.5 |

FIG. 2B

| Gene | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|---|---|---|---|---|---|
| IPD121Cah | SBL | 1 | 0 | FAW | 2.3 | 2.5 | CEW | 2 | 2 | ECB | 1.8 | 1.5 | VBC | 1.3 | 0.5 |
| IPD121Cai |  | 1 | 0 |  | 1 | 0 |  | 3.5 | 3.8 |  | 1 | 0 |  | 1 | 0 |
| IPD121Caj |  | 1 | 0 |  | 2.5 | 1.3 |  | 1 | 0 |  | 2.3 | 1.5 |  | 1 | 0 |
| IPD121Cak |  | 7.7 | 0.5 |  | 5.5 | 0.5 |  | 5.3 | 1.2 |  | 5.3 | 1 |  | 6.5 | 0.5 |
| IPD121Cal |  | 1 | 0 |  | 1.2 | 0.4 |  | 1 | 0 |  | 3.2 | 1.6 |  | 5.7 | 0.8 |
| IPD121Cam |  | 7.3 | 0.8 |  | 5.3 | 1 |  | 5.2 | 0.8 |  | 6.2 | 0.4 |  | 6 | 0 |
| IPD121Can |  | 7.8 | 1 |  | 5.2 | 0.8 |  | 3.5 | 1.4 |  | 7.2 | 1.2 |  | 5.5 | 0.5 |
| IPD121Cap |  | 1 | 2.6 |  | 3 | 3.6 |  | 1 | 2.6 |  | 1 | 2.6 |  | 1 | 2.6 |
| IPD121Cat |  | 7.2 | 0.8 |  | 5.3 | 1.2 |  | 4.5 | 0.8 |  | 6.3 | 0.5 |  | 6.2 | 1 |
| IPD121Cau |  | 7.8 | 1 |  | 5.5 | 0.5 |  | 4.5 | 1.9 |  | 6 | 0 |  | 5.5 | 0.8 |
| IPD121Cav |  | 5.8 | 3.3 |  | 1.5 | 0.8 |  | 1 | 0 |  | 4.5 | 1.7 |  | 2.2 | 1.9 |
| IPD121Caw |  | 5 | 2.5 |  | 4.3 | 1.6 |  | 3.8 | 1.6 |  | 5 | 0 |  | 2 | 1.3 |
| IPD121Cay |  | 6.5 | 1.4 |  | 5.3 | 0.4 |  | 3.7 | 0.8 |  | 6.8 | 1.9 |  | 1.5 | 0.8 |
| IPD121Caz |  | 3.3 | 2.6 |  | 1.2 | 0.5 |  | 1.3 | 0.5 |  | 3.7 | 1.3 |  | 1.2 | 0.4 |
| IPD121Cba |  | 2.3 | 2 |  | 1.7 | 0.5 |  | 1.7 | 0.5 |  | 3 | 1.6 |  | 1 | 0.8 |
| IPD121Cbc |  | 1 | 0.8 |  | 1.5 | 0.8 |  | 1.2 | 0.8 |  | 1.2 | 0.8 |  | 1.7 | 0.8 |
| IPD121Cbd |  | 7.7 | 1.5 |  | 2 | 1.1 |  | 4.2 | 0.4 |  | 2 | 1.4 |  | 1 | 1.2 |
| IPD121Cbe |  | 7.7 | 1.1 |  | 3.8 | 1.3 |  | 4.5 | 0.5 |  | 6 | 0.4 |  | 5 | 1.8 |
| IPD121Cbf |  | 7.3 | 0.7 |  | 2.8 | 1.6 |  | 3.3 | 1.5 |  | 5.3 | 0.8 |  | 5.7 | 1.7 |
| IPD121Cbh |  | 8.2 | 0.6 |  | 2.7 | 1.7 |  | 3 | 1.9 |  | 5 | 1.1 |  | 4.7 | 2 |
| IPD121Cbk |  | 7.8 | 0.4 |  | 1.5 | 2.6 |  | 2.2 | 2.3 |  | 4 | 2.3 |  | 3.8 | 2.1 |
| IPD121Cbm |  | 5.2 | 2.9 |  | 1.8 | 0.5 |  | 2.2 | 1.2 |  | 4.7 | 1.7 |  | 4 | 1.9 |
| IPD121Cbo |  | 7.8 | 2.2 |  | 2 | 0.6 |  | 1.5 | 1.1 |  | 4.7 | 1.3 |  | 2 | 1.4 |
| IPD121Da |  | 2 | 2.4 |  | 1 | 0 |  | 1 | 0 |  | 1 | 0 |  | 1 | 0 |
| IPD121Db |  | 1 | 0 |  | 1 | 0 |  | 2 | 2.4 |  | 1.3 | 0.5 |  | 1 | 0 |

FIG. 2C

| Gene | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|---|---|---|---|---|---|
| IPD121Dc | SBL | 1 | 0 | FAW | 1 | 0 | CEW | 3.8 | 4 | ECB | 1.7 | 0.8 | VBC | 1 | 0 |
| IPD121Dd | | 1 | 0 | | 1 | 0 | | 1.8 | 2 | | 1 | 0 | | 1 | 0 |
| IPD121De | | 1 | 0.8 | | 1.5 | 1 | | 1 | 0.8 | | 3.2 | 1.8 | | 1 | 0.8 |
| IPD121Df | | 1 | 1.1 | | 1 | 1.1 | | 1 | 1.1 | | 1.2 | 1.1 | | 1 | 1.1 |
| IPD121Dg | | 8.2 | 1.3 | | 2 | 1.4 | | 3 | 2.3 | | 3.7 | 0.7 | | 3.3 | 2.1 |
| IPD121Dh | | 3 | 1.6 | | 1.3 | 1.8 | | 2.5 | 3.2 | | 4.3 | 1.5 | | 2.7 | 2.4 |
| IPD121Ea | | 1 | 0 | | 2.3 | 1 | | 2.5 | 2.6 | | 1.8 | 0.5 | | 2.3 | 1.5 |
| IPD121Eb | | 1 | 0 | | 4 | 2.2 | | 1 | 1.8 | | 1.8 | 0.5 | | 2 | 2 |
| IPD121Ec | | 1 | 0 | | 2.3 | 1.9 | | 1 | 0 | | 1.3 | 0.5 | | 1 | 0 |
| IPD121Ed | | 1.3 | 0.5 | | 3.5 | 1 | | 1.5 | 0.9 | | 1.5 | 1 | | 1.5 | 1 |
| Negative | | 1.2 | 0.4 | | 1 | 0 | | 1.7 | 0.8 | | 4.2 | 1 | | 1 | 0 |

FIG. 2D

SEQUENCE LISTING

<160> NUMBER OF SEQ ID NOS: 249

<210> SEQ ID NO 1
<211> LENGTH: 637
<212> TYPE: DNA
<213> ORGANISM: Polystichum tripteron

<400> SEQUENCE: 1

```
atgggcaggt catggggagt tgtggctatt atggtgttgt gcgccagcgg cctgctgggc    60
gtagcgagcg gccatggcac catgaacgac cccatcagtc gcgtctacgc ctgcaggcag   120
gagaatccgg agcgacccac tacgccggct tgcatagcgg cggtggcgct gagtggggcc   180
caagcgttct atgattggaa tgaggtgaac ctgccctttg tcaatggccg gcaccgccag   240
ttcattccgg atgggaaact ctgcagcgcc gggcggaaca agtatagggg tctcgacctg   300
gcacgctccg actggacagc cacaaacttg tcctccggcg tcgcctacac attcctctac   360
agggtcaccg cccagcacag gggcttcttc gagttctacg tcaccgtgga tggttacgac   420
cccactgagc cgctcaaatg ggcagacttg gaggaaacgc cgttcatcaa cgtcaccgac   480
cccacagttg taggcctcaa ctatgtaatc cccggtacca cgcctgccag caagaccggc   540
cgccacctca tctacgtcat ttggcagcgc tccgacagcc ccgaggcctt ctactcctgc   600
tccgacgtca actttcccga tgccctgtct ctccact                            637
```

<210> SEQ ID NO 2
<211> LENGTH: 637
<212> TYPE: DNA
<213> ORGANISM: Polystichum tripteron

<400> SEQUENCE: 2

```
atgggcaggt catggggagt tgtggctatt atggtgttgt gcgccagcgg cctgctgggc    60
gtagcgagcg gccatggcac catgaacgac cccatcagtc gcgtctacgc ctgcaggcag   120
gagaatccgg agcgacccac tacgccggct tgcatagcgg cggtggcgct gagtggggcc   180
caagcgttct atgattggaa tgaggtgaac attcctaatg cccctggtcg gcaccgtgag   240
```

```
ctcatttctg atggctacct atgcagcgcc aatcggacca agtatgcagg tctcgacctg    300
gcacgctccg actggacagc cacaaacttg tcctccggcg tcgcctacac attcctctac    360
agggtcaccg cccagcacag gggcttcttc gagttctacg tcaccgtgga tggttacgac    420
cccactgagc cgctcaaatg gcagacttg gaggaaacgc cgttcatcaa cgtcaccgac    480
cccacagttg taggcctcaa ctatgtaatc cccggtacca cgcctgccag caagaccggc    540
cgccacctca tctacgtcat ttggcagcgc tccgacagcc ccgaggcctt ctactcctgc    600
tccgacgtca actttcccga tgccctgtct ctccact                             637
```

<210> SEQ ID NO 3
<211> LENGTH: 643
<212> TYPE: DNA
<213> ORGANISM: Davallia fejeensis

<400> SEQUENCE: 3

```
atgggcaggt catggggagt tgttgcaatt atggtggtgt gcatcatgag tggcctggtg     60
ggcatagtga gtggccatgg cagcatggag gaccccatca gtcgcgtcta tagatgctac    120
ttagagaatc cggagcgtcc tgtatcggca gcttgccaag cagcggtggc gatgagtggt    180
acccaagcct tctacgattg gaatgaggtg aacattccta acgccgctgg ccggcaccgt    240
gagctcattt ccgatggcca actatgcagc gccaatcgca caaagtatgc aggccttgac    300
ttggcacgcg ctgactggct aggcacccc ttgtcctcgg gtgtctcctt cacatttgcc    360
tacaaggcca ccgcaccaca cttgggcttt tcgagttct acgttacccg ggatggttac    420
gagcccaccg agccgctcaa atgggcggac ttagaggact cgcccttat caatgtcacc    480 gaccccacac ttgaaaatgg cgcctaccaa atctctggca ctacaccttc tggtaagtcg    540
gggcgccact tgatgtatgt catttggcag cgctctgata gccctgaggc gttctactcg    600
tgctccgatg ttgacttcga cgtcgatgcc ctctctctcc act                      643
```

<210> SEQ ID NO 4
<211> LENGTH: 635
<212> TYPE: DNA
<213> ORGANISM: Didymochlaena truncatula

<400> SEQUENCE: 4

```
atgggcaggt catggggagt tgtggctatt atggtgttgt cgccagcgg cctgctgggc     60 gtagcgagtg ccatggcag catggaggac ctatcagtc gcgtctacgc ctgctacctg    120
gagaatccgg agcgtccac gtcggcagct tgccaagcgg cggtggcagt gagtgggacc    180
caagcgttct atgattggaa tgaggtgaac cagcccttcg ccgctggccg gcaccgcgag    240
ctcattccgg atgcgaact gtgcagcggc gggcgggaga agtataaggg cctcgacttg    300
gcacgcgccg actggccagc cacctccttg ccctccggtg tcaactacac atacctctac    360
aaggccaccg ccccgcactt gggcttcttc gagttctaca tcacccggga tggctacgag    420
cccactgagc cgctcaaatg gcagacttg gaggacttgc cgttcatcaa catcaccaac    480
cccacgcttg tcagcggctc ctaccaaatc cccggcacca cgcatgccag caagactggc    540
cggcacctcc tctatgtcat ttggcagcgc tccgacagct cgaggcctt ctactcctgc    600 tccgacgtcg acttcgtcaa tgccctctct ctcca                               635
```

<210> SEQ ID NO 5
<211> LENGTH: 636
<212> TYPE: DNA

<213> ORGANISM: Didymochlaena truncatula

<400> SEQUENCE: 5

| | |
|---|---|
| atgggcaggt catggggagt tgtggctatt atggtgttgt gcgccagcgg cctgctgggc | 60 |
| gtagcgagtg gccatggcag catggaggac cctatcagtc gcgtctacgc ctgctacctg | 120 |
| gagaatccgg agcgtcccac gtcggcagct tgccaagcgg cggtggcagt gagtgggacc | 180 |
| caagcgttct atgattggaa tgaggtgaac cagcccttcg ccgctggccg gcaccgcgag | 240 |
| ctcattccgg atggcgaact gtgcagcggc gggcgggaga agtataaggg cctcgacttg | 300 |
| gcacgcgccg actggccagc cacctccttg ccctccggtg tcaactacac atacctctac | 360 |
| aaggccaccg ccccgcactt gggcttcttc gagttctaca tcacccggga tggctacgag | 420 |
| cccactgagc cgctcaaatg gcagacttg gaggacttgc cgttcatcaa catcaccaac | 480 |
| cccacgcttg tcagcggctc ctaccaaatc cccggcacca cgcctgccag caagactggc | 540 |
| cggcacctcc tctatgtcat ttggcagcgc tccgacagct cgaggccttc tactcctgc | 600 |
| tccgacgtcg acttcgtcaa tgccctctct ctccac | 636 |

<210> SEQ ID NO 6
<211> LENGTH: 636
<212> TYPE: DNA
<213> ORGANISM: Humata tyermanii

<400> SEQUENCE: 6

| | |
|---|---|
| atgggcaggt catggggagt tgtggctatt atggtgatgt acattggtgg cctgctaagc | 60 |
| atagcaagcg gccatggcag catggaggac cccatcagcc gcgtctatag gtgctacttg | 120 |
| gagaatccgg agagtcccac atcggcagct tgccaagcgg cagtggcagt gagtggggcc | 180 |
| caagccttct acgattggaa tgaggtgaac attgctgacg ccaatggccg acaccgggag | 240 |
| ctcatttctg atggccaact atgtagcgca aatcggagta agtatgcggg cctcgacctg | 300 |
| gcacgcgcag attggctagg caccaccttg tcctcgggcg cctccttcac atttgcctac | 360 |
| aaggccaccg cgccgcactt gggcttcttt gagttctacg tcacccggga tggttacgag | 420 |
| cccaccgacc cgctcaaatg gcagacttg gaggactcgc ccttcatcaa cgtcaccaac | 480 |
| cccacacttg ataatggcgc ctaccagatc tccggcacca cgcctgccgg taagtcgggg | 540 |
| cgtcatctga tctacgtcat ttggcagcgc tctgatagcc cagaggcatt ctattcgtgc | 600 |
| tccgacgtcg actttgtcga tgctctctct ctccac | 636 |

<210> SEQ ID NO 7
<211> LENGTH: 726
<212> TYPE: DNA
<213> ORGANISM: Cyrtomium fortunei

<400> SEQUENCE: 7

| | |
|---|---|
| atggggagtt gtggctatta tggtgttgtg cgccagcggc ctgctgggcg tggcggcaat | 60 |
| tctgttggtc atagtgtggg gatggggagg tcatggggag ttgtggctat tatggtgctg | 120 |
| tgcaccagcg gcctgctggg cgtggcgagc ggccatggca ccatgggcga cccatcagc | 180 |
| cgcgtctaca actgcttcca ggagaatccg gagagaccca gtcggcagc ttgcatcgcg | 240 |
| gcggtggcgc tcagtggaac ccaagcgttc tatgattgga tgaggtgaa cctgcccgac | 300 |
| gtcaatggcc gccaccgcga gttcattccg gatggccaac tgtgcagcgc cgggcgggac | 360 |
| aagtataagg gtctcgacct ggcacgctcc gactggacag ccaccaactt gtcctccggc | 420 |
| gtcgcctaca cattcctcta cagggtcacc gcccagcaca ggggcttctt cgagttctac | 480 |

```
gtcaccgtgg atgattacga tcccactgtg gcgctcaaat gggaggactt ggaggaaaca    540
ccgttcctca acgtcaccga ccccacggtt gtaggcgtca actaccaaat ctccggcacc    600
acgcctgcca gcaagaccgg ccgccacctc atctacgtca tttggcagcg ctccgacagc    660
cctgaggcct tctacgcctg ctccgatgtc gacttcgtcg atgccgtctc tctccactcc    720
accacc                                                               726

<210> SEQ ID NO 8
<211> LENGTH: 741
<212> TYPE: DNA
<213> ORGANISM: Adiantum hispidulum

<400> SEQUENCE: 8
atgaagaagt catggggact tgcagtagta gtaggttcac atctgattgt aaggatgaag     60
aagtcatggg gagttgcagt agtagtagga gtagtagctt tgtgcctgct gggcatggca    120
agcggccatg gcagcatgca ggaccccatc agtcgcgtct acaactgcta cctagagggc    180
ccggagcgcc aacgtcggc agcttgcata gctgcggtgg caatgagtgg cacacaacca    240
ttctacgatt ggaatgaggt gaacttgccc gacgccgctg gccggcaccg cgagctcatc    300
cccgatggca agctgtgcag cgccggccgg gataagtatc agggcctcga cctggcgcgc    360
gacgactggg tagcctcctt atcctctggc gtcgcctaca cattcccttta ccgagtcact    420 gcccagcact tgggcttctt tgaaatttac gtcacccgtg acacctacga ccccactcag    480
gcgctaacat gggatgacct ggaagactcg cccttcatca acgttaccaa ccctccgtt    540 gtcagtacga cgttgggtaa cgcctacgca atccccaccc ccacgccatc cggcaagact    600
ggtcgccacc tcatctacgt aatctggcag cgcagcgaca gccccgaggc gttctactcc    660
tgctccgacg tcgagttcga cgtggcatcg acagtcgagg acgacgtcat catctctctc    720
cgctccgcag ctctagacgt c                                               741

<210> SEQ ID NO 9
<211> LENGTH: 750
<212> TYPE: DNA
<213> ORGANISM: Polystichum acrostichoides

<400> SEQUENCE: 9
atggtcacct atatatatat gtgtgaaatg catgttggaa ggtgtagcaa tatgcgtgca     60
gtaattagag aagccaatta tattgatcat agtgtgagtg tgagcatggg gaggtcatgg    120
ggagttgtgc ctattatggt gttgtgcgct agcggcctgc tgggtgtagc gagcggccat    180
ggcagcatga acgacccccat cagccgcgtc tacaactgcc gtctggagaa tccggagagt    240
cccacgtcag cagcttgcat agcggcggtg gcgctgagtg ggacccaagc gttctatgat    300
tggaatgagg tgaacctgcc cgacgtcaat ggccggcacc gccagctcat tccggatggc    360
aaattgtgca gcgccgggcg ggacaagtat aagggcctcg acctggcacg ctccgactgg    420
gtagccacca acttgtcctc cggcgtcgcc ttcacattcc tctacagggt caccgcccag    480
cacaggggct tcttcgagtt ctacgtcacc gtggatgatt acgaccccac tgagctgctc    540
aaatgggaag acttggagga aacgccgttc atgaacgtca ccgaccccac ggttgtaggc    600
gtcaactacg aaatccccgg caccacgcct gccaataaga ccggccgcca tctcatctat    660
gtcatttggc agcgctccga cagccccgag gccttctact cctgctccga cgttgacttc    720
gtcgatgccg tgtctctcca ctccaccacc                                     750
```

<210> SEQ ID NO 10
<211> LENGTH: 729
<212> TYPE: DNA
<213> ORGANISM: Thelypteris kunthii

<400> SEQUENCE: 10

| | | | |
|---|---|---|---|
| atgcatgttg gaatatacag cacgagtgca gtagtaggga ggatgagaga aagcaatatt | 60 |
| ggtcataaca ccgtgaggat ggagagggct gcatggggcg ttgtgggcat tattatggtg | 120 |
| ttgtgcgcca gcggcctgct gggcgtagcg agtggccacg gcagcatgga ggaccccatc | 180 |
| agtcgcgtct acctctgcta cctcgagaat ccggagcgtc ccacgtcggc agcttgccaa | 240 |
| gcggcggtgg cgctgagtgg gacccaagca ttctatgatt ggaatgaggt gaacatcgcc | 300 |
| gacgccgctg ccggcaccg cgagctcatt ccggatggcc aactgtgcag cgccgggcgg | 360 |
| gacaagtata agggcctcga cctggcacgc tccgactggg tagccaccaa cttgtcctcc | 420 |
| ggcgtcgcct tcacattcct ctacagggtc accgccgagc acaggggctt cttcgagttc | 480 |
| tacgtcaccg tggatgatta cgaccccact gagctgctca aatgggaaga cttggaggca | 540 |
| acgccgttca tgaatgtcac cgaccccacg gttgtaggcg acaactacga aatccccggc | 600 |
| accacgcctg ccaacaagac cggccgccat ctcatctatg tcatttggca cgctccgac | 660 |
| agccccgagg ccttctactc ctgctctgac gtcgtcttcg ccgatgccgt gtctctccac | 720 |
| tccaccacc | 729 |

<210> SEQ ID NO 11
<211> LENGTH: 747
<212> TYPE: DNA
<213> ORGANISM: Cyrtomium fortune (clivicola)

<400> SEQUENCE: 11

| | | | |
|---|---|---|---|
| atgcattctg gaatgggcag cagtatgcgt gcagcaatta ggaggacgag acaaggcaat | 60 |
| tatactggtc atagtgtgag gatggggaca ttggggaggt catggggagc tgtggctatt | 120 |
| atggtgttgt gcgccagcgg tctcctgggc gtagccagcg gccatggcag catgaacgac | 180 |
| cccatcagcc gcgtctacaa ctgctacctg gagaatccgg agagaccac ctcggcagct | 240 |
| tgcatagcgg ccgtggcgct cagtgggacc caagcgttct atgattggaa tgaggtgaat | 300 |
| ctgcccgacg ccaatggccg gcaccgccag ctcattccgg atggccaact gtgcagcgcc | 360 |
| gggcgggaca agtataaagg cctcgacctc gcacgctccg actggacggc caccaattta | 420 |
| tcctccggcg tcgccttcac attcctctac agggtcaccg cccagcacag ggcttcttc | 480 |
| gagttctacg tcaccgtgga tgattacgat cccactgtgg cgctcaaatg ggaggacttg | 540 |
| gaggaaacac cgttcctcaa cgtcaccgac cccacggttg taggcgtcaa ctaccaaatc | 600 |
| tccggcacca cgcctgccag caagaccggc cgccacctca tctacgtcat ttggcagcgc | 660 |
| tccgacagcc ccgaggcttt ctatgcctgc tccgacgtcg actttgtcga tgccgtctct | 720 |
| ctccactcca ccaccttgac cctgatc | 747 |

<210> SEQ ID NO 12
<211> LENGTH: 729
<212> TYPE: DNA
<213> ORGANISM: Polystichum tripteron

<400> SEQUENCE: 12

| | | | |
|---|---|---|---|
| atgcatgttg gaatgtgcag caatatgctt gcagtaatta ggaggacgag acatttaggc | 60 |
| acttattttg gtcatagtgt gaggatgggc aggtcatggg gagttgtggc tattatggtg | 120 |

```
ttgttttcca gtggcctgct gggagtagca agcggccatg gcagcatggg cgaccccatc    180
agtcgcgtct acaactgcag gcaggagaat ccggagcgac ccactacgcc ggcttgcata    240
gcggcggtgg cgctgagtgg ggcccaagcg ttctatgatt ggaatgaggt gaacctgccc    300
tttgtcaatg gccggcaccg ccagttcatt ccggatggga actctgcag cgccgggcgg     360 aacaagtata ggggtctcga cctggcacgc tccgactgga cagccacaaa cttgtcctcc    420
ggcgtcgcct acacattcct ctacagggtc accgcccagc acaggggctt cttcgagttc    480
tacgtcaccg tggatggtta cgaccccact gagccgctca atgggcaga cttggaggaa     540 acgccgttca tcaacgtcac cgaccccaca gtagaaggcc tcaactatgt tcgagttcta    600
cgtcaccgtg gatgcaagag tggccgccac ctcatctacg tcatttggca gcgctccgac    660
agccccgagg ccttctactc ctgctccgac gtcaactttc ccgatgccct gtctctccac    720
tccgccacc                                                            729

<210> SEQ ID NO 13
<211> LENGTH: 744
<212> TYPE: DNA
<213> ORGANISM: Didymochlaena truncatula

<400> SEQUENCE: 13
atgatcacct gtatatatat gtgtgaaatg catgttgaaa tgtgcaacat gcgtgcagta     60
gggaggctga caaggcaa tattggtcat agtgtgagga tggggagatc atggggagtt     120
gtggctatta tggtgttgtg cgccagcggc ctgctgggcg tagcgagtgg ccatggcagc    180
atggaggacc ctatcagtcg cgtctacgcc tgctacctgg agaatccgga gcgtcccacg    240
tcggcagctt gccaagcggc ggtggcagtg agtgggaccc aagcgttcta tgattggaat    300
gaggtgaacc agcccttcgc cgctggccgg caccgcgagc tcattccgga tggcgaactg    360
tgcagcggcg ggcgggagaa gtataagggc ctcgacttgg cacgcgccga ctggccagcc    420
acctccttgc cctccggtgt caactacaca tacctctaca aggccaccgc cccgcacttg    480
ggcttcttcg agttctacat cacccgggat ggctacgagc ccactgagcc gctcaaatgg    540
gcagacttgg aggacttgcc gttcatcaac atcaccaacc ccacgcttgt cagcggctcc    600
taccaaatcc ccggcaccac gcctgccagc aagactggcc ggcacctcct ctatgtcatt    660
tggcagcgct ccgacagctt cgaggccttc tactcctgct ccgacgtcga cttcgtcaat    720
gccctctctc tccactccac cacc                                           744

<210> SEQ ID NO 14
<211> LENGTH: 750
<212> TYPE: DNA
<213> ORGANISM: Asplenium antiquum

<400> SEQUENCE: 14
atgtcgagac gctggctgtc attcaatcac acaaacattg ggttgcattt tttgagtagt     60
gctatgagaa tggggaggtc ggcatcttgc atcagagcta atatggcgat catgctggtg    120
ttgttttggg ctagctgctc ctgcctgctg gcatagtga gcgggcatgg cagcatggag     180
gatcccatca gtcgtgtcta cgcctgcttc ttggagaatc cggagaggcc cacatctgca    240
gcttgcatag cggcggtggc gttgagtggg acgcaagcgt tctacgattg aacgaggtt     300 aaccagccca cgccgccgg tcggcaccgc gagatcattc cggatggcca gctttgcggc    360
gccgacgggg acaagtataa gggcctcaac ttggcacgtg ccgactggcc ggcaaccacc    420
```

-continued

| | |
|---|---|
| ttgtcctccg acatcagctt cacataccte ttcaaggcaa ccgcccctca ccgcggtttc | 480 |
| ttcgagttct acgtcacccg ggatggttac gatcccaccg agcccctcaa atgggcggac | 540 |
| ttggaggacc caccattcct caacgtcacc gaccccacgc ttgcttccgg ctcctaccaa | 600 |
| atccccggca ccacaccagc cggcaagact ggccgccatc tcatttacgt catatggcag | 660 |
| cgctccgata gccccgaagc cttctactct tgctctgacg tggactttga cagcagcgat | 720 |
| accgtgatct ctctccgctc tgccaccacc | 750 |

<210> SEQ ID NO 15
<211> LENGTH: 720
<212> TYPE: DNA
<213> ORGANISM: Cyrtomium falcatum (Butterfieldii)

<400> SEQUENCE: 15

| | |
|---|---|
| atgttggaat gtgcagcaaa tatgcgtgca gtaattagca ggacgagaca aggcaattct | 60 |
| attgtgagtg tgaggatggg gaggtcatgg ggagttgtgg ctattatggt gttgtgcgcc | 120 |
| accggcctcc tgggcgtggc gagcggccat ggcagcatgg gcgaccccat cagccgcgtc | 180 |
| tacaactgct ccctggagaa tcctgagaga cccacgtcgg cagcttgcat cgcggccgtt | 240 |
| gcgctcagtg gaacccaagc gttctatgat tggaatgagg tgaacctgcc cgacgtcaat | 300 |
| ggccgccacc gccagttcat tccggatggc caactgtgca gcgccgggcg ggacaagtat | 360 |
| aagggtctcg acctggcacg ctccgactgg acagccacca acttgtcctc cggcatcgcc | 420 |
| tacacattcc tctacagggt caccgcccag cacaggggct tcttcgagtt ctacgtcacc | 480 |
| gtggatgatt acgatcccac tgtggcgctc aaatgggagg acttggagga aacgccgttc | 540 |
| ctcaacgtca ccgaccccac ggttgtaggc gtcaactacc agatcaacgg caccacgcct | 600 |
| gccagcaaga cgggccgcca cctcatctac gtcatttggc agcgctccga cagcccgag | 660 |
| gccttctacg cctgctccga cgtcgacttc gtcgatgccg tctctctcca ctccaccacc | 720 |

<210> SEQ ID NO 16
<211> LENGTH: 741
<212> TYPE: DNA
<213> ORGANISM: Onoclea sensibilis

<400> SEQUENCE: 16

| | |
|---|---|
| atgcgtgcag tcattagtaa gaagatattg agacaaggca atattggtga tattggtgat | 60 |
| agtgtgatca ctgattcagc cttgaggatg gggaggtcat ggggagtggt gcaggctata | 120 |
| attatggtgt tgtgcggcag cggcctgctg gcgtagcga gcggcatgg cagcatggag | 180 |
| gaccccatca gtcgcgtcta caactgctac ctggagaatc ccgagagtcc cacgtcggca | 240 |
| gcttgccaag cggcggtggc gctgagtggg gcccaagcgt tctatgattg gaatgaggtg | 300 |
| aacctggccg acgccgctgg ccggcatcgc gagctcattc cggatggcca actgtgcagc | 360 |
| gccgggcggg agaagtatca gggcctcgac ctggcacgct ccgactggac agccacttcc | 420 |
| ttgtcctccg gcgtctcctt cacataccte tacaaggcca ccgccccgca cttgggcttc | 480 |
| ttcgagttct acgtcaccaa ggatggttac gagcccactg agccgctcaa atgggcagac | 540 |
| ttggaggact cgcccttcat caacgtcacc gaccccacgc ttgtcagcgg ctcctaccaa | 600 |
| atccccggca ccacgccttc cggcaagtcc ggccgccacc tcatctacgt catttggcag | 660 |
| cgctccgaca gccccgaggc cttctactcc tgctccgacg tcgacttcga cgtcgatgcc | 720 |
| ctctctctcc actccaccac c | 741 |

<210> SEQ ID NO 17
<211> LENGTH: 738
<212> TYPE: DNA
<213> ORGANISM: Platycerium superbum

<400> SEQUENCE: 17

| | | | | | |
|---|---|---|---|---|---|
| atggagaagt | tatctgaggt | ggaggaaaag | tggataatgg | agagttggca | gtgggcgaag | 60 |
| gtgctgatgc | aggtgagggt | gagggtgagg | atgaggaggt | catgggtagc | tgtggctgtt | 120 |
| accttggtgg | tgtgcgccgg | cagcctgctg | ggcgtagcga | gcggtcatgg | cagcatggag | 180 |
| gatcccatca | gccgcgtcta | tgggtgctac | ctggagaatc | ggagaatcc | tacgtcggca | 240 |
| gcgtgcatcg | cggcggtggc | ggcaagtggc | actcaagcct | tctacgactg | gaatgaggtg | 300 |
| aatcagccct | tgccgctgg | ccaacaccgc | cagatcattc | ctgacggcca | gctctgcagc | 360 |
| gccgggcggg | acaagtataa | aggcctcgac | ctggcacgcg | ccgactggcc | tgccacctcc | 420 |
| ttatcttcgg | gcgtcgatta | cacttttctc | ttcaaggcca | ccgcccccca | ccggggctac | 480 |
| ttcgagttct | acgtcacccg | cgatagctac | gaccccactg | agccctggc | ctgggccgac | 540 |
| ctggaggaca | cgcccttcat | caacgtcacc | gacccgaccc | ttgtgagcgg | ctcctatcag | 600 |
| atctccagca | ccacgccttc | cggcaagacc | ggccgtcacc | tcatctacgt | catttggcag | 660 |
| cgcaccgaca | gcactgaggc | cttctactcc | tgctccgatg | tcgactttga | cgagaccctc | 720 |
| cgccttcact | ccgccacc | | | | | 738 |

<210> SEQ ID NO 18
<211> LENGTH: 714
<212> TYPE: DNA
<213> ORGANISM: Davallia tyermannii

<400> SEQUENCE: 18

| | | | | | |
|---|---|---|---|---|---|
| atgtggagca | tgcatttgtg | tggagtaagg | aggatcttga | dacaaggcaa | atcggtcat | 60 |
| agtgtgagaa | tggggaggtc | atggggagtt | gtggctatta | tggtgatgta | cattggtggc | 120 |
| ctgctaagca | tagcaagcgg | ccatggcagc | atggaggacc | ccatcagccg | cgtctatagg | 180 |
| tgctacttgg | agaatccgga | gagtcccaca | tcggcagctt | gccaagcggc | agtggcagtg | 240 |
| agtgggccc | aagccttcta | cgattggaat | gaggtgaaca | ttgctgacgc | caatggccgg | 300 |
| caccgcgagc | tcatttccga | tggccaccta | tgtagcgcca | atcgaactaa | gtatgcaggc | 360 |
| ctcgacctgg | catgccccga | ttggctaggc | accctcttgt | tctcgggcgt | ctcctacaca | 420 |
| ttttcctaca | aggccaccgc | gccacacttg | gcttctttg | agttctacgt | cacccgggat | 480 |
| ggttacgagc | ccaccgaccc | gctcaaatgg | gcagacttgg | aggactcgcc | cttcatcaac | 540 |
| gtcaccaacc | ccacacttga | taatggcgcc | taccagatct | ccggcaccac | gcctgccggt | 600 |
| aagtcggggc | gtcatctgat | ctacgtcatt | tggcagcgct | ctgatagccc | agaggcattc | 660 |
| tattcgtgct | ccgacgtcga | ctttgtcgat | gctctctctc | tccactctac | cacc | 714 |

<210> SEQ ID NO 19
<211> LENGTH: 723
<212> TYPE: DNA
<213> ORGANISM: Tectaria milnei

<400> SEQUENCE: 19

| | | | | | |
|---|---|---|---|---|---|
| atgcatcttg | gaatctgcaa | cattcgtgct | gtagggagga | tgagacaagc | caatattgga | 60 |
| gatagtgtga | ggatggggag | gtcatgggga | gtggtggctg | ttatggtggt | gtgcgcaagc | 120 |
| ggcctattga | gcgtagtgag | gggccatgga | agcatggagg | accccatcag | tcgtgtgtat | 180 |

| | |
|---|---|
| gcatgcttcc tagagaatcc ggagcgtccc atatcagcag cttgccaggc ggcagtggca | 240 |
| atgggtggga cgcaagcctt ctatgattgg aatgcggtaa gcctgcccta tgctgctggg | 300 |
| cagcaccgtg aactcatccc ggatggccaa ttgtgcagtg ctgggcgggc aagtatcgg | 360 |
| ggcctggacc tgcctcgtga cgattggcca ggcacctcca atatgacctc cggcgtcgcc | 420 |
| ttcacataca ggtacaaggc caccgcccca cacttgggct ccttccagtt ctatgtcact | 480 |
| cgggatggct acgatcccac cgagccgctc aaatgggcag acttggagga ctcgcctttc | 540 |
| atgaacgcca ccagcacgct tgccccggac tcctacctaa tgtccggcac cacccctagc | 600 |
| ggcaaggctg gccaccacct catctacgcc atttggcagc gcagcgacag ccctgaggcc | 660 |
| ttctactcct gctccgatgt caccttcgac gtcgctgctg tctctgatct ccactccacc | 720 |
| acc | 723 |

<210> SEQ ID NO 20
<211> LENGTH: 720
<212> TYPE: DNA
<213> ORGANISM: Cyrtomium falcatum

<400> SEQUENCE: 20

| | |
|---|---|
| atgttggaat gtgcagcaaa tatgcgtgca gtaattagca ggacgagaca aggcaattct | 60 |
| attgtgagtg tgaggatggg gaggtcatgg ggagttgtgg ctattatggt gttgtgcgcc | 120 |
| accggcctcc tgggcgtggc gagcggccat ggcagcatgg cgacccccat cagccgcgtc | 180 |
| tacaactgct tcctggagaa tcctgagaga cccacgtcgg cagcttgcat cgcggccgtt | 240 |
| gcgctcagtg gaacccaagc gttctatgat tggaatgagg tgaacctgcc cgacgtcaat | 300 |
| ggccgccacc gccagttcat tccggatggc caactgtgca gcgccgggcg ggacaagtat | 360 |
| aagggtctcg acctggcacg ctccgactgg acagccacca acttgtcctc cggcatcgcc | 420 |
| tacacattcc tctacagggt caccgcccag cacaggggct tcttcgagtt ctacgtcacc | 480 |
| gtggatgatt acgatcccac tgtggcgctc aaatgggagg acttggagga aacgccgttc | 540 |
| ctcaacgtca ccgaccccac ggttgtaggc gtcaactacc agatcaacgg caccacgcct | 600 |
| gccagcaaga cgggccgcca cctcatctac gtcatttggc agcgctccga cagcccccgag | 660 |
| gccttctacg cctgctccga cgtcgacttc gtcgatgccg tctctctcca ctccaccacc | 720 |

<210> SEQ ID NO 21
<211> LENGTH: 720
<212> TYPE: DNA
<213> ORGANISM: Polystichium tsus-simense

<400> SEQUENCE: 21

| | |
|---|---|
| atgtgcaaca atatgcgtgc agtaattagg agtacgagac aattaggcaa ttatattggt | 60 |
| catagtgtga ggatggggag gtcatggtgg ggagttttgg ctgttatggt gttgtgcgcc | 120 |
| agcggcctgc tgggcgtagc gagcggccat ggcaccatga atgaccccat cagccgcgtc | 180 |
| tacaactgct tcctggagaa tccggagagc ccacgtcgg cagcttgcat agctgcggtg | 240 |
| gcgctgagtg ggacccaagc gttctatgat tggaatgagg tgaacctggc caacgccgct | 300 |
| ggccgacacc gcgagctcat tccggatggc caactgtgca gcgccgggcg ggacaagtat | 360 |
| aagggcctcg acctggcacg ctccgactgg acagccacca acttgtcctc cggcgtcgcc | 420 |
| ttcacattcc tctacagggt caccgcccag cacaggggct tcttcgagtt ctacgtcacc | 480 |
| gtggatgact acgaccccac tgagctgctc aaatgggaag acttggagga aacgcctttt | 540 |
| ctcaacgtca ctgaccccac ggttgtaggc gtcaactatg aaatctccgg caccacgcct | 600 |

```
gccagcaaga ctggccgcca cctcatctac gtcatttggc agcgctccga cagccccgag    660
gccttctact cctgctccga cgtcgacttc gtcgatagcc tctctctcca ctccaccacc    720

<210> SEQ ID NO 22
<211> LENGTH: 720
<212> TYPE: DNA
<213> ORGANISM: Nephrolepis falcata

<400> SEQUENCE: 22
atgcatcatg gaatctgcaa cattcatgca atagggagga ggagacaagc caatattggt     60
cgtagtgtga ggatggggag gtcatggtgg ggagctgtgg ctattgtatt ggcggtgtgc    120
gccagcggcc tgctgagcgt agtgagcggc aaggaagca tggcgtaccc catcagtcgc    180
gtctatggat gcttcctaga gaatccgttg agtcccacgt cagcagcttg caacgcggcc    240
gtggcattga gtgggacgca agccttctat gattggaatg aggtgagcct ggccaatgcc    300
tctggccagc accgccaact cattccggat ggtcagttgt gcagtgccgg caggccaag    360 tatcggggcc tcgacctggc tcgcgacgat tggccaggca cctccttgac ctccggtgtc    420
gcctacacat tctactacta tgccaccacc ctgcacttgg gcttcttcga gttctatgtc    480
actcgggatg gctacgatgc cacccagccc ctcaaatggg cagatctgga ggactcgcct    540
ttcctcaacg tcaccagcac gcttgccgcc tcctccttcc agtggtctag catcactccc    600
agtgacaagt ctggccgcca cctcatctac gtcatttggc agcgcaccga cagccctgag    660
gccttctact cctgctccga cgtcgacttc gactatgccg tctctctcca ctccaccacc    720

<210> SEQ ID NO 23
<211> LENGTH: 717
<212> TYPE: DNA
<213> ORGANISM: Nephrolepis exaltata

<400> SEQUENCE: 23
atgcatcttg gaatctgcaa cattcgtgca atagggagga ggagacaagc caatattggt     60
ggtagtgtga ggatggggag gtcatgggga gttgcggcta ttgtagtggc ggtgtgcgcc    120
agcggcctgt tgagcgtagt gagcggccat ggaagcatgc aggaccccat cagtcgcgtc    180
tatgcatgct acctagagaa tccggagcgt cccacgtcag cagcttgcca ggcggcagtg    240
gcattgagtg ggacgcaagc cttctatgat tggaatgagg tgaacctgcc caatgccgct    300
ggccggcacc gcgaactcat tccggatggt cagttgtgca gtgctgggcg gccaagtat    360 cagggcctcg accaggctcg caacgattgg ccacacaccg acttgatctc cggcgtcgcc    420
ttcacattca actacagggc caccgcccca cacttgggca tcttcgagtt ctatgtcact    480
cgggatgggt acgatgccac ccagcccctc aaatgggcag atctggagga ctcgcctttc    540
ctcaccgcca ccagcacgct tgcccctcc tctaccagt ggcccggcac cactcccagt    600
ggcaagtctg gccgccacct catctacgtc atttggcagc gcaccgacag ccccgaggcc    660
ttctactcct gctccgacgt cgagttcgtc gatgccgtct ctctccactc caccacc       717

<210> SEQ ID NO 24
<211> LENGTH: 717
<212> TYPE: DNA
<213> ORGANISM: Nephrolepis exaltata

<400> SEQUENCE: 24
atgcatcttg gaatcttcaa cattctggca atagggatga gtatgcaagc caatattggt     60
```

| | |
|---|---|
| ggtagtgtga ggatggggag gtcatgggga gttgcggcta ttgtagtggc ggtgtgcgcc | 120 |
| agcggcctgt tgagcgtagt gagcggccat ggaagcatgc aggacccccat cagtcgcgtc | 180 |
| tatgcatgct acctagagaa tccggagcgt cccacgtcag cagcttgcca ggcggcagtg | 240 |
| gcattgagtg ggacgcaagc cttctatgat tggaatgagg tgaacctgcc caatgccgct | 300 |
| ggccggcacc gcgaactcat tccggatggt cagttgtgca gtgctgggcg ggccaagtat | 360 |
| cagggcctcg accaggctcg caacgattgg ccacacaccg acttgatctc cggcgtcgcc | 420 |
| ttcacattca actacagggc caccgcccca cacttgggca tcttcgagtt ctatgtcact | 480 |
| cgggatgggt acgatgccac ccagcccctc aaatgggcag atctggagga ctcgcctttc | 540 |
| ctcaccgcca ccagcacgct tgcccctcc tcctaccagt ggcccggcac cactcccagt | 600 |
| ggcaagtctg gccgccacct catctacgtc atttggcagc gcaccgacag ccccgaggcc | 660 |
| ttctactcct gctccgacgt cgagttcgtc gatgccgtct ctctccactc caccacc | 717 |

<210> SEQ ID NO 25
<211> LENGTH: 744
<212> TYPE: DNA
<213> ORGANISM: Humata termanii

<400> SEQUENCE: 25

| | |
|---|---|
| atgagtatat atatacacac aaatgttcga atgtggagca tgcatttgtg tggagtaagg | 60 |
| aggatcttga gacaaggcaa atcggtcat agtgtgaaga tgggggaggtc atggggagtt | 120 |
| gtggctatta tggtgatgta cattggtggc ctgctaagca tagcaagcgg ccatggcagc | 180 |
| atggaggacc ccatcagccg cgtctatagg tgctacttgg agaatccgga gagtcccaca | 240 |
| tcggcagctt gccaagcggc agtggcagtg agtgggccc aagccttcta cgattggaat | 300 |
| gaggtgaaca ttgctgacgc caatggccga caccgggagc tcatttctga tggccaacta | 360 |
| tgtagcgcaa atcggagtaa gtatgcgggc ctcgacctgg cacgcgcaga ttggctaggc | 420 |
| accaccttgt cctcgggcgc ctccttcaca ttttgcctaca aggccaccgc gccgcacttg | 480 |
| ggcttctttg agttctacgt cacccgggat ggttacgagc ccaccgaccc gctcaaatgg | 540 |
| gcagacttgg aggactcgcc cttcatcaac gtcaccaacc ccacacttga taatggcgcc | 600 |
| taccagatct ccggcaccac gcctgccggt aagtcggggc gtcatctgat ctacgtcatt | 660 |
| tggcagcgct ctgatagccc agaggcattc tattcgtgct ccgacgtcga ctttgtcgat | 720 |
| gctctctctc tccactctac cacc | 744 |

<210> SEQ ID NO 26
<211> LENGTH: 747
<212> TYPE: DNA
<213> ORGANISM: Adiantum tenerum (Scutum Roseum)

<400> SEQUENCE: 26

| | |
|---|---|
| atgactcaag gtgtttcgaa tttgcatacg aatcatctta cggtcctag gtcacctagc | 60 |
| tttattggtc gtagtgtgag tgttagtatg ggctggtgca ggtcatgggg agttgtggct | 120 |
| gtgatggtgt tgtgcaccag cggcctcctg ggcgtagcga gcgggcatgg cagcatgaag | 180 |
| gaccccatca gccgcgtcta caactgctac ctggagaatc cggagaggcc cacgtcggca | 240 |
| gcttgccaag cggcggtggc gctgagcggg acccaagcat tctatgattg gaatgaggtg | 300 |
| aacctgccca cgccgcgggt cggcaccgt gagctcattc ggatggcga actgtgcagc | 360 |
| gccgggcggg aaaagtatca gggcctcgac ctggcgcgcg ccgactggac agccacgtcc | 420 |
| ttgacctccg gcctcgactc gttcacatgg ctctacaagg ccaccgctcc gcacttgggc | 480 |

| | |
|---|---|
| ttcttcgagt tctacgttac ccgggacggt tacgacccga ccgaggcgct cacatgggca | 540 |
| gacctggagg actcgccgtt cataaacgtc accaaccccg cgcttgtcag cggcgactac | 600 |
| caaatctccg gcaccatacc tgccggcaag agcggccgcc acctcatcta cgtcatttgg | 660 |
| cagcgctccg acagcccgga ggccttctac tcctgctccg acgtcgactt cgtcgatgat | 720 |
| gccctgatct ctctccgctc cgccaca | 747 |

<210> SEQ ID NO 27
<211> LENGTH: 723
<212> TYPE: DNA
<213> ORGANISM: Polystichum setiferum (compacta)

<400> SEQUENCE: 27

| | |
|---|---|
| atgtatatat gtgaaatgca tgttggaatg tgcagcaata tgcgtgcagt agttagacac | 60 |
| ggcaatcata gtgtgaggat ggggaggtca tggggagttg cggctattat ggtgttgtgc | 120 |
| gccagcggcc tgctgggtgt agcgagcggc atggcacca tgcatgaccc catcagtcgt | 180 |
| gtctacaact gcttcctgga gaatccagag agtcccacgt cggcagcttg catagaggcg | 240 |
| gtggaggtga gtgggaccca accattctat gattggaatg aggtgaacct ggccaacgcc | 300 |
| gctggccggc accgcgagct cattccggat ggcaaactgt gcagcgccgg cgggacaag | 360 |
| tataagggcc tcgacctggc acgctccgac tgggtagcca ccaacttgtc ctccggcgtc | 420 |
| gccttcacat tcctctacag ggtcaccgcc gagcacaggg gcttcttcga gttctacgtc | 480 |
| accgtggatg attacgaccc cactgagctg ctcaaatggg aagacttgga ggaaacgccg | 540 |
| ttcatgaatg tcaccgaccc cacggttgta ggcgccaact acgaaatccc cggcaccacg | 600 |
| cctgccaaca agaccggccg ccatctcatc tatgtcattt ggcagcgctc cgacagcccc | 660 |
| gaggccttct actcctgctc cgacgtcgtc ttcgccgatg ccgtgtctct ccactccacc | 720 |
| acc | 723 |

<210> SEQ ID NO 28
<211> LENGTH: 723
<212> TYPE: DNA
<213> ORGANISM: Polystichum setiferum (compacta)

<400> SEQUENCE: 28

| | |
|---|---|
| atgtatatat gtgaaatgca tgttggaatg tgcagcaata tgcgtgcagt agttagacac | 60 |
| ggcaatcata gtgtgaggat ggggaggtca tggggagttg cggctattat ggtgttgtgc | 120 |
| gccagcggcc tgctgggtgt agcgagcggc atggcacca tgcatgaccc catcagtcgt | 180 |
| gtctacaact gcttcctgga gaatccagag agtcccacgt cggcagcttg catagaggcg | 240 |
| gtggaggtga gtgggaccca accattctat gattggaatg aggtgaacct gcctgacgtc | 300 |
| aatggccggc accgcgagct cattccagat ggcaaactgt gcagcgccgg cgggagaag | 360 |
| tataagggcc tcgacctggc acgctccgac tgggtagcca ccaacttgtc ctccggcgtc | 420 |
| gccttcacat tcctctacag ggtcaccgcc gagcacaggg gcttcttcga gttctacgtc | 480 |
| accgtggatg attacgaccc cactgagctg ctcaaatggg aagacttgga ggcaacgccg | 540 |
| ttcatgaatg tcaccgaccc cacggttgta ggcgacaact acgaaatccc cggcaccacg | 600 |
| cctgccaaca agaccggccg ccatctcatc tatgtcattt ggcagcgctc cgacagcccc | 660 |
| gaggccttct actcctgctc cgacgtcgtc ttcgccgatg ccgtgtctct ccactccacc | 720 |
| acc | 723 |

<210> SEQ ID NO 29
<211> LENGTH: 729
<212> TYPE: DNA
<213> ORGANISM: Lepisorus bicolor

<400> SEQUENCE: 29

```
atgtcctggg gagttgtggc tattatggtg ccgtgtgtg ccagcggcct gcttttggta      60
attattttt atagaagtgt gaggatgagg tcctggggag ttgtggctat tatggtggcc     120
gtgtgtgcca gcggcctgct gggcgtcgcg agtggccatg cagcatgtc ggaccccatc     180
agtcgcgtct ataggtgccg cctcgagaat ccggagcgtc ccacgtccgc agcctgcatc    240
gcggcggtgg cgcttagcgg caagcaagcc ttctacgatt ggaatgaggt gaatctgccc    300
ttcgccaatg gccggcaccg cgagctcatc cctgacggta aactttgcag cgccgggcgg    360
gacaaatata aaggcctcga cctgccacgc gccgactggc tggccaccctc cttgtcttct   420
ggctccgcct acacattcct ctaccgggcc accgccccc acctgggcta ctttgagttc     480
tacgtcacgc gggatagcta cgaccccact cagccgctcg catggtcgga cttggaggac    540
tcgccgttca tcaaggtcac caacccgccc ctcgtcagcg gattttacga atttcctggc    600
accacgcctt ccggcaaaac cggccgccac ctcatctacg tcatttggca gcgcaccgac    660
agcaccgagg ctttctactc ctgctccgac gtcgactttg acgaggccct ctctctttcc    720
tccaccatc                                                            729
```

<210> SEQ ID NO 30
<211> LENGTH: 750
<212> TYPE: DNA
<213> ORGANISM: Pyrrosia lingua

<400> SEQUENCE: 30

```
atgagatcct gtataaaaag ggcgggactg aaaggagga gcagcagcga agatcctgag      60
agacatctgg tgcttttag atacagagtg tgtgagagga tgaggacgag ggtatgggga    120
gttgtggctt ttatggtggc cgtgtgtgcc tgcgacctgc tgggcctagc gagtgggcat    180
ggctccatgg ggaccccgt cagtcgcgta ttgaattgct acctcgagaa tccggagagg    240
cccacgtcgg cagcctgcat cgcggcggtg gcgctgagtg gcacccaagc tttctacgac    300
tggaatgagg tgaacctggc ctccgcctgt ggccggcacc gcgagctcat ttctgacggc    360
gaactctgca gcgccgggcg cgacaagtat aaaggcctca acctggcacg cgccgactgg    420
gtggccacct ccctgtcttc gggcgtcgat tacacattcc tctttaacgc caccgccgcc    480
cacctgggct acttcgagtt ctgggtcacc cgtgatagct acgaccccac tcagccgctc    540
gcctgggcgg acttggagga ctcgccattc atcaacatca ccaacccac cattgtcagc    600
gatgcctacc aagtgcccgc caccacgcct tccggcaaga ccggccgcca cctcatctac    660
gtcatttggc agcgcactga cagcaccgag gccttctact cctgctccga cgtcgacttt    720
gacgaggccc tccctctctc ctccaccacc                                     750
```

<210> SEQ ID NO 31
<211> LENGTH: 735
<212> TYPE: DNA
<213> ORGANISM: Blechnum appendiculatum

<400> SEQUENCE: 31

```
atgcaggacc cccgactcac agtttatctt atctgcatgt atacactcac tgatctgatt     60
aggatgaaga agtcatccgg agttgtagta gtggtagtag cagctatatt actgttgtgc   120
```

```
ctgctgggcg tggcaaacgg ccatggcagc atgcaggacc ccatcagtcg cgtctacaac    180
tgcttcctag agaacccgga gagtccgaca tcggcagctt gccaagctgc ggtagcagtg    240
gccgggacgc aaccattcta cgattggaat gaggtgaacc tggccaacgc caatggccgg    300
caccgcgagc tcatttcaga tggcatgctg tgcagcgcca accggtccaa gtatcatggc    360
ctcgacctgg cgcgcgccga ctggacggcc acctccttat cctctggcgt cgcctacaca    420
ttcctgtacc gggtcaccgc ccaccacagg ggtttcttcg agttctacat cacccgtgac    480
agctacgacc ccacccagcc gctcgcatgg gcagacctgg aggactcacc gttcatcaac    540
attaccgacc ccacgactgt gagtacgact ctgggtgaag cctacgaaat ctccggcacc    600
acgcccgcca gcaagagcgg tcgccacctc atctatgtca tctggcagcg cagcgacagc    660
cccgaggcat tctactcctg ctccgacgtc gacttctctg ccgatgccct gatctctctc    720
cgctccgcag tactc                                                    735

<210> SEQ ID NO 32
<211> LENGTH: 717
<212> TYPE: DNA
<213> ORGANISM: Polystichum munitum

<400> SEQUENCE: 32
atgcatcttg gaatgtgcag caatatgcgt gcagtaatta cacaaggcaa ttatattggt     60
catagtgtga ggatggggag gtcatgggga gttgtggcta ttatggtgtt gtgcgctagc    120
ggcctgctgg gcgtagcgag cggccatggc accatgaaca accccatcag ccgcgtctac    180
aactgccgcc tggagaatcc ggagcgtccc acgtcagcag cttgcatagc ggcggtggcg    240
ctgagtggga cccaagcgtt ctatgattgg aatgaggtga acctgcccga cgtcaatggc    300
cggcaccgcg agctcattcc ggatggcaaa ctgtgcagcg ccggcgggga caagtataag    360
ggcctcgacc tggcacgctc cgactgggta gccaccaact tgtcctccgg cgtcgccttc    420
acattcctct acagggtcac cgcccagcac aggggcttct tcgagttcta cgtcaccgtg    480
gatgattacg accccactga gctgctcaaa tgggaagact tggaggaaac gccattcatg    540
aacgtcaccg accccacggt tgtaggcgtc aactacgaaa tcccaggcac cacgcctgca    600
aacaagaccg ccgccatctc atctatgtc atttggcagc gctccgacag ccccgaggcc    660
ttctactcct gctccgacgt agacttcgtc gatgccgtgt ctctccactc caccacc      717

<210> SEQ ID NO 33
<211> LENGTH: 696
<212> TYPE: DNA
<213> ORGANISM: Stenochlaena tenuifolia

<400> SEQUENCE: 33
atgaggcgac acaatactgg ttataatagt gagcgagcac tgtgcatggg gatggggagg     60
tcaaactcat ctaaagttgt agctatcgtg gtgttgtgca gtggcctgct gagcctagtg    120
agcggccatg gcagtatgca gaaccccatc agtcgcgtcc tcaactgcta cctggagaat    180
ccggagcgtc ccacgtcggc agcttgccaa gcggcggtgg cgatgagtgg acccaagcc    240 ttctatgatt ggaatgaggt gaacctgccc aacgccgctg gccggcaccg ccaactcatt    300
cccgatggcc aactgtgcag cgccgggcgg cagaagtatc gggcctcga cttggctcgc    360 gacgactggg aagccaccac cttgtcctcc gggaccgcct tcacatacaa ctacagggcc    420
accgccccgc acctgggctt cttcgagttc tacgtcactc gggatggcta cgagcccact    480
```

| gagcctctca aatggtccga cttgcaggac tcgcccttca tcaacgtcac caccacgctt | 540 |
| tctagcgact cctaccaaat caccggcacc acgcctgctg gcaagtccgg ccgccacctc | 600 |
| atctacgtca tttggcagcg ctccgacagc cccgaggcct ctactcctg ctccgacgtc | 660 |
| gagttcgacg ttgccctctc tctccattcc gccacc | 696 |

<210> SEQ ID NO 34
<211> LENGTH: 693
<212> TYPE: DNA
<213> ORGANISM: Asplenium bulbiferum (G.Forst.)

<400> SEQUENCE: 34

| atgagaatgg ggagatcgac atcttgcatg ggagcaaata tggctttcat gctgctgctg | 60 |
| ctgttgtttt gggctagctg ctgctgcctg ctgggcaaag tgagcgggca tggcagcatg | 120 |
| gaggatccca tcagccgtgt ctacgcctgc ttcttggaga atccggagag ccgacgtcg | 180 |
| gcagcatgcc aagcggcggt ggcgttgagt gggacgcaag cgttctatga ttggaacgag | 240 |
| gtcaaccagc ccaacgctgc cggccggcac cgcgagataa tcccggacgg ccagctctgc | 300 |
| agcggcgggc gggagaagta tcagggcctc gacttggcac gtgacgactg gacggccacc | 360 |
| tccttgtccc caaacgtctc cttcacgttc tctacaagg cgacagcgcc tcaccgcggt | 420 |
| ttcttcgagt tctacgtcac ccgggatggt tacgacccta ccgaggccct cacatgggcc | 480 |
| gacttggagg aaccgccatt catcaacgtc accgacccca cggttgcctc cggcgcctac | 540 |
| cagatccccg gcaccacacc ggccggcaag actggccgcc atctcatcta cgtcatatgg | 600 |
| cagcgctctg atagccccga ggccttctac tcttgctccg acgtcgactt cgagagtgcc | 660 |
| gataccgtca atatctctct ccgctctacc acc | 693 |

<210> SEQ ID NO 35
<211> LENGTH: 699
<212> TYPE: DNA
<213> ORGANISM: Athyrium filix-femina

<400> SEQUENCE: 35

| atgaatattg caggtcatac tagtgtgagg gtgaggatgg ggaggtcatg gggagttgtg | 60 |
| gctattctta tggtgttgtg cggctgcctg ctgggcgtag cgagcgggca tggcagcatg | 120 |
| gaggacccca tcagtcgcgt ctacaactgc tacctcgaga atccggagag tcccacgtcg | 180 |
| gcagcttgcc aagcggcggt ggcgctgggt gggccccaac cgttctatga ttggaatgag | 240 |
| gtgaaccagc ccaacgccga tggccactcc cgcgagatca ttccggatgg ccaactgtgc | 300 |
| agcggcgggc gggagaagta taagggcctc gacctggcac gctccgactg gacagccacc | 360 |
| tccttgtcct ccggcgtcgc cttcacattc tcttcaagg ccactgcccc gcacgcgggc | 420 |
| ttcttcgagt tctacgtcac ccaggatggt tacgacccca ctgagccgct caaatgggca | 480 |
| gacttggagg actcgccctt catcaacgtc accgacccca cgcttctcag cggctcctac | 540 |
| caaatccccg gcaccacgcc tgccggcaag tccggccgcc acctcatcta cgtcatttgg | 600 |
| cagcgctccg acagccccga ggccttctac tcctgctccg acgtcgactt cgtcgatgcc | 660 |
| ctctctagtg atctccactc caccatggca ccaatagct | 699 |

<210> SEQ ID NO 36
<211> LENGTH: 693
<212> TYPE: DNA
<213> ORGANISM: Adiantum capillus-veneris

<400> SEQUENCE: 36

```
atggggatga agatgtcatg ggaagttgca ctagcagaaa tagtagcttt gtgcctactg        60
ggcatggcaa gcagccatgg caccatgcag gaccccataa gtcgtgtcta caactgcttt       120
ctggagaacc cggagaggcc aacgtcggca gcttgtcaag ctgcagtagc gttgggtggc       180
acacaaccac tctatgattg gaatgaggtg aacatccatg atgccgctgg caaccaccgc       240
gatctcatcc ccgatggcaa gctctgcagc gccggccgcc aaaagtttca gggcctcgac       300
ttggcgcgcg cggattggat agcaacctcc ctatcctctg gcgtcgacgt cgactacaca       360
ttcctctacc gcgccaccgc cccgcacttg ggcttctttg aattttacat cacccgtgac       420
acctacgacc ccacccagcc gctcgcatgg ggtgacctgg aagactcgcc cttcatcaac       480
attaccaatc cctccatcgt cagtacgact ttgggtcccg cctactcgat ccccagcact       540
acaccattca gcaaaagtgg tcgccacctc atctacgtca tctggcagcg caccgacagc       600
ctcgaggcgt tctactcctg ctccgacgtc gacttctcga catcttccat cgaggatgat       660
gtcatcgtct ctctccgttc tgcagctcta ctc                                    693
```

`<210>` SEQ ID NO 37
`<211>` LENGTH: 699
`<212>` TYPE: DNA
`<213>` ORGANISM: Coniogramme emeiensis (Golden Zebra)

`<400>` SEQUENCE: 37

```
atgtatacac tcactgatct gattaggatg aagaagtcat ccggagttgt agtagtggta        60
gtagcagcta tattactgtt gtgcctgctg ggcgtggcaa acggccatgg cagcatgcag       120
gaccccatca gtcgcgtcta caactgcttc ctagagaacc cggagagtcc gacatcggca       180
gcttgccaag ctgcggtagc agtggccggg acgcaaccat tctacgattg gaatgaggtg       240
aacctggcca acgccaatgg ccggcaccgc gagctcattt cagatggcat gctgtgcagc       300
gccaaccggt ccaagtatca tggcctcgac ctggcgcgcg ccgactggac ggccacctcc       360
ttatcctctg gcgtcgccta cacattcctg taccgggtca ccgcccacca caggggtttc       420
ttcgagttct acatcacccg tgacagctac gaccccaccc agccgctcgc atgggcagac       480
ctggaggact caccgttcat caacattacc gaccccacga ctgtgagtac gactctgggt       540
gaagcctacg aaatctccgg caccacgccc gccagcaaga gcggtcgcca cctcatctac       600
gtcatttggc agcgcagcga cagccccgag gcattctact cctgctccga cgtcgacttc       660
tctgccgatg ccctgatctc tctccgctcc gcagtactc                             699
```

`<210>` SEQ ID NO 38
`<211>` LENGTH: 693
`<212>` TYPE: DNA
`<213>` ORGANISM: Asplenium nidus var plicatum

`<400>` SEQUENCE: 38

```
atgagaatgg ggagatccat atcacgcatg cagctagga tggctattat gctggtgttg         60
tgctgggcta aagctgctg cctgctgggc acagtgagcg ggcatggcag ctctgaggat       120
cccatgagcc gtgtctatgg gtgctacttg cagaatccgg agaggcccgc atcggcagcc       180
tgccgagcgg cagtggcgat gagtgggacg caagcgttct atgattggaa cgaggtcaac       240
cagccccatg ctgccggtcg gcaccgcgag atcattccgg atggccagct ctgcggcggc       300
gggcgggcga agtatcgggg cctcaacttg gcacgtgccg actggtggtc cacccccttg       360
tactccaaca cccccttcat gttcctctat agggctaccg cccctcacag gggtttcttc       420
```

-continued

| | |
|---|---|
| gagttctatg tcacccggga tggttacgat cccactgaac ccctcaaatg gtcggacttg | 480 |
| gagtacccac cattcatcaa cgtcaccgac cccacgcttg ccttcggcgc ctacaagatc | 540 |
| cccggcttca caccgtatgg caagactggc cgccatctca tctacatcat atggcaacgc | 600 |
| tctgatagcc cagaagcctt ctactcttgc tccgacgtgg acttcgtgga cttcaagagc | 660 |
| gatgaaaccg tgatccctct ccactctacc acc | 693 |

<210> SEQ ID NO 39
<211> LENGTH: 693
<212> TYPE: DNA
<213> ORGANISM: Polystichum polyblepharum

<400> SEQUENCE: 39

| | |
|---|---|
| atgcttgcag taattagaca aggcaattat attggtcata gtgtgaggat ggggaggtca | 60 |
| tggggagttg tggctattat ggtgctgtgc gctagcggcc tgctggacgt agcgagcggc | 120 |
| catggcagca tgaacgaccc catcagccgt gtctacaact gccgcctgga gaatccggag | 180 |
| agtcccacgt cagatgcttg catagcggcg gtggcgctga gtgggaccca agcgttctat | 240 |
| gattggaatg aggtgaacct gcccaacgcc gctggcaggc accgagagct cattccggat | 300 |
| ggcaaactgt gcagcgccgg gcgggacaag tataagggcc tcgacctcgc acgctccgac | 360 |
| tgggtagcca ccaacttgtc ctccggcgtc gccttcacat tcctctacag ggtcaccgcc | 420 |
| cagcacaggg gcttcttcga gttctacgtc accgtggatg attacgaccc cactgagctg | 480 |
| ctcaaatggg aagacttgga ggaaacaccg ttcatgaatg tcaccgaccc cacggttgta | 540 |
| ggcgtcaact acgaaatggc cggcaccacg cctgccaaca agaccggccg ccatctcatc | 600 |
| tatgtcattt ggcagcgctc cgacagcccc gaggccttct actcctgctc cgacgtcgac | 660 |
| ttcgtcgatg ccgtgtctct ccactccagc acc | 693 |

<210> SEQ ID NO 40
<211> LENGTH: 699
<212> TYPE: DNA
<213> ORGANISM: Adiantum venustum

<400> SEQUENCE: 40

| | |
|---|---|
| atggggagac gtcgtgcagt aaggaaaggt cataatagtg tgaggaggat atccatgggg | 60 |
| aggtcatggg gagacgttgt ggctattatg gtgttgtgcg ccagcggcct gctgggcgta | 120 |
| gcgagcggcc atggcagcat gcaggacccc atcagtcgcg tctacaactg ctacctggag | 180 |
| ggtccggaga gtcccacgtc ggcagcttgc atagcggcgg tggcgctgag tgggacccaa | 240 |
| gcattctatg actggaatga ggtgaaccag cccaacgccg ctggccggca ccgcgagatc | 300 |
| atcccggatg ccaactctg cagcggcggg cgggacaagt atagcggcct cgaccttgcg | 360 |
| cgctccgact ggacagccac ctccttgtcc tccaacgtct cctacacata cctcttcaag | 420 |
| gccaccgccc cgcacaaggg cttcttcgag ttttacgtca cccgggacag ctacgagccc | 480 |
| actgaggcgc tcaaatgggc agacttggag gactcaccct tcattaacat caccgacccc | 540 |
| acgcttgaca gcggcgccta ccaaatcccc ggcaccacgc tgccggcaa gtctgggcgc | 600 |
| cacctcatct acgtcatttg gcagcgctcc gacagcggcg aggccttcta cgcctgctgc | 660 |
| gacgtcgact cgatgtcga tgtcctccac tccaccaca | 699 |

<210> SEQ ID NO 41
<211> LENGTH: 699
<212> TYPE: DNA
<213> ORGANISM: Actiniopteris australis

<400> SEQUENCE: 41

```
atgaggcaag gcagtagtat tgctgatatg agtgtgagaa tgggggagt taacgctgtt      60
gctatcatat tgctgttgtg ctgcgctagc agcggcttgc tgggcatagc ccgcgggcat     120
ggcagcatgc aagatcccat cagccgtgtc tacgcctgct acttggagaa tccggagcgt    180
cccacatcgg cagcttgcca agcggcagtg gccttgagtg ggacgcaagc cttctatgac    240
tggaacgagg tgaaccagcc gtttgctgct ggccgccacc gcgagatcat ccccgacggc    300
cagctttgca gcggtgggcg gaccaagtat gcgggcctcg acctggcacg cgacgactgg    360
acagccacct cctgtccgc cggcatctcc tacacattcc tctacagagg caccgccccg     420
caccttggct tcttcgagtt ctacgtcacc cgggatggtt acgatcccac tgagcccctc    480
aaatgggcag acttggagga cccgcctttc atcaacatca ccaaccccac tcttgtcagc    540
ggcgtttacc agatccccgg gaccacacct gccggaaaga ctggccgcca tctcatctac    600
gttatctggc agcgcaccga cagccccgag gcgttctact cctgctccga cgtcgtcttc    660
agcgacgatg ccgccctcta tctccgctct accactgag                           699
```

<210> SEQ ID NO 42
<211> LENGTH: 693
<212> TYPE: DNA
<213> ORGANISM: Marsilea crenata

<400> SEQUENCE: 42

```
atgaggagga gcgggatgag cagcagcgtg ctagccgctg tcgccgccgg agttcttcta    60
gtggcggcac taggcagcca cgtggcgtac gggcacggca gcatgaagga accaatcagc   120
cgcgcttaca actgctacct cgaaattgct gacaatgcca cgtcagacgc gtgcggggcg   180
gcggcagcgc tttgcatccc tgaagccttc aacgactgga cgctgtact tatccctgac    240
gtcgccggcc gccaccgcca gctcatcccg gacggacagc tgtgcagcgc cggaagagcg   300
aagtacgccg gcctgaatct cgcaagtgtg gactgggagg ccgccacctt ggctgccggc   360
gtgaactaca cgtttctgta caaggccgta gtggtccaca aaggctactt cgagttctac   420
gtcaccaagg acggctacga cgccacgcaa gcgctcacat ggtccgactt ggaagacgcc   480
cctttcgtca acgtcaccga tcccatagtc aattccgaca gtgacttcga aattcccggc   540
accattccct ccgggaagtc cggccgccac gtgatctacg tcatttggca gcgcaccgac   600
agccccgaag ctttctactc ctgctcggac gtcgacttcg acgacaccat ctccgacgac   660
accatctccg acaccgtcct acatgccagc tca                               693
```

<210> SEQ ID NO 43
<211> LENGTH: 687
<212> TYPE: DNA
<213> ORGANISM: Asplenium prolongatum x Asplenium antiquum (Kurata)

<400> SEQUENCE: 43

```
atgagaatgg ggaggtcggc atcttgcatc agagctaata tggctatcat gctggtgttg    60
ttttgggcta gctgctgctg cctgctgggc atagtgagcg gcatggcag catggaggat   120
cccatcagtc gtgtctacgc ctgctacttg agaatccgg agcggccac atctgcagct   180
tgcatagcgg cggtggcgtt gagtgggacg caagcgttct acgattggaa cgaggttaac   240
cagcccaacg ccgccggtcg gcaccgcgag atcattccgg atggccagct ttgcagcggt   300
gggcgggaga agtatcaggg cctcgacctg gcacgtgccg actggacggc cacctccctg   360
```

```
acctccggta tcaccttcac tttcctctac aaggcaacag ccccctcaccg tggtttcttt    420 gagttctacg tcacccgcga tacttatgat cccaccgagc ccctcacatg ggcggacttg    480
gaggacacgc cattcatcaa cgccaccgac cccacgcttg cttccggctc ctaccagatc    540
cccggcacca caccagccgg caagactggc cgccatctca tctacgtcat atggcagcgc    600
tctgatagcc ccgaagcctt ctactcttgc tctgacgtgg actttgagag cagcgatacc    660
gtgatctctc tccgctctgc caccacc                                        687

<210> SEQ ID NO 44
<211> LENGTH: 687
<212> TYPE: DNA
<213> ORGANISM: Adiantum raddianum (Fritz Luthi)

<400> SEQUENCE: 44
atggggatga agatgtcatg ggaagttgca ctagcagaaa tagtagcttt gtgcctactg     60
ggcatggcaa gcagccatgg caccatgcag accccataa gtcgtgtcta caactgcttt    120
ctggagaacc cggagaggcc aacgtcggca gcttgtcaag ctgcagtagc gttgggtggc    180
acacaaccac tctatgattg gaatgaggtg aacatccatg atgccgctgg caaccaccgc    240
gatctcatcc ccgatggcaa gctctgcagc gccggccgcc aaaagtttca gggcctcgac    300
ttggcgcgcg cggattggat agcaacctcc ctatcctctg gcgtcgacta cacattcctc    360
taccgcgcca ccgccccgca cttgggcttc tttgaatttt acatcacccg tgacacctac    420
gaccccaccc agccgctcgc atggggtgac ctggaagact cgcccttcat caacattacc    480
aatccctcca tcgtcagtac gactttgggt cccgcctact cgatccccag cactacacca    540
ttcagcaaaa gtggtcgcca cctcatctac gtcatctggc agcgcaccga cagcctcgag    600
gcgttctact cctgctccga cgtcgacttc tcgacatctt ccatcgagga tgatgtcatc    660
gtctctctcc gttctgcagc tctactc                                        687

<210> SEQ ID NO 45
<211> LENGTH: 681
<212> TYPE: DNA
<213> ORGANISM: Asplenium australasicum

<400> SEQUENCE: 45
atgagaatgg ggagatccac atcacgcatg gcagctagga tggctattac gctgctgttg     60
tgctgggcta gctgctgcct gctgggcaca gtgagcgggc atggcagcat gctggatccc    120
atcagtcgca tctacgcctg cttcttggag aatccggaga ggcccacatc ggcagcctgc    180
caggcggcag tggcgttggg tgggacgcaa ccgctctatg attggaacga ggtcaaccag    240
cccaatgctg ccgtcggca ccgcgagatc attccggatg ccagctttg cggcggcggg    300 cgggagaagt atcagggcct caacttggca cgtgccgact ggccggcaac ctccttgtcc    360
tccaacaccg ccttcacgtt cctctacatt gctacagccc ctcaccgcgg tttcttcgag    420
ttctacgtca cccgggatgg ttacgatccc actgagctcc ttaaatgggc ggacttggag    480
tacccaccct tcctcaacgt caccgacccc acgcttgcct ccggcaacta ccagatccct    540
ggcaccacac cagccggcaa gaccggccgc catctcattt acgtcatatg gcagcgctcc    600
gatagccccg aagccttcta ctcctgctcc gacatcgact tcgagagcga tgaaaccgtg    660
atctctctcc actctaccac c                                              681

<210> SEQ ID NO 46
<211> LENGTH: 681
```

```
<212> TYPE: DNA
<213> ORGANISM: Asplenium australasicum

<400> SEQUENCE: 46
atgagaatgg ggagatccac atcacgcatg gcagctagga tggctattac gctgctgttg      60
tgctgggcta gctgctgcct gctgggcaca gtgagcgggc atggcagcat gctggatccc     120
atcagtcgca tctacgcctg cttcttggag aatccggaga ggcccacatc ggcagcctgc     180
caggcggcag tggcgttggg tgggacgcaa ccgctctatg attggaacga ggtcaaccag     240
cccaacgctg ccggccgcca ccgcgagatc attcccgatg ccaactttg cagcggcggg      300 cgggagaagt ataagggctt cgacttgcct cgtgccgact ggccggcaac caccttggtc     360
tccaacatca gcttcacata cctctacaag gcaacagctc ctcaccgtgg tttcttcgag     420
ttctacgtca cccgggatgg ttacgatccc actgagctcc ttaaatgggc ggacttggag     480
tacccaccct tcctcaacgt caccgacccc acgcttgcct ccggcaacta ccagatccct     540
ggcaccacac cagccggcaa gaccggccgc catctcattt acgtcatatg cagcgctcc      600 gatagccccg aagccttcta ctcctgctcc gacatcgact cgagagcga tgaaaccgtg      660 atctctctcc actctatcac c                                               681

<210> SEQ ID NO 47
<211> LENGTH: 687
<212> TYPE: DNA
<213> ORGANISM: Adiantum raddianum (Gracillimum)

<400> SEQUENCE: 47
atggggatga agatgtcatg ggaagttgca ctagcagaaa tagtagcttt gtgcctactg      60
ggcatggcaa gcagccatgg caccatgcag gaccccataa gtcgtgtcta caactgcttt     120
ctggagaacc cggagaggcc aacgtcggca gcttgtcaag ctgcagtagc gttgggtggc     180
acacaaccac tctatgattg gaatgaggtg aacatccatg atgccgctgg caaccaccgc     240
gatctcatcc ccgatggcaa gctctgcagc gccggccgcc aaaagtttca gggcctcgac     300
ttggcgcgcg cggattggat agcaacctcc ctatcctctg cgtcgactac acattcctc      360 taccgcgcca ccgccccgca cttgggcttc tttgaatttt acatcacccg tgacacctac     420
gaccccaccc agccgctcgc atggggtgac ctggaagact cgcccttcat caacattacc     480
aatccctcca tcgtcagtac gactttgggt cccgcctact cgatcccag cactacacca      540 ttcagcaaaa gtggtcgcca cctcatctac gtcatctggc agcgcaccga cagcctcgag     600
gcgttctact cctgctccga cgtcgacttc tcgacatctt ccatcgagga tgatgtcatc     660
gtctctctcc gttctgcagc tctactc                                         687

<210> SEQ ID NO 48
<211> LENGTH: 684
<212> TYPE: DNA
<213> ORGANISM: Thelypteris palustris

<400> SEQUENCE: 48
atgaggcaag gcaattatat aggtcatagt gtgaggatgg ggaggtcatg gggagttgtg      60
ggtattatgg tgttgtgcct gctgggcgta gcgagcggcc atggcaccat gcaggacccc     120
atcagtcgcg tctacaactg ccgcctggag aatccggagc gtcccacgtc ggcagcttgc     180
atagcggccg tggcgctgag tgggacccaa gcgttctatg attggaatga ggtgaacttg     240
gccaacgccg ctggccggca ccgcgagctc attccggatg ccaactgtg cagcgccggg      300
```

```
cgggtcaagt accagggcct cgacctggca cgctccgact ggacagccac ctccttgtcc      360
tccggcgtct ccttcacatt cctctacagg gtcaccgccc agcacttggg cttcttcgag      420
ttctacgtca cccaggatgg ttacgacccc actgagccgc tcaaatgggc agacttggag      480
gactcgccgt tcatcaacgt caccaacccc acggttgtca gcacctccct aggcccccgcc     540 taccaaatcg ctggcaccac gcctgccggc aagtctggcc gccacctcat ctacgtcatt      600
tggcagcgct ccgacagccc cgaggccttc tactcctgct ccgacgtcga cttcgtcgat      660
gccctctctc tccactccac tgcc                                             684
```

<210> SEQ ID NO 49
<211> LENGTH: 687
<212> TYPE: DNA
<213> ORGANISM: Adiantum raddianum (Variegatum)

<400> SEQUENCE: 49

```
atggggatga agatgtcatg ggaagttgca ctagcagaaa tagtagcttt gtgcctactg       60
ggcatggcaa gcagccatgg caccatgcag acccccataa gtcgtgtcta caactgcttt      120
ctggagaacc cggagaggcc aacgtcggca gcttgtcaag ctgcagtagc gttgggtggc      180
acacaaccac tctatgattg aatgaggtg aacatccatg atgccgctgg caaccaccgc       240
gatctcatcc ccgatggcaa gctctgcagc gccggccgcc aaaagtttca gggcctcgac      300
ttggcgcgcg cggattggat agcaacctcc ctatcctctg cgtcgactaa cacattcctc       360
taccgcgcca ccgccccgca cttgggcttc tttgaatttt acatcacccg tgacacctac       420
gaccccaccc agccgctcgc atggggtgac ctggaagact cgcccttcat caacattacc      480
aatccctcca tcgtcagtac gactttgggt cccgcctact cgatcccccag cactacacca    540 ttcagcaaaa gtggtcgcca cctcatctac gtcatctggc agcgcaccga cagcctcgag      600
gcgttctact cctgctccga cgtcgacttc tcgacatctt ccatcgagga tgatgtcatc      660
gtctctctcc gttctgcagc tctactc                                          687
```

<210> SEQ ID NO 50
<211> LENGTH: 690
<212> TYPE: DNA
<213> ORGANISM: Asplenium dimorphum X Asplenium difforme

<400> SEQUENCE: 50

```
atgagaatgg ggagatcgac atcttgcatg ggagctaata tggctatcgt cctgctgctg       60
ctgttgtttt gggctagctg ctgctgcctg ctgggcaaag tgagcgggca tgcagcatg      120 gaggatccca tcagtcgtgt ctacgcctgc ttcctggaga atccggagag gccgacgtcg      180
gcagcctgcc aagcggcggt ggcgttgagt gggacgcaag cgttctatga ttggaacgag      240
gtcaacctgc ccaacgctgc cggccggcac cgcgaaatca tcccggacgg ccagctttgc      300
agcggcgggc gggagaagta taaaggcctc gacttggcac gtgccgactg gacggccacc      360
tccttgtccc caaacgtctc cttcacgttc ctctacaagg ggacagcgcc tcaccgcggt      420
ttcttcgagt tctacgtcac ccgggatggt tacgacccta ccgaggccct cacatgggcc      480
gacttggagg aaccgccatt catcaacgtc accgaccccca cgcttgcctc cggcgcctac      540
cagatccccg gcaccacacc agccggcaag acgggccgcc atctcatcta cgtcatatgg      600
cagcgctctg acagcccga agccttctac tcttgctccg acgtcgactt cgagagtgac      660
gataccgtgg tctctctccg ctctaccacc                                       690
```

```
<210> SEQ ID NO 51
<211> LENGTH: 687
<212> TYPE: DNA
<213> ORGANISM: Matteuccia struthiopteris

<400> SEQUENCE: 51
atgcttgcag taaggaaagg caatattggt gatagcgtga ggatggggag gtcatggggt      60
gttgtagcta ttatggtgtt gtgcgccagc agcctgctgg gcgtagtgag cggccatggc     120
agcatggcgg accccatcag tcgtgtctat gggtgccgtc tggagggtcc ggagagcccc     180
acatcggcag cttgccaagc ggcggtggcg ctgagtggga cccaagcgtt ctatgattgg     240
aatgaggtga accagccctt cgccgctggc cggaccgcg agctcattcc ggatggccaa      300
ctgtgcagcg gcgggcgggt caagtatcag ggcctcgacc tggcacgctc cgactggcca     360
gccaccaact tgtcctccgg cgtctccttc acattcctct acgaggtcac cgccacgcac     420
ttgggctact ttgagttcta cgtcacccgg gatggttacc agccgactga gccgctcaaa     480
tgggcagact ggaggactc gccgttcctc accgccacca caacgcatga gagcagctcc     540
tacataatcc ctggcaccac gccttccgcc aagtccggcc gccacctcat ctacctcatt     600
tggcagcgga ccgacagccc cgaggccttc tactcctgct ccgacgtcga cttcgtcgat     660
gccctctcta gtctccactc caccaac                                         687

<210> SEQ ID NO 52
<211> LENGTH: 684
<212> TYPE: DNA
<213> ORGANISM: Athyrium filix-femina (angustum)

<400> SEQUENCE: 52
atgatgaata ttgcaggtca tactagtgtg aggatgggga ggtcatgggg agttgtggct      60
attcttatgg tgttgtgcgg ctgcctgctg ggcgtagcga gcgggcatgg cagcatggag     120
gaccccatca gtcgcgtcta caactgctac ctggagaatc cggagagtcc cacgtcggca     180
gcttgccaag cggcggtggc gctgggtggc acccaaccgt tgtatgattg aatgaggtg      240 aaccagccca cgccgctgg ccagtcccgc gaaatcattc cggatggcca actgtgcagc      300
ggcgggcggg agaagtatca gggcctcgac ctggcacgct ccgactggac agccacctcc     360
ttgtcctccg gcgtcgcctt cacattcctc ttcaaggcca ccgccccgca cttgggcttc     420
ttcgagttct acgtcaccca ggatggttac gaccccactg agccgctcaa atgggcagac     480
ttggaggact cgcccttcat caacgtcacc gaccccacgc ttctcagcgg ctcctaccaa     540
atccccggca ccacgcctgc cggcaagtcc ggcgccacc taatctacgt catttggcag     600
cgctccgaca gccccgaggc cttctactcc tgctccgacg tcgacttcgt cgatgccctc     660
tctagtgatc tccactccac cacc                                            684

<210> SEQ ID NO 53
<211> LENGTH: 687
<212> TYPE: DNA
<213> ORGANISM: Adiantum monocolor

<400> SEQUENCE: 53
atggggatga agatgtcatg ggaagttgca ctagcagaaa tagtagccttt gtgcctactg      60 ggcatggcaa gcagccatgg caccatgcag acccccataa gtcgtgtcta caactgcttt     120
ctggagaacc cggagaggcc aacgtcggca gcttgtcaag ctgcagtagc gttgggtggc     180
acacaaccac tctatgattg gaatgaggtg aacatccatg atgccgctgg caaccaccgc     240
```

```
gatctcatcc ccgatggcaa gctctgcagc gccggccgcc aaaagtttca gggcctcgac      300
ttggcgcgcg cggattggat agcaacctcc ctatcctctg cgtcgacta cacattcctc      360 taccgcgcca ccgccccgca cttgggcttc tttgaatttt acatcacccg tgacacctac      420
gaccccaccc agccgctcgc atggggtgac ctggaagact cgcccttcat caacattacc      480
aatccctcca tcgtcagtac gactttgggt cccgcctact cgatcccag cactacacca       540 ttcagcaaaa gtggtcgcca cctcatctac gtcatctggc agcgcaccga cagcctcgag      600
gcgttctact cctgctccga cgtcgacttc tcgacatctt ccatcgagga tgatgtcatc      660
gtctctctcc gttctgcagc tctactc                                          687

<210> SEQ ID NO 54
<211> LENGTH: 684
<212> TYPE: DNA
<213> ORGANISM: Adiantum pubescens (Bronze)

<400> SEQUENCE: 54
atgaagaagt cttggggagt tacagctgta gtgggagtaa tagctttgtg cctgctggac       60
gtggcaagcg gccatggcag catgcaggac cccatcagtc gtgtctacaa ctgctttcta      120
gaaaacccgg agcgcccaac gtcggcagct tgcatagctg cggtggcaat gagtggcaca      180
caaccattct acgattggaa tgaggtgaac ttggccgacg ccaatggccg gcaccgcgag      240
ctcatccccg atggcaagct gtgcagcgcc ggcaggata agtatcaggg cctcgaccag       300
gcgcgcgacg actgggtagc aacctcctta tcctctggcg tcgcctacac attcctttac      360
cgggtcactg ccccgcactt gggcttcttt gaattttacg tcacccgtga cacctacgac      420
cccactcagg cgctcgcatg ggatgacctg gaagactcgc ccttcatcaa cattaccaac      480
ccctccgttg tcagtacgac gttgggtaac gcctactcaa ttcccggcac cacgccatcc      540
ggcaagactg gtcgccacct catctacgtc atctggcagc gcagcgacag tcgcgaggcg      600
ttctactcct gctccgacgt cgacttcccg gcatcgacag tcgaggatga cgtcatcatc      660
tctctccgct ccgcagctct agtc                                             684

<210> SEQ ID NO 55
<211> LENGTH: 681
<212> TYPE: DNA
<213> ORGANISM: Blechnum niponicum

<400> SEQUENCE: 55
atgagcgcag taaggaatat tggtcatagt gtgaggatgg aaggtcatg gggagttgtg        60 gctattatgg tgttgtgcgc cagcggcctg ctgggcgtag cgagcggcca tggcagcatg      120
gacgacccca tcagtcgtgt ctacaactgc tacctggaga tccggagcg tcccacgtcg       180 gcagcttgcc aagccgcggt ggcgctgagt gggacccaag cgttctatga ttggaatgag      240
gtgaaccagc cctccgccgc tggccggcac cgcgagatca ttccggatgg ccaactgtgc      300
agcggcgggc gggagaagta tcagggcctg gacctggcac gctccgactg gacagccacc      360
tccttgtcct ccggcgtctc cttcacatac ctgtacaagg ccaccgcccc gcacttgggc      420
ttcttcgagt tctacgtcac cgtggatggt taccagccca ctgagccgct caaatggtca      480
gacttggagg accgccgtt catcaacgtc accaacccca cgcttgtcag cggctcctac       540
caaatccccg gcaccacgcc tgccggcaag accggccgcc acctcatcta cgtcatttgg      600
cagcgctccg acagcccga ggccttctac tcctgctccg acgtcgactt cgccgatgcc       660
ctctctctcc actccaccac c                                                681
```

<210> SEQ ID NO 56
<211> LENGTH: 672
<212> TYPE: DNA
<213> ORGANISM: Platycerium wandae

<400> SEQUENCE: 56

| | | | | | |
|---|---|---|---|---|---|
| atgtatggtg | gtcagcatac | tgggaggatg | gggaagccgt | ggagagtggt | ggtggccatt | 60 |
| gtggtggtgt | gcgccagcgg | cctgctgggc | gtagcgagcg | gccatggcag | catgggtgaa | 120 |
| cccatcagtc | gcgtctataa | ttgctacctg | gagaatccgg | agagacccac | gtcggcagcg | 180 |
| tgcatcgcgg | cggtggcgct | tagtggcacc | caagccttct | acgactggaa | tgaggtgaac | 240 |
| ctgcccttcg | ccgctggccg | gcaccgcgag | ctcattcctg | acggccagct | ctgcagcgcc | 300 |
| gggcgggaca | gtataaagg | cctggacctg | gcacgcgccg | actgggttgc | cacctccctg | 360 |
| tcttcgggcg | tcagctacac | cttcctctac | agggccaccg | ccccccacca | gggctacttt | 420 |
| gagttctacg | tcaccaagga | tagctacgac | cccactgagc | cgctggcctg | gcggacctg | 480 |
| gaggacacgc | ccttcattaa | catcaccgat | ccgaccctttg | tcagcggctc | ttaccagatc | 540 |
| cccagcacca | cgccttccga | caagaccggc | cgccacctca | tctacgtcat | ttggcagcgc | 600 |
| accgacagcc | ctgaggcctt | ctactcctgc | tccgatatcg | actttgacga | caccctcccc | 660 |
| ctacactcca | cc | | | | | 672 |

<210> SEQ ID NO 57
<211> LENGTH: 675
<212> TYPE: DNA
<213> ORGANISM: Nephrolepis cordifolia (Duffii)

<400> SEQUENCE: 57

| | | | | | |
|---|---|---|---|---|---|
| atgaaacaag | ccaatattgg | tcatagtgta | aggatgggga | ggtcatggcg | agttgtggct | 60 |
| attatggtgg | tgtgcgccag | cggcctattg | agtgtagtga | gggccatgg | aagcatggaa | 120 |
| gaccccctta | gtcgcgtcta | tgggtgcttc | ctagagaatc | cagagagtcc | cacgtcagca | 180 |
| gcttgccaag | cggcagtggc | aatgagtggg | accctagctt | tctatgattg | gtttgatgtg | 240 |
| agcttgccca | tgcttctgg | ccggcaccgc | gaactcattc | cggatggcca | attgtgtggt | 300 |
| gctgggctga | ccaagtatca | gggcctcaac | ctggctcgcg | atgattggac | agccacctcc | 360 |
| ttgacctccg | gcgtctcctt | cacatacctc | tacaaggccg | ccgcccgaca | cttgggcttc | 420 |
| tttgagttct | atgtcactcg | ggatggttac | gatcccaccg | agccgctcaa | atgggcagac | 480 |
| ttggaggact | gcctttcat | gaacgtcacc | agcacgcttg | acgaggagtc | ctaccaaatc | 540 |
| cctggcacca | ctcctagtgg | caaggctggc | cgccacctca | tctacgtcat | ttggcagcgc | 600 |
| agcgacagcc | ctgaggcctt | ctactcctgc | tccgatgtcg | acttcgtcga | tgctgtctct | 660 |
| ctccactcca | ccacc | | | | | 675 |

<210> SEQ ID NO 58
<211> LENGTH: 672
<212> TYPE: DNA
<213> ORGANISM: Adiantum raddianum (Fragrans)

<400> SEQUENCE: 58

| | | | | | |
|---|---|---|---|---|---|
| atggggatga | agatgtcatg | gaagttgca | ctagcagaaa | tagtagcttt | gtgcctactg | 60 |
| ggcatggcaa | gcagccatgg | caccatgcag | gaccccataa | gtcgtgtcta | caactgctttt | 120 |
| ctggagaacc | cggagaggcc | aacgtcggca | gcttgtcaag | ctgcagtagc | gttgggtggc | 180 |

-continued

```
acacaaccac tctatgattg aatgaggtg aacatccatg atgccgctgg caaccaccgc      240
gatctcatcc ccgatggcaa gctctgcagc gccggccgcc aaaagtttca gggcctcgac      300
ttggcgcgcg cggattggat agcaacctcc ctatcctctg gcgtcgacta cacattcctc      360
taccgcgcca ccgccccgca cttgggcttc tttgaatttt acatcacccg tgacacctac      420
gaccccaccc agccgctcgc atggggtgac ctggaagact cgcccttcat caacattacc      480
aatccctcca tcgtcagtac gactttgggt cccgcctact cgatcccag cactacacca      540 ttcagcaaaa gtggtcgcca cctcatctac gtcatatggc agcgcagcga cagccccgaa      600
gctttctatg cctgctccga catcgacttc tccacttctt ccgacatgat ttctctccgc      660
tccgcagttc tc                                                          672
```

<210> SEQ ID NO 59
<211> LENGTH: 675
<212> TYPE: DNA
<213> ORGANISM: Platycerium bifurcatum (Netherlands)

<400> SEQUENCE: 59

```
atgtatggtg gtcagcatac tgcgagcatg gggaagccgt ggagagtggt ggtggccatt      60
gtggtggtgt gcgccagcgg cctgctgggc gtagcgagcg ccatggcag catgggggat      120 cccatcagtc gcgtctataa ttgctacctg gagaatccgg agaggcccac atcggcagcg      180
tgcatcgcgg cggtggcgct tagtggcacc caagccttct acgactggaa tgaggtgaac      240
ctgcccttcg ccgctggccg gcaccgcgag ctcattcctg acggccagct ctgcagcgcc      300
gggcgggaca gtataaagg cctggacctg gcacgcgccg actgggttgc cacctccttg      360
tcttcgggcg tcagctacac cttcctctac agggttaccg cccccaccg gggctacttt      420 gagttctacg tcaccaagga tagctacgac cccactgagc cgctggcctg gcggacctg      480 gaggacacgc ccttcattaa catcaccgac ccgaccattg tcagcggctc ttaccagatc      540
tccagcacca cgccttccga caagaccggc cgccacctca tctacgtcat ttggcagcgc      600
accgacagcc ctgaggcctt ctactcctgc tccgatgtcg actttgacga caccctcccc      660
ctccactcct ccacc                                                       675
```

<210> SEQ ID NO 60
<211> LENGTH: 663
<212> TYPE: DNA
<213> ORGANISM: Pyrrosia polydactyla

<400> SEQUENCE: 60

```
atgaggatgg ggatgaggat gaggttatgg ggagttgtgg ctttttatggt ggccgtgtgt      60 gccggcgagc tgctggacca agcgagtggg catggctcca tgggggaccc cgtcagtcgc      120
gtcttgaatt gctacctcga gaatccggag aacccctcgt cggctgcctg catcgctgcg      180
gtggcggcga gtggcaccca agccttctac gactggaatg aggtgaatct ggccttcgcc      240
gctggccagc accgcacgct cattcctgat ggcgaactct gcagcgccgg tcgggagaag      300
tataaaggcc tcaatctggc acgcgccgac tgggtagcca cttcattgtc ttcaggcgcc      360
aactacacat tcctctacag ggccaccgcc ccccacctgg gctacttcga gttctacgtc      420
acgcaagata gctacgaccc cactgagccg ctcgcatggg cggacttgga ggactcgccg      480
ttcatcaatg tcaccaaccc gggcctcgtc agcggctcct accgaattgc tggcaccacg      540
ccttccggca aaaccggccg ccacctcatc tacgtcattt ggcagcgcac cgacagcccc      600
gaggccttct actcctgctc cgacgtcgac tttgacgagg ccgtctctct ttcttccacc      660
```

```
acc                                                                      663

<210> SEQ ID NO 61
<211> LENGTH: 666
<212> TYPE: DNA
<213> ORGANISM: Blechnum brasiliense

<400> SEQUENCE: 61
atgaagaagc catggggagt tgtagtagta gtagctatat tactgttgtg cctgctgggc         60
gtggcaagcg gccatggcag catgcaggac cccatcagtc gagtctacaa ctgctaccta        120
gagaacccag agaggccgac atcggcagct tgccaagctg cggtggcgat gagcgggacg        180
caagcattct acgattggaa tgaggtgaac ctggccaacg cttctggccg gcaccgcgag        240
ctcattcctg atggcaagct gtgcagtgcc ggccgggaca agtatcgggg cctcgacctg        300
gcgcgcgccg actggacggc cacctcctta tcctctggcg tcgcctacac attcctccac        360
cgggtcaccg cccggcactt gggattcttc gagttctaca tcacccgtga cagctacgac        420
cccaccgagc tgctcacatg ggcagacctg gaggactcgc cgttcatcaa cattaccaac        480
cccacgactg tgagtacgtc tctgggtaac gcctaccaga tccccggcac cacgcccgcc        540
ggcaagagcg gtcgtcacct catctacgtc atctggcagc gcagcgacag ccctgaggca        600
ttctactcct gctgcgacgt cgacttctct tctgataccc tgatctctct ccgctctgca        660
gcactc                                                                   666

<210> SEQ ID NO 62
<211> LENGTH: 666
<212> TYPE: DNA
<213> ORGANISM: Blechnum sp. (Silver Lady)

<400> SEQUENCE: 62
atgaagaagc catggggagt tgtagtagta gtagctatat tactgttgtg cctgctgggc         60
gtggcaagcg gccatggcag catgcaggac cccatcagtc gagtctacaa ctgctaccta        120
gagaacccag agaggccgac atcggcagct tgccaagctg cggtggcgat gagcgggacg        180
caagcattct acgattggaa tgaggtgaac ctggccaacg cttctggccg gcaccgcgag        240
ctcattcctg atggcaagct gtgcagtgcc ggccgggaca agtatcgggg cctcgacctg        300
gcgcgcgccg actggacggc cacctcctta tcctctggcg tcgcctacac attcctccac        360
cgggtcaccg cccggcactt gggattcttc gagttctaca tcacccgtga cagttacgac        420
cccaccgagc cctcacatg ggcagacctg gaggattcgc cgttcctcaa cattaccgac        480
cccacgactg tgggtacgcc tctgggtgat gcctacgaaa tccccggcac cacgcccgac        540
ggcaagagcg gtcgccacct catctatgtc atctggcagc gcagcgacag ccctgaggca        600
ttctactcct gctgcgacgt cgacttctct tctgataccc tgatctctct ccgctctgca        660
gcactc                                                                   666

<210> SEQ ID NO 63
<211> LENGTH: 669
<212> TYPE: DNA
<213> ORGANISM: Pteris cretica (Mayi)

<400> SEQUENCE: 63
atggggtcga ggtcagtggg cggcggagga gctggggcta tttattgtat gctgctaata         60
tgctgcgtta gcagcgggct gctgggcata gcgagcggcc atggcaccat gctggacccc        120
```

```
tttagtcgtg tgtacgcctg ccgcttcttc gagaatccgg agcgtcccac atcgccagca    180
tgccaagcag cagtggcggc gagtggaacg caagcgttct atgactggaa cgaggtgaac    240
cagcccttcg ccgctggccg gcaccgcgag atcattccgg acggccaact tgcagcggt     300 gggcgggaca gtataaaggg cctcgacctg cacgcaacg actggccagc cacctccttg     360
tcctccaaca tccccttcac atacctgtac attgccagcg ctccgcaccg cggcttcttc    420
gagttctacg tcacccagga tggttacgat cccactcagc ccctcaaatg gcagatttg     480 gagtacccgc cattcatcaa catcaccgac cccacgctgc tcagcggctc ctaccaaatc    540
cccggcacca cgccgccgg caagtctggc cgccatctca tctacgtcat ttggcagcgc     600
tccgacagcc ccgaggcctt ctactcctgc tccgacgtcg acttcgtcga ctctctccac    660
gcctccgtc                                                            669

<210> SEQ ID NO 64
<211> LENGTH: 663
<212> TYPE: DNA
<213> ORGANISM: Cystopteris fragilis

<400> SEQUENCE: 64
atggggagag ttaaccttct ggctattctg gtgttgtgcg ccagctgctg cgccggcctg     60
ctgggcgtag ccagcggcca tggcaccatg gaggaccca tcagtcgcgt ctacaactgc    120
ttcctggaga acccggagcg tcccacgtcg gcagcttgcc aagcggcggt tgcgctgagt    180
ggcacccaag cgttctatga ctggaatgag gtgaacctgg cggacgccgc tggccggcat    240
cgcgagctca ttccggatgg ccaactgtgc agcgccgggc gggagaagta tcggggcctg    300
gacctggcac gctccgactg ggtagccacc tccttgtcct ccggcgtctc caccacattc    360
ctctacaagg ccacggctcc gcacttgggc ttcttcgagt tctacgtcac ccgggatgga    420 tacgaccca ccgaggcgct caaatggtca gacttggagg actcgccgtt cctcaacgtc    480
accgacccca cccttctcag cagccctac gtctaccaaa tccctggcac cacgcctgcc    540
ggcaagtccg gcgccacct gatctacgtc atttggcagc gctccgacag ccctgaggcc    600
ttctactcct gctccgacgt cgccttcgac gatgcccagc ttgtctctct ccactccacc    660
acc                                                                  663

<210> SEQ ID NO 65
<211> LENGTH: 660
<212> TYPE: DNA
<213> ORGANISM: Dryopteris filix-mas

<400> SEQUENCE: 65
atggggaggt catggggagt ggtgcaggct ataattatgg tgttgtgcgg cagcggcctg     60
ctgggcgtag cgagcggcca tggcagcatg gaggaccca tcagtcgcgt ctacaactgc    120
tacctggaga atcccgagag tcccacgtcg gcagcttgcc aagcggcggt ggcgctgagt    180
ggggcccaag cgttctatga ttggaatgag gtgaacctgg ccgacgccgc tggccggcat    240
cgcgagctca ttccggatgg ccaactgtgc agcgccgggc gggagaagta tcagggcctc    300
gacctggcac gctccgactg gacagccact tccttgtcct ccggcgtctc cttcacatac    360
ctctacaagg ccaccgcccc gcacttgggc ttcttcgagt tctacgtcac caaggatggt    420
tacgagccca ctgagccgct caaatgggca gacttggagg actcgccctt catcaacgtc    480
accgacccca cgcttgtcag cggctcctac caaatccccg gcaccacgcc ttccggcaag    540
tccggccgcc acctcatcta cgtcatttgg cagcgctccg acagccccga ggccttctac    600
```

```
tcctgctccg acgtcgactt ctcttccgat gccctcatct ctctcggctc cgcggtactc    660
```

<210> SEQ ID NO 66
<211> LENGTH: 657
<212> TYPE: DNA
<213> ORGANISM: Bolbitis cladorrhizans

<400> SEQUENCE: 66

```
atggggaggt cattgggagc tgtggttatt acattggtgc tgtgcgcggg cggcctgctg     60
agcttagcga gcggccatgg cagcatggag gatcccatca gtcgcgttta caggtgctac    120
cttgagaatc cggagagtcc gacttcggcg gcttgccaag cggcggtggc gctgagtggc    180
accgaagcct ctctggtta tgcttggagt gcggtattgg ccaacgctgc aggccagcac    240
cgccagctca ttccagatgg ccaattgtgc agcgcagggc aggagctgta tgcgggccta    300
gacctgccac gcgccgactg gccagccacc tccttgtcct ctggcgttgc cttcacatat    360
ctctacaagg ccgcgatccc gcacatgggc ttcttcgagt ctacatcac ccgggatggt    420
tatgagccca cagagccgct caagtgggca gatttggagg actcgccctt cctcaacgtc    480
actgaccccc cgcttgtcag tagttcctac cagatccctg ctccacacc tgccggcaag    540
tctggccgcc accttatcta tgtcatttgg cagcgctccg acagccccca ggccttctac    600
tcctgttccg atgtcgactt tgttgatgcc accctctctc agctccactc caccacc      657
```

<210> SEQ ID NO 67
<211> LENGTH: 660
<212> TYPE: DNA
<213> ORGANISM: Dryopteris filix-mas

<400> SEQUENCE: 67

```
atgaagaagt catggggagt tgttgtagta gtagtagtag ctctagtact gttgtgcctg     60
ctgggcacgg caagcggcca tgcagcatg caggacccca tcagtcgtgt ctacaactgc    120
tacctagaga atcctgagaa cccaacgtcg gcagcttgca aagctgtggt ggcggtgggg    180
ggcacgcaac cactctacga ttggaatgag gtgaacctgg ccaacgccgc tggccggcac    240
cgtgagctca ttcctgatgg caggctgtgc agtgctggcc gggacaaata tcggggcctc    300
gacctggctc gcgacgactg gccagccacc tccttatcct ctggtgtcga ctacacattc    360
ctctaccgcg ccactgcccc tcacttgggc ttcttcgagt tctatgtcac ccgcgacagc    420
tacgacccca cccagccgct cgcatgggca gacctggagg acttgccgtt catcaacgtt    480
accaaccctg ccctaaatgc tggtgcctac caaatccccg gcaccatgcc ggccggaaag    540
agcggtcgcc acctcatcta cgtcatctgg cagcgcagcg acagccccga ggcattctac    600
tcctgctccg acgtcgactt ctcttccgat gccctcatct ctctccgctc cgcggtactc    660
```

<210> SEQ ID NO 68
<211> LENGTH: 654
<212> TYPE: DNA
<213> ORGANISM: Pyrrosia lanceolata

<400> SEQUENCE: 68

```
atgaggacga ggtcatgggg agttgtggct tttatggtag ctgtgtgtgc cggcgacctg     60
ctaggcctcg cgagtgggca tggctccatg ggctaccccg tcagtcgcgt cttgaactgc    120
ttccttgaga atccggagag ccccacgtcg gctgcctgca ccgcggcggt ggctatgagt    180
ggcacccaag ccttctacga ctggaatgag gtcaatctgc cctttgccaa tggccagcac    240
```

-continued

| cgcgacctca ttcctgacgg ccaactctgc agcgccgggc gcgccaagta tgcaggcctg | 300 |
| gacctggcac gcgacgactg ggaagccact tttttgtctt cggccaccag ctacacactc | 360 |
| ctctacaggg tcaccgctcg ccacctgggc tacttcgagt tctacgtcac tcgcgatagc | 420 |
| tacaactcca ctcagccgct cgcctgggcg gacttggagg attcgccctt catcaacatc | 480 |
| accaacccta ccgttgacag cggctactac caagtgcctg tcgacacgcc ttccggcaag | 540 |
| actggccgcc acctcatcta cgtcatttgg cagcacaccg acagcctcga ggccttctac | 600 |
| tcctgctccg acgttgaatt tgacgtcgag gtccctctc tccgctccac cacc | 654 |

<210> SEQ ID NO 69
<211> LENGTH: 654
<212> TYPE: DNA
<213> ORGANISM: Athyrium filix-femina

<400> SEQUENCE: 69

| atggggaggt catggggggg agttgtggct attatggtgt tgtgcggctg cctgctgggc | 60 |
| gtagcgagcg ggcatggcag catggaggac cccatcagtc gcgtctacaa ctgctacctg | 120 |
| gagaatccgg agagtcccac gtcggcagct tgccaagcgg cggtggcgct gagtgggacc | 180 |
| caagcgttct atgattggaa tgaggtgaac cagcccttcg ccgctggcca gtcccgcgag | 240 |
| atcattccgg atggccaact gtgcagcggc gggcgggaga agtataaggg cctcgacctg | 300 |
| gcacgctccg actggacagc cacctccttg tcctccggcg tcgccttcac attcctcttc | 360 |
| aaggccaccg ccccgcacgc gggcttcttc gaattctacg tcacccagga tggttacgac | 420 |
| cccactgagc cgctcaaatg gcagacttg gaggactcgc ccttcatcaa cgtcaccgac | 480 |
| cccacgcttg tcagcggctc ctaccaaatc tccggcacca cgcctgccgg caagtccggc | 540 |
| cgccacctca tctacgtcat ttggcagcgc tccgacagcc ccgaggcctt ctactcctgc | 600 |
| tccgacgtcg aattcgtcga cgatgccctc tctagtgatc tccactccac cacc | 654 |

<210> SEQ ID NO 70
<211> LENGTH: 654
<212> TYPE: DNA
<213> ORGANISM: Colysis wrightii (Monstifera)

<400> SEQUENCE: 70

| atggggagag catgggtagt tgtggctatt atggtcgccg tgtgcgccag cgggctgctg | 60 |
| agcttcgcca gtcgcacacg gggccatggc agcatggggg accccatcag tcgagtactt | 120 |
| aggtgccgcg aagagaatcc ggagaatccc acgtcgccag cctgcatcgc ggcggtggcg | 180 |
| ctcagcggca acaagccctt ctacgattgg aatgaagtga atctgcccct cgccgatggc | 240 |
| cagcaccaaa agctcatccc tgacggccaa ctttgcggcg ctgggcgtga caagtataaa | 300 |
| ggcctcaacc tggcacgtgc cgactggctg gctacctcct tgtctgccgg cgcccctac | 360 |
| acattcctct tcctggcctc cgccccccac ctgggctact cgagttcta cgtcactcgg | 420 |
| gatagttacg accccactca gccgctcgca tgggcggact ggaggactc gccgttcctc | 480 |
| actaccacca cgaccctcga cagcagctcc tacataattc aggcaccac gcccgctggc | 540 |
| aaaaccggcc gccacctcat ctacctcatt tggcagcgca ccgacagccc tgaggccttc | 600 |
| tactcctgct ccgacgtcga cttgaggag gccatctctc tttcctccac cacc | 654 |

<210> SEQ ID NO 71
<211> LENGTH: 657
<212> TYPE: DNA
<213> ORGANISM: Coniogramme venusta

<400> SEQUENCE: 71

```
atggggagga gctcgtcgtg ggagggagta ctagtagtag tggtgtgctg cgccagcggc      60
ctgctgggcg tagcgagcgg ccatggcagc atgggcagcc ccatcagtcg cgtctacaac     120
tgccgccagg agaatccgga gcgtcccacc tcggcagctt gcagagaggc ggtgaggatt     180
agtgggaccc aagcgttcta tgattggaat gaggtgaacc tgcccgtcgc ctctggccgg     240
caccgcgagc tcattccgga tggcaagctc tgcagcgccg ggcggactaa gtatgcgggc     300
ctcgacttgg cacgctccga ctgggtatcc accgtcttgc cctccggcgt ccctacaca      360
ttcctctaca gggtcaccgc tcgccacgtg ggcttcttcg agttctacgt cacccgggat     420
ggttaccagc cctctgagcc cctcaaatgg tcagacttgg aagagcctcc gttcatcaac     480
gtcaccaatc ccacgatgtc cggcggcttc tatcgaatcc ccggaaccac gccacccgcc     540
aaggccggcc gccacctcat ctacgtcatt tggcagcgct ccgacagccc cgaggccttc     600
tactcctgct ccgacgctgt cttcggcgac gccctctctc tccagtactc ctccacc       657
```

<210> SEQ ID NO 72
<211> LENGTH: 651
<212> TYPE: DNA
<213> ORGANISM: Platycerium coronarium

<400> SEQUENCE: 72

```
atgaggaggt cttggggagt gtggctgtt attatgttgg cagtgtgcgc cgtcggcatg       60
ctgggcgtag ccagcgggca tggtagcatg gaggatccca tcagtcgcgt gtataggtgc     120
ttcctggaga acccggagag gcccacgtca gcagcgtgca tcgccgcggt ggcgcttagt     180
ggcacccaag ccttctacga ctggaatgag gtaaatctgc ccttcgcagc tggccgacac     240
cgcgagctca ttcctgacgg tcagctctgc agcgccgggc gggacaagta taaaggcctc     300
gacctggcac gcgacgactg ggtggccacc tctttgtcct ccggcgtcaa ctacaccttc     360
ctctacaagg ccaccgcccc catcggggc tacttcgagt tctacgtcac ccgggatagc      420
tacgacccca ctgagccgct ggcctgggcg gacctggaag acacgccctt catcaacgtc     480
accgacccgg acctcgccag tggctcctac cagatctcca gcaccacgcc ttccggcaag     540
accggccgcc accttatcta cgtcatttgg cagcgcaccg acagccccga ggccttctac     600
tcctgctccg acatccttt cgacgaggcc gtcgctctct actctaccgc t                651
```

<210> SEQ ID NO 73
<211> LENGTH: 654
<212> TYPE: DNA
<213> ORGANISM: Cystopteris bulbifera

<400> SEQUENCE: 73

```
atggggagag tcaaccttat ggctattttg gcgttgtgcg ccagcttctg cgccgccctg      60
ctgggcgttg ccagcggcca tggcagcatg caggaccccca tcagtcgcgt ctacaactgc    120
ttcctggaga acccggagcg tcccacgtcg gcagcttgcc aagcggcggt tgcgctgagt     180
ggcacccaag cgttctatga ctggaatgag gtgaacctgg cgaacgccga tggtcggcat     240
cgcgagctca ttccggatgg ccaactgtgc agcgccggga gggagaagta tcagggcctg     300
gacctggcac gcgccgactg gacagccacc tccttgtcct ccggcatctc ctacacattc     360
ctctacaagg ccaccgctcc gcacctgggc ttcttcgagt tctacgtcac ccgggatggt     420
tacgacccca ccgaggcgct caaatggtca gacttggagg actcgccgtt cctcaacgtc     480
```

| | |
|---|---:|
| accaacccca cccttgtcag cggctcctac caaatccccg ttaccacgcc tgccgccaag | 540 |
| tccggccgcc acctgatcta cgtcatttgg cagcgctccg acagccccga ggccttctac | 600 |
| tcctgctccg acgtcgactt cgacgatgcc ctagtctctc tccactccac cacc | 654 |

<210> SEQ ID NO 74
<211> LENGTH: 651
<212> TYPE: DNA
<213> ORGANISM: Platycerium ridleyi

<400> SEQUENCE: 74

| | |
|---|---:|
| atgaggaggt catggggagt tatggctgtt attttgttgg cggtgtgcgc ctgcggcctg | 60 |
| ctgggcgtag cgagcgggca tggcagcatg gaggatccca tcagtcgcgt gtatgggtgc | 120 |
| tacctggaga tccggagag ccccacgtcg cagcgtgca tcgcggcggt ggcgctcagt | 180 |
| ggcacccaag ccttctacga ctggaatgag gtgaatcagc cctttgcagc tggccgacac | 240 |
| cgcgagctca ttcctgacgg tcagctctgc agcggcgggc gggacaagta taaaggcctc | 300 |
| gacctggcgc gcgacgactg ggaggccacc tccttgtctt ctggcgccaa ctacagcttc | 360 |
| ctcttcaagg ccaccgcccc catcggggc tacttcgagt tctacgtcac ccaggatagc | 420 |
| tacgacccca ctgagccgct ggcctggggg gacctggaga gcacgccctt catcaatgtt | 480 |
| acggacccgg acctttcag cggctcctac cagatctcca gcaccaccc tcccggcaag | 540 |
| accggccgcc acctcatcta cgtcatctgg cagcgcaccg acagtcccga ggctttctac | 600 |
| tcctgctccg acgtcctttt cgacgaggcc gtcgctctct actctaccgc t | 651 |

<210> SEQ ID NO 75
<211> LENGTH: 645
<212> TYPE: DNA
<213> ORGANISM: Dryopteris marginalis

<400> SEQUENCE: 75

| | |
|---|---:|
| atggggaggt catggggagt tgtggctatt attatggtgt tgtgcggcag cggcctgctg | 60 |
| ggcgtagcga gcggccatgg cagcatgcag gaccccatca gtcgcgtcta caactgctac | 120 |
| ctggagaatc cggagcgtcc cacgtcggca gcttgccaag cggcggtggc gctcagtggg | 180 |
| acccaagcgt ctatgattg gaatgaggtg aaccagccct tcgcggctgg ccggcaccgc | 240 |
| gaaatcattc cggatggcca actgtgcagc gccgggcggg agaagtatcg gggcctcgac | 300 |
| ctggcacgct ccgactgggt agccacctcc ttgtcctcgg gcgtcaacta cacataccct | 360 |
| tacaaggcca ccgccccgca cttgggcttc ttcgagttct acgtcaccca ggatggttac | 420 |
| aattcctctg agccgctcaa atgggcagac ttggaggact cgccgttcat caacgtcacc | 480 |
| accacgcttg acagcgcctc ctaccaaatc ccggcacca cgcctgcggg caagaacggc | 540 |
| cgccacctca tctacgtcat ttggcagcgc tccgacagcc ccgaggcctt ctactcctgc | 600 |
| tccgacgtcg acttcgccga tgccctctct ctccactcca ccacc | 645 |

<210> SEQ ID NO 76
<211> LENGTH: 648
<212> TYPE: DNA
<213> ORGANISM: Microsorum musifolium (Blume)

<400> SEQUENCE: 76

| | |
|---|---:|
| atgagaaggt catggggagt tctggctatc gtgatggccg tgtgcgcaag cggcctgttt | 60 |
| ggcgtcgcga gtggccatgg ctctatggag caccccatta gtcgcgtcta tcaatgctac | 120 |
| cgcgagggtc cggaaaatcc caagtcgcca gcctgcatcg cggcaaaggg gcttagcggc | 180 |

```
gctcaagcct tctacgattg gaatgaagtg aatcagccct tcgccgatgg ccgccaccag    240
gagatcatcc atgacggcca tctttgcagc ggcgggcgcg acaagtatag aggcctcgac    300
ctgccacgtg ccgactgggt ggctacctct ttgtctgccg gaaaacccta cacattcctc    360 tacccgggcca ccgccacca cctgggctac ttcgagttct acgtcactcg ggacggctac    420
gaccccacta agccgctcgc atgggcggac ttggaggact cgccgtttat caatgtcacc    480
aacccgaccc tcgtcagcgg cagctaccga attccacaca ccacgcccgc cagcaaaact    540
ggccggcacc tcatctacgt catttggcag cgcaccgaca gcttcgaggc tttctactcc    600
tgctccgacg tcgtctttga tgaggccctc tctctttcct ccaccatc                 648
```

<210> SEQ ID NO 77
<211> LENGTH: 648
<212> TYPE: DNA
<213> ORGANISM: Elaphoglossum sp.

<400> SEQUENCE: 77

```
atgcggagat catgggaagt tgtggctcta attatggtgg tgtgcgcctg cggcctgctg    60
ggcgtagcga gtggccatgg cagcatggag acccccatca gtcgtgtcta caggtgctac    120
ctcgagggag tggagaatcc cacgtcggca gcctgcatag cggccattga ggtgagtggc    180
aagcaagcct tctacgactg gaatgaagtg aatcagccct tggccgctgg ccggcaccgc    240
gaaatcattc ctgacggcga gctgtgcagc ggcgggcggg agaagtataa aggcctcgac    300
ttggcacgcg ccgactggtt agccacctcc ttgtcttcgg gtgtcgacta cacattcctc    360
tacaaagcca ccgccgaaca aagggctac ttcgagttct acgtcactca ggatagttac    420
gaccccacgg agcctctcaa atggtcggac ctggaggaca cgcccttcat taacgtcacc    480 caaccttgc ttgtcagcgg ctcctaccaa attcccggca ccacgccttc cggcaaaacc    540
ggccgccacc tcatctacgt catctggcag cgcaccgata cgccgaagc cttctactcc    600 tgctccgatg tcaactttga cgacgccctc cctatctact ctgccacc                 648
```

<210> SEQ ID NO 78
<211> LENGTH: 645
<212> TYPE: DNA
<213> ORGANISM: Nephrolepis exaltata (Tiger Fern)

<400> SEQUENCE: 78

```
atggggaggt catgggagt tgcggctatt gtagtggcgg tgtgcgccag cggcctgttg    60
agcgtagtga gcggccatgg aagcatgcag acccccatca gtcgcgtcta tgcatgctac    120
ctagagaatc cggagcgtcc cacgtcagca gcttgccagg cggcagtggc attgagtggg    180
acgcaagcct tctatgattg gaatgaggtg aacctgccca tgccgctgg ccggcaccgc    240 gaactcattc cggatggtca gttgtgcagt gctgggcggg ccaagtatca gggcctcgac    300
caggctcgca acgattggcc acacaccgac ttgatctccg gcgtcgcctt cacattcaac    360
tacagggcca ccgccccaca cttgggcatc ttcgagttct atgtcactcg ggatgggtac    420
gatgccaccc agcccctcaa atgggcagat ctggaggact cgcctttcct caccgccacc    480
agcacgcttg cccccctcctc ctaccagtgg cccggcacca ctcccagtgg caagtctggc    540
cgccacctca tctacgtcat ttggcagcgc accgacagcc ccgaggcctt ctactcctgc    600
tccgacgtcg agttcgtcga tgccgtctct ctccactcca ccacc                    645
```

<210> SEQ ID NO 79

<211> LENGTH: 642
<212> TYPE: DNA
<213> ORGANISM: Dryopteris lepidopoda

<400> SEQUENCE: 79

```
atggggaggt catggggagt tgtggctatt atggtgttgt gcggcagcgg cctgctgggc    60
gtggcgagcg ccatggcag catggaggac cccatcagtc gcgtctacaa ctgctacctg   120
gagaatccgg agcgtccac gtcggcagct tgccaagcgg cggtggcgct gagtgggacc   180
caagcgttct atgattggaa tgaggtgaac cagcccttcg cggctggccg caccgcgaa   240
atcattccgg atggccaact gtgcagcggc gggcgggaga agtatcgggg cctggacctg   300
gcacgctccg actgggaagc cacctccttg tcctccggcg tcagctacac atacctctac   360
aaggccaccg ccccgcactt gggcttcttc gagttctacg tcacccagga tggttacaac   420
tcctctgagc cgctcgaatg gcagacttg gaggactcac cgttcatcaa cgtcaccacc   480
acgcttgaca cgcctccta ccaaatcccc ggtaccacgc tgccggcaa gaccggccgc   540
cacctcatct acgtcatttg gcagcgctcc gacagccccg aggcattcta ctcctgctcc   600
gacgtcgact cgtcgatgc cctctctctc cactccacca cc                      642
```

<210> SEQ ID NO 80
<211> LENGTH: 642
<212> TYPE: DNA
<213> ORGANISM: Polystichum lepidocaulon

<400> SEQUENCE: 80

```
atgggcaggt catggggagt tgtggctatt atggtgttgt tgccagcgc tagcggcctg    60
ctgggcgtag cgaacggcca tggctccatg gcaaccccca tcagtcgcgt ctacaactgc   120
aggctggaga atccggagag acccacgtcg gcagcttgca tagcggcggt ggcgctgagt   180
ggcacctatg attggagtga ggtgaacctg cccaacgcca atggccggca ccgcgagctc   240
attccggatg gcaaactgtg cagcgccggg cgggacaagt ataagggcct cgacctggct   300
cgctccgact ggacagccac caacttgtcc tccggcgtcg cctacacatt cctctacagg   360
gtcaccgccg agcacagggg gttcttcgag ttctacgtca ccgtggatga ttacgaaccc   420
actgagctgc tcaaatggga agacttggag gaaacgccgt tcctcaacgt gagtgaccc   480
acggtcgtag caacaacta cgaaatctcc ggcaccacgc tgccagcaa gactggccgc   540
cacctcatct acgtcatttg gcagcgctcc gacagccccg aggccttcta ctcctgctcc   600
gacgtcgact cgtcgatac cctgtctctc cactccacca cc                      642
```

<210> SEQ ID NO 81
<211> LENGTH: 645
<212> TYPE: DNA
<213> ORGANISM: Polystichum acrostichoides

<400> SEQUENCE: 81

```
atggggaggt catggggagt tgtggctatt atggtgttgt gcgctagcgg cctgctgggt    60
gtagcgagcg ccatggcag catgaacgac cccatcagcc gcgtctacaa ctgccgtctg   120
gagaatccgg agagtccac gtcagcagct tgcatagcgg cggtggcgct gagtgggacc   180
caagcgttct atgattggaa tgaggtgaac ctgcccgacg tcaatggccg gcaccgccag   240
ctcattccgg atggcaaatt gtgcagcgcc gggcgggaca agtataaggg cctcgacctg   300
gcacgctccg actgggtagc caccaacttg tcctccggcg tcgccttcac attcctctac   360
agggtcaccg cccagcacag gggcttcttc gagttctacg tcaccgtgga tgattacgac   420
```

```
cccactgagc tgctcaaatg ggaagacttg gaggaaacgc cgttcatgaa cgtcaccgac      480
cccacggttg taggcgtcaa ttacgaaatc cccggcacca cgcctgccaa taagaccggc      540
cgccatctca tctatgtcat ttggcagcgc tccgacagcc ccgaggcctt ctactcctgc      600
tccgacgttg acttcgtcga tgccgtgtct ctccactcca ccacc                     645
```

<210> SEQ ID NO 82
<211> LENGTH: 645
<212> TYPE: DNA
<213> ORGANISM: Davallia tyermannii

<400> SEQUENCE: 82

```
atggggaggt catggggagt tgtggctatt atggtgatgt acattggtgg cctgctaagc      60
atagcaagcg gccatggcag catggaggac cccatcagcc gcgtctatag gtgctacttg      120
gagaatccgg agagtcccac atcggcagct tgccaagcgg cagtggcagt gagtggggcc      180
caagccttct acgattggaa tgaggtgaac attgctgacg ccaatggccg acaccgggag      240
ctcatttctg atggccaact atgtagcgca atcggagta agtatgcggg cctcgacctg       300
gcacgcgcag attggctagg caccaccttg tcctcgggcg cctccttcac atttgcctac      360
aaggccaccg cgccgcactt gggcttcttt gagttctacg tcacccggga tggttacgag      420
cccaccgacc cgctcaaatg gcagacttg gaggactcgc ccttcatcaa cgtcaccaac       480
cccacacttg ataatggcgc ctaccagatc tccggcacca cgcctgccgg taagtcgggg     540
cgtcatctga tctacgtcat ttggcagcgc tctgatagcc cagaggcatt ctattcgtgc     600
tccgacgtcg actttgtcga tgctctctct ctccactcta ccacc                     645
```

<210> SEQ ID NO 83
<211> LENGTH: 645
<212> TYPE: DNA
<213> ORGANISM: Polystichum polyblepharum (C.)

<400> SEQUENCE: 83

```
atggggaggt catggggagt tgtggctatt atggtgttgt gcgctagcgg cctgctcggc      60
gtagcgagcg gccatggcac catgaatgac cccatcagcc gcgtctacaa ctgccgcctg      120
gagaatccgg agagtcccac gtcagcagct tgcatagcgg cggtggcgct gagtgggacc      180
caagcgttct atgattggaa tgaggtgaac ctgcccaacg ccgctggcag gcaccgagag      240
ctcattccgg atggcaaact gtgcagcgcc gggcgggaca agtataaggg cctcgacctc      300
gcacgctccg actgggtagc caccaacttg tcctccggcg tcgccttcac attcctctac     360
agggtcaccg cccagcacag gggcttcttc gagttctacg tcaccgtgga tgattacgac      420
cccactgagc tgctcaaatg ggaagacttg gaggaaacac cgttcatgaa tgtcaccgac      480
cccacggttg taggcgtcaa ctacgaaatg gccggcacca cgcctgccaa caagaccggc      540
cgccatctca tctatgtcat ttggcagcgc tccgacagcc ccgaggcctt ctactcctgc      600
tccgacgtcg acttcgtcga tgccgtgtct ctccactcca gcacc                     645
```

<210> SEQ ID NO 84
<211> LENGTH: 648
<212> TYPE: DNA
<213> ORGANISM: Lecanopteris sinuosa

<400> SEQUENCE: 84

```
atgatgaggt catggggagt tgcggcaatt atgatggccg tctgcgccag tggcctgctg      60
```

```
ggcgttgcaa gtgggcatgg cagcatggcg accccatca gtcgggtgta caggtgccgc    120
ctcgagaatc ccgaaaggcc cacgtcgcca gcctgcattg cggcggtggc gcttagcggc    180
actcaagcct tctacgactg gaatgaagtg aatcttccct tcgctgctgg ccgccaccgc    240
cagctcatcc ccgacggaca actttgcagc gccgggcgga acaagtataa aggcctcgac    300
ctcgcacgcg ccgactggct agccacctcc ctgtctcccg cgccaatta cacattcctc    360 taccgggcga ccgcccccca cgcgggctac tttgagttct acgtcactcg tgatagctac    420
gaccccactg agcagctcgc ttgggcggac ttggaagact cgccgttcat caccatcacc    480
aacccgaccc ttgtcaacgg ctactaccag attcccaaca ccgtccctgc cggcaaaact    540
ggccgtcacc ttatctacgt catttggcaa cgcacagaca gtcccgaagc cttctactcc    600
tgctccgacg tcgactttga cgatgccctc cgtctccact actccacc                648

<210> SEQ ID NO 85
<211> LENGTH: 645
<212> TYPE: DNA
<213> ORGANISM: Aglaomorpha splendens

<400> SEQUENCE: 85
atgaggaggt catggggagt ggtggtgatt ttggtggtgt gcgtctgcgg cctgctgggc     60
gtggcgagtg ggcatggctc catggggac cccatcagtc gcgtctatgg gtgccgcctt    120
gagaatccgg agagtccac gtcggcagcc tgcatagcgg cggtggcggt gagtggcacc    180
caagccttct acgattggaa tgaggtgaat cagcccaacg ccaatggccg gcaccgcgag    240
atcattccag atggcgaact gtgcagcgcc gggcgggtaa aatatgcagg cctcgatctg    300
gcacgcgacg actgggtagc cacctccttg tcttctggcg tcaactacac attcctcttc    360
gtagccaccg ccccccactt gggctacttc gagttctacg tcactcagga tagctacgac    420
cccacccagc cgctcaaatg gtcggacttg gaggccaccc cgttcatcaa cgtcaccgat    480
cccacgcttc ttaacggctc ctaccaaatt cccagctcca cgcctccgg caaaaccggc    540 cgccacctca tctacgtcat ttggcagcgc actgacagcc ctgaggcctt ctactcctgc    600
tccgacgtcg actttgatgt ggccctccct ctttactcct ccacc                    645

<210> SEQ ID NO 86
<211> LENGTH: 645
<212> TYPE: DNA
<213> ORGANISM: Nephrolepis exaltata

<400> SEQUENCE: 86
atggggaggt catggggagt tgcggctatt gtagtggcgg tgtgcgccag cggcctgttg     60
agcgtagtga gcggccatgg aagcatgcag accccatca gtcgcgtcta tgcatgctac    120
ctagagaatc cggagcgtcc cacgtcagca gcttgccagg cggcagtggc attgagtggg    180
acgcaagcct tctatgattg gaatgaggtg aacctgccca tgccgctgg ccggcaccgc    240 gaactcattc cggatggtca gttgtgcagt gctgggcggg ccaagtatca gggcctcgac    300
caggctcgca acgattggcc acacaccgac ttgatctccg gcgtcgcctt cacattcaac    360
tacagggcca ccgccccaca cttgggcatc ttcgagttct atgtcactcg ggatgggtac    420
gatgccaccc agcccctcaa atgggcagat ctggaggact cgcctttcct caccgccacc    480
agcacgcttg ccccctcctc ctaccagtgg cccggcacca ctcccagtgg caagtctggc    540
cgccacctca tctacgtcat ttggcagcgc accgacagcc ccgaggcctt ctactcctgc    600
tccgacgtcg agttcgtcga tgccgtctct ctccactcca ccacc                    645
```

<210> SEQ ID NO 87
<211> LENGTH: 645
<212> TYPE: DNA
<213> ORGANISM: Aglaomorpha splendens

<400> SEQUENCE: 87

```
atgaggaggt catggggagt ggtggtgatt ttggtggtgt gcgtctgcgg cctgctgggc      60
gtggcgagtg ggcatggctc catgggggac cccatcagtc gcgtctatgg gtgccgcctt     120
gagaatccgg agagtcccac gtcggcagcc tgcatagcgg cggtggcggt gagtggcacc     180
caagccttct acgattggaa tgaggtgaat cagcccaacg ccaatggccg gcaccgcgag     240
atcattccag atggcgaact gtgcagcgcc gggcgggtaa aatatgcagg cctcgatctg     300
gcacgcgacg actgggtagc cacctccttg tcttctggcg tcaactacac attcctcttc     360
gtagccaccg cccccactt gggctacttc gagttctacg tcactcagga tagctacgac     420
cccacccagc cgctcaaatg gtcggacttg gaggccaccc cgttcatcaa cgtcaccgat     480
cccacgcttc ttaacggctc ctaccaaatt cccagctcca cgcctccgg caaaaccggc      540
cgccacctca tctacgtcat ttggcagcgc actgacagcc ctgaggcctt ctactcctgc     600
tccgacgtcg actttgatgt ggccctccct ctttactcct ccacc                    645
```

<210> SEQ ID NO 88
<211> LENGTH: 648
<212> TYPE: DNA
<213> ORGANISM: Polypodium formosanum

<400> SEQUENCE: 88

```
atgaagagat cgtggggagt tgctgctatt gtgatggccc tgagcacttg cggcttgata     60
ggcgtagcaa gtggccatgg ctccatggga gaccccatca gtcgcgtcta taggtgctac    120
cgagagaatc cggagcgtcc cacgtcgcca gcctgcattg cggcggtggc gctgagtggc    180
aagcaagcct tctacgattg gaatgcggtg aatctgttca cgccaacgg tcgacaccgc     240
gagctcattc ctgacggcca gctctgcagt gccgggcggg ccaagtataa aggccttgac    300
ctcccacgcg ccgattggct agccaccctc ttatcctccg cgtcaacttt cacattcctc    360
tacagggtca ccgcccgcca cctgggctat ttcgagttct acgtcactcg cgatggctac    420
gaccccagtg aaccgctcgc atgggcggac ttggaggact cgccgttcat caaaatcacc    480
aacccatccg ttgtcagcaa ctcctatgta attcccggca tcacgcctgc cggcaaaact    540
ggccgccacc ttatttacgt catttggcag cgcaccgaca gccaggaggc cttctactcc    600
tgctccgaca tcgactttga cgaggccgtc cctctctact ccaccacc                648
```

<210> SEQ ID NO 89
<211> LENGTH: 642
<212> TYPE: DNA
<213> ORGANISM: Nephrolepis obliterata (Sunjest)

<400> SEQUENCE: 89

```
atggggaggt catggggagt tgtggctatt atggtggtgt gcgcttgcgg cctattgagc     60
gtagtgaggg gccatggaag catggaggac cccattagtc gcgtctatgg gtgctaccta    120
gagaatccag agagtcccaa gtcagcagct tgccaagcgg cagtggcatt gagtgggacc    180
caagcgttct atgattggaa tgaggtgaac ttgcccgatg ttgctggccg gcaccgcgca    240
gtcattccgg atggccaatt gtgcagtgct gggcgggcta agtatcaggg cctcaacttg    300
```

```
gctcgcgccg attggccagc cacctccttg acctcaggcg tgtccttcac atacctctac      360
aaggtcaccg caaaacactt gggcttcttt gagttctatg tcactcaaga tggttacgat      420
cccaccgaac cgctcaaatg gcagacttg gaggacttgc ctttcatgaa cgtcaccagc       480
acgtttgacg atgagtccta ccaaatgtct ggcaccactc ctagtggcaa ggctggccgc      540
cacctcatct acgtcatttg gcagcgcagc gacagccctg aggccttcta ctcctgctcc      600
gatgtcgact cgtcgatgc cgtctctctc cgctccacca cc                         642
```

<210> SEQ ID NO 90
<211> LENGTH: 645
<212> TYPE: DNA
<213> ORGANISM: Deparia acrostichoides

<400> SEQUENCE: 90

```
atggggaggt catggggagt tgtggctatt atggtgttgt gcgccagcgg tctgctgggc      60
gtagcgagcg gccatggcag catggagggc cccatcagtc gcgtcctcaa ctgctacctg      120
gagaatccgg agagacccac gtcggagct tgcatagcgg cggtgcgct gggtgggaca       180 caaccgtttt atgattggaa tgaggtgaac ctggccgatg ccgatggccg gcaccgcgag     240
ctcattccgg atggccaact gtgcagcgcc ggacgggaga agtttaaggg cctcgacctg    300
gcacgctccg actggccagc cacctccttg tcctccggcg tcgccttcac atacctctac    360
aaggccaccg ccccacacgc tggcttcttc gagttctacg tcacccggga tggttacaag   420
cccactgagc cgctcaaatg gcagacttg gaggagccac cgttcatcaa cgtcaccgac    480
cccaagcttg tcagcggctc ctaccaaatc cccggcacca cgcctgccgg caaggctggc    540
cgccacctca tctacgtcat ttggcagcgc tccgacagcc ccgaggcctt ctactcctgc   600
tccgacgtcg acttcgtcga agccctctct ctccactcca ccacc                     645
```

<210> SEQ ID NO 91
<211> LENGTH: 648
<212> TYPE: DNA
<213> ORGANISM: Aglaomorpha sp. (Roberts)

<400> SEQUENCE: 91

```
atgaggaggt catggccggg agtggtggcg attatggtgg tgtgtgcctg cggcctgctg      60
ggcgtggcga gtggccatgg ctccatgcag gaccccatca gtcgggtcta taggtgccgc    120
cttgagaatc cggagcggcc cacgtcggca gcctgcatag cggcggtggc gctgagtggc    180
acccaagcct tctacgactg gaatgaggtg aatcagccct cgccaatgg ccgccaccgc    240 gagatcattc cggacggcca actgtgcagc gccgggcggg caaagtatag aggcctcgac    300
ctggcacgcg ccgactggct agcccccctcc ttgtcttctg cgtcgactac acatttctc    360 tacatagcca ctgcccccca tttgggctac ttcgagttct acatcactcg ggatagctac   420
gaccccaccg agccgctcaa atggtcggac ttggaggact ctccgttcat caacgtcacc   480 aaccccctcgc ttgtcagcgg ctcctaccaa attcccggca ccacgccctc caacaaaacc   540
ggccgccacc tcatgtacgt catttggcag cgcaccgaca gccccgaggc cttctacgcc    600
tgctctgacg tcgactttga tgtggccctc cctctctact ccaccact                 648
```

<210> SEQ ID NO 92
<211> LENGTH: 642
<212> TYPE: DNA
<213> ORGANISM: Nephrolepis obliterata

<400> SEQUENCE: 92

```
atggggaggt catggggagt tgtggctatt atggtggtgt gcgcttgcgg cctattgagc      60
gtagtgaggg gccatggaag catggaggac cccattagtc gcgtctatgg gtgctaccta     120
gagaatccag agagtcccaa gtcagcagct tgccaagcgg cagtggcatt gagtgggacc     180
caagcgttct atgattggaa tgaggtgaac ttgcccgatg ttgctggccg caccgcgca      240 gtcattccgg atggccaatt gtgcagtgct gggcgggcta agtatcaggg cctcaacttg     300
gctcgcgccg attggccagc cacctccttg acctcaggcg tgtccttcac atacctctac     360
aaggtcaccg caaaacactt gggcttcttt gagttctatg tcactcaaga tggttacgat     420
cccaccgaac cgctcaaatg gcagacttg gaggacttgc ctttcatgaa cgtcaccagc      480
acgtttgacg atgagtccta ccaaatgtct ggcaccactc ctagtggcaa ggctggccgc     540
cacctcatct acgtcatttg gcagcgcagc gacagccctg aggccttcta ctcctgctcc     600
gatgtcgact cgtcgatgc cgtctctctc cgctccacca cc                         642
```

```
<210> SEQ ID NO 93
<211> LENGTH: 645
<212> TYPE: DNA
<213> ORGANISM: Polypodium attenuatum (Falax)

<400> SEQUENCE: 93
atggggaagg gatgggaagt tgtgggtata atggtggtgt cgcctgcgg cctgctgggc      60 gtggccagtg ggcatggcac catggaggac cccatcagtc gcgtctacag gtgccgcctt    120
gagaatccgg agcgacccac gtcgccagcc tgcatagcgg cggtggcgct gagcggcact    180
caagccttct acgattggaa tgaggtgaat ctgcccttcg ccgccggccg gcaccgcgag    240
atcattcccg acggccagct gtgcagcgcc gggcgcgcca agtataggg gctggatctg     300 gcacgcgatg actggctagc cacctccttg tcttccggcg tcgactacac attcgtctac    360
agagtcaccg cgcccaccg tggctacttc gagttctacg tcactcggga cacctacgac    420
cccactgagc ccctcaaatg gtcggacttg gaggagcccc ccttcatcaa cgttacccaa    480
ccctcgcttg tcagcggctc ctaccagatt cccggcgcca cgcctaccgg taagaccggc    540
cgccacctca tctacgtcat ctggcagcgc actgacagcc ccgaagcctt ttactcctgt    600
tccgacgtcg actttggcga ggctctccgt ctcgacgcca ccgcc                    645
```

```
<210> SEQ ID NO 94
<211> LENGTH: 645
<212> TYPE: DNA
<213> ORGANISM: Arachniodes simplicior (variegata)

<400> SEQUENCE: 94
atggggaggt catggggagt tgtggctatt atagtgttgt gcgccagcgg cctgctgggc     60
gtagcgagcg gccatggcag catggaggac cccatcagtc gcgtctacaa ctgcttcctg    120
gagggtccgg agaatccccac gtcggacgct tgcatagcag ctgtggcgct gagtgggacc    180
caagcgttct atgattggac ggaggtgaac ctggccgacg ccgatggcca tcaccgcgag    240
ctcattccgg atggccaact gtgcagcgcc gggcgggaca agtacaaggg cctcgacctc    300
gcacgctccg actggacagc cacgtcattg tcctccggcg tcgactacac attcctcttc    360
aaggccaccg cccgcacttt gggctccttc gagttctacg tcactgtgga tggttacgag    420
cccactgagc cgctcaaatg gcagacttg gaggcaacgc cattcatcaa cgtcaccgac    480
cccacgcttg acagcggctc ctaccaaatc cctggtacca cacctgccgg caagaccggc    540
```

```
cgccacctca tctacgtgat ttggcagcgc tccgacagtg ccgaggcctt ctactcctgc      600
tccgacgtcg acttcactga tgccctctct ctccactcca ccacc                     645

<210> SEQ ID NO 95
<211> LENGTH: 648
<212> TYPE: DNA
<213> ORGANISM: Campyloneurum angustifolium

<400> SEQUENCE: 95
atgaggaggt catgggaggt tgtggggatg atggtgctgt gcgcctgcgg cctgctgggt       60
gtagcgagcg gccatggcag catggaggac cccatcagtc gcgtctatag gtgccgcctt      120
gagggtccgg agaggccaac gtcgccggcc tgcatagcgg cggtggcggt gaatggcact      180
caggccttct acgactggaa tgaggtgaat cagcccttcg ccgctgggcg gcaccgtgag      240
atcattcccg acgccagct ctgcagcgcc gggcgggaca agtataaagg gttggacctg       300
gcgcgcgccg actggctagc cgtctccttg tcttccggcg ccgactacac attcctctac      360
ctagccaccg ccacccacag gggctacttc gagttctacg tcactcggga tagctacgat      420
cccactgagc cgctcaaatg gtcggacttg gaggactccc cgttcatcaa cgtcacggat      480
cccacagaag tcggccccgt gtaccaaatt cccggcacca cgcctgccgg caaaactggc      540
cgccacctca tctacgtcat ttggcagcgc accgacagcc cgaagccttt ctactcctgc      600
tccgacgtcg actttggcga gtctctctcc ctctactccg tcaccgag                   648

<210> SEQ ID NO 96
<211> LENGTH: 645
<212> TYPE: DNA
<213> ORGANISM: Colysis wrightii (Ching)

<400> SEQUENCE: 96
atgaggaagt cattggaagt tgtggctatt atggtggccg tgtgcgccag cggcctactg       60
ggcgtcgcga gtggccatgg caccatgctg acccccatca gtcgcgtcta taggtgctac      120
ctcgagaatc cggagcgtcc cacgtcccca gcctgcatcg cggcggtggc gctcagcggc      180
aaacaagcct tctacgattg gaatgaagtg aatctgccct tcgcggctgg ccgtcaccgc      240
gagctcatcc ctgacggcca actttgcagc gctgggcggg acaagtataa aggcctcgat      300
caggcacgtg acgactggct ggctacctcc ttgccttccg cgccaactac atattccgc       360 tttgaggtca ccgccgtcca ccgtggctac ttcgagtttt acgtcactcg cgatggttac      420
gaccccactc agccgctcgc atgggcggac ttggaggact cgccgttcct cactaccacc      480
acgaccctcg acagcagctc ctacataatt ccaggcacca cgcccgctgg caaaaccggc      540
cgccacctca tctacctcat ttggcagcgc accgacagcc ctgaggcctt ctactcctgc      600
tccgacgtcg actttgagga ggccatctct ctttcctcca ccacc                     645

<210> SEQ ID NO 97
<211> LENGTH: 645
<212> TYPE: DNA
<213> ORGANISM: Colysis wrightii (Ching)

<400> SEQUENCE: 97
atggggaggt catgggtagt tgtggctatt atggtcaccg tgtgcgccag cggcctgctg       60
ggcttcgcca gtggccatgg cagcatgggg acccccatca gtcgagtact aggtgccgc       120 gaagagaatc cggagaatcc cacgtcgcca gcctgcatcg cggcggtggc gctcagcggc      180
aaacaagcct tctacgattg gaatgaagtg aatctgccct tcgcggctgg ccgtcaccgc      240
```

```
gagctcatcc ctgacggcca actttgcagc gctgggcggg ccaagtataa aggcctcgat      300
ctggcacgtg acgactggct ggctacccccc ttgccttccg gcgccgccta cacattccgc     360
tatcgggtca ccgccgccca ccgtggctac ttcgagttct acgtcactcg ggatggttac     420
gaccccactc agccgctcgc atgggcggac ttggaggact cgccgttcct cactaccacc     480
acgaccctcg acagcagctc ctacataatt ccaggcacca cgcccgctgg caaaaccggc     540
cgccacctca tctacctcat ttggcagcgc accgacagcc ctgaggcctt ctactcctgc     600
tccgacgtcg actttgagga ggccatctct ctttcctcca ccacc                     645
```

<210> SEQ ID NO 98
<211> LENGTH: 648
<212> TYPE: DNA
<213> ORGANISM: Platycerium elephantotis

<400> SEQUENCE: 98

```
atgaggaggt catgggggggt tgtggctgtt atgttggcga tctgcgccag cggcctgctg      60
ggcgtagcga gcggccatgg cagcatgctg gatcccatca gtcgcgtgta acgtgctat     120
ttggagaatc cggagaggcc cacgtcggca gcgtgcatcg cggcggtggc ggtcagtggc     180
tcccaagcgt tctacgattg gaatgaggtg aatctggccg atgcagatgg ccagcaccgc     240
cagctcattc ctgacggcaa gctctgcagc gccgggcggg aaaagtacag aggcctcgac     300
ctcgcacgcg atgattggcc tgccacctcc ttgtcttctg gagtcaatta caccttcctc     360
tacagggcca ccgccccccca cctgggcttc ttcgagttct acgtcacccg tgatagctac     420
gaccccactc agcccctggc ctgggcggac ctggaagacc ccccctttat caacatcacc     480
gacccaaccc ttgccagcgg ctcctaccag attgttaaca ccacgccttc caacaagacc     540
ggccgccacc tcatctacgt catctggcag cgtactgaca gccccgaggc cttctactcc     600
tgctccgacg tcgacttcga cgaagatgac tctcttctct ccgcagtt                  648
```

<210> SEQ ID NO 99
<211> LENGTH: 645
<212> TYPE: DNA
<213> ORGANISM: Platycerium madagascariense

<400> SEQUENCE: 99

```
atgaggaggt cgtggggggt tgtggctgtt atcttggcaa tgtgcgccgg tagcctgctc      60
ggcgtagcaa gcggccatgg tagcatggag gatcccatca gtcgcgtgta tgcgtgcttc     120
ctggagaatc cggagagacc cacgtcggca gcatgcatcg cggcggtggc gctgagtggc     180
acccaagcct tctacgactg gaatgaggtg aatcagccca atgccgctgg caaccacaca     240
atcattcccg acgccagct ctgcagtgcc gggcgggaga agtacaaagg cctcgacctc     300
ccacgcgccg actggtctgc catctccttg tcttccggcg taaactacac cttcctttac     360
aaggctaccg cccccccaccg gggctacttt gagttctacg tcacccgtga tagctacgac     420
cccactgagc cccttgcctg gcggacctg gaagacaccc ccttcatcaa catcaccgac     480
ccagaccttg tcagcggctc ctaccggatt gctaacacca ccccttccgg caagaccggc     540
cgccacctca tctacgtcat ttggcagcgt accgacagcc ccgaggcctt ctactcctgc     600
tccgacgtcg tcttcgacga ggatgtctct ctcgtctccg cagct                     645
```

<210> SEQ ID NO 100
<211> LENGTH: 648
<212> TYPE: DNA

<213> ORGANISM: Microsorum musifolium (Blume)

<400> SEQUENCE: 100

| | |
|---|---|
| atgagaaggt catggggagt tctggctatc gtggtggccg tgtgcgcaag cggcctgttt | 60 |
| ggcgtcgcga gtggccatgg ctctatggag cacccccatta gtcgcgtcta tcaatgctac | 120 |
| cgcgagggtc cggaaaatcc caagtcgcca gcctgcatcg cggcaaaggg gcttagcggc | 180 |
| gctcaagcct tctacgattg gaatgaagtg aatcagccct cgccgatgg ccgccaccag | 240 |
| gagatcatcc atgacggcca tctttgcagc ggcgggcgcg acaagtatag aggcctcgac | 300 |
| ctgccacgtg ccgactgggt ggctacctct ttgtctgccg gaaaacccta cacattcctc | 360 |
| taccgtgcca ccgcccccca cttgggctac ttccagtttt acgtcactcg cgacggctac | 420 |
| aaccccacta gccgctcgc atgggcggac ttggaggact cgccgtttat caatgtcacc | 480 |
| aacccgaccc tcgtcagcgg cagctaccga attccacaca ccacgcccgc cagcaaaact | 540 |
| ggccggcacc tcatctacgt catttggcag cgcaccgaca gccccgaagc cttctactcc | 600 |
| tgctcggacg tcgtctttga tgaagccctc tctctctcct ccaccatc | 648 |

<210> SEQ ID NO 101
<211> LENGTH: 657
<212> TYPE: DNA
<213> ORGANISM: Lygodium flexuosum

<400> SEQUENCE: 101

| | |
|---|---|
| atggggagct ggcagtgggg atcagtgaat gtggccattg ttgtttttat gatgttgtgc | 60 |
| ggcgtagcga gcggccatgg caccatgggg gaccccatca gtcgcgtcta caggtgctac | 120 |
| cttgagaatc cggagaggcc cacgtcggca gcttgccaag cggcggtggc gctgagtggg | 180 |
| acccaagcct tctacgactg gaatgaggta aacctgccca cgccgctgg ccggcaccgc | 240 |
| cagctcattc cggatggcca actgtgcagc gccgggcggg ccaagtatca gggcctcgac | 300 |
| ctggcacgcg ccgactggct agccgccagc ctgtcctccg cgtctcccta cacattcctc | 360 |
| tacagggtca ccgcccagca ccgtggcttc ttcgagttct acgtcacccg ggatggttac | 420 |
| gagcccactg agccgctcaa atggtcagac ttggaggagt cgccgttcat caacgtcacc | 480 |
| gaccccacgg ctgtcagcgg ctcctaccag atccccggca ccacgcctgc cggcaagtcc | 540 |
| ggccgccacc tcatctacgt catttggcag cgctccgaca gccccgaggc cttctactcc | 600 |
| tgctccgacg tcgacttcga cgtcgagggc gccgccgtct ctctccgctc taccacc | 657 |

<210> SEQ ID NO 102
<211> LENGTH: 645
<212> TYPE: DNA
<213> ORGANISM: Polystichum polyblepharum

<400> SEQUENCE: 102

| | |
|---|---|
| atgaacaggt catggggagt tgtggctatt atggtgctgt gcgctagcgg cctgctcggc | 60 |
| gtagcgagcg gccatggcac catgaatgac cccatcagcc gtgtctacaa ctgccgcctg | 120 |
| gagaatccgg agagtcccac gtcagcagct tgcatagcgg cggtggcgct gagtgggacc | 180 |
| caagcgttct atgattggaa tgaggtgaac ctggccaacg tcgctggccg gcaccgcgag | 240 |
| ctcattccgg atggcaaact gtgcagcgcc gggcgggaca agtataaggg cctcgacctc | 300 |
| gcacgctccg actgggtagc caccaacttg tcctccggcg tcgccttcac attcctctac | 360 |
| agggtcaccg cccagcacag gggcttcttc gagttctacg tcaccgtgga tgattacgac | 420 |
| cccactgagc tgctcaaatg ggaagacttg gaggaaacgc cgttcatgaa tgtcaccgac | 480 |

```
cccacgcttg taggcctcaa ctacgaaatg cccggcacca cgcctgccaa caagaccggc    540
cgccatctca tctatgtcat ttggcagcgc tccgacagcc ccgaggcctt ctactcctgc    600
tccgacgtcg acttcgtcga tgccgtgtct ctccactcca gcacc                   645
```

<210> SEQ ID NO 103
<211> LENGTH: 654
<212> TYPE: DNA
<213> ORGANISM: Diplazium pycnocarpon

<400> SEQUENCE: 103

```
atggggaagt catggggagt tgtggctatt atattggtgt tgtgcgccag cggcctgctg    60
ggtgtagcga gcggccatgg cagcatggcg gaccccatca gtcgcattta caactgcaga   120
caggagaatc cggagcgtcc cacgtcggca gcttgccaag cggcagtggc gctgagtgga   180
acccaagcgt tctatgattg gaatgaggtg aaccagccca cgccgctgg ccggcaccgc    240 gagatcattc cggatggcca actgtgcagc gccggcggg acaagtatcg ggcctcgac    300 ctggcaagcg ccgactggca gtggcctgcc acctccttgt cctccggcgt ctccttcaca   360
taccgctaca gggccaccgc cgcgcactac ggctacttcc agttctatat cacccgggat   420
ggttaccagc ccactcagcc gctcaaatgg gcagacttgg agcagctgcc attccttacc   480
gtctacaacc ccacgcttgt caacggcttc tacgaaatgc aggggaccac gcctgctggc   540
aagaccggcc gccacctcat ctatgtcatc tggcagcgct ccgacagccc cgaggccttc   600
tactcctgct ccgacgtcga cttcgtgggt gccctctctc tccattccac cacc         654
```

<210> SEQ ID NO 104
<211> LENGTH: 648
<212> TYPE: DNA
<213> ORGANISM: Polystichum braunii

<400> SEQUENCE: 104

```
atggggaggt catggggagt tgtggctatt atggtgttgt gtgctagcgg cctgctgggc    60
gcagcgagcg gccatggcac catgtacgac ccattcagcc gcgtctacaa ctgccgcttc   120
cgggagaatc cggagcgtcc cacgtcagca gcttgcatag cggcggtggc gttgagtggg   180
acccaagcgt tctatgattg gaatgaggtg aacctggcca cgccgctgg ccggcaccgc    240 gagctcattc cggatggcaa actgtgcagc gccggcggg acaagtataa gggcctcgac    300
ctggcacgct ccgactgggt agccaccaac ttgtcctccg cgtcgccctt cacattcctc   360
tacagggtca ccgcccagca caggggcttc ttcgagttct acgtcaccgt ggatgattac   420
gaccccactg agtcgctcaa atgggaagac ttggaggaaa cgccgttcct caacgtcacc   480
gaccccacgg ttgtaggcgt caactaccaa atctccggca ccacgcctgc cagcaagacc   540
ggccgccacc tcatctacgt tatatggcag cgctccgata gccctgaggc cttctactcc   600
tgctccgacg tcgacttcgt cgatgccctg tctctccaat ccaccacc                648
```

<210> SEQ ID NO 105
<211> LENGTH: 645
<212> TYPE: DNA
<213> ORGANISM: Platycerium hillii

<400> SEQUENCE: 105

```
atggggaagc gtggagagt ggtggtggcc attgtggtgg tgtgcgccag cggcctgctg     60
ggcgtagcga gcggccatgg cagcatgggt gaacccatca gtcgcgtcta taattgctac   120
```

| | |
|---|---|
| ctggagaatc cggagagacc cacgtcggca gcgtgcatcg cggcggtggc gcttagtggc | 180 |
| acccaagcct tctacgactg gaatgaggtg aacctgccct tcgccgctgg ccggcaccgc | 240 |
| gagctcattc ctgacggcca gctctgcagc gccggcgggg acaagtataa aggcctggac | 300 |
| ctggcacgcg ccgactgggt tgccacctcc ttgtcttcgg gcgtcagcta caccttcctc | 360 |
| tacagggtta ccgcccccca ccggggctac tttgagttct acgtcaccaa ggatagctac | 420 |
| gaccccactg agccgctggc ctgggcagac ctggaggaca cgcccttcat taacatcacc | 480 |
| gacccgacca ttgtcagcgg ctcttaccag atctccagca ccacgccttc cgacaagacc | 540 |
| ggccgccacc tcatctacgt catttggcag cgcaccgaca gccctgaggc cttctactcc | 600 |
| tgctccgata tcgactttga cgacaccctc cccctacact ccacc | 645 |

<210> SEQ ID NO 106
<211> LENGTH: 681
<212> TYPE: DNA
<213> ORGANISM: Drynaria rigidula (whitei)

<400> SEQUENCE: 106

| | |
|---|---|
| atggggagga cgtactcatg gggggctgtg gctgttatgg tggtgctgtg cgccagcggc | 60 |
| ctgctgggca tagcgagcgg ccatggcagc atggacagcc ccatcagtcg cgtctaccgg | 120 |
| tgctatctag agaatccgga gaatcccacg tcggcagcct gccaagcggc ggtggcgctg | 180 |
| agtgggaccc aagccttcta cgactggaat gaggtgaaca tcgccgacgc tgcgggccgc | 240 |
| caccgcgagc tcattccgga tggccaactg tgcagcgccg ggcgggaaaa gtatcaaggt | 300 |
| ctcgacctgg cacgcgccga ctggctagcc gactccttgt cctccggcgt ctccttcact | 360 |
| ttcctctaca aggctactgc cgcgcacttg ggcttcttcg agttctacgt cacccgggat | 420 |
| gcctacgacc ccactgagcc gctcaaatgg gcagacctgg aggactcgcc cttcctcaac | 480 |
| gtcaccgacc ccacgcttgt cagcggctac taccagatcc ctggcaccac gcctgccggc | 540 |
| aagtccggcc gccacctcct ctacgtcatc tggcagcgct ccgacagccc cgaggccttc | 600 |
| tactcctgct ccgacgtcga cttcgacgac gatgccgctg ccgcccagca catgataatc | 660 |
| tctctccgcc actccaccac c | 681 |

<210> SEQ ID NO 107
<211> LENGTH: 687
<212> TYPE: DNA
<213> ORGANISM: Adiantum monocolor

<400> SEQUENCE: 107

| | |
|---|---|
| atggggatga agatgtcatg ggaagttgca ctagcagaaa tagtagcttt gtgcctactg | 60 |
| ggcatggcaa gcagccatgg caccatgcag gaccccataa gtcgtgtcta caactgcttt | 120 |
| ctggagaacc ggagaggcc aacgtcggca gcttgtcaag ctgcagtagc gttgggtggc | 180 |
| acacaaccac tctatgattg gaatgaggtg aacatccatg atgccgctgg caaccaccgc | 240 |
| gatctcatcc ccgatggcaa gctctgcagc gccggccgcc aaaagtttca gggcctcgac | 300 |
| ttggcgcgcg cggattggat agcaacctcc ctatcctctg gcgtcgacta cacattcctc | 360 |
| taccgcgcca ccgcccgca cttgggcttc tttgaatttt acatcacccg tgacacctac | 420 |
| gaccccaccc agccgctcgc atggggtgac ctggaagact cgcccttcat caacattacc | 480 |
| aatccctcca tcgtcagtac gactttgggt cccgcctact cgatcccag cactacacca | 540 |
| ttcagcaaaa gtggtcgcca cctcatctac gtcatctggc agcgcaccga cagcctcgag | 600 |
| gcgttctact cctgctccga cgtcgacttc tcgacatctt ccatcgagga tgatgtcatc | 660 |

```
gtctctctcc gttctgcagc tctactc                                     687

<210> SEQ ID NO 108
<211> LENGTH: 669
<212> TYPE: DNA
<213> ORGANISM: Pellaea rotundifolia

<400> SEQUENCE: 108
atgcagaggt catgcatgtg gggggaatcc gtagtggcta ttatgtgcat ggtgttgggc   60
cttctgggcg acgtagcgag cggccatggc agcatggcca gccccatcag tcgcgtcttc  120
aactgctacc tcgagaatcc agagagtccc acctcggaag cttgcaaagc ggctgtggag  180
gagagtggca cccaagcttt ctatgattgg gctgaggtga gcctgcccaa cgccgctgga  240
cgccaccgcg agctcattcc ggatggccaa ctctgcagcg ccgggctggc caagtatgcg  300
ggcctcgacc tggcgcgcgc cgactggaca gccacctcct tgacctccaa catctcctac  360
acgttcatct tcgaggccac cgccggcccg cacttgggct ccttcgagtt ctacgtcacc  420
aatgatgatt acgagcccgc tgaggcgctc aactgggcag acttggagga cactccgttc  480
atcatcgtca ccaaccccac gcttgtgagc ggctcctacc tcatcccggg cactacgcct  540
gccggcaaga ccggccgcca tcatctctac gtcatttggc agcgctccga cagccccgag  600
gctttctact cctgctccga catcgacttc gtggaggagg atcccgtggt ccctctccac  660
tctaccacc                                                          669

<210> SEQ ID NO 109
<211> LENGTH: 645
<212> TYPE: DNA
<213> ORGANISM: Platycerium bifurcatum

<400> SEQUENCE: 109
atggggaagc cgtggagagt ggtggtggcc attgtggtgg tgtgcgccag cggcctgctg   60
ggcgtagcga gcggccatgg cagcatgggt gaacccatca gtcgcgtcta taattgctac  120
ctggagaatc cggagagacc cacgtcggca gcgtgcatcg cggcggtggc gcttagtggc  180
acccaagcct tctacgactg gaatgaggtg aacctgccct cgccgctgg ccggcaccgc   240 gagctcattc ctgacggcca gctctgcagc gccgggcggg acaagtataa aggcctggac  300
ctggcacgcg ccgactgggt tgccacctcc ctgtcttcgg gcgtcagcta caccttcctc  360
tacagggcca ccgccccccca ccagggctac tttgagttct acgtcaccaa ggatagctac  420
gaccccactg agccgctggc ctgggcggac ctggaggaca cgcccttcat taacatcacc  480
gatccgaccc ttgtcagcgg ctcttaccag atccccagca ccacgccttc gacaagacc   540 ggccgccacc tcatctacgt catttggcag cgcaccgaca gccctgaggc cttctactcc  600
tgctccgata tcgactttga cgacacccct cccctacact ccacc                  645

<210> SEQ ID NO 110
<211> LENGTH: 648
<212> TYPE: DNA
<213> ORGANISM: Microsorum punctatum

<400> SEQUENCE: 110
atgaggaggt catggggagt tctggctatt gtggtggccg tgtgcgcaag cggcctgttt   60
ggcgtcgcga gtggtcatgg ctccatggag gacccatta gtcgcgtcta tcaatgctac  120
gacgagggtc cggaaaatcc caagtcgcca gcctgcatcg cggcggtggg gcttagcggc  180
```

```
gctcaagcct tctacgattg gaatgaagtg aatcagccct tcgccgctgg ccagcacaag    240
gagatcatcc atgacggcca tctttgcagc ggcgggcgcg acaagtatag aggcctcgac    300
ctgccacgtg ccgactgggt ggctacctct ttgtctgccg gcgcacccta cacattcctc    360
taccgcgcca ccgcccacca cctgggctac ttcgagttct acgtcactcg ggacggctac    420
gaccccacta gccgctcgc atgggcggac ttggaggact cgccgtttat caatgtcacc    480
aacccgcccc tcgtcagcgg cagctaccga attccagaca ccacgcccgc cctcaaaact    540
ggccggcacc tcatctacgt catttggcag cgcaccgaca gccccgaagc cttctactcc    600
tgctcggacg tcgtctttgc tgaggccctc tctctttcct ccaccacc                 648

<210> SEQ ID NO 111
<211> LENGTH: 651
<212> TYPE: DNA
<213> ORGANISM: Woodwardia fimbriata

<400> SEQUENCE: 111
atggggaggt caatatgggg agttgtggct atgatggtgt tgtgcgccag cggcctgctg    60
cgcatagcga gcgggcatgg cagcatggag aaccccatca gtcgcgtcta caactgctat    120
ctggagggtc cggagaatcc caagtcggca gcttgcaaag cggcggtggc ggcgagtggg    180
acccaagcgt ctatgattg gaatgaggtg aacctggcca acgccgctgg ccgccaccgc    240
gagctcattc cggatggcca actgtgcagc gccgggcggc agaagtatca gggcctcgac    300
ctcgtacgct ccgactggcc agccacctcc ttgtcctccg gcgtccccct cacattcctc    360
tacaggatca ccgcccagca cttgggcttc ttcgagttct acgtcacccg cgatggttac    420
cagcccactg cggcgctcac ttgggcagac ttggaggact cccgttcat gaacgtcacc    480 ggcgacccca cgtttatcac cggctcctgg gaaatccccg gcacctcgcc tgccggcaag    540
tctggccgcc accttatcta cgtcatctgg cagcgctccg acagccccga ggccttctac    600
gcctgctgcg acgtcgactt cgtcgacgcc ctctctctcc actccaccac t             651

<210> SEQ ID NO 112
<211> LENGTH: 639
<212> TYPE: DNA
<213> ORGANISM: Dryopteris celsa

<400> SEQUENCE: 112
atggggaggt catcattggg agttgtggct attatggtgt tgtgcctggt gggcgtagcg    60
agcggtcatg gcagcatgca ggaccccatc agtcgcgtct acaactgcta cctcgagaat    120
ccggagagtc ccacgtcggc agcttgccaa gcggcggtgg cgctgagtgg cacccaagcg    180
ttctatgact ggaatgaggt gaaccagccc gaagccgatg gtcggtcccg cgaaatcatt    240
ccggatggcc aactgtgcag cggcgggcgg agaagtatc agggcctgga cctggcgcgc    300
tccgactggg aagccaccac cttgtcctcc agcgtcaact acacattcct ctacaaggcc    360
acagccccgc acttgggctt cttcgagttc tacgtcaccc aggatggtta cgatcccact    420
gaggtgctca atgggcagat ctggaggac tcgccgttcc tcaacgtcac cgaccccacg    480
cttgacagcg gcgcctacca aatccccggc accacgcctg ccgtaagac cggccgccac    540 ctcatctacg tcatttggca gcgctccgac agccccgagg ccttctactc ctgctccgac    600
gtcgacttcc ccgatgccct ctctctccac tccaccacc                          639

<210> SEQ ID NO 113
<211> LENGTH: 648
```

```
<212> TYPE: DNA
<213> ORGANISM: Campyloneurum angustifolium

<400> SEQUENCE: 113
atgaggaggt catgggaggt tgtggggatg atggtgctgt gcgcctgcgg cctgctgggt      60
gtagcgagcg gccatggcag catggaggac cccatcagtc gcgtctatag gtgccgcctt     120
gagaatccgg agagacccac gtcaccagct tgcagagcgg cggtggcgtt gagtggcact     180
caggccttct acgactggaa tgaggtgaat cagcccttcg ccgctgggcg gcaccgtgag     240
atcattcccg acggccagct ctgcagcgcc gggcgggaca agtataaagg gttggacctg     300
gcgcgcgccg actggctagc cgtctccttg tcttccggcg ccgactacac attcctctac     360
ctagccaccg ccacccacag gggctacttc gagttctacg tcactcggga tagctacgat     420
cccactgagc cgctcaaatg gtcggacttg gaggactccc cgttcatcaa cgtcacggat     480
cccacagaag tcggccccgt gtaccaaatt cccggcacca cgcctgccgg caaaactggc     540
cgccacctca tctacgtcat ttggcagcgc accgacagcc ccgaagcctt ctactcctgc     600
tccgacgtcg actttggcga gtctctctcc ctctactccg tcaccgag                  648

<210> SEQ ID NO 114
<211> LENGTH: 654
<212> TYPE: DNA
<213> ORGANISM: Onoclea sensibilis

<400> SEQUENCE: 114
atggggaggt catggggagt ggtgcaggct ataattatgg tgttgtgcgg cagcggcctg      60
ctgggcgtag cgagcggcca tgcagcatg gaggacccca tcagtcgcgt ctacaactgc      120
tacctggaga atcccgagag tcccacgtcg gcagcttgcc aagcggcggt ggcgctgagt     180
ggggcccaag cgttctatga ttggaatgag gtgaacctgg ccgacgccgc tggccggcat     240
cgcgagctca ttccggatgg ccaactgtgc agcgccgggc gggagaagta tcagggcctc     300
gacctggcac gctccgactg gacagccact tccttgtcct ccggcgtctc cttcacatac     360
ctctacaagg ccaccgcccc gcacttgggc ttcttcgagt tctacgtcac caaggatggt     420
tacgagccca ctgagccgct caaatgggca gacttggagg actcgcccct catcaacgtc     480
accgaccccca cgcttgtcag cggctcctac caaatcccg gcaccacgcc ttccggcaag     540
tccggccgcc acctcatcta cgtcatttgg cagcgctccg acagcccga ggccttctac     600
tcctgctccg acgtcgactt cgacgtcgat gccctctctc tccactccac cacc           654

<210> SEQ ID NO 115
<211> LENGTH: 705
<212> TYPE: DNA
<213> ORGANISM: Onoclea sensibilis

<400> SEQUENCE: 115
atggggaggt catggggagt ggtgcaggct ataattatgg tgttgtgcgg cagcggcctg      60
ctgggcgtag cgagcggcca tgcagcatg gaggacccca tcagtcgcgt ctacaactgc      120
tacctggaga atcccgagag tcccacgtcg gcagcttgcc aagcggcggt ggcgctgagt     180
ggggcccaag cgttctatga ttggaatgag gtgaacctgg ccgacgccgc tggccggcat     240
cgcgagctca ttccggatgg ccaactgtgc agcgccgggc gggagaagta tcagggcctc     300
gacctggcac gctccgactg gacagccact tccttgtcct ccggcgtctc cttcacatac     360
ctctacaagg ccaccgcccc gcacttgggc ttcttcgagt tctacgtcac caaggatggt     420
```

```
tacgagccca ctgagccgct caaatgggca gacttggagg actcgccctt catcaacgtc      480
accgacccca cgcttgtcag cggctcctac caaatccccg gcaccacgcc ttccggcaag      540
tccggccgcc acctcatcta cgtcatttgg cagcgctccg acagcccga ggccttctac       600 tcctgctccg acgtcgactt cgacgtcgat gccctctctc tccactccac acctaatcta     660
gacttgtcat cttctggatt ggccaactta attaatgtat gtgta                     705

<210> SEQ ID NO 116
<211> LENGTH: 688
<212> TYPE: DNA
<213> ORGANISM: Onoclea sensibilis

<400> SEQUENCE: 116
atggggaggt catggggagt ggtgcaggct ataattatgg tgttgtgcgg cagcggcctg      60
ctgggcgtag cgagcggcca tggcagcatg gaggacccca tcagtcgcgt ctacaactgc     120
tacctggaga atcccgagag tcccacgtcg gcagcttgcc aagcggcggt ggcgctgagt     180
ggggcccaag cgttctatga ttggaatgag gtgaacctgg ccgacgccgc tggccggcat     240
cgcgagctca ttccggatgg ccaactgtgc agcgccgggc gggagaagta tcagggcctc     300
gacctggcac gctccgactg gacagccact tccttgtcct ccggcgtctc cttcacatac     360
ctctacaagg ccaccgcccc gcacttgggc ttcttcgagt tctacgtcac caaggatggt     420
tacgagccca ctgagccgct caaatgggca gacttggagg actcgccctt catcaacgtc      480
accgacccca cgcttgtcag cggctcctac caaatccccg gcaccacgcc ttccggcaag      540
tccggccgcc acctcatcta cgtcatttgg cagcgctccg acagcccga ggccttctac       600 tcctgctccg acgtcgactt cgacgtcgat gccctctctc tccactccac acctaatcta     660
gacttgtcca ttctggattg gccaactt                                        688

<210> SEQ ID NO 117
<211> LENGTH: 645
<212> TYPE: DNA
<213> ORGANISM: Polystichum tripteron

<400> SEQUENCE: 117
atgggcaggt catggggagt tgtggctatt atggtgttgt gcgccagcgg cctgctgggc      60
gtagcgagcg ccatggcac catgaacgac cccatcagtc gcgtctacgc ctgcaggcag      120
gagaatccgg agcgacccac tacgccggct tgcatagcgg cggtggcgct gagtggggcc     180
caagcgttct atgattggaa tgaggtgaac ctgcccttg tcaatggccg gcaccgccag      240
ttcattccgg atgggaaact ctgcagcgcc gggcggaaca agtatagggg tctcgacctg     300
gcacgctccg actggacagc cacaaacttg tcctccggcg tcgcctacac attcctctac     360
agggtcaccg cccagcacag gggcttcttc gagttctacg tcaccgtgga tggttacgac     420
cccactgagc cgctcaaatg gcagacttg gaggaaacgc cgttcatcaa cgtcaccgac      480
cccacagttg taggcctcaa ctatgtaatc cccggtacca cgcctgccag caagaccggc     540
cgccacctca tctacgtcat ttggcagcgc tccgacagcc ccgaggcctt ctactcctgc     600
tccgacgtca actttcccga tgccctgtct ctccactccg ccacc                    645

<210> SEQ ID NO 118
<211> LENGTH: 645
<212> TYPE: DNA
<213> ORGANISM: Polystichum tripteron

<400> SEQUENCE: 118
```

```
atgggcaggt catggggagt tgtggctatt atggtgttgt gcgccagcgg cctgctgggc      60
gtagcgagcg gccatggcac catgaacgac cccatcagtc gcgtctacgc ctgcaggcag     120
gagaatccgg agcgacccac tacgccggct tgcatagcgg cggtggcgct gagtggggcc     180
caagcgttct atgattggaa tgaggtgaac ctgccctttg tcaatggccg gcaccgccag     240
ttcattccgg atgggaaact ctgcagcgcc gggcggaaca agtatagggg tctcgacctg     300
gcacgctccg actggacagc cacaaacttg tcctccggcg tcgcctacac attcctctac     360
agggtcaccg cccagcacag gggcttcttc gagttctacg tcaccgtgga tggttacgac     420
cccactgagc cgctcaaatg gcagacttg gaggaaacgc cgttcatcaa cgtcaccgac     480
cccacagttg taggcctcaa ctatgtaatc tccggcacca cgcctgccag caagaccggc     540
cgccacctca tctacgtcat ttggcagcgt accgacagcc ccgaggcctt ctactcctgc     600
tccgacgtca actttcccga tgccctgtct ctccactccg ccacc                     645

<210> SEQ ID NO 119
<211> LENGTH: 645
<212> TYPE: DNA
<213> ORGANISM: Polystichum tripteron

<400> SEQUENCE: 119
atgggcaggt catggggagt tgtggctatt atgatgttgt gcgccagcgg cctgctgggc      60
gtagcgagcg gccatggcac catgaacgac cccatcagtc gcgtctacgc ctgcaggcag     120
gagaatccgg agcgacccac tacgccggct tgcatagcgg cggtggcgct gagtggggcc     180
caagcgttct atgattggaa tgaggtgaac ctgccctttg tcaatggccg gcaccgccag     240
ttcattccgg atgggaaact ctgcagcgcc gggcggaaca agtatagggg tctcgacctg     300
gcacgctccg actggacagc cacaaacttg tcctccggcg tcgcctacac attcctctac     360
agggtcaccg cccagcacag gggcttcttc gagttctacg tcaccgtgga tggttacgac     420
cccactgagc cgctcaaatg gcagacttg gaggaaacgc cgttcatcaa cgtcaccgac     480
cccacagttg taggcctcaa ctatgtaatc cccggtacca cgcctgccag caagaccggc     540
cgccacctca tctacgtcat ttggcagcgc tccgacagcc ccgaggcctt ctactcctgc     600
tccgacgtca actttcccga tgccctgtct ctccactccg ccacc                     645

<210> SEQ ID NO 120
<211> LENGTH: 645
<212> TYPE: DNA
<213> ORGANISM: Polystichum tripteron

<400> SEQUENCE: 120
atgggcaggt catggggagt tgtggctatt atggtgttgt gcgccagcgg cctgctgggc      60
gtagcgagcg gccatggcac catgaacgac cccatcagtc gcgtctacgc ctgcaggcag     120
gagaatccgg agcgacccac tacgccggct tgcatagcgg cggtggcgct gagtggggcc     180
caagcgttct atgattggaa tgaggtgaac ctgccctttg tcaatggccg gcaccgccag     240
ttcattccgg atgggaaact ctgcagcgcc gggcggaaca agtatagggg tctcgacctg     300
gcacgctccg actggacagc cacaaacttg tcctccggcg tcgcctacac attcctctac     360
agggtcaccg cccagcacag gggcttcttc gagttctacg tcaccgtgga tggttacgac     420
cccactgagc cgctcaaatg gcagacttg gaggaaacgc cgttcatcaa cgtcgccaac     480
cccacagttg taggcctcaa ctatgtaatc tccggcacca cgcctgccag caagaccggc     540
```

```
cgccacctca tctacgtcat ttggcagcgt accgacagcc ccgaggcctt ctactcctgc      600
tccgacgtca acttcgtcga tgccctgtct ctccactccg ccacc                     645

<210> SEQ ID NO 121
<211> LENGTH: 651
<212> TYPE: DNA
<213> ORGANISM: Tectaria milnei

<400> SEQUENCE: 121
atggggaggt catggggagt ggtggctgtt atggtggtgt gcgcaagcgg cctattgagc       60
gtagtgaggg gccatggaag catggaggac cccatcagtc gtgtgtatgc atgcttccta      120
gagaatccgg agcgtcccat atcagcagct tgccaggcgg cagtggcaat gggtgggacg      180
caagccttct atgattggaa tgcggtaagc ctgccctatg ctgctgggcg gcaccgtgaa      240
ctcatcccgg atggccaatt gtgcagtgct gggcgggcca agtatcgggg cctggacctg      300
cctcgtgacg attggccagg cacctccaat atgacctccg gcgtcgcctt cacatacagg      360
tacaaggcca ccgccccaca cttgggctcc ttccagttct atgtcactcg ggatggctac      420
gatcccaccg agccgctcaa atgggcagac ttggaggact cgccttcat gaacgccacc       480 agcacgcttg ccccggactc ctacctaatg tccggcacca ccctagcgg caaggctggc       540 caccacctca tctacgccat ttggcagcgc agcgacagcc ctgaggcctt ctactcctgc      600
tccgatgtca ccttcgacgt cgctgctgtc tctgatctcc actccaccac c              651

<210> SEQ ID NO 122
<211> LENGTH: 651
<212> TYPE: DNA
<213> ORGANISM: Tectaria milnei

<400> SEQUENCE: 122
atggggaggt catggggagt ggtggctgtt atggtggtgt gcgcaagcgg cctattgagc       60
gtagtgaggg gccatggaag catggaggac cccatcagtc gtgtgtatgc atgcttccta      120
gagaatccgg agcgtcccat atcagcagct tgccaggcgg cagtggcaat gggtgggacg      180
caagccttct atgattggaa tgcggtaagc ctgccctatg ctgctgggcg gcaccgtgaa      240
ctcatcccgg atggccaatt gtgcagtgct gggcgggcca agtatcgggg cctggacctg      300
cctcgtgacg attggccagg cacctccaat atgacctccg gcgtcgcctt cacatacagg      360
tacaaggcca ccgccccaca cttgggctcc ttccagttcc atgtcactcg ggatggctac      420
gatcccaccg agccgctcaa atgggcagac ttggaggact cgccttcat gaacgccacc       480 agcacgcttg ccccggactc ctacctaatg tccggcacca ccctagcgg caaggctggc       540 caccacctca tctacgccat ttggcagcgc agcgacagcc ctgaggcctt ctactcctgc      600
tccgatgtca ccttcgacgt cgctgctgtc tctgatctcc actccaccac c              651

<210> SEQ ID NO 123
<211> LENGTH: 651
<212> TYPE: DNA
<213> ORGANISM: Tectaria milnei

<400> SEQUENCE: 123
atggggaggt catggggagt ggtggctgtt atggtggtgt gcgcaagcgg cctattgagc       60
gtagtgaggg gccatggaag catggaggac cccatcagtc gtgtgtatgc atgcttccta      120
gagaatccgg agcgtcccat atcagcagct tgccaggcgg cagtggcaat gggtgggacg      180
caagccttct atgattggaa tgcggtaagc ctgccctatg ctgctgggcg gcaccgtgaa      240
```

-continued

```
ctcatcccgg atggccaatt gtgcagtgct gggcgggcca agtatcgggg cctggacctg    300
cctcgtgacg attggccagg cacctccaat atgacctccg gcgtcgcctt cacatacagg    360
tacaaggcca ccgccccaca cttgggctcc ttccagttct atgtcactcg ggatggctac    420
gatcccaccg agccgctcaa atgggcagac ttggaggact cgcctctcat gaacgccacc    480
agcacgcttg ccccggactc ctacctaatg tccggcacca ccctagcgg caaggctggc    540 caccacctca tctacgccat ttggcagcgc agcgacagcc ctgaggcctt ctactcctgc    600
tccgatgtca ccttcgacgt cgctgctgtc tctgatctcc actccaccac c             651
```

<210> SEQ ID NO 124
<211> LENGTH: 215
<212> TYPE: PRT
<213> ORGANISM: Polystichum tripteron

<400> SEQUENCE: 124

```
Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Ala Cys Arg Gln Glu Asn Pro Glu Arg Pro Thr Thr
        35                  40                  45

Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
        115                 120                 125

Phe Phe Glu Phe Tyr Val Thr Val Asp Gly Tyr Asp Pro Thr Glu Pro
    130                 135                 140

Leu Lys Trp Ala Asp Leu Glu Glu Thr Pro Phe Ile Asn Val Thr Asp
145                 150                 155                 160

Pro Thr Val Val Gly Leu Asn Tyr Val Ile Pro Gly Thr Thr Pro Ala
                165                 170                 175

Ser Lys Thr Gly Arg His Leu Ile Tyr Val Ile Trp Gln Arg Ser Asp
            180                 185                 190

Ser Pro Glu Ala Phe Tyr Ser Cys Ser Asp Val Asn Phe Pro Asp Ala
        195                 200                 205

Leu Ser Leu His Ser Thr Thr
    210                 215
```

<210> SEQ ID NO 125
<211> LENGTH: 212
<212> TYPE: PRT
<213> ORGANISM: Polystichum tripteron

<400> SEQUENCE: 125

```
Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30
```

```
Ser Arg Val Tyr Ala Cys Arg Gln Glu Asn Pro Glu Arg Pro Thr Thr
         35                  40                  45

Pro Ala Cys Ile Ala Ala Val Ala Leu Ser Gly Ala Gln Ala Phe Tyr
 50                      55                  60

Asp Trp Asn Glu Val Asn Ile Pro Asn Ala Pro Gly Arg His Arg Glu
 65                  70                  75                  80

Leu Ile Ser Asp Gly Tyr Leu Cys Ser Ala Asn Arg Thr Lys Tyr Ala
                 85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
            115                 120                 125

Phe Phe Glu Phe Tyr Val Thr Val Asp Gly Tyr Asp Pro Thr Glu Pro
130                 135                 140

Leu Lys Trp Ala Asp Leu Glu Glu Thr Pro Phe Ile Asn Val Thr Asp
145                 150                 155                 160

Pro Thr Val Val Gly Leu Asn Tyr Val Ile Pro Gly Thr Thr Pro Ala
                165                 170                 175

Ser Lys Thr Gly Arg His Leu Ile Tyr Val Ile Trp Gln Arg Ser Asp
            180                 185                 190

Ser Pro Glu Ala Phe Tyr Ser Cys Ser Asp Val Asn Phe Pro Asp Ala
            195                 200                 205

Leu Ser Leu His
        210

<210> SEQ ID NO 126
<211> LENGTH: 214
<212> TYPE: PRT
<213> ORGANISM: Davallia fejeensis

<400> SEQUENCE: 126

Met Gly Arg Ser Trp Gly Val Val Ala Ile Met Val Val Cys Ile Met
 1               5                  10                  15

Ser Gly Leu Val Gly Ile Val Ser Gly His Gly Ser Met Glu Asp Pro
             20                  25                  30

Ile Ser Arg Val Tyr Arg Cys Tyr Leu Glu Asn Pro Glu Arg Pro Val
         35                  40                  45

Ser Ala Ala Cys Gln Ala Ala Val Ala Met Ser Gly Thr Gln Ala Phe
 50                      55                  60

Tyr Asp Trp Asn Glu Val Asn Ile Pro Asn Ala Ala Gly Arg His Arg
 65                  70                  75                  80

Glu Leu Ile Ser Asp Gly Gln Leu Cys Ser Ala Asn Arg Thr Lys Tyr
                 85                  90                  95

Ala Gly Leu Asp Leu Ala Arg Ala Asp Trp Leu Gly Thr Pro Leu Ser
            100                 105                 110

Ser Gly Val Ser Phe Thr Phe Ala Tyr Lys Ala Thr Ala Pro His Leu
            115                 120                 125

Gly Phe Phe Glu Phe Tyr Val Thr Arg Asp Gly Tyr Glu Pro Thr Glu
130                 135                 140

Pro Leu Lys Trp Ala Asp Leu Glu Asp Ser Pro Phe Ile Asn Val Thr
145                 150                 155                 160

Asp Pro Thr Leu Glu Asn Gly Ala Tyr Gln Ile Ser Gly Thr Thr Pro
                165                 170                 175

Ser Gly Lys Ser Gly Arg His Leu Met Tyr Val Ile Trp Gln Arg Ser
            180                 185                 190
```

```
Asp Ser Pro Glu Ala Phe Tyr Ser Cys Ser Asp Val Asp Phe Asp Val
        195                 200                 205

Asp Ala Leu Ser Leu His
        210
```

<210> SEQ ID NO 127
<211> LENGTH: 212
<212> TYPE: PRT
<213> ORGANISM: Didymochlaena truncatula

<400> SEQUENCE: 127

```
Met Gly Arg Ser Trp Gly Val Val Ala Ile Met Val Leu Cys Ala Ser
1               5                   10                  15

Gly Leu Leu Gly Val Ala Ser Gly His Gly Ser Met Glu Asp Pro Ile
            20                  25                  30

Ser Arg Val Tyr Ala Cys Tyr Leu Glu Asn Pro Glu Arg Pro Thr Ser
        35                  40                  45

Ala Ala Cys Gln Ala Ala Val Ala Val Ser Gly Thr Gln Ala Phe Tyr
    50                  55                  60

Asp Trp Asn Glu Val Asn Gln Pro Phe Ala Ala Gly Arg His Arg Glu
65                  70                  75                  80

Leu Ile Pro Asp Gly Glu Leu Cys Ser Gly Gly Arg Glu Lys Tyr Lys
                85                  90                  95

Gly Leu Asp Leu Ala Arg Ala Asp Trp Pro Ala Thr Ser Leu Pro Ser
            100                 105                 110

Gly Val Asn Tyr Thr Tyr Leu Tyr Lys Ala Thr Ala Pro His Leu Gly
        115                 120                 125

Phe Phe Glu Phe Tyr Ile Thr Arg Asp Gly Tyr Glu Pro Thr Glu Pro
    130                 135                 140

Leu Lys Trp Ala Asp Leu Glu Asp Leu Pro Phe Ile Asn Ile Thr Asn
145                 150                 155                 160

Pro Thr Leu Val Ser Gly Ser Tyr Gln Ile Pro Gly Thr Thr His Ala
                165                 170                 175

Ser Lys Thr Gly Arg His Leu Leu Tyr Val Ile Trp Gln Arg Ser Asp
            180                 185                 190

Ser Phe Glu Ala Phe Tyr Ser Cys Ser Asp Val Asp Phe Val Asn Ala
        195                 200                 205

Leu Ser Leu His
    210
```

<210> SEQ ID NO 128
<211> LENGTH: 212
<212> TYPE: PRT
<213> ORGANISM: Didymochlaena truncatula

<400> SEQUENCE: 128

```
Met Gly Arg Ser Trp Gly Val Val Ala Ile Met Val Leu Cys Ala Ser
1               5                   10                  15

Gly Leu Leu Gly Val Ala Ser Gly His Gly Ser Met Glu Asp Pro Ile
            20                  25                  30

Ser Arg Val Tyr Ala Cys Tyr Leu Glu Asn Pro Glu Arg Pro Thr Ser
        35                  40                  45

Ala Ala Cys Gln Ala Ala Val Ala Val Ser Gly Thr Gln Ala Phe Tyr
    50                  55                  60

Asp Trp Asn Glu Val Asn Gln Pro Phe Ala Ala Gly Arg His Arg Glu
65                  70                  75                  80
```

```
Leu Ile Pro Asp Gly Glu Leu Cys Ser Gly Arg Glu Lys Tyr Lys
            85                  90                  95

Gly Leu Asp Leu Ala Arg Ala Asp Trp Pro Ala Thr Ser Leu Pro Ser
                100                 105                 110

Gly Val Asn Tyr Thr Tyr Leu Tyr Lys Ala Thr Ala Pro His Leu Gly
            115                 120                 125

Phe Phe Glu Phe Tyr Ile Thr Arg Asp Gly Tyr Glu Pro Thr Glu Pro
    130                 135                 140

Leu Lys Trp Ala Asp Leu Glu Asp Leu Pro Phe Ile Asn Ile Thr Asn
145                 150                 155                 160

Pro Thr Leu Val Ser Gly Ser Tyr Gln Ile Pro Gly Thr Thr Pro Ala
                165                 170                 175

Ser Lys Thr Gly Arg His Leu Leu Tyr Val Ile Trp Gln Arg Ser Asp
                180                 185                 190

Ser Phe Glu Ala Phe Tyr Ser Cys Ser Asp Val Asp Phe Val Asn Ala
                195                 200                 205

Leu Ser Leu His
            210

<210> SEQ ID NO 129
<211> LENGTH: 212
<212> TYPE: PRT
<213> ORGANISM: Humata tyermanii

<400> SEQUENCE: 129

Met Gly Arg Ser Trp Gly Val Val Ala Ile Met Val Met Tyr Ile Gly
1               5                   10                  15

Gly Leu Leu Ser Ile Ala Ser Gly His Gly Ser Met Glu Asp Pro Ile
            20                  25                  30

Ser Arg Val Tyr Arg Cys Tyr Leu Glu Asn Pro Glu Ser Pro Thr Ser
        35                  40                  45

Ala Ala Cys Gln Ala Ala Val Ala Val Ser Gly Ala Gln Ala Phe Tyr
    50                  55                  60

Asp Trp Asn Glu Val Asn Ile Ala Asp Ala Asn Gly Arg His Arg Glu
65                  70                  75                  80

Leu Ile Ser Asp Gly Gln Leu Cys Ser Ala Asn Arg Ser Lys Tyr Ala
            85                  90                  95

Gly Leu Asp Leu Ala Arg Ala Asp Trp Leu Gly Thr Thr Leu Ser Ser
                100                 105                 110

Gly Ala Ser Phe Thr Phe Ala Tyr Lys Ala Thr Ala Pro His Leu Gly
            115                 120                 125

Phe Phe Glu Phe Tyr Val Thr Arg Asp Gly Tyr Glu Pro Thr Asp Pro
    130                 135                 140

Leu Lys Trp Ala Asp Leu Glu Asp Ser Pro Phe Ile Asn Val Thr Asn
145                 150                 155                 160

Pro Thr Leu Asp Asn Gly Ala Tyr Gln Ile Ser Gly Thr Thr Pro Ala
                165                 170                 175

Gly Lys Ser Gly Arg His Leu Ile Tyr Val Ile Trp Gln Arg Ser Asp
                180                 185                 190

Ser Pro Glu Ala Phe Tyr Ser Cys Ser Asp Val Asp Phe Val Asp Ala
                195                 200                 205

Leu Ser Leu His
            210
```

```
<210> SEQ ID NO 130
<211> LENGTH: 215
<212> TYPE: PRT
<213> ORGANISM: Cyrtomium fortunei

<400> SEQUENCE: 130
```

Met Gly Arg Ser Trp Gly Val Val Ala Ile Met Val Leu Cys Thr Ser
1               5                   10                  15

Gly Leu Leu Gly Val Ala Ser Gly His Gly Thr Met Gly Asp Pro Ile
            20                  25                  30

Ser Arg Val Tyr Asn Cys Phe Gln Glu Asn Pro Glu Arg Pro Thr Ser
        35                  40                  45

Ala Ala Cys Ile Ala Ala Val Ala Leu Ser Gly Thr Gln Ala Phe Tyr
    50                  55                  60

Asp Trp Asn Glu Val Asn Leu Pro Asp Val Asn Gly Arg His Arg Glu
65                  70                  75                  80

Phe Ile Pro Asp Gly Gln Leu Cys Ser Ala Gly Arg Asp Lys Tyr Lys
                85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
        115                 120                 125

Phe Phe Glu Phe Tyr Val Thr Val Asp Asp Tyr Asp Pro Thr Val Ala
    130                 135                 140

Leu Lys Trp Glu Asp Leu Glu Glu Thr Pro Phe Leu Asn Val Thr Asp
145                 150                 155                 160

Pro Thr Val Val Gly Val Asn Tyr Gln Ile Ser Gly Thr Thr Pro Ala
                165                 170                 175

Ser Lys Thr Gly Arg His Leu Ile Tyr Val Ile Trp Gln Arg Ser Asp
            180                 185                 190

Ser Pro Glu Ala Phe Tyr Ala Cys Ser Asp Val Asp Phe Val Asp Ala
        195                 200                 205

Val Ser Leu His Ser Thr Thr
    210                 215

```
<210> SEQ ID NO 131
<211> LENGTH: 229
<212> TYPE: PRT
<213> ORGANISM: Adiantum hispidulum

<400> SEQUENCE: 131
```

Met Lys Lys Ser Trp Gly Val Ala Val Val Gly Val Ala Leu
1               5                   10                  15

Cys Leu Leu Gly Met Ala Ser Gly His Gly Ser Met Gln Asp Pro Ile
            20                  25                  30

Ser Arg Val Tyr Asn Cys Tyr Leu Glu Gly Pro Glu Arg Pro Thr Ser
        35                  40                  45

Ala Ala Cys Ile Ala Ala Val Ala Met Ser Gly Thr Gln Pro Phe Tyr
    50                  55                  60

Asp Trp Asn Glu Val Asn Leu Pro Asp Ala Ala Gly Arg His Arg Glu
65                  70                  75                  80

Leu Ile Pro Asp Gly Lys Leu Cys Ser Ala Gly Arg Asp Lys Tyr Gln
                85                  90                  95

Gly Leu Asp Leu Ala Arg Asp Asp Trp Val Ala Ser Leu Ser Ser Gly
            100                 105                 110

Val Ala Tyr Thr Phe Leu Tyr Arg Val Thr Ala Gln His Leu Gly Phe

```
                115                 120                 125
Phe Glu Ile Tyr Val Thr Arg Asp Thr Tyr Asp Pro Thr Gln Ala Leu
            130                 135                 140

Thr Trp Asp Asp Leu Glu Asp Ser Pro Phe Ile Asn Val Thr Asn Pro
145                 150                 155                 160

Ser Val Val Ser Thr Thr Leu Gly Asn Ala Tyr Ala Ile Pro Thr Pro
                165                 170                 175

Thr Pro Ser Gly Lys Thr Gly Arg His Leu Ile Tyr Val Ile Trp Gln
            180                 185                 190

Arg Ser Asp Ser Pro Glu Ala Phe Tyr Ser Cys Ser Asp Val Glu Phe
                195                 200                 205

Asp Val Ala Ser Thr Val Glu Asp Val Ile Ile Ser Leu Arg Ser
            210                 215                 220

Ala Ala Leu Asp Val
225

<210> SEQ ID NO 132
<211> LENGTH: 215
<212> TYPE: PRT
<213> ORGANISM: Polystichum acrostichoides

<400> SEQUENCE: 132

Met Gly Arg Ser Trp Gly Val Val Ala Ile Met Val Leu Cys Ala Ser
1                   5                  10                  15

Gly Leu Leu Gly Val Ala Ser Gly His Gly Ser Met Asn Asp Pro Ile
                20                  25                  30

Ser Arg Val Tyr Asn Cys Arg Leu Glu Asn Pro Glu Ser Pro Thr Ser
            35                  40                  45

Ala Ala Cys Ile Ala Ala Val Ala Leu Ser Gly Thr Gln Ala Phe Tyr
        50                  55                  60

Asp Trp Asn Glu Val Asn Leu Pro Asp Val Asn Gly Arg His Arg Gln
65                  70                  75                  80

Leu Ile Pro Asp Gly Lys Leu Cys Ser Ala Gly Arg Asp Lys Tyr Lys
                85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Gln His Arg Gly
        115                 120                 125

Phe Phe Glu Phe Tyr Val Thr Val Asp Asp Tyr Asp Pro Thr Glu Leu
130                 135                 140

Leu Lys Trp Glu Asp Leu Glu Glu Thr Pro Phe Met Asn Val Thr Asp
145                 150                 155                 160

Pro Thr Val Val Gly Val Asn Tyr Glu Ile Pro Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Val Ser Leu His Ser Thr Thr
            210                 215

<210> SEQ ID NO 133
<211> LENGTH: 217
<212> TYPE: PRT
<213> ORGANISM: Thelypteris kunthii
```

```
<400> SEQUENCE: 133

Met Glu Arg Ala Ala Trp Gly Val Val Ile Ile Met Val Leu Cys
1               5                   10                  15

Ala Ser Gly Leu Leu Gly Val Ala Ser Gly His Gly Ser Met Glu Asp
            20                  25                  30

Pro Ile Ser Arg Val Tyr Leu Cys Tyr Leu Glu Asn Pro Glu Arg Pro
        35                  40                  45

Thr Ser Ala Ala Cys Gln Ala Val Ala Leu Ser Gly Thr Gln Ala
    50                  55                  60

Phe Tyr Asp Trp Asn Glu Val Asn Ile Ala Asp Ala Ala Gly Arg His
65              70                  75                  80

Arg Glu Leu Ile Pro Asp Gly Gln Leu Cys Ser Ala Gly Arg Asp Lys
                85                  90                  95

Tyr Lys Gly Leu Asp Leu Ala Arg Ser Asp Trp Val Ala Thr Asn Leu
            100                 105                 110

Ser Ser Gly Val Ala Phe Thr Phe Leu Tyr Arg Val Thr Ala Glu His
        115                 120                 125

Arg Gly Phe Phe Glu Phe Tyr Val Thr Val Asp Asp Tyr Asp Pro Thr
    130                 135                 140

Glu Leu Leu Lys Trp Glu Asp Leu Glu Ala Thr Pro Phe Met Asn Val
145             150                 155                 160

Thr Asp Pro Thr Val Val Gly Asp Asn Tyr Glu Ile Pro Gly Thr Thr
                165                 170                 175

Pro Ala Asn Lys Thr Gly Arg His Leu Ile Tyr Val Ile Trp Gln Arg
            180                 185                 190

Ser Asp Ser Pro Glu Ala Phe Tyr Ser Cys Ser Asp Val Val Phe Ala
        195                 200                 205

Asp Ala Val Ser Leu His Ser Thr Thr
    210                 215

<210> SEQ ID NO 134
<211> LENGTH: 222
<212> TYPE: PRT
<213> ORGANISM: Cyrtomium fortune (clivicola)

<400> SEQUENCE: 134

Met Gly Thr Leu Gly Arg Ser Trp Gly Ala Val Ala Ile Met Val Leu
1               5                   10                  15

Cys Ala Ser Gly Leu Leu Gly Val Ala Ser Gly His Gly Ser Met Asn
            20                  25                  30

Asp Pro Ile Ser Arg Val Tyr Asn Cys Tyr Leu Glu Asn Pro Glu Arg
        35                  40                  45

Pro Thr Ser Ala Ala Cys Ile Ala Ala Val Ala Leu Ser Gly Thr Gln
    50                  55                  60

Ala Phe Tyr Asp Trp Asn Glu Val Asn Leu Pro Asp Ala Asn Gly Arg
65              70                  75                  80

His Arg Gln Leu Ile Pro Asp Gly Gln Leu Cys Ser Ala Gly Arg Asp
                85                  90                  95

Lys Tyr Lys Gly Leu Asp Leu Ala Arg Ser Asp Trp Thr Ala Thr Asn
            100                 105                 110

Leu Ser Ser Gly Val Ala Phe Thr Phe Leu Tyr Arg Val Thr Ala Gln
        115                 120                 125

His Arg Gly Phe Phe Glu Phe Tyr Val Thr Val Asp Asp Tyr Asp Pro
    130                 135                 140
```

```
Thr Val Ala Leu Lys Trp Glu Asp Leu Glu Glu Thr Pro Phe Leu Asn
145                 150                 155                 160

Val Thr Asp Pro Thr Val Gly Val Asn Tyr Gln Ile Ser Gly Thr
                165                 170                 175

Thr Pro Ala Ser Lys Thr Gly Arg His Leu Ile Tyr Val Ile Trp Gln
                180                 185                 190

Arg Ser Asp Ser Pro Glu Ala Phe Tyr Ala Cys Ser Asp Val Asp Phe
            195                 200                 205

Val Asp Ala Val Ser Leu His Ser Thr Thr Leu Thr Leu Ile
        210                 215                 220
```

<210> SEQ ID NO 135
<211> LENGTH: 215
<212> TYPE: PRT
<213> ORGANISM: Polystichum tripteron

<400> SEQUENCE: 135

```
Met Gly Arg Ser Trp Gly Val Val Ala Ile Met Val Leu Phe Ser Ser
1               5                   10                  15

Gly Leu Leu Gly Val Ala Ser Gly His Gly Ser Met Gly Asp Pro Ile
                20                  25                  30

Ser Arg Val Tyr Asn Cys Arg Gln Glu Asn Pro Glu Arg Pro Thr Thr
            35                  40                  45

Pro Ala Cys Ile Ala Ala Val Ala Leu Ser Gly Ala Gln Ala Phe Tyr
        50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
        115                 120                 125

Phe Phe Glu Phe Tyr Val Thr Val Asp Gly Tyr Asp Pro Thr Glu Pro
130                 135                 140

Leu Lys Trp Ala Asp Leu Glu Glu Thr Pro Phe Ile Asn Val Thr Asp
145                 150                 155                 160

Pro Thr Val Glu Gly Leu Asn Tyr Val Arg Val Leu Arg His Arg Gly
                165                 170                 175

Cys Lys Ser Gly Arg His Leu Ile Tyr Val Ile Trp Gln Arg Ser Asp
            180                 185                 190

Ser Pro Glu Ala Phe Tyr Ser Cys Ser Asp Val Asn Phe Pro Asp Ala
        195                 200                 205

Leu Ser Leu His Ser Ala Thr
        210                 215
```

<210> SEQ ID NO 136
<211> LENGTH: 215
<212> TYPE: PRT
<213> ORGANISM: Didymochlaena truncatula

<400> SEQUENCE: 136

```
Met Gly Arg Ser Trp Gly Val Val Ala Ile Met Val Leu Cys Ala Ser
1               5                   10                  15

Gly Leu Leu Gly Val Ala Ser Gly His Gly Ser Met Glu Asp Pro Ile
                20                  25                  30
```

```
Ser Arg Val Tyr Ala Cys Tyr Leu Glu Asn Pro Glu Arg Pro Thr Ser
        35                  40                  45

Ala Ala Cys Gln Ala Ala Val Ala Val Ser Gly Thr Gln Ala Phe Tyr
 50                  55                  60

Asp Trp Asn Glu Val Asn Gln Pro Phe Ala Ala Gly Arg His Arg Glu
 65                  70                  75                  80

Leu Ile Pro Asp Gly Glu Leu Cys Ser Gly Gly Arg Glu Lys Tyr Lys
                85                  90                  95

Gly Leu Asp Leu Ala Arg Ala Asp Trp Pro Ala Thr Ser Leu Pro Ser
                100                 105                 110

Gly Val Asn Tyr Thr Tyr Leu Tyr Lys Ala Thr Ala Pro His Leu Gly
                115                 120                 125

Phe Phe Glu Phe Tyr Ile Thr Arg Asp Gly Tyr Glu Pro Thr Glu Pro
    130                 135                 140

Leu Lys Trp Ala Asp Leu Glu Asp Leu Pro Phe Ile Asn Ile Thr Asn
145                 150                 155                 160

Pro Thr Leu Val Ser Gly Ser Tyr Gln Ile Pro Gly Thr Thr Pro Ala
                165                 170                 175

Ser Lys Thr Gly Arg His Leu Leu Tyr Val Ile Trp Gln Arg Ser Asp
                180                 185                 190

Ser Phe Glu Ala Phe Tyr Ser Cys Ser Asp Val Asp Phe Val Asn Ala
                195                 200                 205

Leu Ser Leu His Ser Thr Thr
                210                 215

<210> SEQ ID NO 137
<211> LENGTH: 229
<212> TYPE: PRT
<213> ORGANISM: Asplenium antiquum

<400> SEQUENCE: 137

Met Arg Met Gly Arg Ser Ala Ser Cys Ile Arg Ala Asn Met Ala Ile
 1               5                  10                  15

Met Leu Val Leu Phe Trp Ala Ser Cys Ser Cys Leu Leu Gly Ile Val
                20                  25                  30

Ser Gly His Gly Ser Met Glu Asp Pro Ile Ser Arg Val Tyr Ala Cys
                35                  40                  45

Phe Leu Glu Asn Pro Glu Arg Pro Thr Ser Ala Ala Cys Ile Ala Ala
         50                  55                  60

Val Ala Leu Ser Gly Thr Gln Ala Phe Tyr Asp Trp Asn Glu Val Asn
 65                  70                  75                  80

Gln Pro Asn Ala Ala Gly Arg His Arg Glu Ile Ile Pro Asp Gly Gln
                85                  90                  95

Leu Cys Gly Ala Gly Arg Asp Lys Tyr Lys Gly Leu Asn Leu Ala Arg
                100                 105                 110

Ala Asp Trp Pro Ala Thr Thr Leu Ser Ser Asp Ile Ser Phe Thr Tyr
                115                 120                 125

Leu Phe Lys Ala Thr Ala Pro His Arg Gly Phe Phe Glu Phe Tyr Val
    130                 135                 140

Thr Arg Asp Gly Tyr Asp Pro Thr Glu Pro Leu Lys Trp Ala Asp Leu
145                 150                 155                 160

Glu Asp Pro Pro Phe Leu Asn Val Thr Asp Pro Thr Leu Ala Ser Gly
                165                 170                 175

Ser Tyr Gln Ile Pro Gly Thr Thr Pro Ala Gly Lys Thr Gly Arg His
                180                 185                 190
```

```
Leu Ile Tyr Val Ile Trp Gln Arg Ser Asp Ser Pro Glu Ala Phe Tyr
        195                 200                 205

Ser Cys Ser Asp Val Asp Phe Asp Ser Ser Asp Thr Val Ile Ser Leu
210                 215                 220

Arg Ser Ala Thr Thr
225

<210> SEQ ID NO 138
<211> LENGTH: 215
<212> TYPE: PRT
<213> ORGANISM: Cyrtomium falcatum (Butterfieldii)

<400> SEQUENCE: 138

Met Gly Arg Ser Trp Gly Val Val Ala Ile Met Val Leu Cys Ala Thr
1               5                   10                  15

Gly Leu Leu Gly Val Ala Ser Gly His Gly Ser Met Gly Asp Pro Ile
            20                  25                  30

Ser Arg Val Tyr Asn Cys Phe Leu Glu Asn Pro Glu Arg Pro Thr Ser
        35                  40                  45

Ala Ala Cys Ile Ala Ala Val Ala Leu Ser Gly Thr Gln Ala Phe Tyr
    50                  55                  60

Asp Trp Asn Glu Val Asn Leu Pro Asp Val Asn Gly Arg His Arg Gln
65                  70                  75                  80

Phe Ile Pro Asp Gly Gln Leu Cys Ser Ala Gly Arg Asp Lys Tyr Lys
                85                  90                  95

Gly Leu Asp Leu Ala Arg Ser Asp Trp Thr Ala Thr Asn Leu Ser Ser
            100                 105                 110

Gly Ile Ala Tyr Thr Phe Leu Tyr Arg Val Thr Ala Gln His Arg Gly
        115                 120                 125

Phe Phe Glu Phe Tyr Val Thr Val Asp Asp Tyr Asp Pro Thr Val Ala
    130                 135                 140

Leu Lys Trp Glu Asp Leu Glu Glu Thr Pro Phe Leu Asn Val Thr Asp
145                 150                 155                 160

Pro Thr Val Val Gly Val Asn Tyr Gln Ile Asn Gly Thr Thr Pro Ala
                165                 170                 175

Ser Lys Thr Gly Arg His Leu Ile Tyr Val Ile Trp Gln Arg Ser Asp
            180                 185                 190

Ser Pro Glu Ala Phe Tyr Ala Cys Ser Asp Val Asp Phe Val Asp Ala
        195                 200                 205

Val Ser Leu His Ser Thr Thr
    210                 215

<210> SEQ ID NO 139
<211> LENGTH: 218
<212> TYPE: PRT
<213> ORGANISM: Onoclea sensibilis

<400> SEQUENCE: 139

Met Gly Arg Ser Trp Gly Val Val Gln Ala Ile Ile Met Val Leu Cys
1               5                   10                  15

Gly Ser Gly Leu Leu Gly Val Ala Ser Gly His Gly Ser Met Glu Asp
            20                  25                  30

Pro Ile Ser Arg Val Tyr Asn Cys Tyr Leu Glu Asn Pro Glu Ser Pro
        35                  40                  45

Thr Ser Ala Ala Cys Gln Ala Val Ala Leu Ser Gly Ala Gln Ala
    50                  55                  60
```

Phe Tyr Asp Trp Asn Glu Val Asn Leu Ala Asp Ala Ala Gly Arg His
65                  70                  75                  80

Arg Glu Leu Ile Pro Asp Gly Gln Leu Cys Ser Ala Gly Arg Glu Lys
                85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
        115                 120                 125

Leu Gly Phe Phe Glu Phe Tyr Val Thr Lys Asp Gly Tyr Glu Pro Thr
130                 135                 140

Glu Pro Leu Lys Trp Ala Asp Leu Glu Asp Ser Pro Phe Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
        195                 200                 205

Val Asp Ala Leu Ser Leu His Ser Thr Thr
210                 215

<210> SEQ ID NO 140
<211> LENGTH: 216
<212> TYPE: PRT
<213> ORGANISM: Platycerium superbum

<400> SEQUENCE: 140

Met Arg Arg Ser Trp Val Ala Val Ala Val Thr Leu Val Val Cys Ala
1               5                   10                  15

Gly Ser Leu Leu Gly Val Ala Ser Gly His Gly Ser Met Glu Asp Pro
            20                  25                  30

Ile Ser Arg Val Tyr Gly Cys Tyr Leu Glu Asn Pro Glu Asn Pro Thr
        35                  40                  45

Ser Ala Ala Cys Ile Ala Ala Val Ala Ala Ser Gly Thr Gln Ala Phe
    50                  55                  60

Tyr Asp Trp Asn Glu Val Asn Gln Pro Phe Ala Ala Gly Gln His Arg
65                  70                  75                  80

Gln Ile Ile Pro Asp Gly Gln Leu Cys Ser Ala Gly Arg Asp Lys Tyr
                85                  90                  95

Lys Gly Leu Asp Leu Ala Arg Ala Asp Trp Pro Ala Thr Ser Leu Ser
            100                 105                 110

Ser Gly Val Asp Tyr Thr Phe Leu Phe Lys Ala Thr Ala Pro His Arg
        115                 120                 125

Gly Tyr Phe Glu Phe Tyr Val Thr Arg Asp Ser Tyr Asp Pro Thr Glu
130                 135                 140

Pro Leu Ala Trp Ala Asp Leu Glu Asp Thr Pro Phe Ile Asn Val Thr
145                 150                 155                 160

Asp Pro Thr Leu Val Ser Gly Ser Tyr Gln Ile Ser Ser Thr Thr Pro
                165                 170                 175

Ser Gly Lys Thr Gly Arg His Leu Ile Tyr Val Ile Trp Gln Arg Thr
            180                 185                 190

Asp Ser Thr Glu Ala Phe Tyr Ser Cys Ser Asp Val Asp Phe Asp Glu
        195                 200                 205

Thr Leu Arg Leu His Ser Ala Thr

<210> SEQ ID NO 141
<211> LENGTH: 215
<212> TYPE: PRT
<213> ORGANISM: Davallia tyermannii

<400> SEQUENCE: 141

Met Gly Arg Ser Trp Gly Val Val Ala Ile Met Val Met Tyr Ile Gly
1               5                   10                  15

Gly Leu Leu Ser Ile Ala Ser Gly His Gly Ser Met Glu Asp Pro Ile
            20                  25                  30

Ser Arg Val Tyr Arg Cys Tyr Leu Glu Asn Pro Glu Ser Pro Thr Ser
        35                  40                  45

Ala Ala Cys Gln Ala Ala Val Ala Val Ser Gly Ala Gln Ala Phe Tyr
    50                  55                  60

Asp Trp Asn Glu Val Asn Ile Ala Asp Ala Asn Gly Arg His Arg Glu
65                  70                  75                  80

Leu Ile Ser Asp Gly His Leu Cys Ser Ala Asn Arg Thr Lys Tyr Ala
                85                  90                  95

Gly Leu Asp Leu Ala Cys Pro Asp Trp Leu Gly Thr Leu Leu Phe Ser
            100                 105                 110

Gly Val Ser Tyr Thr Phe Ser Tyr Lys Ala Thr Ala Pro His Leu Gly
        115                 120                 125

Phe Phe Glu Phe Tyr Val Thr Arg Asp Gly Tyr Glu Pro Thr Asp Pro
    130                 135                 140

Leu Lys Trp Ala Asp Leu Glu Asp Ser Pro Phe Ile Asn Val Thr Asn
145                 150                 155                 160

Pro Thr Leu Asp Asn Gly Ala Tyr Gln Ile Ser Gly Thr Thr Pro Ala
                165                 170                 175

Gly Lys Ser Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Leu Ser Leu His Ser Thr Thr
    210                 215

<210> SEQ ID NO 142
<211> LENGTH: 217
<212> TYPE: PRT
<213> ORGANISM: Tectaria milnei

<400> SEQUENCE: 142

Met Gly Arg Ser Trp Gly Val Val Ala Val Met Val Val Cys Ala Ser
1               5                   10                  15

Gly Leu Leu Ser Val Val Arg Gly His Gly Ser Met Glu Asp Pro Ile
            20                  25                  30

Ser Arg Val Tyr Ala Cys Phe Leu Glu Asn Pro Glu Arg Pro Ile Ser
        35                  40                  45

Ala Ala Cys Gln Ala Ala Val Ala Met Gly Gly Thr Gln Ala Phe Tyr
    50                  55                  60

Asp Trp Asn Ala Val Ser Leu Pro Tyr Ala Gly Gln His Arg Glu
65                  70                  75                  80

Leu Ile Pro Asp Gly Gln Leu Cys Ser Ala Gly Arg Ala Lys Tyr Arg
                85                  90                  95

Gly Leu Asp Leu Pro Arg Asp Asp Trp Pro Gly Thr Ser Asn Met Thr

```
                100             105             110
Ser Gly Val Ala Phe Thr Tyr Arg Tyr Lys Ala Thr Ala Pro His Leu
            115                 120                 125

Gly Ser Phe Gln Phe Tyr Val Thr Arg Asp Gly Tyr Asp Pro Thr Glu
            130                 135                 140

Pro Leu Lys Trp Ala Asp Leu Glu Asp Ser Pro Phe Met Asn Ala Thr
145                 150                 155                 160

Ser Thr Leu Ala Pro Asp Ser Tyr Leu Met Ser Gly Thr Thr Pro Ser
            165                 170                 175

Gly Lys Ala Gly His His Leu Ile Tyr Ala Ile Trp Gln Arg Ser Asp
            180                 185                 190

Ser Pro Glu Ala Phe Tyr Ser Cys Ser Asp Val Thr Phe Asp Val Ala
            195                 200                 205

Ala Val Ser Asp Leu His Ser Thr Thr
            210                 215

<210> SEQ ID NO 143
<211> LENGTH: 216
<212> TYPE: PRT
<213> ORGANISM: Polystichium tsus-simense

<400> SEQUENCE: 143

Met Gly Arg Ser Trp Trp Gly Val Leu Ala Val Met Val Leu Cys Ala
1               5                   10                  15

Ser Gly Leu Leu Gly Val Ala Ser Gly His Gly Thr Met Asn Asp Pro
            20                  25                  30

Ile Ser Arg Val Tyr Asn Cys Phe Leu Glu Asn Pro Glu Ser Pro Thr
            35                  40                  45

Ser Ala Ala Cys Ile Ala Ala Val Ala Leu Ser Gly Thr Gln Ala Phe
        50                  55                  60

Tyr Asp Trp Asn Glu Val Asn Leu Ala Asn Ala Ala Gly Arg His Arg
65                  70                  75                  80

Glu Leu Ile Pro Asp Gly Gln Leu Cys Ser Ala Gly Arg Asp Lys Tyr
                85                  90                  95

Lys Gly Leu Asp Leu Ala Arg Ser Asp Trp Thr Ala Thr Asn Leu Ser
            100                 105                 110

Ser Gly Val Ala Phe Thr Phe Leu Tyr Arg Val Thr Ala Gln His Arg
            115                 120                 125

Gly Phe Phe Glu Phe Tyr Val Thr Val Asp Asp Tyr Asp Pro Thr Glu
            130                 135                 140

Leu Leu Lys Trp Glu Asp Leu Glu Glu Thr Pro Phe Leu Asn Val Thr
145                 150                 155                 160

Asp Pro Thr Val Val Gly Val Asn Tyr Glu Ile Ser Gly Thr Thr Pro
            165                 170                 175

Ala Ser Lys Thr Gly Arg His Leu Ile Tyr Val Ile Trp Gln Arg Ser
            180                 185                 190

Asp Ser Pro Glu Ala Phe Tyr Ser Cys Ser Asp Val Asp Phe Val Asp
            195                 200                 205

Ser Leu Ser Leu His Ser Thr Thr
            210                 215

<210> SEQ ID NO 144
<211> LENGTH: 216
<212> TYPE: PRT
<213> ORGANISM: Nephrolepis falcata
```

-continued

```
<400> SEQUENCE: 144

Met Gly Arg Ser Trp Gly Ala Val Ala Ile Val Leu Ala Val Cys
1               5                   10                  15

Ala Ser Gly Leu Leu Ser Val Val Ser Gly Gln Gly Ser Met Ala Tyr
            20                  25                  30

Pro Ile Ser Arg Val Tyr Gly Cys Phe Leu Glu Asn Pro Leu Ser Pro
            35                  40                  45

Thr Ser Ala Ala Cys Asn Ala Val Ala Leu Ser Gly Thr Gln Ala
    50                  55                  60

Phe Tyr Asp Trp Asn Glu Val Ser Leu Ala Asn Ala Ser Gly Gln His
65                  70                  75                  80

Arg Gln Leu Ile Pro Asp Gly Gln Leu Cys Ser Ala Gly Gln Ala Lys
                85                  90                  95

Tyr Arg Gly Leu Asp Leu Ala Arg Asp Asp Trp Pro Gly Thr Ser Leu
            100                 105                 110

Thr Ser Gly Val Ala Tyr Thr Phe Tyr Tyr Ala Thr Thr Leu His
        115                 120                 125

Leu Gly Phe Phe Glu Phe Tyr Val Thr Arg Asp Gly Tyr Asp Ala Thr
130                 135                 140

Gln Pro Leu Lys Trp Ala Asp Leu Glu Asp Ser Pro Phe Leu Asn Val
145                 150                 155                 160

Thr Ser Thr Leu Ala Ala Ser Ser Phe Gln Trp Ser Ser Ile Thr Pro
                165                 170                 175

Ser Asp Lys Ser Gly Arg His Leu Ile Tyr Val Ile Trp Gln Arg Thr
            180                 185                 190

Asp Ser Pro Glu Ala Phe Tyr Ser Cys Ser Asp Val Asp Phe Asp Tyr
        195                 200                 205

Ala Val Ser Leu His Ser Thr Thr
    210                 215

<210> SEQ ID NO 145
<211> LENGTH: 213
<212> TYPE: PRT
<213> ORGANISM: Nephrolepis exaltata (compacta)

<400> SEQUENCE: 145

Met Gly Arg Ser Trp Gly Val Ala Ala Ile Val Val Ala Val Cys Ala
1               5                   10                  15

Ser Gly Leu Leu Ser Val Val Ser Gly His Gly Ser Met Gln Asp Pro
            20                  25                  30

Ile Ser Arg Val Tyr Ala Cys Tyr Leu Glu Asn Pro Glu Arg Pro Thr
        35                  40                  45

Ser Ala Ala Cys Gln Ala Ala Val Ala Leu Ser Gly Thr Gln Ala Phe
    50                  55                  60

Tyr Asp Trp Asn Glu Val Asn Leu Pro Asn Ala Ala Gly Arg His Arg
65                  70                  75                  80

Glu Leu Ile Pro Asp Gly Gln Leu Cys Ser Ala Gly Arg Ala Lys Tyr
                85                  90                  95

Gln Gly Leu Asp Gln Ala Arg Asn Asp Trp Pro His Thr Asp Leu Ile
            100                 105                 110

Ser Gly Val Ala Phe Thr Phe Asn Tyr Arg Ala Thr Ala Pro His Leu
        115                 120                 125

Gly Ile Phe Glu Phe Tyr Val Thr Arg Asp Gly Tyr Asp Ala Thr Gln
130                 135                 140
```

```
Pro Leu Lys Trp Ala Asp Leu Glu Asp Ser Pro Phe Leu Thr Ala Thr
145                 150                 155                 160

Ser Thr Leu Ala Pro Ser Ser Tyr Gln Trp Pro Gly Thr Thr Pro Ser
                165                 170                 175

Gly Lys Ser Gly Arg His Leu Ile Tyr Val Ile Trp Gln Arg Thr Asp
            180                 185                 190

Ser Pro Glu Ala Phe Tyr Ser Cys Ser Asp Val Glu Phe Val Asp Ala
        195                 200                 205

Val Ser Leu His Ser
    210

<210> SEQ ID NO 146
<211> LENGTH: 215
<212> TYPE: PRT
<213> ORGANISM: Nephrolepis exaltata (Tiger Fern)

<400> SEQUENCE: 146

Met Gly Arg Ser Trp Gly Val Ala Ala Ile Val Ala Val Cys Ala
1               5                   10                  15

Ser Gly Leu Leu Ser Val Val Ser Gly His Gly Ser Met Gln Asp Pro
                20                  25                  30

Ile Ser Arg Val Tyr Ala Cys Tyr Leu Glu Asn Pro Glu Arg Pro Thr
            35                  40                  45

Ser Ala Ala Cys Gln Ala Val Ala Leu Ser Gly Thr Gln Ala Phe
        50                  55                  60

Tyr Asp Trp Asn Glu Val Asn Leu Pro Asn Ala Ala Gly Arg His Arg
65                  70                  75                  80

Glu Leu Ile Pro Asp Gly Gln Leu Cys Ser Ala Gly Arg Ala Lys Tyr
                85                  90                  95

Gln Gly Leu Asp Gln Ala Arg Asn Asp Trp Pro His Thr Asp Leu Ile
            100                 105                 110

Ser Gly Val Ala Phe Thr Phe Asn Tyr Arg Ala Thr Ala Pro His Leu
        115                 120                 125

Gly Ile Phe Glu Phe Tyr Val Thr Arg Asp Gly Tyr Asp Ala Thr Gln
    130                 135                 140

Pro Leu Lys Trp Ala Asp Leu Glu Asp Ser Pro Phe Leu Thr Ala Thr
145                 150                 155                 160

Ser Thr Leu Ala Pro Ser Ser Tyr Gln Trp Pro Gly Thr Thr Pro Ser
                165                 170                 175

Gly Lys Ser Gly Arg His Leu Ile Tyr Val Ile Trp Gln Arg Thr Asp
            180                 185                 190

Ser Pro Glu Ala Phe Tyr Ser Cys Ser Asp Val Glu Phe Val Asp Ala
        195                 200                 205

Val Ser Leu His Ser Thr Thr
    210                 215

<210> SEQ ID NO 147
<211> LENGTH: 215
<212> TYPE: PRT
<213> ORGANISM: Humata termanii

<400> SEQUENCE: 147

Met Gly Arg Ser Trp Gly Val Val Ala Ile Met Val Met Tyr Ile Gly
1               5                   10                  15

Gly Leu Leu Ser Ile Ala Ser Gly His Gly Ser Met Glu Asp Pro Ile
                20                  25                  30
```

```
Ser Arg Val Tyr Arg Cys Tyr Leu Glu Asn Pro Glu Ser Pro Thr Ser
        35                  40                  45

Ala Ala Cys Gln Ala Ala Val Ala Val Ser Gly Ala Gln Ala Phe Tyr
50                  55                  60

Asp Trp Asn Glu Val Asn Ile Ala Asp Ala Asn Gly Arg His Arg Glu
65                  70                  75                  80

Leu Ile Ser Asp Gly Gln Leu Cys Ser Ala Asn Arg Ser Lys Tyr Ala
                85                  90                  95

Gly Leu Asp Leu Ala Arg Ala Asp Trp Leu Gly Thr Thr Leu Ser Ser
                100                 105                 110

Gly Ala Ser Phe Thr Phe Ala Tyr Lys Ala Thr Ala Pro His Leu Gly
                115                 120                 125

Phe Phe Glu Phe Tyr Val Thr Arg Asp Gly Tyr Glu Pro Thr Asp Pro
            130                 135                 140

Leu Lys Trp Ala Asp Leu Glu Asp Ser Pro Phe Ile Asn Val Thr Asn
145                 150                 155                 160

Pro Thr Leu Asp Asn Gly Ala Tyr Gln Ile Ser Gly Thr Thr Pro Ala
                165                 170                 175

Gly Lys Ser Gly Arg His Leu Ile Tyr Val Ile Trp Gln Arg Ser Asp
                180                 185                 190

Ser Pro Glu Ala Phe Tyr Ser Cys Ser Asp Val Asp Phe Val Asp Ala
            195                 200                 205

Leu Ser Leu His Ser Thr Thr
                210                 215

<210> SEQ ID NO 148
<211> LENGTH: 220
<212> TYPE: PRT
<213> ORGANISM: Adiantum tenerum (Scutum Roseum)

<400> SEQUENCE: 148

Met Gly Trp Cys Arg Ser Trp Gly Val Ala Val Met Val Leu Cys
1               5                   10                  15

Thr Ser Gly Leu Leu Gly Val Ala Ser Gly His Gly Ser Met Lys Asp
                20                  25                  30

Pro Ile Ser Arg Val Tyr Asn Cys Tyr Leu Glu Asn Pro Glu Arg Pro
            35                  40                  45

Thr Ser Ala Ala Cys Gln Ala Val Ala Leu Ser Gly Thr Gln Ala
            50                  55                  60

Phe Tyr Asp Trp Asn Glu Val Asn Leu Pro Asn Ala Ala Gly Arg His
65                  70                  75                  80

Arg Glu Leu Ile Pro Asp Gly Glu Leu Cys Ser Ala Gly Arg Glu Lys
                85                  90                  95

Tyr Gln Gly Leu Asp Leu Ala Arg Ala Asp Trp Thr Ala Thr Ser Leu
                100                 105                 110

Thr Ser Gly Leu Asp Ser Phe Thr Trp Leu Tyr Lys Ala Thr Ala Pro
                115                 120                 125

His Leu Gly Phe Phe Glu Phe Tyr Val Thr Arg Asp Gly Tyr Asp Pro
            130                 135                 140

Thr Glu Ala Leu Thr Trp Ala Asp Leu Glu Asp Ser Pro Phe Ile Asn
145                 150                 155                 160

Val Thr Asn Pro Ala Leu Val Ser Gly Asp Tyr Gln Ile Ser Gly Thr
                165                 170                 175

Ile Pro Ala Gly Lys Ser Gly Arg His Leu Ile Tyr Val Ile Trp Gln
                180                 185                 190
```

Arg Ser Asp Ser Pro Glu Ala Phe Tyr Ser Cys Ser Asp Val Asp Phe
        195                 200                 205

Val Asp Asp Ala Leu Ile Ser Leu Arg Ser Ala Thr
    210                 215                 220

<210> SEQ ID NO 149
<211> LENGTH: 215
<212> TYPE: PRT
<213> ORGANISM: Polystichum setiferum (compacta)

<400> SEQUENCE: 149

Met Gly Arg Ser Trp Gly Val Ala Ala Ile Met Val Leu Cys Ala Ser
1               5                   10                  15

Gly Leu Leu Gly Val Ala Ser Gly His Gly Thr Met His Asp Pro Ile
            20                  25                  30

Ser Arg Val Tyr Asn Cys Phe Leu Glu Asn Pro Glu Ser Pro Thr Ser
        35                  40                  45

Ala Ala Cys Ile Glu Ala Val Glu Val Ser Gly Thr Gln Pro Phe Tyr
    50                  55                  60

Asp Trp Asn Glu Val Asn Leu Ala Asn Ala Ala Gly Arg His Arg Glu
65                  70                  75                  80

Leu Ile Pro Asp Gly Lys Leu Cys Ser Ala Gly Arg Asp Lys Tyr Lys
                85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Glu His Arg Gly
        115                 120                 125

Phe Phe Glu Phe Tyr Val Thr Val Asp Asp Tyr Asp Pro Thr Glu Leu
    130                 135                 140

Leu Lys Trp Glu Asp Leu Glu Glu Thr Pro Phe Met Asn Val Thr Asp
145                 150                 155                 160

Pro Thr Val Val Gly Ala Asn Tyr Glu Ile Pro Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Val Phe Ala Asp Ala
        195                 200                 205

Val Ser Leu His Ser Thr Thr
    210                 215

<210> SEQ ID NO 150
<211> LENGTH: 215
<212> TYPE: PRT
<213> ORGANISM: Polystichum setiferum (compacta)

<400> SEQUENCE: 150

Met Gly Arg Ser Trp Gly Val Ala Ala Ile Met Val Leu Cys Ala Ser
1               5                   10                  15

Gly Leu Leu Gly Val Ala Ser Gly His Gly Thr Met His Asp Pro Ile
            20                  25                  30

Ser Arg Val Tyr Asn Cys Phe Leu Glu Asn Pro Glu Ser Pro Thr Ser
        35                  40                  45

Ala Ala Cys Ile Glu Ala Val Glu Val Ser Gly Thr Gln Pro Phe Tyr
    50                  55                  60

Asp Trp Asn Glu Val Asn Leu Pro Asp Val Asn Gly Arg His Arg Glu
65                  70                  75                  80

```
Leu Ile Pro Asp Gly Lys Leu Cys Ser Ala Gly Arg Glu Lys Tyr Lys
                85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Glu His Arg Gly
            115                 120                 125

Phe Phe Glu Phe Tyr Val Thr Val Asp Asp Tyr Asp Pro Thr Glu Leu
130                 135                 140

Leu Lys Trp Glu Asp Leu Glu Ala Thr Pro Phe Met Asn Val Thr Asp
145                 150                 155                 160

Pro Thr Val Val Gly Asp Asn Tyr Glu Ile Pro Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Val Phe Ala Asp Ala
            195                 200                 205

Val Ser Leu His Ser Thr Thr
            210             215

<210> SEQ ID NO 151
<211> LENGTH: 215
<212> TYPE: PRT
<213> ORGANISM: Lepisorus bicolor

<400> SEQUENCE: 151

Met Arg Ser Trp Gly Val Val Ala Ile Met Val Ala Val Cys Ala Ser
1               5                   10                  15

Gly Leu Leu Gly Val Ala Ser Gly His Gly Ser Met Ser Asp Pro Ile
            20                  25                  30

Ser Arg Val Tyr Arg Cys Arg Leu Glu Asn Pro Glu Arg Pro Thr Ser
            35                  40                  45

Ala Ala Cys Ile Ala Ala Val Ala Leu Ser Gly Lys Gln Ala Phe Tyr
        50                  55                  60

Asp Trp Asn Glu Val Asn Leu Pro Phe Ala Asn Gly Arg His Arg Glu
65                  70                  75                  80

Leu Ile Pro Asp Gly Lys Leu Cys Ser Ala Gly Arg Asp Lys Tyr Lys
                85                  90                  95

Gly Leu Asp Leu Pro Arg Ala Asp Trp Leu Ala Thr Ser Leu Ser Ser
            100                 105                 110

Gly Ser Ala Tyr Thr Phe Leu Tyr Arg Ala Thr Ala Pro His Leu Gly
            115                 120                 125

Tyr Phe Glu Phe Tyr Val Thr Arg Asp Ser Tyr Asp Pro Thr Gln Pro
130                 135                 140

Leu Ala Trp Ser Asp Leu Glu Asp Ser Pro Phe Ile Lys Val Thr Asn
145                 150                 155                 160

Pro Pro Leu Val Ser Gly Phe Tyr Glu Phe Pro Gly Thr Thr Pro Ser
                165                 170                 175

Gly Lys Thr Gly Arg His Leu Ile Tyr Val Ile Trp Gln Arg Thr Asp
            180                 185                 190

Ser Thr Glu Ala Phe Tyr Ser Cys Ser Asp Val Asp Phe Asp Glu Ala
            195                 200                 205

Leu Ser Leu Ser Ser Thr Ile
            210             215
```

<210> SEQ ID NO 152
<211> LENGTH: 217
<212> TYPE: PRT
<213> ORGANISM: Pyrrosia lingua (Ogon)

<400> SEQUENCE: 152

Met Arg Thr Arg Val Trp Gly Val Val Ala Phe Met Val Ala Val Cys
1               5                   10                  15

Ala Cys Asp Leu Leu Gly Leu Ala Ser Gly His Gly Ser Met Gly Asp
            20                  25                  30

Pro Val Ser Arg Val Leu Asn Cys Tyr Leu Glu Asn Pro Glu Arg Pro
        35                  40                  45

Thr Ser Ala Ala Cys Ile Ala Val Ala Leu Ser Gly Thr Gln Ala
    50                  55                  60

Phe Tyr Asp Trp Asn Glu Val Asn Leu Ala Ser Ala Cys Gly Arg His
65                  70                  75                  80

Arg Glu Leu Ile Ser Asp Gly Glu Leu Cys Ser Ala Gly Arg Asp Lys
                85                  90                  95

Tyr Lys Gly Leu Asn Leu Ala Arg Ala Asp Trp Val Ala Thr Ser Leu
            100                 105                 110

Ser Ser Gly Val Asp Tyr Thr Phe Leu Phe Asn Ala Thr Ala Ala His
        115                 120                 125

Leu Gly Tyr Phe Glu Phe Trp Val Thr Arg Asp Ser Tyr Asp Pro Thr
130                 135                 140

Gln Pro Leu Ala Trp Ala Asp Leu Glu Asp Ser Pro Phe Ile Asn Ile
145                 150                 155                 160

Thr Asn Pro Thr Ile Val Ser Asp Ala Tyr Gln Val Pro Ala Thr Thr
                165                 170                 175

Pro Ser Gly Lys Thr Gly Arg His Leu Ile Tyr Val Ile Trp Gln Arg
            180                 185                 190

Thr Asp Ser Thr Glu Ala Phe Tyr Ser Cys Ser Asp Val Asp Phe Asp
        195                 200                 205

Glu Ala Leu Pro Leu Ser Ser Thr Thr
    210                 215

<210> SEQ ID NO 153
<211> LENGTH: 224
<212> TYPE: PRT
<213> ORGANISM: Blechnum appendiculatum

<400> SEQUENCE: 153

Met Lys Lys Ser Ser Gly Val Val Val Val Ala Ala Ile Leu
1               5                   10                  15

Leu Leu Cys Leu Leu Gly Val Ala Asn Gly His Gly Ser Met Gln Asp
            20                  25                  30

Pro Ile Ser Arg Val Tyr Asn Cys Phe Leu Glu Asn Pro Glu Ser Pro
        35                  40                  45

Thr Ser Ala Ala Cys Gln Ala Val Ala Val Ala Gly Thr Gln Pro
    50                  55                  60

Phe Tyr Asp Trp Asn Glu Val Asn Leu Ala Asn Ala Asn Gly Arg His
65                  70                  75                  80

Arg Glu Leu Ile Ser Asp Gly Met Leu Cys Ser Ala Asn Arg Ser Lys
                85                  90                  95

Tyr His Gly Leu Asp Leu Ala Arg Ala Asp Trp Thr Ala Thr Ser Leu
            100                 105                 110

Ser Ser Gly Val Ala Tyr Thr Phe Leu Tyr Arg Val Thr Ala His His

-continued

```
                115                 120                 125
Arg Gly Phe Phe Glu Phe Tyr Ile Thr Arg Asp Ser Tyr Asp Pro Thr
            130                 135                 140

Gln Pro Leu Ala Trp Ala Asp Leu Glu Asp Ser Pro Phe Ile Asn Ile
145                 150                 155                 160

Thr Asp Pro Thr Thr Val Ser Thr Thr Leu Gly Glu Ala Tyr Glu Ile
                165                 170                 175

Ser Gly Thr Thr Pro Ala Ser Lys Ser Gly Arg His Leu Ile Tyr Val
                180                 185                 190

Ile Trp Gln Arg Ser Asp Ser Pro Glu Ala Phe Tyr Ser Cys Ser Asp
            195                 200                 205

Val Asp Phe Ser Ala Asp Ala Leu Ile Ser Leu Arg Ser Ala Val Leu
        210                 215                 220

<210> SEQ ID NO 154
<211> LENGTH: 215
<212> TYPE: PRT
<213> ORGANISM: Polystichum munitum

<400> SEQUENCE: 154

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asn Pro Ile
                20                  25                  30

Ser Arg Val Tyr Asn Cys Arg Leu Glu Asn Pro Glu Arg Pro Thr Ser
            35                  40                  45

Ala Ala Cys Ile Ala Ala Val Ala Leu Ser Gly Thr Gln Ala Phe Tyr
        50                  55                  60

Asp Trp Asn Glu Val Asn Leu Pro Asp Val Asn Gly Arg His Arg Glu
65                  70                  75                  80

Leu Ile Pro Asp Gly Lys Leu Cys Ser Ala Gly Arg Asp Lys Tyr Lys
                85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Gln His Arg Gly
        115                 120                 125

Phe Phe Glu Phe Tyr Val Thr Val Asp Asp Tyr Asp Pro Thr Glu Leu
130                 135                 140

Leu Lys Trp Glu Asp Leu Glu Glu Thr Pro Phe Met Asn Val Thr Asp
145                 150                 155                 160

Pro Thr Val Val Gly Val Asn Tyr Glu Ile Pro Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Val Ser Leu His Ser Thr Thr
        210                 215

<210> SEQ ID NO 155
<211> LENGTH: 217
<212> TYPE: PRT
<213> ORGANISM: Stenochlaena tenuifolia

<400> SEQUENCE: 155

Met Gly Met Gly Arg Ser Asn Ser Ser Lys Val Val Ala Ile Val Val
```

```
  1               5                  10                   15
Leu Cys Ser Gly Leu Leu Ser Leu Val Ser Gly His Gly Ser Met Gln
                20                  25                  30

Asn Pro Ile Ser Arg Val Leu Asn Cys Tyr Leu Glu Asn Pro Glu Arg
                35                  40                  45

Pro Thr Ser Ala Ala Cys Gln Ala Val Ala Met Ser Gly Thr Gln
                50                  55                  60

Ala Phe Tyr Asp Trp Asn Glu Val Asn Leu Pro Asn Ala Ala Gly Arg
 65                  70                  75                  80

His Arg Gln Leu Ile Pro Asp Gly Gln Leu Cys Ser Ala Gly Arg Gln
                85                  90                  95

Lys Tyr Arg Gly Leu Asp Leu Ala Arg Asp Asp Trp Glu Ala Thr Thr
                100                 105                 110

Leu Ser Ser Gly Thr Ala Phe Thr Tyr Asn Tyr Arg Ala Thr Ala Pro
                115                 120                 125

His Leu Gly Phe Phe Glu Phe Tyr Val Thr Arg Asp Gly Tyr Glu Pro
                130                 135                 140

Thr Glu Pro Leu Lys Trp Ser Asp Leu Gln Asp Ser Pro Phe Ile Asn
145                 150                 155                 160

Val Thr Thr Thr Leu Ser Ser Asp Ser Tyr Gln Ile Thr Gly Thr Thr
                    165                 170                 175

Pro Ala Gly Lys Ser Gly Arg His Leu Ile Tyr Val Ile Trp Gln Arg
                180                 185                 190

Ser Asp Ser Pro Glu Ala Phe Tyr Ser Cys Ser Asp Val Glu Phe Asp
                195                 200                 205

Val Ala Leu Ser Leu His Ser Ala Thr
210                 215
```

<210> SEQ ID NO 156
<211> LENGTH: 231
<212> TYPE: PRT
<213> ORGANISM: Asplenium bulbiferum (G.Forst.)

<400> SEQUENCE: 156

```
Met Arg Met Gly Arg Ser Thr Ser Cys Met Gly Ala Asn Met Ala Phe
 1               5                  10                  15

Met Leu Leu Leu Leu Leu Phe Trp Ala Ser Cys Cys Cys Leu Leu Gly
                20                  25                  30

Lys Val Ser Gly His Gly Ser Met Glu Asp Pro Ile Ser Arg Val Tyr
                35                  40                  45

Ala Cys Phe Leu Glu Asn Pro Glu Arg Pro Thr Ser Ala Ala Cys Gln
 50                  55                  60

Ala Ala Val Ala Leu Ser Gly Thr Gln Ala Phe Tyr Asp Trp Asn Glu
 65                  70                  75                  80

Val Asn Gln Pro Asn Ala Ala Gly Arg His Arg Glu Ile Ile Pro Asp
                85                  90                  95

Gly Gln Leu Cys Ser Gly Gly Arg Glu Lys Tyr Gln Gly Leu Asp Leu
                100                 105                 110

Ala Arg Asp Asp Trp Thr Ala Thr Ser Leu Ser Pro Asn Val Ser Phe
                115                 120                 125

Thr Phe Leu Tyr Lys Ala Thr Ala Pro His Arg Gly Phe Phe Glu Phe
                130                 135                 140

Tyr Val Thr Arg Asp Gly Tyr Asp Pro Thr Glu Ala Leu Thr Trp Ala
145                 150                 155                 160
```

```
Asp Leu Glu Glu Pro Pro Phe Ile Asn Val Thr Asp Pro Thr Val Ala
                165                 170                 175

Ser Gly Ala Tyr Gln Ile Pro Gly Thr Thr Pro Ala Gly Lys Thr Gly
            180                 185                 190

Arg His Leu Ile Tyr Val Ile Trp Gln Arg Ser Asp Ser Pro Glu Ala
        195                 200                 205

Phe Tyr Ser Cys Ser Asp Val Asp Phe Glu Ser Ala Asp Thr Val Asn
    210                 215                 220

Ile Ser Leu Arg Ser Thr Thr
225                 230

<210> SEQ ID NO 157
<211> LENGTH: 221
<212> TYPE: PRT
<213> ORGANISM: Athyrium filix-femina

<400> SEQUENCE: 157

Met Gly Arg Ser Trp Gly Val Val Ala Ile Leu Met Val Leu Cys Gly
1               5                   10                  15

Cys Leu Leu Gly Val Ala Ser Gly His Gly Ser Met Glu Asp Pro Ile
            20                  25                  30

Ser Arg Val Tyr Asn Cys Tyr Leu Glu Asn Pro Glu Ser Pro Thr Ser
        35                  40                  45

Ala Ala Cys Gln Ala Ala Val Ala Leu Gly Gly Pro Gln Pro Phe Tyr
    50                  55                  60

Asp Trp Asn Glu Val Asn Gln Pro Asn Ala Asp Gly His Ser Arg Glu
65                  70                  75                  80

Ile Ile Pro Asp Gly Gln Leu Cys Ser Gly Gly Arg Glu Lys Tyr Lys
                85                  90                  95

Gly Leu Asp Leu Ala Arg Ser Asp Trp Thr Ala Thr Ser Leu Ser Ser
            100                 105                 110

Gly Val Ala Phe Thr Phe Leu Phe Lys Ala Thr Ala Pro His Ala Gly
        115                 120                 125

Phe Phe Glu Phe Tyr Val Thr Gln Asp Gly Tyr Asp Pro Thr Glu Pro
    130                 135                 140

Leu Lys Trp Ala Asp Leu Glu Asp Ser Pro Phe Ile Asn Val Thr Asp
145                 150                 155                 160

Pro Thr Leu Leu Ser Gly Ser Tyr Gln Ile Pro Gly Thr Thr Pro Ala
                165                 170                 175

Gly Lys Ser Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Leu Ser Ser Asp Leu His Ser Thr Met Ala Pro Ile Ala
    210                 215                 220

<210> SEQ ID NO 158
<211> LENGTH: 231
<212> TYPE: PRT
<213> ORGANISM: Adiantum capillus-veneris

<400> SEQUENCE: 158

Met Gly Met Lys Met Ser Trp Glu Val Ala Leu Ala Glu Ile Val Ala
1               5                   10                  15

Leu Cys Leu Leu Gly Met Ala Ser Ser His Gly Thr Met Gln Asp Pro
            20                  25                  30
```

Ile Ser Arg Val Tyr Asn Cys Phe Leu Glu Asn Pro Glu Arg Pro Thr
        35                  40                  45

Ser Ala Ala Cys Gln Ala Ala Val Ala Leu Gly Gly Thr Gln Pro Leu
 50                  55                  60

Tyr Asp Trp Asn Glu Val Asn Ile His Asp Ala Ala Gly Asn His Arg
65                  70                  75                  80

Asp Leu Ile Pro Asp Gly Lys Leu Cys Ser Ala Gly Arg Gln Lys Phe
                85                  90                  95

Gln Gly Leu Asp Leu Ala Arg Ala Asp Trp Ile Ala Thr Ser Leu Ser
            100                 105                 110

Ser Gly Val Asp Val Asp Tyr Thr Phe Leu Tyr Arg Ala Thr Ala Pro
            115                 120                 125

His Leu Gly Phe Phe Glu Phe Tyr Ile Thr Arg Asp Thr Tyr Asp Pro
130                 135                 140

Thr Gln Pro Leu Ala Trp Gly Asp Leu Glu Asp Ser Pro Phe Ile Asn
145                 150                 155                 160

Ile Thr Asn Pro Ser Ile Val Ser Thr Thr Leu Gly Pro Ala Tyr Ser
                165                 170                 175

Ile Pro Ser Thr Thr Pro Phe Ser Lys Ser Gly Arg His Leu Ile Tyr
            180                 185                 190

Val Ile Trp Gln Arg Thr Asp Ser Leu Glu Ala Phe Tyr Ser Cys Ser
            195                 200                 205

Asp Val Asp Phe Ser Thr Ser Ser Ile Glu Asp Val Ile Val Ser
            210                 215                 220

Leu Arg Ser Ala Ala Leu Leu
225                 230

<210> SEQ ID NO 159
<211> LENGTH: 231
<212> TYPE: PRT
<213> ORGANISM: Asplenium nidus var plicatum

<400> SEQUENCE: 159

Met Arg Met Gly Arg Ser Ile Ser Arg Met Ala Ala Arg Met Ala Ile
1               5                   10                  15

Met Leu Val Leu Cys Trp Ala Ile Ser Cys Cys Leu Leu Gly Thr Val
                20                  25                  30

Ser Gly His Gly Ser Ser Glu Asp Pro Met Ser Arg Val Tyr Gly Cys
            35                  40                  45

Tyr Leu Gln Asn Pro Glu Arg Pro Ala Ser Ala Cys Arg Ala Ala
 50                  55                  60

Val Ala Met Ser Gly Thr Gln Ala Phe Tyr Asp Trp Asn Glu Val Asn
65                  70                  75                  80

Gln Pro His Ala Ala Gly Arg His Arg Glu Ile Ile Pro Asp Gly Gln
                85                  90                  95

Leu Cys Gly Gly Gly Arg Ala Lys Tyr Arg Gly Leu Asn Leu Ala Arg
            100                 105                 110

Ala Asp Trp Trp Ser Thr Pro Leu Tyr Ser Asn Thr Pro Phe Met Phe
            115                 120                 125

Leu Tyr Arg Ala Thr Ala Pro His Arg Gly Phe Phe Glu Phe Tyr Val
130                 135                 140

Thr Arg Asp Gly Tyr Asp Pro Thr Glu Pro Leu Lys Trp Ser Asp Leu
145                 150                 155                 160

Glu Tyr Pro Pro Phe Ile Asn Val Thr Asp Pro Thr Leu Ala Phe Gly
                165                 170                 175

```
Ala Tyr Lys Ile Pro Gly Phe Thr Pro Tyr Gly Lys Thr Gly Arg His
            180                 185                 190

Leu Ile Tyr Ile Ile Trp Gln Arg Ser Asp Ser Pro Glu Ala Phe Tyr
            195                 200                 205

Ser Cys Ser Asp Val Asp Phe Val Asp Phe Lys Ser Asp Glu Thr Val
            210                 215                 220

Ile Pro Leu His Ser Thr Thr
225                 230
```

<210> SEQ ID NO 160
<211> LENGTH: 215
<212> TYPE: PRT
<213> ORGANISM: Polystichum polyblepharum

<400> SEQUENCE: 160

```
Met Gly Arg Ser Trp Gly Val Val Ala Ile Met Val Leu Cys Ala Ser
1               5                   10                  15

Gly Leu Leu Asp Val Ala Ser Gly His Gly Ser Met Asn Asp Pro Ile
            20                  25                  30

Ser Arg Val Tyr Asn Cys Arg Leu Glu Asn Pro Glu Ser Pro Thr Ser
            35                  40                  45

Asp Ala Cys Ile Ala Ala Val Ala Leu Ser Gly Thr Gln Ala Phe Tyr
50                  55                  60

Asp Trp Asn Glu Val Asn Leu Pro Asn Ala Ala Gly Arg His Arg Glu
65                  70                  75                  80

Leu Ile Pro Asp Gly Lys Leu Cys Ser Ala Gly Arg Asp Lys Tyr Lys
            85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Gln His Arg Gly
            115                 120                 125

Phe Phe Glu Phe Tyr Val Thr Val Asp Asp Tyr Asp Pro Thr Glu Leu
            130                 135                 140

Leu Lys Trp Glu Asp Leu Glu Glu Thr Pro Phe Met Asn Val Thr Asp
145                 150                 155                 160

Pro Thr Val Val Gly Val Asn Tyr Glu Met Ala Gly Thr Thr Pro Ala
            165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
            195                 200                 205

Val Ser Leu His Ser Ser Thr
            210                 215
```

<210> SEQ ID NO 161
<211> LENGTH: 215
<212> TYPE: PRT
<213> ORGANISM: Adiantum venustum

<400> SEQUENCE: 161

```
Met Gly Arg Ser Trp Gly Asp Val Ala Ile Met Val Leu Cys Ala
1               5                   10                  15

Ser Gly Leu Leu Gly Val Ala Ser Gly His Gly Ser Met Gln Asp Pro
            20                  25                  30

Ile Ser Arg Val Tyr Asn Cys Tyr Leu Glu Gly Pro Glu Ser Pro Thr
            35                  40                  45
```

```
Ser Ala Ala Cys Ile Ala Ala Val Ala Leu Ser Gly Thr Gln Ala Phe
 50                  55                  60

Tyr Asp Trp Asn Glu Val Asn Gln Pro Asn Ala Ala Gly Arg His Arg
 65                  70                  75                  80

Glu Ile Ile Pro Asp Gly Gln Leu Cys Ser Gly Gly Arg Asp Lys Tyr
                 85                  90                  95

Ser Gly Leu Asp Leu Ala Arg Ser Asp Trp Thr Ala Thr Ser Leu Ser
            100                 105                 110

Ser Asn Val Ser Tyr Thr Tyr Leu Phe Lys Ala Thr Ala Pro His Lys
            115                 120                 125

Gly Phe Phe Glu Phe Tyr Val Thr Arg Asp Ser Tyr Glu Pro Thr Glu
        130                 135                 140

Ala Leu Lys Trp Ala Asp Leu Glu Asp Ser Pro Phe Ile Asn Ile Thr
145                 150                 155                 160

Asp Pro Thr Leu Asp Ser Gly Ala Tyr Gln Ile Pro Gly Thr Thr Pro
                165                 170                 175

Ala Gly Lys Ser Gly Arg His Leu Ile Tyr Val Ile Trp Gln Arg Ser
            180                 185                 190

Asp Ser Gly Glu Ala Phe Tyr Ala Cys Cys Asp Val Asp Phe Asp Val
            195                 200                 205

Asp Val Leu His Ser Thr Thr
            210                 215

<210> SEQ ID NO 162
<211> LENGTH: 233
<212> TYPE: PRT
<213> ORGANISM: Actiniopteris australis

<400> SEQUENCE: 162

Met Arg Gln Gly Ser Ser Ile Ala Asp Met Ser Val Arg Met Gly Gly
 1               5                  10                  15

Val Asn Ala Val Ala Ile Ile Leu Leu Cys Cys Ala Ser Ser Gly
                 20                  25                  30

Leu Leu Gly Ile Ala Arg Gly His Gly Ser Met Gln Asp Pro Ile Ser
            35                  40                  45

Arg Val Tyr Ala Cys Tyr Leu Glu Asn Pro Glu Arg Pro Thr Ser Ala
 50                  55                  60

Ala Cys Gln Ala Ala Val Ala Leu Ser Gly Thr Gln Ala Phe Tyr Asp
 65                  70                  75                  80

Trp Asn Glu Val Asn Gln Pro Phe Ala Ala Gly Arg His Arg Glu Ile
                 85                  90                  95

Ile Pro Asp Gly Gln Leu Cys Ser Gly Gly Arg Thr Lys Tyr Ala Gly
            100                 105                 110

Leu Asp Leu Ala Arg Asp Asp Trp Thr Ala Thr Ser Leu Ser Ala Gly
            115                 120                 125

Ile Ser Tyr Thr Phe Leu Tyr Arg Gly Thr Ala Pro His Leu Gly Phe
        130                 135                 140

Phe Glu Phe Tyr Val Thr Arg Asp Gly Tyr Asp Pro Thr Glu Pro Leu
145                 150                 155                 160

Lys Trp Ala Asp Leu Glu Asp Pro Pro Phe Ile Asn Ile Thr Asn Pro
                165                 170                 175

Thr Leu Val Ser Gly Val Tyr Gln Ile Pro Gly Thr Thr Pro Ala Gly
            180                 185                 190

Lys Thr Gly Arg His Leu Ile Tyr Val Ile Trp Gln Arg Thr Asp Ser
```

```
                195                 200                 205
Pro Glu Ala Phe Tyr Ser Cys Ser Asp Val Val Phe Ser Asp Asp Ala
    210                 215                 220

Ala Leu Tyr Leu Arg Ser Thr Thr Glu
225                 230

<210> SEQ ID NO 163
<211> LENGTH: 231
<212> TYPE: PRT
<213> ORGANISM: Marsilea crenata

<400> SEQUENCE: 163

Met Arg Arg Ser Gly Met Ser Ser Val Leu Ala Ala Val Ala Ala
1               5                   10                  15

Gly Val Leu Leu Val Ala Ala Leu Gly Ser His Val Ala Tyr Gly His
                20                  25                  30

Gly Ser Met Lys Glu Pro Ile Ser Arg Ala Tyr Asn Cys Tyr Leu Glu
            35                  40                  45

Ile Ala Asp Asn Ala Thr Ser Asp Ala Cys Gly Ala Ala Ala Ala Leu
        50                  55                  60

Cys Ile Pro Glu Ala Phe Asn Asp Trp Asn Ala Val Leu Ile Pro Asp
65                  70                  75                  80

Val Ala Gly Arg His Arg Gln Leu Ile Pro Asp Gly Gln Leu Cys Ser
                85                  90                  95

Ala Gly Arg Ala Lys Tyr Ala Gly Leu Asn Leu Ala Ser Val Asp Trp
            100                 105                 110

Glu Ala Ala Thr Leu Ala Ala Gly Val Asn Tyr Thr Phe Leu Tyr Lys
        115                 120                 125

Ala Val Val Val His Lys Gly Tyr Phe Glu Phe Tyr Val Thr Lys Asp
    130                 135                 140

Gly Tyr Asp Ala Thr Gln Ala Leu Thr Trp Ser Asp Leu Glu Asp Ala
145                 150                 155                 160

Pro Phe Val Asn Val Thr Asp Pro Ile Val Asn Ser Asp Ser Asp Phe
                165                 170                 175

Glu Ile Pro Gly Thr Ile Pro Ser Gly Lys Ser Gly Arg His Val Ile
            180                 185                 190

Tyr Val Ile Trp Gln Arg Thr Asp Ser Pro Glu Ala Phe Tyr Ser Cys
        195                 200                 205

Ser Asp Val Asp Phe Asp Thr Ile Ser Asp Thr Ile Ser Asp
    210                 215                 220

Thr Val Leu His Ala Ser Ser
225                 230

<210> SEQ ID NO 164
<211> LENGTH: 229
<212> TYPE: PRT
<213> ORGANISM: Asplenium prolongatum x Asplenium antiquum (Kurata)

<400> SEQUENCE: 164

Met Arg Met Gly Arg Ser Ala Ser Cys Ile Arg Ala Asn Met Ala Ile
1               5                   10                  15

Met Leu Val Leu Phe Trp Ala Ser Cys Cys Leu Leu Gly Ile Val
                20                  25                  30

Ser Gly His Gly Ser Met Glu Asp Pro Ile Ser Arg Val Tyr Ala Cys
            35                  40                  45

Tyr Leu Glu Asn Pro Glu Arg Pro Thr Ser Ala Ala Cys Ile Ala Ala
```

Val Ala Leu Ser Gly Thr Gln Ala Phe Tyr Asp Trp Asn Glu Val Asn
65                  70                  75                  80

Gln Pro Asn Ala Ala Gly Arg His Arg Glu Ile Ile Pro Asp Gly Gln
                85                  90                  95

Leu Cys Ser Gly Gly Arg Glu Lys Tyr Gln Gly Leu Asp Leu Ala Arg
            100                 105                 110

Ala Asp Trp Thr Ala Thr Ser Leu Thr Ser Gly Ile Thr Phe Thr Phe
            115                 120                 125

Leu Tyr Lys Ala Thr Ala Pro His Arg Gly Phe Phe Glu Phe Tyr Val
        130                 135                 140

Thr Arg Asp Thr Tyr Asp Pro Thr Glu Pro Leu Thr Trp Ala Asp Leu
145                 150                 155                 160

Glu Asp Thr Pro Phe Ile Asn Ala Thr Asp Pro Thr Leu Ala Ser Gly
                165                 170                 175

Ser Tyr Gln Ile Pro Gly Thr Thr Pro Ala Gly Lys Thr Gly Arg His
            180                 185                 190

Leu Ile Tyr Val Ile Trp Gln Arg Ser Asp Ser Pro Glu Ala Phe Tyr
        195                 200                 205

Ser Cys Ser Asp Val Asp Phe Glu Ser Ser Asp Thr Val Ile Ser Leu
210                 215                 220

Arg Ser Ala Thr Thr
225

<210> SEQ ID NO 165
<211> LENGTH: 229
<212> TYPE: PRT
<213> ORGANISM: Adiantum raddianum (Fritz Luthi)

<400> SEQUENCE: 165

Met Gly Met Lys Met Ser Trp Glu Val Ala Leu Ala Glu Ile Val Ala
1               5                   10                  15

Leu Cys Leu Leu Gly Met Ala Ser Ser His Gly Thr Met Gln Asp Pro
            20                  25                  30

Ile Ser Arg Val Tyr Asn Cys Phe Leu Glu Asn Pro Gly Arg Pro Thr
        35                  40                  45

Ser Ala Ala Cys Gln Ala Ala Val Ala Leu Gly Gly Thr Gln Pro Leu
    50                  55                  60

Tyr Asp Trp Asn Glu Val Asn Ile His Asp Ala Ala Gly Asn His Arg
65                  70                  75                  80

Asp Leu Ile Pro Asp Gly Lys Leu Cys Ser Ala Gly Arg Gln Lys Phe
                85                  90                  95

Gln Gly Leu Asp Leu Ala Arg Ala Asp Trp Ile Ala Thr Ser Leu Ser
            100                 105                 110

Ser Gly Val Asp Tyr Thr Phe Leu Tyr Arg Ala Thr Ala Pro His Leu
            115                 120                 125

Gly Phe Phe Glu Phe Tyr Ile Thr Arg Asp Thr Tyr Asp Pro Thr Gln
        130                 135                 140

Pro Leu Ala Trp Gly Asp Leu Glu Asp Ser Pro Phe Ile Asn Ile Thr
145                 150                 155                 160

Asn Pro Ser Ile Val Ser Thr Thr Leu Gly Pro Ala Tyr Ser Ile Pro
                165                 170                 175

Ser Thr Thr Pro Phe Ser Lys Ser Gly Arg His Leu Ile Tyr Val Ile
            180                 185                 190

Trp Gln Arg Thr Asp Ser Leu Glu Ala Phe Tyr Ser Cys Ser Asp Val
            195                 200                 205

Asp Phe Ser Thr Ser Ser Ile Glu Asp Val Ile Val Ser Leu Arg
210                 215                 220

Ser Ala Ala Leu Leu
225

<210> SEQ ID NO 166
<211> LENGTH: 227
<212> TYPE: PRT
<213> ORGANISM: Asplenium australasicum

<400> SEQUENCE: 166

Met Arg Met Gly Arg Ser Thr Ser Arg Met Ala Ala Arg Met Ala Ile
1               5                   10                  15

Thr Leu Leu Leu Cys Trp Ala Ser Cys Cys Leu Leu Gly Thr Val Ser
            20                  25                  30

Gly His Gly Ser Met Leu Asp Pro Ile Ser Arg Ile Tyr Ala Cys Phe
        35                  40                  45

Leu Glu Asn Pro Glu Arg Pro Thr Ser Ala Ala Cys Gln Ala Ala Val
50                  55                  60

Ala Leu Gly Gly Thr Gln Pro Leu Tyr Asp Trp Asn Glu Val Asn Gln
65                  70                  75                  80

Pro Asn Ala Ala Gly Arg His Arg Glu Ile Ile Pro Asp Gly Gln Leu
                85                  90                  95

Cys Gly Gly Gly Arg Glu Lys Tyr Gln Gly Leu Asn Leu Ala Arg Ala
            100                 105                 110

Asp Trp Pro Ala Thr Ser Leu Ser Ser Asn Thr Ala Phe Thr Phe Leu
        115                 120                 125

Tyr Ile Ala Thr Ala Pro His Arg Gly Phe Phe Glu Phe Tyr Val Thr
130                 135                 140

Arg Asp Gly Tyr Asp Pro Thr Glu Leu Leu Lys Trp Ala Asp Leu Glu
145                 150                 155                 160

Tyr Pro Pro Phe Leu Asn Val Thr Asp Pro Thr Leu Ala Ser Gly Asn
                165                 170                 175

Tyr Gln Ile Pro Gly Thr Thr Pro Ala Gly Lys Thr Gly Arg His Leu
            180                 185                 190

Ile Tyr Val Ile Trp Gln Arg Ser Asp Ser Pro Glu Ala Phe Tyr Ser
        195                 200                 205

Cys Ser Asp Ile Asp Phe Glu Ser Asp Glu Thr Val Ile Ser Leu His
210                 215                 220

Ser Thr Thr
225

<210> SEQ ID NO 167
<211> LENGTH: 227
<212> TYPE: PRT
<213> ORGANISM: Asplenium australasicum

<400> SEQUENCE: 167

Met Arg Met Gly Arg Ser Thr Ser Arg Met Ala Ala Arg Met Ala Ile
1               5                   10                  15

Thr Leu Leu Leu Cys Trp Ala Ser Cys Cys Leu Leu Gly Thr Val Ser
            20                  25                  30

Gly His Gly Ser Met Leu Asp Pro Ile Ser Arg Ile Tyr Ala Cys Phe
        35                  40                  45

-continued

```
Leu Glu Asn Pro Glu Arg Pro Thr Ser Ala Ala Cys Gln Ala Ala Val
 50                  55                  60
Ala Leu Gly Gly Thr Gln Pro Leu Tyr Asp Trp Asn Glu Val Asn Gln
 65                  70                  75                  80
Pro Asn Ala Ala Gly Arg His Arg Glu Ile Ile Pro Asp Gly Gln Leu
                 85                  90                  95
Cys Ser Gly Gly Arg Glu Lys Tyr Lys Gly Phe Asp Leu Pro Arg Ala
            100                 105                 110
Asp Trp Pro Ala Thr Thr Leu Val Ser Asn Ile Ser Phe Thr Tyr Leu
            115                 120                 125
Tyr Lys Ala Thr Ala Pro His Arg Gly Phe Phe Glu Phe Tyr Val Thr
130                 135                 140
Arg Asp Gly Tyr Asp Pro Thr Glu Leu Leu Lys Trp Ala Asp Leu Glu
145                 150                 155                 160
Tyr Pro Pro Phe Leu Asn Val Thr Asp Pro Thr Leu Ala Ser Gly Asn
                165                 170                 175
Tyr Gln Ile Pro Gly Thr Thr Pro Ala Gly Lys Thr Gly Arg His Leu
            180                 185                 190
Ile Tyr Val Ile Trp Gln Arg Ser Asp Ser Pro Glu Ala Phe Tyr Ser
        195                 200                 205
Cys Ser Asp Ile Asp Phe Glu Ser Asp Glu Thr Val Ile Ser Leu His
210                 215                 220
Ser Ile Thr
225

<210> SEQ ID NO 168
<211> LENGTH: 216
<212> TYPE: PRT
<213> ORGANISM: Thelypteris palustris

<400> SEQUENCE: 168

Met Gly Arg Ser Trp Gly Val Val Gly Ile Met Val Leu Cys Leu Leu
1               5                   10                  15
Gly Val Ala Ser Gly His Gly Thr Met Gln Asp Pro Ile Ser Arg Val
            20                  25                  30
Tyr Asn Cys Arg Leu Glu Asn Pro Glu Arg Pro Thr Ser Ala Ala Cys
        35                  40                  45
Ile Ala Ala Val Ala Leu Ser Gly Thr Gln Ala Phe Tyr Asp Trp Asn
 50                  55                  60
Glu Val Asn Leu Ala Asn Ala Ala Gly Arg His Arg Glu Leu Ile Pro
 65                  70                  75                  80
Asp Gly Gln Leu Cys Ser Ala Gly Arg Val Lys Tyr Gln Gly Leu Asp
                 85                  90                  95
Leu Ala Arg Ser Asp Trp Thr Ala Thr Ser Leu Ser Ser Gly Val Ser
            100                 105                 110
Phe Thr Phe Leu Tyr Arg Val Thr Ala Gln His Leu Gly Phe Phe Glu
            115                 120                 125
Phe Tyr Val Thr Gln Asp Gly Tyr Asp Pro Thr Glu Pro Leu Lys Trp
130                 135                 140
Ala Asp Leu Glu Asp Ser Pro Phe Ile Asn Val Thr Asn Pro Thr Val
145                 150                 155                 160
Val Ser Thr Ser Leu Gly Pro Ala Tyr Gln Ile Ala Gly Thr Thr Pro
                165                 170                 175
Ala Gly Lys Ser Gly Arg His Leu Ile Tyr Val Ile Trp Gln Arg Ser
            180                 185                 190
```

```
Asp Ser Pro Glu Ala Phe Tyr Ser Cys Ser Asp Val Asp Phe Val Asp
        195                 200                 205

Ala Leu Ser Leu His Ser Thr Ala
    210                 215
```

<210> SEQ ID NO 169
<211> LENGTH: 230
<212> TYPE: PRT
<213> ORGANISM: Asplenium dimorphum x Asplenium difforme

<400> SEQUENCE: 169

```
Met Arg Met Gly Arg Ser Thr Ser Cys Met Gly Ala Asn Met Ala Ile
1               5                   10                  15

Val Leu Leu Leu Leu Phe Trp Ala Ser Cys Cys Leu Leu Gly
                20                  25                  30

Lys Val Ser Gly His Gly Ser Met Glu Asp Pro Ile Ser Arg Val Tyr
            35                  40                  45

Ala Cys Phe Leu Glu Asn Pro Glu Arg Pro Thr Ser Ala Ala Cys Gln
    50                  55                  60

Ala Ala Val Ala Leu Ser Gly Thr Gln Ala Phe Tyr Asp Trp Asn Glu
65                  70                  75                  80

Val Asn Leu Pro Asn Ala Ala Gly Arg His Arg Glu Ile Ile Pro Asp
                85                  90                  95

Gly Gln Leu Cys Ser Gly Gly Arg Glu Lys Tyr Lys Gly Leu Asp Leu
            100                 105                 110

Ala Arg Ala Asp Trp Thr Ala Thr Ser Leu Ser Pro Asn Val Ser Phe
        115                 120                 125

Thr Phe Leu Tyr Lys Gly Thr Ala Pro His Arg Gly Phe Phe Glu Phe
    130                 135                 140

Tyr Val Thr Arg Asp Gly Tyr Asp Pro Thr Glu Ala Leu Thr Trp Ala
145                 150                 155                 160

Asp Leu Glu Glu Pro Pro Phe Ile Asn Val Thr Asp Pro Thr Leu Ala
                165                 170                 175

Ser Gly Ala Tyr Gln Ile Pro Gly Thr Thr Pro Ala Gly Lys Thr Gly
            180                 185                 190

Arg His Leu Ile Tyr Val Ile Trp Gln Arg Ser Asp Ser Pro Glu Ala
        195                 200                 205

Phe Tyr Ser Cys Ser Asp Val Asp Phe Glu Ser Asp Asp Thr Val Val
    210                 215                 220

Ser Leu Arg Ser Thr Thr
225                 230
```

<210> SEQ ID NO 170
<211> LENGTH: 215
<212> TYPE: PRT
<213> ORGANISM: Matteuccia struthiopteris

<400> SEQUENCE: 170

```
Met Gly Arg Ser Trp Gly Val Val Ala Ile Met Val Leu Cys Ala Ser
1               5                   10                  15

Ser Leu Leu Gly Val Val Ser Gly His Gly Ser Met Ala Asp Pro Ile
                20                  25                  30

Ser Arg Val Tyr Gly Cys Arg Leu Glu Gly Pro Glu Ser Pro Thr Ser
            35                  40                  45

Ala Ala Cys Gln Ala Ala Val Ala Leu Ser Gly Thr Gln Ala Phe Tyr
    50                  55                  60
```

```
Asp Trp Asn Glu Val Asn Gln Pro Phe Ala Ala Gly Arg His Arg Glu
 65                  70                  75                  80

Leu Ile Pro Asp Gly Gln Leu Cys Ser Gly Gly Arg Val Lys Tyr Gln
                 85                  90                  95

Gly Leu Asp Leu Ala Arg Ser Asp Trp Pro Ala Thr Asn Leu Ser Ser
                100                 105                 110

Gly Val Ser Phe Thr Phe Leu Tyr Glu Val Thr Ala Thr His Leu Gly
                115                 120                 125

Tyr Phe Glu Phe Tyr Val Thr Arg Asp Gly Tyr Gln Pro Thr Glu Pro
    130                 135                 140

Leu Lys Trp Ala Asp Leu Glu Asp Ser Pro Phe Leu Thr Ala Thr Thr
145                 150                 155                 160

Thr His Glu Ser Ser Ser Tyr Ile Ile Pro Gly Thr Thr Pro Ser Ala
                165                 170                 175

Lys Ser Gly Arg His Leu Ile Tyr Leu Ile Trp Gln Arg Thr Asp Ser
                180                 185                 190

Pro Glu Ala Phe Tyr Ser Cys Ser Asp Val Asp Phe Val Asp Ala Leu
                195                 200                 205

Ser Ser Leu His Ser Thr Asn
    210                 215

<210> SEQ ID NO 171
<211> LENGTH: 217
<212> TYPE: PRT
<213> ORGANISM: Athyrium filix-femina (angustum)

<400> SEQUENCE: 171

Met Gly Arg Ser Trp Gly Val Val Ala Ile Leu Met Val Leu Cys Gly
  1               5                  10                  15

Cys Leu Leu Gly Val Ala Ser Gly His Gly Ser Met Glu Asp Pro Ile
                 20                  25                  30

Ser Arg Val Tyr Asn Cys Tyr Leu Glu Asn Pro Glu Ser Pro Thr Ser
                 35                  40                  45

Ala Ala Cys Gln Ala Ala Val Ala Leu Gly Gly Thr Gln Pro Leu Tyr
 50                  55                  60

Asp Trp Asn Glu Val Asn Gln Pro Asn Ala Ala Gly Gln Ser Arg Glu
 65                  70                  75                  80

Ile Ile Pro Asp Gly Gln Leu Cys Ser Gly Gly Arg Glu Lys Tyr Gln
                 85                  90                  95

Gly Leu Asp Leu Ala Arg Ser Asp Trp Thr Ala Thr Ser Leu Ser Ser
                100                 105                 110

Gly Val Ala Phe Thr Phe Leu Phe Lys Ala Thr Ala Pro His Leu Gly
                115                 120                 125

Phe Phe Glu Phe Tyr Val Thr Gln Asp Gly Tyr Asp Pro Thr Glu Pro
    130                 135                 140

Leu Lys Trp Ala Asp Leu Glu Asp Ser Pro Phe Ile Asn Val Thr Asp
145                 150                 155                 160

Pro Thr Leu Leu Ser Gly Ser Tyr Gln Ile Pro Gly Thr Thr Pro Ala
                165                 170                 175

Gly Lys Ser Gly Arg His Leu Ile Tyr Val Ile Trp Gln Arg Ser Asp
                180                 185                 190

Ser Pro Glu Ala Phe Tyr Ser Cys Ser Asp Val Asp Phe Val Asp Ala
                195                 200                 205

Leu Ser Ser Asp Leu His Ser Thr Thr
```

<210> SEQ ID NO 172
<211> LENGTH: 228
<212> TYPE: PRT
<213> ORGANISM: Adiantum pubescens (Bronze)

<400> SEQUENCE: 172

Met Lys Lys Ser Trp Gly Val Thr Ala Val Gly Val Ile Ala Leu
1               5                   10                  15

Cys Leu Leu Asp Val Ala Ser Gly His Gly Ser Met Gln Asp Pro Ile
                20                  25                  30

Ser Arg Val Tyr Asn Cys Phe Leu Glu Asn Pro Glu Arg Pro Thr Ser
            35                  40                  45

Ala Ala Cys Ile Ala Ala Val Ala Met Ser Gly Thr Gln Pro Phe Tyr
        50                  55                  60

Asp Trp Asn Glu Val Asn Leu Ala Asp Ala Asn Gly Arg His Arg Glu
65                  70                  75                  80

Leu Ile Pro Asp Gly Lys Leu Cys Ser Ala Gly Arg Asp Lys Tyr Gln
                85                  90                  95

Gly Leu Asp Gln Ala Arg Asp Asp Trp Val Ala Thr Ser Leu Ser Ser
            100                 105                 110

Gly Val Ala Tyr Thr Phe Leu Tyr Arg Val Thr Ala Pro His Leu Gly
        115                 120                 125

Phe Phe Glu Phe Tyr Val Thr Arg Asp Thr Tyr Asp Pro Thr Gln Ala
130                 135                 140

Leu Ala Trp Asp Asp Leu Glu Asp Ser Pro Phe Ile Asn Ile Thr Asn
145                 150                 155                 160

Pro Ser Val Val Ser Thr Thr Leu Gly Asn Ala Tyr Ser Ile Pro Gly
                165                 170                 175

Thr Thr Pro Ser Gly Lys Thr Gly Arg His Leu Ile Tyr Val Ile Trp
            180                 185                 190

Gln Arg Ser Asp Ser Arg Glu Ala Phe Tyr Ser Cys Ser Asp Val Asp
        195                 200                 205

Phe Pro Ala Ser Thr Val Glu Asp Asp Val Ile Ile Ser Leu Arg Ser
    210                 215                 220

Ala Ala Leu Val
225

<210> SEQ ID NO 173
<211> LENGTH: 215
<212> TYPE: PRT
<213> ORGANISM: Blechnum niponicum

<400> SEQUENCE: 173

Met Gly Arg Ser Trp Gly Val Val Ala Ile Met Val Leu Cys Ala Ser
1               5                   10                  15

Gly Leu Leu Gly Val Ala Ser Gly His Gly Ser Met Asp Asp Pro Ile
                20                  25                  30

Ser Arg Val Tyr Asn Cys Tyr Leu Glu Asn Pro Glu Arg Pro Thr Ser
            35                  40                  45

Ala Ala Cys Gln Ala Ala Val Ala Leu Ser Gly Thr Gln Ala Phe Tyr
        50                  55                  60

Asp Trp Asn Glu Val Asn Gln Pro Phe Ala Ala Gly Arg His Arg Glu
65                  70                  75                  80

Ile Ile Pro Asp Gly Gln Leu Cys Ser Gly Gly Arg Glu Lys Tyr Gln 85                  90                  95
Gly Leu Asp Leu Ala Arg Ser Asp Trp Thr Ala Thr Ser Leu Ser Ser
                100                 105                 110

Gly Val Ser Phe Thr Tyr Leu Tyr Lys Ala Thr Ala Pro His Leu Gly
            115                 120                 125

Phe Phe Glu Phe Tyr Val Thr Val Asp Gly Tyr Gln Pro Thr Glu Pro
130                 135                 140

Leu Lys Trp Ser Asp Leu Glu Asp Pro Pro Phe Ile Asn Val Thr Asn
145                 150                 155                 160

Pro Thr Leu Val Ser Gly Ser Tyr Gln Ile Pro Gly Thr Thr Pro Ala
                165                 170                 175

Gly Lys Thr Gly Arg His Leu Ile Tyr Val Ile Trp Gln Arg Ser Asp
                180                 185                 190

Ser Pro Glu Ala Phe Tyr Ser Cys Ser Asp Val Asp Phe Ala Asp Ala
                195                 200                 205

Leu Ser Leu His Ser Thr Thr
                210                 215

<210> SEQ ID NO 174
<211> LENGTH: 215
<212> TYPE: PRT
<213> ORGANISM: Platycerium wandae

<400> SEQUENCE: 174

Met Gly Lys Pro Trp Arg Val Val Ala Ile Val Val Cys Ala
1               5                   10                  15

Ser Gly Leu Leu Gly Val Ala Ser Gly His Gly Ser Met Gly Glu Pro
                20                  25                  30

Ile Ser Arg Val Tyr Asn Cys Tyr Leu Glu Asn Pro Glu Arg Pro Thr
            35                  40                  45

Ser Ala Ala Cys Ile Ala Ala Val Ala Leu Ser Gly Thr Gln Ala Phe
        50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Asp Lys Tyr
                85                  90                  95

Lys Gly Leu Asp Leu Ala Arg Ala Asp Trp Val Ala Thr Ser Leu Ser
                100                 105                 110

Ser Gly Val Ser Tyr Thr Phe Leu Tyr Arg Ala Thr Ala Pro His Gln
            115                 120                 125

Gly Tyr Phe Glu Phe Tyr Val Thr Lys Asp Ser Tyr Asp Pro Thr Glu
        130                 135                 140

Pro Leu Ala Trp Ala Asp Leu Glu Asp Thr Pro Phe Ile Asn Ile Thr
145                 150                 155                 160

Asp Pro Thr Leu Val Ser Gly Ser Tyr Gln Ile Pro Ser Thr Thr Pro
                165                 170                 175

Ser Asp Lys Thr Gly Arg His Leu Ile Tyr Val Ile Trp Gln Arg Thr
                180                 185                 190

Asp Ser Pro Glu Ala Phe Tyr Ser Cys Ser Asp Ile Asp Phe Asp Asp
                195                 200                 205

Thr Leu Pro Leu His Ser Thr
                210                 215

<210> SEQ ID NO 175
<211> LENGTH: 214

<212> TYPE: PRT
<213> ORGANISM: Nephrolepis cordifolia (Duffii)

<400> SEQUENCE: 175

```
Met Gly Arg Ser Trp Arg Val Val Ala Ile Met Val Val Cys Ala Ser
1               5                   10                  15

Gly Leu Leu Ser Val Val Arg Gly His Gly Ser Met Glu Asp Pro Leu
            20                  25                  30

Ser Arg Val Tyr Gly Cys Phe Leu Glu Asn Pro Glu Ser Pro Thr Ser
        35                  40                  45

Ala Ala Cys Gln Ala Ala Val Ala Met Ser Gly Thr Leu Ala Phe Tyr
    50                  55                  60

Asp Trp Phe Asp Val Ser Leu Pro Asn Ala Ser Gly Arg His Arg Glu
65                  70                  75                  80

Leu Ile Pro Asp Gly Gln Leu Cys Gly Ala Gly Leu Thr Lys Tyr Gln
                85                  90                  95

Gly Leu Asn Leu Ala Arg Asp Asp Trp Thr Ala Thr Ser Leu Thr Ser
            100                 105                 110

Gly Val Ser Phe Thr Tyr Leu Tyr Lys Ala Ala Ala Arg His Leu Gly
        115                 120                 125

Phe Phe Glu Phe Tyr Val Thr Arg Asp Gly Tyr Asp Pro Thr Glu Pro
    130                 135                 140

Leu Lys Trp Ala Asp Leu Glu Asp Leu Pro Phe Met Asn Val Thr Ser
145                 150                 155                 160

Thr Leu Asp Glu Glu Ser Tyr Gln Ile Pro Gly Thr Thr Pro Ser Gly
                165                 170                 175

Lys Ala Gly Arg His Leu Ile Tyr Val Ile Trp Gln Arg Ser Asp Ser
            180                 185                 190

Pro Glu Ala Phe Tyr Ser Cys Ser Asp Val Asp Phe Val Asp Ala Val
        195                 200                 205

Ser Leu His Ser Thr Thr
    210
```

<210> SEQ ID NO 176
<211> LENGTH: 224
<212> TYPE: PRT
<213> ORGANISM: Adiantum raddianum (Fragrans)

<400> SEQUENCE: 176

```
Met Gly Met Lys Met Ser Trp Glu Val Ala Leu Ala Glu Ile Val Ala
1               5                   10                  15

Leu Cys Leu Leu Gly Met Ala Ser Ser His Gly Thr Met Gln Asp Pro
            20                  25                  30

Ile Ser Arg Val Tyr Asn Cys Phe Leu Glu Asn Pro Glu Arg Pro Thr
        35                  40                  45

Ser Ala Ala Cys Gln Ala Ala Val Ala Leu Gly Gly Thr Gln Pro Leu
    50                  55                  60

Tyr Asp Trp Asn Glu Val Asn Ile His Asp Ala Ala Gly Asn His Arg
65                  70                  75                  80

Asp Leu Ile Pro Asp Gly Lys Leu Cys Ser Ala Gly Arg Gln Lys Phe
                85                  90                  95

Gln Gly Leu Asp Leu Ala Arg Ala Asp Trp Ile Ala Thr Ser Leu Ser
            100                 105                 110

Ser Gly Val Asp Tyr Thr Phe Leu Tyr Arg Ala Thr Ala Pro His Leu
        115                 120                 125
```

```
Gly Phe Phe Glu Phe Tyr Ile Thr Arg Asp Thr Tyr Asp Pro Thr Gln
            130                 135                 140

Pro Leu Ala Trp Gly Asp Leu Glu Asp Ser Pro Phe Ile Asn Ile Thr
145                 150                 155                 160

Asn Pro Ser Ile Val Ser Thr Thr Leu Gly Pro Ala Tyr Ser Ile Pro
                165                 170                 175

Ser Thr Thr Pro Phe Ser Lys Ser Gly Arg His Leu Ile Tyr Val Ile
                180                 185                 190

Trp Gln Arg Ser Asp Ser Pro Glu Ala Phe Tyr Ala Cys Ser Asp Ile
                195                 200                 205

Asp Phe Ser Thr Ser Ser Asp Met Ile Ser Leu Arg Ser Ala Val Leu
210                 215                 220
```

<210> SEQ ID NO 177
<211> LENGTH: 216
<212> TYPE: PRT
<213> ORGANISM: Platycerium bifurcatum (Netherlands)

<400> SEQUENCE: 177

```
Met Gly Lys Pro Trp Arg Val Val Ala Ile Val Val Val Val Cys Ala
1               5                   10                  15

Ser Gly Leu Leu Gly Val Ala Ser Gly His Gly Ser Met Gly Asp Pro
                20                  25                  30

Ile Ser Arg Val Tyr Asn Cys Tyr Leu Glu Asn Pro Glu Arg Pro Thr
            35                  40                  45

Ser Ala Ala Cys Ile Ala Ala Val Ala Leu Ser Gly Thr Gln Ala Phe
        50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Asp Lys Tyr
                85                  90                  95

Lys Gly Leu Asp Leu Ala Arg Ala Asp Trp Val Ala Thr Ser Leu Ser
            100                 105                 110

Ser Gly Val Ser Tyr Thr Phe Leu Tyr Arg Val Thr Ala Pro His Arg
        115                 120                 125

Gly Tyr Phe Glu Phe Tyr Val Thr Lys Asp Ser Tyr Asp Pro Thr Glu
            130                 135                 140

Pro Leu Ala Trp Ala Asp Leu Glu Asp Thr Pro Phe Ile Asn Ile Thr
145                 150                 155                 160

Asp Pro Thr Ile Val Ser Gly Ser Tyr Gln Ile Ser Ser Thr Thr Pro
                165                 170                 175

Ser Asp Lys Thr Gly Arg His Leu Ile Tyr Val Ile Trp Gln Arg Thr
            180                 185                 190

Asp Ser Pro Glu Ala Phe Tyr Ser Cys Ser Asp Val Asp Phe Asp Asp
        195                 200                 205

Thr Leu Pro Leu His Ser Ser Thr
210                 215
```

<210> SEQ ID NO 178
<211> LENGTH: 221
<212> TYPE: PRT
<213> ORGANISM: Pyrrosia polydactyla

<400> SEQUENCE: 178

```
Met Arg Met Gly Met Arg Met Arg Leu Trp Gly Val Val Ala Phe Met
1               5                   10                  15
```

Val Ala Val Cys Ala Gly Glu Leu Leu Asp Gln Ala Ser His Gly
            20                  25                  30

Ser Met Gly Asp Pro Val Ser Arg Val Leu Asn Cys Tyr Leu Glu Asn
            35                  40                  45

Pro Glu Asn Pro Ser Ser Ala Ala Cys Ile Ala Ala Val Ala Ala Ser
 50                  55                  60

Gly Thr Gln Ala Phe Tyr Asp Trp Asn Glu Val Asn Leu Ala Phe Ala
 65                  70                  75                  80

Ala Gly Gln His Arg Thr Leu Ile Pro Asp Gly Glu Leu Cys Ser Ala
            85                  90                  95

Gly Arg Glu Lys Tyr Lys Gly Leu Asn Leu Ala Arg Ala Asp Trp Val
            100                 105                 110

Ala Thr Ser Leu Ser Ser Gly Ala Asn Tyr Thr Phe Leu Tyr Arg Ala
            115                 120                 125

Thr Ala Pro His Leu Gly Tyr Phe Glu Phe Tyr Val Thr Gln Asp Ser
 130                 135                 140

Tyr Asp Pro Thr Glu Pro Leu Ala Trp Ala Asp Leu Glu Asp Ser Pro
145                 150                 155                 160

Phe Ile Asn Val Thr Asn Pro Ala Leu Val Ser Gly Ser Tyr Arg Ile
            165                 170                 175

Ala Gly Thr Thr Pro Ser Gly Lys Thr Gly Arg His Leu Ile Tyr Val
            180                 185                 190

Ile Trp Gln Arg Thr Asp Ser Pro Glu Ala Phe Tyr Ser Cys Ser Asp
            195                 200                 205

Val Asp Phe Asp Glu Ala Val Ser Leu Ser Ser Thr Thr
 210                 215                 220

<210> SEQ ID NO 179
<211> LENGTH: 222
<212> TYPE: PRT
<213> ORGANISM: Blechnum brasiliense

<400> SEQUENCE: 179

Met Lys Lys Pro Trp Gly Val Val Val Ala Ile Leu Leu Leu
1               5                   10                  15

Cys Leu Leu Gly Val Ala Ser Gly His Gly Ser Met Gln Asp Pro Ile
            20                  25                  30

Ser Arg Val Tyr Asn Cys Tyr Leu Glu Asn Pro Glu Arg Pro Thr Ser
            35                  40                  45

Ala Ala Cys Gln Ala Ala Val Ala Met Ser Gly Thr Gln Ala Phe Tyr
 50                  55                  60

Asp Trp Asn Glu Val Asn Leu Ala Asn Ala Ser Gly Arg His Arg Glu
 65                  70                  75                  80

Leu Ile Pro Asp Gly Lys Leu Cys Ser Ala Gly Arg Asp Lys Tyr Arg
            85                  90                  95

Gly Leu Asp Leu Ala Arg Ala Asp Trp Thr Ala Thr Ser Leu Ser Ser
            100                 105                 110

Gly Val Ala Tyr Thr Phe Leu His Arg Val Thr Ala Arg His Leu Gly
            115                 120                 125

Phe Phe Glu Phe Tyr Ile Thr Arg Asp Ser Tyr Asp Pro Thr Glu Leu
 130                 135                 140

Leu Thr Trp Ala Asp Leu Glu Asp Ser Pro Phe Ile Asn Ile Thr Asn
145                 150                 155                 160

Pro Thr Thr Val Ser Thr Ser Leu Gly Asn Ala Tyr Gln Ile Pro Gly
            165                 170                 175

```
Thr Thr Pro Ala Gly Lys Ser Gly Arg His Leu Ile Tyr Val Ile Trp
            180                 185                 190

Gln Arg Ser Asp Ser Pro Glu Ala Phe Tyr Ser Cys Cys Asp Val Asp
        195                 200                 205

Phe Ser Ser Asp Thr Leu Ile Ser Leu Arg Ser Ala Ala Leu
    210                 215                 220

<210> SEQ ID NO 180
<211> LENGTH: 222
<212> TYPE: PRT
<213> ORGANISM: Blechnum SP. (Silver Lady)

<400> SEQUENCE: 180

Met Lys Lys Pro Trp Gly Val Val Val Ala Ile Leu Leu Leu
1               5                   10                  15

Cys Leu Leu Gly Val Ala Ser Gly His Gly Ser Met Gln Asp Pro Ile
            20                  25                  30

Ser Arg Val Tyr Asn Cys Tyr Leu Glu Asn Pro Glu Arg Pro Thr Ser
        35                  40                  45

Ala Ala Cys Gln Ala Ala Val Ala Met Ser Gly Thr Gln Ala Phe Tyr
    50                  55                  60

Asp Trp Asn Glu Val Asn Leu Ala Asn Ala Ser Gly Arg His Arg Glu
65                  70                  75                  80

Leu Ile Pro Asp Gly Lys Leu Cys Ser Ala Gly Arg Asp Lys Tyr Arg
                85                  90                  95

Gly Leu Asp Leu Ala Arg Ala Asp Trp Thr Ala Thr Ser Leu Ser Ser
            100                 105                 110

Gly Val Ala Tyr Thr Phe Leu His Arg Val Thr Ala Arg His Leu Gly
        115                 120                 125

Phe Phe Glu Phe Tyr Ile Thr Arg Asp Ser Tyr Asp Pro Thr Glu Pro
    130                 135                 140

Leu Thr Trp Ala Asp Leu Glu Asp Ser Pro Phe Leu Asn Ile Thr Asp
145                 150                 155                 160

Pro Thr Thr Val Gly Thr Pro Leu Gly Asp Ala Tyr Glu Ile Pro Gly
                165                 170                 175

Thr Thr Pro Asp Gly Lys Ser Gly Arg His Leu Ile Tyr Val Ile Trp
            180                 185                 190

Gln Arg Ser Asp Ser Pro Glu Ala Phe Tyr Ser Cys Cys Asp Val Asp
        195                 200                 205

Phe Ser Ser Asp Thr Leu Ile Ser Leu Arg Ser Ala Ala Leu
    210                 215                 220

<210> SEQ ID NO 181
<211> LENGTH: 223
<212> TYPE: PRT
<213> ORGANISM: Pteris cretica (Mayi)

<400> SEQUENCE: 181

Met Gly Ser Arg Ser Val Gly Gly Gly Ala Gly Ala Ile Tyr Cys
1               5                   10                  15

Met Leu Leu Ile Cys Cys Val Ser Gly Leu Leu Gly Ile Ala Ser
            20                  25                  30

Gly His Gly Thr Met Leu Asp Pro Phe Ser Arg Val Tyr Ala Cys Arg
        35                  40                  45

Phe Phe Glu Asn Pro Glu Arg Pro Thr Ser Pro Ala Cys Gln Ala Ala
    50                  55                  60
```

```
Val Ala Ala Ser Gly Thr Gln Ala Phe Tyr Asp Trp Asn Glu Val Asn
 65                  70                  75                  80

Gln Pro Phe Ala Ala Gly Arg His Arg Glu Ile Ile Pro Asp Gly Gln
                 85                  90                  95

Leu Cys Ser Gly Gly Arg Asp Lys Tyr Lys Gly Leu Asp Leu Ala Arg
            100                 105                 110

Asn Asp Trp Pro Ala Thr Ser Leu Ser Ser Asn Ile Pro Phe Thr Tyr
            115                 120                 125

Leu Tyr Ile Ala Ser Ala Pro His Arg Gly Phe Phe Glu Phe Tyr Val
        130                 135                 140

Thr Gln Asp Gly Tyr Asp Pro Thr Gln Pro Leu Lys Trp Ala Asp Leu
145                 150                 155                 160

Glu Tyr Pro Pro Phe Ile Asn Ile Thr Asp Pro Thr Leu Leu Ser Gly
                165                 170                 175

Ser Tyr Gln Ile Pro Gly Thr Thr Pro Ala Gly Lys Ser Gly Arg His
            180                 185                 190

Leu Ile Tyr Val Ile Trp Gln Arg Ser Asp Ser Pro Glu Ala Phe Tyr
        195                 200                 205

Ser Cys Ser Asp Val Asp Phe Val Asp Ser Leu His Ala Ser Val
    210                 215                 220

<210> SEQ ID NO 182
<211> LENGTH: 221
<212> TYPE: PRT
<213> ORGANISM: Cystopteris fragilis

<400> SEQUENCE: 182

Met Gly Arg Val Asn Leu Leu Ala Ile Leu Val Leu Cys Ala Ser Cys
1               5                   10                  15

Cys Ala Gly Leu Leu Gly Val Ala Ser Gly His Gly Thr Met Glu Asp
            20                  25                  30

Pro Ile Ser Arg Val Tyr Asn Cys Phe Leu Glu Asn Pro Glu Arg Pro
        35                  40                  45

Thr Ser Ala Ala Cys Gln Ala Ala Val Ala Leu Ser Gly Thr Gln Ala
    50                  55                  60

Phe Tyr Asp Trp Asn Glu Val Asn Leu Ala Asp Ala Ala Gly Arg His
65                  70                  75                  80

Arg Glu Leu Ile Pro Asp Gly Gln Leu Cys Ser Ala Gly Arg Glu Lys
                85                  90                  95

Tyr Arg Gly Leu Asp Leu Ala Arg Ser Asp Trp Val Ala Thr Ser Leu
            100                 105                 110

Ser Ser Gly Val Ser Thr Thr Phe Leu Tyr Lys Ala Thr Ala Pro His
        115                 120                 125

Leu Gly Phe Phe Glu Phe Tyr Val Thr Arg Asp Gly Tyr Asp Pro Thr
    130                 135                 140

Glu Ala Leu Lys Trp Ser Asp Leu Glu Asp Ser Pro Phe Leu Asn Val
145                 150                 155                 160

Thr Asp Pro Thr Leu Leu Ser Ser Pro Tyr Val Tyr Gln Ile Pro Gly
                165                 170                 175

Thr Thr Pro Ala Gly Lys Ser Gly Arg His Leu Ile Tyr Val Ile Trp
            180                 185                 190

Gln Arg Ser Asp Ser Pro Glu Ala Phe Tyr Ser Cys Ser Asp Val Ala
        195                 200                 205

Phe Asp Asp Ala Gln Leu Val Ser Leu His Ser Thr Thr
```

```
              210                 215                 220

<210> SEQ ID NO 183
<211> LENGTH: 220
<212> TYPE: PRT
<213> ORGANISM: Dryopteris filix-mas

<400> SEQUENCE: 183

Met Gly Arg Ser Trp Gly Val Val Gln Ala Ile Ile Met Val Leu Cys
1               5                   10                  15

Gly Ser Gly Leu Leu Gly Val Ala Ser Gly His Gly Ser Met Glu Asp
            20                  25                  30

Pro Ile Ser Arg Val Tyr Asn Cys Tyr Leu Glu Asn Pro Glu Ser Pro
        35                  40                  45

Thr Ser Ala Ala Cys Gln Ala Val Ala Leu Ser Gly Ala Gln Ala
    50                  55                  60

Phe Tyr Asp Trp Asn Glu Val Asn Leu Ala Asp Ala Ala Gly Arg His
65              70                  75                  80

Arg Glu Leu Ile Pro Asp Gly Gln Leu Cys Ser Ala Gly Arg Glu Lys
                85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
        115                 120                 125

Leu Gly Phe Phe Glu Phe Tyr Val Thr Lys Asp Gly Tyr Glu Pro Thr
130             135                 140

Glu Pro Leu Lys Trp Ala Asp Leu Glu Asp Ser Pro Phe Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Ser
        195                 200                 205

Ser Asp Ala Leu Ile Ser Leu Gly Ser Ala Val Leu
    210                 215                 220

<210> SEQ ID NO 184
<211> LENGTH: 219
<212> TYPE: PRT
<213> ORGANISM: Bolbitis cladorrhizans

<400> SEQUENCE: 184

Met Gly Arg Ser Leu Gly Ala Val Val Ile Thr Leu Val Leu Cys Ala
1               5                   10                  15

Gly Gly Leu Leu Ser Leu Ala Ser Gly His Gly Ser Met Glu Asp Pro
            20                  25                  30

Ile Ser Arg Val Tyr Arg Cys Tyr Leu Glu Asn Pro Glu Ser Pro Thr
        35                  40                  45

Ser Ala Ala Cys Gln Ala Val Ala Leu Ser Gly Thr Glu Ala Phe
    50                  55                  60

Ser Gly Tyr Ala Trp Ser Ala Val Leu Ala Asn Ala Gly Gln His
65              70                  75                  80

Arg Gln Leu Ile Pro Asp Gly Gln Leu Cys Ser Ala Gly Gln Glu Leu
                85                  90                  95

Tyr Ala Gly Leu Asp Leu Pro Arg Ala Asp Trp Pro Ala Thr Ser Leu
```

```
                100             105             110
Ser Ser Gly Val Ala Phe Thr Tyr Leu Tyr Lys Ala Ala Ile Pro His
        115             120             125

Met Gly Phe Phe Glu Phe Tyr Ile Thr Arg Asp Gly Tyr Glu Pro Thr
        130             135             140

Glu Pro Leu Lys Trp Ala Asp Leu Glu Asp Ser Pro Phe Leu Asn Val
145             150             155             160

Thr Asp Pro Pro Leu Val Ser Ser Tyr Gln Ile Pro Gly Ser Thr
                165             170             175

Pro Ala Gly Lys Ser Gly Arg His Leu Ile Tyr Val Ile Trp Gln Arg
                180             185             190

Ser Asp Ser Pro Gln Ala Phe Tyr Ser Cys Ser Asp Val Asp Phe Val
        195             200             205

Asp Ala Thr Leu Ser Gln Leu His Ser Thr Thr
        210             215

<210> SEQ ID NO 185
<211> LENGTH: 220
<212> TYPE: PRT
<213> ORGANISM: Dryopteris filix-mas

<400> SEQUENCE: 185

Met Lys Lys Ser Trp Gly Val Val Val Val Val Ala Leu Val
1               5                   10                  15

Leu Leu Cys Leu Leu Gly Thr Ala Ser Gly His Gly Ser Met Gln Asp
            20                  25                  30

Pro Ile Ser Arg Val Tyr Asn Cys Tyr Leu Glu Asn Pro Glu Asn Pro
        35                  40                  45

Thr Ser Ala Ala Cys Lys Ala Val Val Ala Val Gly Gly Thr Gln Pro
    50                  55                  60

Leu Tyr Asp Trp Asn Glu Val Asn Leu Ala Asn Ala Ala Gly Arg His
65                  70                  75                  80

Arg Glu Leu Ile Pro Asp Gly Arg Leu Cys Ser Ala Gly Arg Asp Lys
                85                  90                  95

Tyr Arg Gly Leu Asp Leu Ala Arg Asp Asp Trp Pro Ala Thr Ser Leu
            100                 105                 110

Ser Ser Gly Val Asp Tyr Thr Phe Leu Tyr Arg Ala Thr Ala Pro His
        115                 120                 125

Leu Gly Phe Phe Glu Phe Tyr Val Thr Arg Asp Ser Tyr Asp Pro Thr
        130                 135                 140

Gln Pro Leu Ala Trp Ala Asp Leu Glu Asp Leu Pro Phe Ile Asn Val
145                 150                 155                 160

Thr Asn Pro Ala Leu Asn Ala Gly Ala Tyr Gln Ile Pro Gly Thr Met
                165                 170                 175

Pro Ala Gly Lys Ser Gly Arg His Leu Ile Tyr Val Ile Trp Gln Arg
                180                 185                 190

Ser Asp Ser Pro Glu Ala Phe Tyr Ser Cys Ser Asp Val Asp Phe Ser
        195                 200                 205

Ser Asp Ala Leu Ile Ser Leu Arg Ser Ala Val Leu
        210                 215                 220

<210> SEQ ID NO 186
<211> LENGTH: 218
<212> TYPE: PRT
<213> ORGANISM: Pyrrosia lanceolata
```

```
<400> SEQUENCE: 186

Met Arg Thr Arg Ser Trp Gly Val Val Ala Phe Met Val Ala Val Cys
1               5                   10                  15

Ala Gly Asp Leu Leu Gly Leu Ala Ser Gly His Gly Ser Met Gly Tyr
            20                  25                  30

Pro Val Ser Arg Val Leu Asn Cys Phe Leu Glu Asn Pro Glu Ser Pro
        35                  40                  45

Thr Ser Ala Ala Cys Thr Ala Val Ala Met Ser Gly Thr Gln Ala
    50                  55                  60

Phe Tyr Asp Trp Asn Glu Val Asn Leu Pro Phe Ala Asn Gly Gln His
65              70                  75                  80

Arg Asp Leu Ile Pro Asp Gly Gln Leu Cys Ser Ala Gly Arg Ala Lys
                85                  90                  95

Tyr Ala Gly Leu Asp Leu Ala Arg Asp Asp Trp Glu Ala Thr Phe Leu
            100                 105                 110

Ser Ser Ala Thr Ser Tyr Thr Leu Leu Tyr Arg Val Thr Ala Arg His
        115                 120                 125

Leu Gly Tyr Phe Glu Phe Tyr Val Thr Arg Asp Ser Tyr Asn Ser Thr
    130                 135                 140

Gln Pro Leu Ala Trp Ala Asp Leu Glu Asp Ser Pro Phe Ile Asn Ile
145             150                 155                 160

Thr Asn Pro Thr Val Asp Ser Gly Tyr Tyr Gln Val Pro Val Asp Thr
                165                 170                 175

Pro Ser Gly Lys Thr Gly Arg His Leu Ile Tyr Val Ile Trp Gln His
            180                 185                 190

Thr Asp Ser Leu Glu Ala Phe Tyr Ser Cys Ser Asp Val Glu Phe Asp
        195                 200                 205

Val Glu Val Pro Ser Leu Arg Ser Thr Thr
    210                 215

<210> SEQ ID NO 187
<211> LENGTH: 218
<212> TYPE: PRT
<213> ORGANISM: Athyrium filix-femina

<400> SEQUENCE: 187

Met Gly Arg Ser Trp Gly Val Val Ala Ile Met Val Leu Cys Gly
1               5                   10                  15

Cys Leu Leu Gly Val Ala Ser Gly His Gly Ser Met Glu Asp Pro Ile
            20                  25                  30

Ser Arg Val Tyr Asn Cys Tyr Leu Glu Asn Pro Glu Ser Pro Thr Ser
        35                  40                  45

Ala Ala Cys Gln Ala Ala Val Ala Leu Ser Gly Thr Gln Ala Phe Tyr
    50                  55                  60

Asp Trp Asn Glu Val Asn Gln Pro Phe Ala Ala Gly Gln Ser Arg Glu
65              70                  75                  80

Ile Ile Pro Asp Gly Gln Leu Cys Ser Gly Arg Glu Lys Tyr Lys
                85                  90                  95

Gly Leu Asp Leu Ala Arg Ser Asp Trp Thr Ala Thr Ser Leu Ser Ser
            100                 105                 110

Gly Val Ala Phe Thr Phe Leu Phe Lys Ala Thr Ala Pro His Ala Gly
        115                 120                 125

Phe Phe Glu Phe Tyr Val Thr Gln Asp Gly Tyr Asp Pro Thr Glu Pro
    130                 135                 140
```

```
Leu Lys Trp Ala Asp Leu Glu Asp Ser Pro Phe Ile Asn Val Thr Asp
145                 150                 155                 160

Pro Thr Leu Val Ser Gly Ser Tyr Gln Ile Ser Gly Thr Thr Pro Ala
                165                 170                 175

Gly Lys Ser Gly Arg His Leu Ile Tyr Val Ile Trp Gln Arg Ser Asp
            180                 185                 190

Ser Pro Glu Ala Phe Tyr Ser Cys Ser Asp Val Glu Phe Val Asp Asp
        195                 200                 205

Ala Leu Ser Ser Asp Leu His Ser Thr Thr
    210                 215

<210> SEQ ID NO 188
<211> LENGTH: 218
<212> TYPE: PRT
<213> ORGANISM: Colysis wrightii (Monstifera)

<400> SEQUENCE: 188

Met Gly Arg Ala Trp Val Val Ala Ile Met Val Ala Val Cys Ala
1               5                   10                  15

Ser Gly Leu Leu Ser Phe Ala Ser Arg Thr Arg Gly His Gly Ser Met
            20                  25                  30

Gly Asp Pro Ile Ser Arg Val Leu Arg Cys Arg Glu Glu Asn Pro Glu
        35                  40                  45

Asn Pro Thr Ser Pro Ala Cys Ile Ala Ala Val Ala Leu Ser Gly Lys
    50                  55                  60

Gln Ala Phe Tyr Asp Trp Asn Glu Val Asn Leu Pro Phe Ala Asp Gly
65                  70                  75                  80

Gln His Gln Lys Leu Ile Pro Asp Gly Gln Leu Cys Gly Ala Gly Arg
                85                  90                  95

Asp Lys Tyr Lys Gly Leu Asn Leu Ala Arg Ala Asp Trp Leu Ala Thr
            100                 105                 110

Ser Leu Ser Ala Gly Ala Pro Tyr Thr Phe Leu Phe Leu Ala Ser Ala
        115                 120                 125

Pro His Leu Gly Tyr Phe Glu Phe Tyr Val Thr Arg Asp Ser Tyr Asp
    130                 135                 140

Pro Thr Gln Pro Leu Ala Trp Ala Asp Leu Glu Asp Ser Pro Phe Leu
145                 150                 155                 160

Thr Thr Thr Thr Thr Leu Asp Ser Ser Ser Tyr Ile Ile Pro Gly Thr
                165                 170                 175

Thr Pro Ala Gly Lys Thr Gly Arg His Leu Ile Tyr Leu Ile Trp Gln
            180                 185                 190

Arg Thr Asp Ser Pro Glu Ala Phe Tyr Ser Cys Ser Asp Val Asp Phe
        195                 200                 205

Glu Glu Ala Ile Ser Leu Ser Ser Thr Thr
    210                 215

<210> SEQ ID NO 189
<211> LENGTH: 219
<212> TYPE: PRT
<213> ORGANISM: Coniogramme venusta

<400> SEQUENCE: 189

Met Gly Arg Ser Ser Ser Trp Glu Gly Val Leu Val Val Val Cys
1               5                   10                  15

Cys Ala Ser Gly Leu Leu Gly Val Ala Ser Gly His Gly Ser Met Gly
            20                  25                  30
```

Ser Pro Ile Ser Arg Val Tyr Asn Cys Arg Gln Glu Asn Pro Glu Arg
            35                  40                  45

Pro Thr Ser Ala Ala Cys Arg Glu Ala Val Arg Ile Ser Gly Thr Gln
 50                  55                  60

Ala Phe Tyr Asp Trp Asn Glu Val Asn Leu Pro Val Ala Ser Gly Arg
 65                  70                  75                  80

His Arg Glu Leu Ile Pro Asp Gly Lys Leu Cys Ser Ala Gly Arg Thr
                 85                  90                  95

Lys Tyr Ala Gly Leu Asp Leu Ala Arg Ser Asp Trp Val Ser Thr Val
                100                 105                 110

Leu Pro Ser Gly Val Pro Tyr Thr Phe Leu Tyr Arg Val Thr Ala Arg
                115                 120                 125

His Val Gly Phe Phe Glu Phe Tyr Val Thr Arg Asp Gly Tyr Gln Pro
                130                 135                 140

Ser Glu Pro Leu Lys Trp Ser Asp Leu Glu Glu Pro Pro Phe Ile Asn
145                 150                 155                 160

Val Thr Asn Pro Thr Met Ser Gly Gly Phe Tyr Arg Ile Pro Gly Thr
                165                 170                 175

Thr Pro Pro Ala Lys Ala Gly Arg His Leu Ile Tyr Val Ile Trp Gln
                180                 185                 190

Arg Ser Asp Ser Pro Glu Ala Phe Tyr Ser Cys Ser Asp Ala Val Phe
                195                 200                 205

Gly Asp Ala Leu Ser Leu Gln Tyr Ser Ser Thr
                210                 215

<210> SEQ ID NO 190
<211> LENGTH: 217
<212> TYPE: PRT
<213> ORGANISM: Platycerium coronarium

<400> SEQUENCE: 190

Met Arg Arg Ser Trp Gly Val Val Ala Val Ile Met Leu Ala Val Cys
 1               5                  10                  15

Ala Val Gly Met Leu Gly Val Ala Ser Gly His Gly Ser Met Glu Asp
                20                  25                  30

Pro Ile Ser Arg Val Tyr Arg Cys Phe Leu Glu Asn Pro Glu Arg Pro
            35                  40                  45

Thr Ser Ala Ala Cys Ile Ala Val Ala Leu Ser Gly Thr Gln Ala
 50                  55                  60

Phe Tyr Asp Trp Asn Glu Val Asn Leu Pro Phe Ala Ala Gly Arg His
 65                  70                  75                  80

Arg Glu Leu Ile Pro Asp Gly Gln Leu Cys Ser Ala Gly Arg Asp Lys
                 85                  90                  95

Tyr Lys Gly Leu Asp Leu Ala Arg Asp Asp Trp Val Ala Thr Ser Leu
                100                 105                 110

Ser Ser Gly Val Asn Tyr Thr Phe Leu Tyr Lys Ala Thr Ala Pro His
                115                 120                 125

Arg Gly Tyr Phe Glu Phe Tyr Val Thr Arg Asp Ser Tyr Asp Pro Thr
                130                 135                 140

Glu Pro Leu Ala Trp Ala Asp Leu Glu Asp Thr Pro Phe Ile Asn Val
145                 150                 155                 160

Thr Asp Pro Asp Leu Ala Ser Gly Ser Tyr Gln Ile Ser Ser Thr Thr
                165                 170                 175

Pro Ser Gly Lys Thr Gly Arg His Leu Ile Tyr Val Ile Trp Gln Arg
                180                 185                 190

Thr Asp Ser Pro Glu Ala Phe Tyr Ser Cys Ser Asp Ile Leu Phe Asp
        195                 200                 205

Glu Ala Val Ala Leu Tyr Ser Thr Ala
    210                 215

<210> SEQ ID NO 191
<211> LENGTH: 218
<212> TYPE: PRT
<213> ORGANISM: Cystopteris bulbifera

<400> SEQUENCE: 191

Met Gly Arg Val Asn Leu Met Ala Ile Leu Ala Leu Cys Ala Ser Phe
1               5                   10                  15

Cys Ala Ala Leu Leu Gly Val Ala Ser Gly His Gly Ser Met Gln Asp
            20                  25                  30

Pro Ile Ser Arg Val Tyr Asn Cys Phe Leu Glu Asn Pro Glu Arg Pro
        35                  40                  45

Thr Ser Ala Ala Cys Gln Ala Val Ala Leu Ser Gly Thr Gln Ala
    50                  55                  60

Phe Tyr Asp Trp Asn Glu Val Asn Leu Ala Asn Ala Asp Gly Arg His
65                  70                  75                  80

Arg Glu Leu Ile Pro Asp Gly Gln Leu Cys Ser Ala Gly Arg Glu Lys
                85                  90                  95

Tyr Gln Gly Leu Asp Leu Ala Arg Ala Asp Trp Thr Ala Thr Ser Leu
            100                 105                 110

Ser Ser Gly Ile Ser Tyr Thr Phe Leu Tyr Lys Ala Thr Ala Pro His
        115                 120                 125

Leu Gly Phe Phe Glu Phe Tyr Val Thr Arg Asp Gly Tyr Asp Pro Thr
    130                 135                 140

Glu Ala Leu Lys Trp Ser Asp Leu Glu Asp Ser Pro Phe Leu Asn Val
145                 150                 155                 160

Thr Asn Pro Thr Leu Val Ser Gly Ser Tyr Gln Ile Pro Val Thr Thr
                165                 170                 175

Pro Ala Ala Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
        195                 200                 205

Asp Ala Leu Val Ser Leu His Ser Thr Thr
    210                 215

<210> SEQ ID NO 192
<211> LENGTH: 217
<212> TYPE: PRT
<213> ORGANISM: Platycerium ridleyi

<400> SEQUENCE: 192

Met Arg Arg Ser Trp Gly Val Met Ala Val Ile Leu Leu Ala Val Cys
1               5                   10                  15

Ala Cys Gly Leu Leu Gly Val Ala Ser Gly His Gly Ser Met Glu Asp
            20                  25                  30

Pro Ile Ser Arg Val Tyr Gly Cys Tyr Leu Glu Asn Pro Glu Arg Pro
        35                  40                  45

Thr Ser Ala Ala Cys Ile Ala Ala Val Ala Leu Ser Gly Thr Gln Ala
    50                  55                  60

Phe Tyr Asp Trp Asn Glu Val Asn Gln Pro Phe Ala Ala Gly Arg His
65                  70                  75                  80

Arg Glu Leu Ile Pro Asp Gly Gln Leu Cys Ser Gly Arg Asp Lys
                85                  90                  95

Tyr Lys Gly Leu Asp Leu Ala Arg Asp Asp Trp Glu Ala Thr Ser Leu
            100                 105                 110

Ser Ser Gly Ala Asn Tyr Ser Phe Leu Phe Lys Ala Thr Ala Pro His
            115                 120                 125

Arg Gly Tyr Phe Glu Phe Tyr Val Thr Gln Asp Ser Tyr Asp Pro Thr
        130                 135                 140

Glu Pro Leu Ala Trp Gly Asp Leu Glu Ser Thr Pro Phe Ile Asn Val
145                 150                 155                 160

Thr Asp Pro Asp Leu Phe Ser Gly Ser Tyr Gln Ile Ser Ser Thr Thr
                165                 170                 175

Pro Pro Gly Lys Thr Gly Arg His Leu Ile Tyr Val Ile Trp Gln Arg
            180                 185                 190

Thr Asp Ser Pro Glu Ala Phe Tyr Ser Cys Ser Asp Val Leu Phe Asp
        195                 200                 205

Glu Ala Val Ala Leu Tyr Ser Thr Ala
    210                 215

<210> SEQ ID NO 193
<211> LENGTH: 215
<212> TYPE: PRT
<213> ORGANISM: Dryopteris marginalis

<400> SEQUENCE: 193

Met Gly Arg Ser Trp Gly Val Val Ala Ile Ile Met Val Leu Cys Gly
1               5                   10                  15

Ser Gly Leu Leu Gly Val Ala Ser Gly His Gly Ser Met Gln Asp Pro
            20                  25                  30

Ile Ser Arg Val Tyr Asn Cys Tyr Leu Glu Asn Pro Glu Arg Pro Thr
        35                  40                  45

Ser Ala Ala Cys Gln Ala Ala Val Ala Leu Ser Gly Thr Gln Ala Phe
    50                  55                  60

Tyr Asp Trp Asn Glu Val Asn Gln Pro Phe Ala Ala Gly Arg His Arg
65                  70                  75                  80

Glu Ile Ile Pro Asp Gly Gln Leu Cys Ser Ala Gly Arg Glu Lys Tyr
                85                  90                  95

Arg Gly Leu Asp Leu Ala Arg Ser Asp Trp Val Ala Thr Ser Leu Ser
            100                 105                 110

Ser Gly Val Asn Tyr Thr Tyr Leu Tyr Lys Ala Thr Ala Pro His Leu
            115                 120                 125

Gly Phe Phe Glu Phe Tyr Val Thr Gln Asp Gly Tyr Asn Ser Ser Glu
        130                 135                 140

Pro Leu Lys Trp Ala Asp Leu Glu Asp Ser Pro Phe Ile Asn Val Thr
145                 150                 155                 160

Thr Thr Leu Asp Ser Ala Ser Tyr Gln Ile Pro Gly Thr Pro Ala
                165                 170                 175

Gly Lys Asn Gly Arg His Leu Ile Tyr Val Ile Trp Gln Arg Ser Asp
            180                 185                 190

Ser Pro Glu Ala Phe Tyr Ser Cys Ser Asp Val Asp Phe Ala Asp Ala
        195                 200                 205

Leu Ser Leu His Ser Thr Thr
    210                 215

<210> SEQ ID NO 194
<211> LENGTH: 216
<212> TYPE: PRT
<213> ORGANISM: Microsorum musifolium (Blume)

<400> SEQUENCE: 194

Met Arg Arg Ser Trp Gly Val Leu Ala Ile Val Met Ala Val Cys Ala
1               5                   10                  15

Ser Gly Leu Phe Gly Val Ala Ser Gly His Gly Ser Met Glu His Pro
            20                  25                  30

Ile Ser Arg Val Tyr Gln Cys Tyr Arg Glu Gly Pro Glu Asn Pro Lys
        35                  40                  45

Ser Pro Ala Cys Ile Ala Ala Lys Gly Leu Ser Gly Ala Gln Ala Phe
    50                  55                  60

Tyr Asp Trp Asn Glu Val Asn Gln Pro Phe Ala Asp Gly Arg His Gln
65                  70                  75                  80

Glu Ile Ile His Asp Gly His Leu Cys Ser Gly Gly Arg Asp Lys Tyr
                85                  90                  95

Arg Gly Leu Asp Leu Pro Arg Ala Asp Trp Val Ala Thr Ser Leu Ser
            100                 105                 110

Ala Gly Lys Pro Tyr Thr Phe Leu Tyr Arg Ala Thr Ala His His Leu
        115                 120                 125

Gly Tyr Phe Glu Phe Tyr Val Thr Arg Asp Gly Tyr Asp Pro Thr Lys
    130                 135                 140

Pro Leu Ala Trp Ala Asp Leu Glu Asp Ser Pro Phe Ile Asn Val Thr
145                 150                 155                 160

Asn Pro Thr Leu Val Ser Gly Ser Tyr Arg Ile Pro His Thr Thr Pro
                165                 170                 175

Ala Ser Lys Thr Gly Arg His Leu Ile Tyr Val Ile Trp Gln Arg Thr
            180                 185                 190

Asp Ser Phe Glu Ala Phe Tyr Ser Cys Ser Asp Val Val Phe Asp Glu
        195                 200                 205

Ala Leu Ser Leu Ser Ser Thr Ile
    210                 215

<210> SEQ ID NO 195
<211> LENGTH: 216
<212> TYPE: PRT
<213> ORGANISM: Elaphoglossum SP.

<400> SEQUENCE: 195

Met Arg Arg Ser Trp Glu Val Val Ala Leu Ile Met Val Val Cys Ala
1               5                   10                  15

Cys Gly Leu Leu Gly Val Ala Ser Gly His Gly Ser Met Glu Asp Pro
            20                  25                  30

Ile Ser Arg Val Tyr Arg Cys Tyr Leu Glu Gly Val Glu Asn Pro Thr
        35                  40                  45

Ser Ala Ala Cys Ile Ala Ala Ile Glu Val Ser Gly Lys Gln Ala Phe
    50                  55                  60

Tyr Asp Trp Asn Glu Val Asn Gln Pro Leu Ala Ala Gly Arg His Arg
65                  70                  75                  80

Glu Ile Ile Pro Asp Gly Glu Leu Cys Ser Gly Gly Arg Glu Lys Tyr
                85                  90                  95

Lys Gly Leu Asp Leu Ala Arg Ala Asp Trp Leu Ala Thr Ser Leu Ser
            100                 105                 110

Ser Gly Val Asp Tyr Thr Phe Leu Tyr Lys Ala Thr Ala Glu His Lys

```
            115                 120                 125
Gly Tyr Phe Glu Phe Tyr Val Thr Gln Asp Ser Tyr Asp Pro Thr Glu
            130                 135                 140

Pro Leu Lys Trp Ser Asp Leu Glu Asp Thr Pro Phe Ile Asn Val Thr
145                 150                 155                 160

Gln Pro Leu Leu Val Ser Gly Ser Tyr Gln Ile Pro Gly Thr Thr Pro
                    165                 170                 175

Ser Gly Lys Thr Gly Arg His Leu Ile Tyr Val Ile Trp Gln Arg Thr
            180                 185                 190

Asp Ser Ala Glu Ala Phe Tyr Ser Cys Ser Asp Val Asn Phe Asp Asp
                195                 200                 205

Ala Leu Pro Ile Tyr Ser Ala Thr
            210                 215

<210> SEQ ID NO 196
<211> LENGTH: 214
<212> TYPE: PRT
<213> ORGANISM: Dryopteris lepidopoda

<400> SEQUENCE: 196

Met Gly Arg Ser Trp Gly Val Val Ala Ile Met Val Leu Cys Gly Ser
1               5                   10                  15

Gly Leu Leu Gly Val Ala Ser Gly His Gly Ser Met Glu Asp Pro Ile
                20                  25                  30

Ser Arg Val Tyr Asn Cys Tyr Leu Glu Asn Pro Glu Arg Pro Thr Ser
            35                  40                  45

Ala Ala Cys Gln Ala Ala Val Ala Leu Ser Gly Thr Gln Ala Phe Tyr
        50                  55                  60

Asp Trp Asn Glu Val Asn Gln Pro Phe Ala Ala Gly Arg His Arg Glu
65                  70                  75                  80

Ile Ile Pro Asp Gly Gln Leu Cys Ser Gly Gly Arg Glu Lys Tyr Arg
                85                  90                  95

Gly Leu Asp Leu Ala Arg Ser Asp Trp Glu Ala Thr Ser Leu Ser Ser
            100                 105                 110

Gly Val Ser Tyr Thr Tyr Leu Tyr Lys Ala Thr Ala Pro His Leu Gly
        115                 120                 125

Phe Phe Glu Phe Tyr Val Thr Gln Asp Gly Tyr Asn Ser Ser Glu Pro
    130                 135                 140

Leu Glu Trp Ala Asp Leu Glu Asp Ser Pro Phe Ile Asn Val Thr Thr
145                 150                 155                 160

Thr Leu Asp Ser Ala Ser Tyr Gln Ile Pro Gly Thr Thr Pro Ala Gly
                165                 170                 175

Lys Thr Gly Arg His Leu Ile Tyr Val Ile Trp Gln Arg Ser Asp Ser
            180                 185                 190

Pro Glu Ala Phe Tyr Ser Cys Ser Asp Val Asp Phe Val Asp Ala Leu
        195                 200                 205

Ser Leu His Ser Thr Thr
            210

<210> SEQ ID NO 197
<211> LENGTH: 214
<212> TYPE: PRT
<213> ORGANISM: Polystichum lepidocaulon

<400> SEQUENCE: 197

Met Gly Arg Ser Trp Gly Val Val Ala Ile Met Val Leu Phe Ala Ser
```

```
            1               5                  10                 15
Ala Ser Gly Leu Leu Gly Val Ala Asn Gly His Gly Ser Met Gly Asn
                20                  25                 30

Pro Ile Ser Arg Val Tyr Asn Cys Arg Leu Glu Asn Pro Glu Arg Pro
                35                  40                 45

Thr Ser Ala Ala Cys Ile Ala Val Ala Leu Ser Gly Thr Tyr Asp
            50                  55                 60

Trp Ser Glu Val Asn Leu Pro Asn Ala Asn Gly Arg His Arg Glu Leu
65                  70                  75                  80

Ile Pro Asp Gly Lys Leu Cys Ser Ala Gly Arg Asp Lys Tyr Lys Gly
                85                  90                  95

Leu Asp Leu Ala Arg Ser Asp Trp Thr Ala Thr Asn Leu Ser Ser Gly
                100                 105                110

Val Ala Tyr Thr Phe Leu Tyr Arg Val Thr Ala Glu His Arg Gly Phe
                115                 120                125

Phe Glu Phe Tyr Val Thr Val Asp Asp Tyr Glu Pro Thr Glu Leu Leu
                130                 135                140

Lys Trp Glu Asp Leu Glu Glu Thr Pro Phe Leu Asn Val Ser Asp Pro
145                 150                 155                 160

Thr Val Val Gly Asn Asn Tyr Glu Ile Ser Gly Thr Thr Pro Ala Ser
                165                 170                 175

Lys Thr Gly Arg His Leu Ile Tyr Val Ile Trp Gln Arg Ser Asp Ser
                180                 185                 190

Pro Glu Ala Phe Tyr Ser Cys Ser Asp Val Asp Phe Val Asp Thr Leu
                195                 200                 205

Ser Leu His Ser Thr Thr
                210

<210> SEQ ID NO 198
<211> LENGTH: 215
<212> TYPE: PRT
<213> ORGANISM: Polystichum polyblepharum (C.)

<400> SEQUENCE: 198

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
                20                  25                  30

Ser Arg Val Tyr Asn Cys Arg Leu Glu Asn Pro Glu Ser Pro Thr Ser
                35                  40                  45

Ala Ala Cys Ile Ala Ala Val Ala Leu Ser Gly Thr Gln Ala Phe Tyr
            50                  55                  60

Asp Trp Asn Glu Val Asn Leu Pro Asn Ala Ala Gly Arg His Arg Glu
65                  70                  75                  80

Leu Ile Pro Asp Gly Lys Leu Cys Ser Ala Gly Arg Asp Lys Tyr Lys
                85                  90                  95

Gly Leu Asp Leu Ala Arg Ser Asp Trp Val Ala Thr Asn Leu Ser Ser
                100                 105                 110

Gly Val Ala Phe Thr Phe Leu Tyr Arg Val Thr Ala Gln His Arg Gly
                115                 120                 125

Phe Phe Glu Phe Tyr Val Thr Val Asp Asp Tyr Asp Pro Thr Glu Leu
                130                 135                 140

Leu Lys Trp Glu Asp Leu Glu Glu Thr Pro Phe Met Asn Val Thr Asp
145                 150                 155                 160
```

```
Pro Thr Val Val Gly Val Asn Tyr Glu Met Ala Gly Thr Thr Pro Ala
            165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
            195                 200                 205

Val Ser Leu His Ser Ser Thr
            210                 215

<210> SEQ ID NO 199
<211> LENGTH: 216
<212> TYPE: PRT
<213> ORGANISM: Lecanopteris sinuosa

<400> SEQUENCE: 199

Met Met Arg Ser Trp Gly Val Ala Ala Ile Met Met Ala Val Cys Ala
1               5                   10                  15

Ser Gly Leu Leu Gly Val Ala Ser Gly His Gly Ser Met Ala Asp Pro
            20                  25                  30

Ile Ser Arg Val Tyr Arg Cys Arg Leu Glu Asn Pro Glu Arg Pro Thr
            35                  40                  45

Ser Pro Ala Cys Ile Ala Ala Val Ala Leu Ser Gly Thr Gln Ala Phe
        50                  55                  60

Tyr Asp Trp Asn Glu Val Asn Leu Pro Phe Ala Ala Gly Arg His Arg
65                  70                  75                  80

Gln Leu Ile Pro Asp Gly Gln Leu Cys Ser Ala Gly Arg Asn Lys Tyr
            85                  90                  95

Lys Gly Leu Asp Leu Ala Arg Ala Asp Trp Leu Ala Thr Ser Leu Ser
            100                 105                 110

Pro Gly Ala Asn Tyr Thr Phe Leu Tyr Arg Ala Thr Ala Pro His Ala
            115                 120                 125

Gly Tyr Phe Glu Phe Tyr Val Thr Arg Asp Ser Tyr Asp Pro Thr Glu
            130                 135                 140

Gln Leu Ala Trp Ala Asp Leu Glu Asp Ser Pro Phe Ile Thr Ile Thr
145                 150                 155                 160

Asn Pro Thr Leu Val Asn Gly Tyr Tyr Gln Ile Pro Asn Thr Val Pro
            165                 170                 175

Ala Gly Lys Thr Gly Arg His Leu Ile Tyr Val Ile Trp Gln Arg Thr
            180                 185                 190

Asp Ser Pro Glu Ala Phe Tyr Ser Cys Ser Asp Val Asp Phe Asp Asp
            195                 200                 205

Ala Leu Arg Leu His Tyr Ser Thr
            210                 215

<210> SEQ ID NO 200
<211> LENGTH: 215
<212> TYPE: PRT
<213> ORGANISM: Aglaomorpha splendens

<400> SEQUENCE: 200

Met Arg Arg Ser Trp Gly Val Val Ile Leu Val Val Cys Val Cys
1               5                   10                  15

Gly Leu Leu Gly Val Ala Ser Gly His Gly Ser Met Gly Asp Pro Ile
            20                  25                  30

Ser Arg Val Tyr Gly Cys Arg Leu Glu Asn Pro Glu Ser Pro Thr Ser
            35                  40                  45
```

```
Ala Ala Cys Ile Ala Ala Val Ala Ser Gly Thr Gln Ala Phe Tyr
    50                  55                  60

Asp Trp Asn Glu Val Asn Gln Pro Asn Ala Asn Gly Arg His Arg Glu
65                  70                  75                  80

Ile Ile Pro Asp Gly Glu Leu Cys Ser Ala Gly Arg Val Lys Tyr Ala
                    85                  90                  95

Gly Leu Asp Leu Ala Arg Asp Asp Trp Val Ala Thr Ser Leu Ser Ser
                100                 105                 110

Gly Val Asn Tyr Thr Phe Leu Phe Val Ala Thr Ala Pro His Leu Gly
                115                 120                 125

Tyr Phe Glu Phe Tyr Val Thr Gln Asp Ser Tyr Asp Pro Thr Gln Pro
    130                 135                 140

Leu Lys Trp Ser Asp Leu Glu Ala Thr Pro Phe Ile Asn Val Thr Asp
145                 150                 155                 160

Pro Thr Leu Leu Asn Gly Ser Tyr Gln Ile Pro Ser Ser Thr Pro Ser
                    165                 170                 175

Gly Lys Thr Gly Arg His Leu Ile Tyr Val Ile Trp Arg Thr Asp
                180                 185                 190

Ser Pro Glu Ala Phe Tyr Ser Cys Ser Asp Val Asp Phe Asp Val Ala
    195                 200                 205

Leu Pro Leu Tyr Ser Ser Thr
    210                 215

<210> SEQ ID NO 201
<211> LENGTH: 216
<212> TYPE: PRT
<213> ORGANISM: Polypodium formosanum

<400> SEQUENCE: 201

Met Lys Arg Ser Trp Gly Val Ala Ala Ile Val Met Ala Leu Ser Thr
1               5                   10                  15

Cys Gly Leu Ile Gly Val Ala Ser Gly His Gly Ser Met Gly Asp Pro
                20                  25                  30

Ile Ser Arg Val Tyr Arg Cys Tyr Arg Glu Asn Pro Glu Arg Pro Thr
            35                  40                  45

Ser Pro Ala Cys Ile Ala Ala Val Ala Leu Ser Gly Lys Gln Ala Phe
    50                  55                  60

Tyr Asp Trp Asn Ala Val Asn Leu Phe Asn Ala Asn Gly Arg His Arg
65                  70                  75                  80

Glu Leu Ile Pro Asp Gly Gln Leu Cys Ser Ala Gly Arg Ala Lys Tyr
                    85                  90                  95

Lys Gly Leu Asp Leu Pro Arg Ala Asp Trp Leu Ala Thr Ser Leu Ser
                100                 105                 110

Ser Gly Val Asn Phe Thr Phe Leu Tyr Arg Val Thr Ala Arg His Leu
                115                 120                 125

Gly Tyr Phe Glu Phe Tyr Val Thr Arg Asp Gly Tyr Asp Pro Ser Glu
    130                 135                 140

Pro Leu Ala Trp Ala Asp Leu Glu Asp Ser Pro Phe Ile Lys Ile Thr
145                 150                 155                 160

Asn Pro Ser Val Val Ser Asn Ser Tyr Val Ile Pro Gly Ile Thr Pro
                    165                 170                 175

Ala Gly Lys Thr Gly Arg His Leu Ile Tyr Val Ile Trp Gln Arg Thr
                180                 185                 190

Asp Ser Gln Glu Ala Phe Tyr Ser Cys Ser Asp Ile Asp Phe Asp Glu
    195                 200                 205
```

```
Ala Val Pro Leu Tyr Ser Thr Thr
        210             215

<210> SEQ ID NO 202
<211> LENGTH: 214
<212> TYPE: PRT
<213> ORGANISM: Nephrolepis obliterata (Sunjest)

<400> SEQUENCE: 202

Met Gly Arg Ser Trp Gly Val Val Ala Ile Met Val Cys Ala Cys
1               5                   10                  15

Gly Leu Leu Ser Val Val Arg Gly His Gly Ser Met Glu Asp Pro Ile
            20                  25                  30

Ser Arg Val Tyr Gly Cys Tyr Leu Glu Asn Pro Glu Ser Pro Lys Ser
        35                  40                  45

Ala Ala Cys Gln Ala Ala Val Ala Leu Ser Gly Thr Gln Ala Phe Tyr
    50                  55                  60

Asp Trp Asn Glu Val Asn Leu Pro Asp Val Ala Gly Arg His Arg Ala
65                  70                  75                  80

Val Ile Pro Asp Gly Gln Leu Cys Ser Ala Gly Arg Ala Lys Tyr Gln
                85                  90                  95

Gly Leu Asn Leu Ala Arg Ala Asp Trp Pro Ala Thr Ser Leu Thr Ser
            100                 105                 110

Gly Val Ser Phe Thr Tyr Leu Tyr Lys Val Thr Ala Lys His Leu Gly
        115                 120                 125

Phe Phe Glu Phe Tyr Val Thr Gln Asp Gly Tyr Asp Pro Thr Glu Pro
    130                 135                 140

Leu Lys Trp Ala Asp Leu Glu Asp Leu Pro Phe Met Asn Val Thr Ser
145                 150                 155                 160

Thr Phe Asp Asp Glu Ser Tyr Gln Met Ser Gly Thr Thr Pro Ser Gly
                165                 170                 175

Lys Ala Gly Arg His Leu Ile Tyr Val Ile Trp Gln Arg Ser Asp Ser
            180                 185                 190

Pro Glu Ala Phe Tyr Ser Cys Ser Asp Val Asp Phe Val Asp Ala Val
        195                 200                 205

Ser Leu Arg Ser Thr Thr
    210

<210> SEQ ID NO 203
<211> LENGTH: 215
<212> TYPE: PRT
<213> ORGANISM: Deparia acrostichoides

<400> SEQUENCE: 203

Met Gly Arg Ser Trp Gly Val Val Ala Ile Met Val Leu Cys Ala Ser
1               5                   10                  15

Gly Leu Leu Gly Val Ala Ser Gly His Gly Ser Met Glu Gly Pro Ile
            20                  25                  30

Ser Arg Val Leu Asn Cys Tyr Leu Glu Asn Pro Glu Arg Pro Thr Ser
        35                  40                  45

Gly Ala Cys Ile Ala Ala Val Ala Leu Gly Gly Thr Gln Pro Phe Tyr
    50                  55                  60

Asp Trp Asn Glu Val Asn Leu Ala Asp Ala Asp Gly Arg His Arg Glu
65                  70                  75                  80

Leu Ile Pro Asp Gly Gln Leu Cys Ser Ala Gly Arg Glu Lys Phe Lys
                85                  90                  95
```

Gly Leu Asp Leu Ala Arg Ser Asp Trp Pro Ala Thr Ser Leu Ser Ser
            100                 105                 110

Gly Val Ala Phe Thr Tyr Leu Tyr Lys Ala Thr Ala Pro His Ala Gly
            115                 120                 125

Phe Phe Glu Phe Tyr Val Thr Arg Asp Gly Tyr Lys Pro Thr Glu Pro
            130                 135                 140

Leu Lys Trp Ala Asp Leu Glu Glu Pro Pro Phe Ile Asn Val Thr Asp
145                 150                 155                 160

Pro Lys Leu Val Ser Gly Ser Tyr Gln Ile Pro Gly Thr Thr Pro Ala
            165                 170                 175

Gly Lys Ala Gly Arg His Leu Ile Tyr Val Ile Trp Gln Arg Ser Asp
            180                 185                 190

Ser Pro Glu Ala Phe Tyr Ser Cys Ser Asp Val Asp Phe Val Glu Ala
            195                 200                 205

Leu Ser Leu His Ser Thr Thr
            210                 215

<210> SEQ ID NO 204
<211> LENGTH: 216
<212> TYPE: PRT
<213> ORGANISM: Aglaomorpha sp. (Roberts)

<400> SEQUENCE: 204

Met Arg Arg Ser Trp Pro Gly Val Val Ala Ile Met Val Val Cys Ala
1               5                   10                  15

Cys Gly Leu Leu Gly Val Ala Ser Gly His Gly Ser Met Gln Asp Pro
            20                  25                  30

Ile Ser Arg Val Tyr Arg Cys Arg Leu Glu Asn Pro Glu Arg Pro Thr
        35                  40                  45

Ser Ala Ala Cys Ile Ala Ala Val Ala Leu Ser Gly Thr Gln Ala Phe
    50                  55                  60

Tyr Asp Trp Asn Glu Val Asn Gln Pro Phe Ala Asn Gly Arg His Arg
65                  70                  75                  80

Glu Ile Ile Pro Asp Gly Gln Leu Cys Ser Ala Gly Arg Ala Lys Tyr
                85                  90                  95

Arg Gly Leu Asp Leu Ala Arg Ala Asp Trp Leu Ala Pro Ser Leu Ser
            100                 105                 110

Ser Gly Val Asp Tyr Thr Phe Leu Tyr Ile Ala Thr Ala Pro His Leu
            115                 120                 125

Gly Tyr Phe Glu Phe Tyr Ile Thr Arg Asp Ser Tyr Asp Pro Thr Glu
            130                 135                 140

Pro Leu Lys Trp Ser Asp Leu Glu Asp Ser Pro Phe Ile Asn Val Thr
145                 150                 155                 160

Asn Pro Ser Leu Val Ser Gly Ser Tyr Gln Ile Pro Gly Thr Thr Pro
            165                 170                 175

Ser Asn Lys Thr Gly Arg His Leu Met Tyr Val Ile Trp Gln Arg Thr
            180                 185                 190

Asp Ser Pro Glu Ala Phe Tyr Ala Cys Ser Asp Val Asp Phe Asp Val
            195                 200                 205

Ala Leu Pro Leu Tyr Ser Thr Thr
            210                 215

<210> SEQ ID NO 205
<211> LENGTH: 215
<212> TYPE: PRT

<213> ORGANISM: Polypodium attenuatum (Falax)

<400> SEQUENCE: 205

Met Gly Lys Gly Trp Glu Val Val Gly Ile Met Val Val Cys Ala Cys
1               5                   10                  15

Gly Leu Leu Gly Val Ala Ser Gly His Gly Thr Met Glu Asp Pro Ile
            20                  25                  30

Ser Arg Val Tyr Arg Cys Arg Leu Glu Asn Pro Glu Arg Pro Thr Ser
        35                  40                  45

Pro Ala Cys Ile Ala Ala Val Ala Leu Ser Gly Thr Gln Ala Phe Tyr
    50                  55                  60

Asp Trp Asn Glu Val Asn Leu Pro Phe Ala Ala Gly Arg His Arg Glu
65                  70                  75                  80

Ile Ile Pro Asp Gly Gln Leu Cys Ser Ala Gly Arg Ala Lys Tyr Arg
                85                  90                  95

Gly Leu Asp Leu Ala Arg Asp Asp Trp Leu Ala Thr Ser Leu Ser Ser
            100                 105                 110

Gly Val Asp Tyr Thr Phe Val Tyr Arg Val Thr Ala Pro His Arg Gly
        115                 120                 125

Tyr Phe Glu Phe Tyr Val Thr Arg Asp Thr Tyr Asp Pro Thr Glu Pro
130                 135                 140

Leu Lys Trp Ser Asp Leu Glu Pro Pro Phe Ile Asn Val Thr Gln
145                 150                 155                 160

Pro Ser Leu Val Ser Gly Ser Tyr Gln Ile Pro Gly Ala Thr Pro Thr
                165                 170                 175

Gly Lys Thr Gly Arg His Leu Ile Tyr Val Ile Trp Gln Arg Thr Asp
            180                 185                 190

Ser Pro Glu Ala Phe Tyr Ser Cys Ser Asp Val Asp Phe Gly Glu Ala
        195                 200                 205

Leu Arg Leu Asp Ala Thr Ala
    210                 215

<210> SEQ ID NO 206
<211> LENGTH: 215
<212> TYPE: PRT
<213> ORGANISM: Arachniodes simplicior (variegata)

<400> SEQUENCE: 206

Met Gly Arg Ser Trp Gly Val Val Ala Ile Ile Val Leu Cys Ala Ser
1               5                   10                  15

Gly Leu Leu Gly Val Ala Ser Gly His Gly Ser Met Glu Asp Pro Ile
            20                  25                  30

Ser Arg Val Tyr Asn Cys Phe Leu Glu Gly Pro Glu Asn Pro Thr Ser
        35                  40                  45

Asp Ala Cys Ile Ala Ala Val Ala Leu Ser Gly Thr Gln Ala Phe Tyr
    50                  55                  60

Asp Trp Thr Glu Val Asn Leu Ala Asp Ala Asp Gly His His Arg Glu
65                  70                  75                  80

Leu Ile Pro Asp Gly Gln Leu Cys Ser Ala Gly Arg Asp Lys Tyr Lys
                85                  90                  95

Gly Leu Asp Leu Ala Arg Ser Asp Trp Thr Ala Thr Ser Leu Ser Ser
            100                 105                 110

Gly Val Asp Tyr Thr Phe Leu Phe Lys Ala Thr Ala Pro His Leu Gly
        115                 120                 125

Ser Phe Glu Phe Tyr Val Thr Val Asp Gly Tyr Glu Pro Thr Glu Pro

```
              130                 135                 140
Leu Lys Trp Ala Asp Leu Glu Ala Thr Pro Phe Ile Asn Val Thr Asp
145                 150                 155                 160

Pro Thr Leu Asp Ser Gly Ser Tyr Gln Ile Pro Gly Thr Thr Pro Ala
                165                 170                 175

Gly Lys Thr Gly Arg His Leu Ile Tyr Val Ile Trp Gln Arg Ser Asp
            180                 185                 190

Ser Ala Glu Ala Phe Tyr Ser Cys Ser Asp Val Asp Phe Thr Asp Ala
        195                 200                 205

Leu Ser Leu His Ser Thr Thr
    210                 215

<210> SEQ ID NO 207
<211> LENGTH: 216
<212> TYPE: PRT
<213> ORGANISM: Campyloneurum angustifolium

<400> SEQUENCE: 207

Met Arg Arg Ser Trp Glu Val Val Gly Met Met Val Leu Cys Ala Cys
1               5                   10                  15

Gly Leu Leu Gly Val Ala Ser Gly His Gly Ser Met Glu Asp Pro Ile
            20                  25                  30

Ser Arg Val Tyr Arg Cys Arg Leu Glu Gly Pro Glu Arg Pro Thr Ser
        35                  40                  45

Pro Ala Cys Ile Ala Ala Val Ala Val Asn Gly Thr Gln Ala Phe Tyr
    50                  55                  60

Asp Trp Asn Glu Val Asn Gln Pro Phe Ala Ala Gly Arg His Arg Glu
65                  70                  75                  80

Ile Ile Pro Asp Gly Gln Leu Cys Ser Ala Gly Arg Asp Lys Tyr Lys
                85                  90                  95

Gly Leu Asp Leu Ala Arg Ala Asp Trp Leu Ala Val Ser Leu Ser Ser
            100                 105                 110

Gly Ala Asp Tyr Thr Phe Leu Tyr Leu Ala Thr Ala Thr His Arg Gly
        115                 120                 125

Tyr Phe Glu Phe Tyr Val Thr Arg Asp Ser Tyr Asp Pro Thr Glu Pro
    130                 135                 140

Leu Lys Trp Ser Asp Leu Glu Asp Ser Pro Phe Ile Asn Val Thr Asp
145                 150                 155                 160

Pro Thr Glu Val Gly Pro Val Tyr Gln Ile Pro Gly Thr Thr Pro Ala
                165                 170                 175

Gly Lys Thr Gly Arg His Leu Ile Tyr Val Ile Trp Gln Arg Thr Asp
            180                 185                 190

Ser Pro Glu Ala Phe Tyr Ser Cys Ser Asp Val Asp Phe Gly Glu Ser
        195                 200                 205

Leu Ser Leu Tyr Ser Val Thr Glu
    210                 215

<210> SEQ ID NO 208
<211> LENGTH: 215
<212> TYPE: PRT
<213> ORGANISM: Colysis wrightii (Ching)

<400> SEQUENCE: 208

Met Arg Lys Ser Leu Glu Val Val Ala Ile Met Val Ala Val Cys Ala
1               5                   10                  15

Ser Gly Leu Leu Gly Val Ala Ser Gly His Gly Thr Met Leu Asp Pro
```

```
            20                  25                  30
Ile Ser Arg Val Tyr Arg Cys Tyr Leu Glu Asn Pro Glu Arg Pro Thr
        35                  40                  45

Ser Pro Ala Cys Ile Ala Ala Val Ala Leu Ser Gly Lys Gln Ala Phe
    50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Asp Lys Tyr
                85                  90                  95

Lys Gly Leu Asp Gln Ala Arg Asp Asp Trp Leu Ala Thr Ser Leu Pro
            100                 105                 110

Ser Gly Ala Asn Tyr Ile Phe Arg Phe Glu Val Thr Ala Val His Arg
        115                 120                 125

Gly Tyr Phe Glu Phe Tyr Val Thr Arg Asp Gly Tyr Asp Pro Thr Gln
    130                 135                 140

Pro Leu Ala Trp Ala Asp Leu Glu Asp Ser Pro Phe Leu Thr Thr Thr
145                 150                 155                 160

Thr Thr Leu Asp Ser Ser Ser Tyr Ile Ile Pro Gly Thr Thr Pro Ala
                165                 170                 175

Gly Lys Thr Gly Arg His Leu Ile Tyr Leu Ile Trp Gln Arg Thr Asp
            180                 185                 190

Ser Pro Glu Ala Phe Tyr Ser Cys Ser Asp Val Asp Phe Glu Glu Ala
        195                 200                 205

Ile Ser Leu Ser Ser Thr Thr
    210                 215

<210> SEQ ID NO 209
<211> LENGTH: 246
<212> TYPE: PRT
<213> ORGANISM: Colysis wrightii (Ching)

<400> SEQUENCE: 209

Met Gly Arg Ser Trp Val Val Ala Ile Met Val Thr Val Cys Ala
1               5                   10                  15

Ser Gly Leu Leu Gly Phe Ala Ser Gly His Gly Ser Met Gly Asp Pro
            20                  25                  30

Ile Ser Arg Val Leu Arg Cys Arg Glu Glu Asn Pro Glu Asn Pro Thr
        35                  40                  45

Ser Pro Ala Cys Ile Ala Ala Val Ala Leu Ser Gly Lys Gln Ala Phe
    50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Ala Lys Tyr
                85                  90                  95

Lys Gly Leu Asp Leu Ala Arg Asp Asp Trp Leu Ala Thr Pro Leu Pro
            100                 105                 110

Ser Gly Ala Ala Tyr Thr Phe Arg Tyr Arg Val Thr Ala Ala His Arg
        115                 120                 125

Gly Tyr Phe Glu Phe Tyr Val Thr Arg Asp Gly Tyr Asp Pro Thr Gln
    130                 135                 140

Pro Leu Ala Trp Ala Asp Leu Glu Asp Ser Pro Phe Leu Thr Thr Thr
145                 150                 155                 160

Thr Thr Leu Asp Ser Ser Ser Tyr Ile Ile Pro Gly Thr Thr Pro Ala
                165                 170                 175
```

```
Gly Lys Thr Gly Arg His Leu Ile Tyr Leu Ile Trp Gln Arg Thr Asp
            180                 185                 190

Ser Pro Glu Ala Phe Tyr Ser Cys Ser Asp Val Asp Phe Glu Glu Ala
        195                 200                 205

Ile Ser Leu Ser Ser Thr Thr Leu Ser Leu Ala Gly Gly Leu Ser Gly
210                 215                 220

Met Ala Thr Tyr Cys Lys Gly His Ala Ala Ala Pro Val Leu Thr Trp
225                 230                 235                 240

Arg Met Glu Cys Cys Cys
                245

<210> SEQ ID NO 210
<211> LENGTH: 216
<212> TYPE: PRT
<213> ORGANISM: Platycerium elephantotis

<400> SEQUENCE: 210

Met Arg Arg Ser Trp Gly Val Val Ala Val Met Leu Ala Ile Cys Ala
1               5                   10                  15

Ser Gly Leu Leu Gly Val Ala Ser Gly His Gly Ser Met Leu Asp Pro
            20                  25                  30

Ile Ser Arg Val Tyr Thr Cys Tyr Leu Glu Asn Pro Glu Arg Pro Thr
        35                  40                  45

Ser Ala Ala Cys Ile Ala Ala Val Ala Val Ser Gly Ser Gln Ala Phe
    50                  55                  60

Tyr Asp Trp Asn Glu Val Asn Leu Ala Asp Ala Asp Gly Gln His Arg
65                  70                  75                  80

Gln Leu Ile Pro Asp Gly Lys Leu Cys Ser Ala Gly Arg Glu Lys Tyr
                85                  90                  95

Arg Gly Leu Asp Leu Ala Arg Asp Asp Trp Pro Ala Thr Ser Leu Ser
            100                 105                 110

Ser Gly Val Asn Tyr Thr Phe Leu Tyr Arg Ala Thr Ala Pro His Leu
        115                 120                 125

Gly Phe Phe Glu Phe Tyr Val Thr Arg Asp Ser Tyr Asp Pro Thr Gln
    130                 135                 140

Pro Leu Ala Trp Ala Asp Leu Glu Asp Pro Pro Phe Ile Asn Ile Thr
145                 150                 155                 160

Asp Pro Thr Leu Ala Ser Gly Ser Tyr Gln Ile Val Asn Thr Thr Pro
                165                 170                 175

Ser Asn Lys Thr Gly Arg His Leu Ile Tyr Val Ile Trp Gln Arg Thr
            180                 185                 190

Asp Ser Pro Glu Ala Phe Tyr Ser Cys Ser Asp Val Asp Phe Asp Glu
        195                 200                 205

Asp Asp Ser Leu Leu Ser Ala Val
    210                 215

<210> SEQ ID NO 211
<211> LENGTH: 215
<212> TYPE: PRT
<213> ORGANISM: Platycerium madagascariense

<400> SEQUENCE: 211

Met Arg Arg Ser Trp Gly Val Val Ala Val Ile Leu Ala Met Cys Ala
1               5                   10                  15

Gly Ser Leu Leu Gly Val Ala Ser Gly His Gly Ser Met Glu Asp Pro
            20                  25                  30
```

-continued

```
Ile Ser Arg Val Tyr Ala Cys Phe Leu Glu Asn Pro Glu Arg Pro Thr
        35                  40                  45

Ser Ala Ala Cys Ile Ala Ala Val Ala Leu Ser Gly Thr Gln Ala Phe
 50                  55                  60

Tyr Asp Trp Asn Glu Val Asn Gln Pro Asn Ala Ala Gly Asn His Thr
 65                  70                  75                  80

Ile Ile Pro Asp Gly Gln Leu Cys Ser Ala Gly Arg Glu Lys Tyr Lys
                 85                  90                  95

Gly Leu Asp Leu Pro Arg Ala Asp Trp Ser Ala Ile Ser Leu Ser Ser
                100                 105                 110

Gly Val Asn Tyr Thr Phe Leu Tyr Lys Ala Thr Ala Pro His Arg Gly
                115                 120                 125

Tyr Phe Glu Phe Tyr Val Thr Arg Asp Ser Tyr Asp Pro Thr Glu Pro
        130                 135                 140

Leu Ala Trp Ala Asp Leu Glu Asp Thr Pro Phe Ile Asn Ile Thr Asp
145                 150                 155                 160

Pro Asp Leu Val Ser Gly Ser Tyr Arg Ile Ala Asn Thr Thr Pro Ser
                165                 170                 175

Gly Lys Thr Gly Arg His Leu Ile Tyr Val Ile Trp Gln Arg Thr Asp
                180                 185                 190

Ser Pro Glu Ala Phe Tyr Ser Cys Ser Asp Val Val Phe Asp Glu Asp
        195                 200                 205

Val Ser Leu Val Ser Ala Ala
        210                 215

<210> SEQ ID NO 212
<211> LENGTH: 216
<212> TYPE: PRT
<213> ORGANISM: Microsorum musifolium (Blume)

<400> SEQUENCE: 212

Met Arg Arg Ser Trp Gly Val Leu Ala Ile Val Val Ala Val Cys Ala
 1                   5                  10                  15

Ser Gly Leu Phe Gly Val Ala Ser Gly His Gly Ser Met Glu His Pro
                 20                  25                  30

Ile Ser Arg Val Tyr Gln Cys Tyr Arg Glu Gly Pro Glu Asn Pro Lys
        35                  40                  45

Ser Pro Ala Cys Ile Ala Ala Lys Gly Leu Ser Gly Ala Gln Ala Phe
 50                  55                  60

Tyr Asp Trp Asn Glu Val Asn Gln Pro Phe Ala Asp Gly Arg His Gln
 65                  70                  75                  80

Glu Ile Ile His Asp Gly His Leu Cys Ser Gly Gly Arg Asp Lys Tyr
                 85                  90                  95

Arg Gly Leu Asp Leu Pro Arg Ala Asp Trp Val Ala Thr Ser Leu Ser
                100                 105                 110

Ala Gly Lys Pro Tyr Thr Phe Leu Tyr Arg Ala Thr Ala Pro His Leu
                115                 120                 125

Gly Tyr Phe Gln Phe Tyr Val Thr Arg Asp Gly Tyr Asn Pro Thr Lys
        130                 135                 140

Pro Leu Ala Trp Ala Asp Leu Glu Asp Ser Pro Phe Ile Asn Val Thr
145                 150                 155                 160

Asn Pro Thr Leu Val Ser Gly Ser Tyr Arg Ile Pro His Thr Thr Pro
                165                 170                 175

Ala Ser Lys Thr Gly Arg His Leu Ile Tyr Val Ile Trp Gln Arg Thr
                180                 185                 190
```

Asp Ser Pro Glu Ala Phe Tyr Ser Cys Ser Asp Val Val Phe Asp Glu
        195                 200                 205

Ala Leu Ser Leu Ser Ser Thr Ile
        210                 215

<210> SEQ ID NO 213
<211> LENGTH: 219
<212> TYPE: PRT
<213> ORGANISM: Lygodium flexuosum

<400> SEQUENCE: 213

Met Gly Ser Trp Gln Trp Gly Ser Val Asn Val Ala Ile Val Val Phe
1               5                   10                  15

Met Met Leu Cys Gly Val Ala Ser Gly His Gly Thr Met Gly Asp Pro
            20                  25                  30

Ile Ser Arg Val Tyr Arg Cys Tyr Leu Glu Asn Pro Glu Arg Pro Thr
        35                  40                  45

Ser Ala Ala Cys Gln Ala Ala Val Ala Leu Ser Gly Thr Gln Ala Phe
    50                  55                  60

Tyr Asp Trp Asn Glu Val Asn Leu Pro Asn Ala Ala Gly Arg His Arg
65                  70                  75                  80

Gln Leu Ile Pro Asp Gly Gln Leu Cys Ser Ala Gly Arg Ala Lys Tyr
                85                  90                  95

Gln Gly Leu Asp Leu Ala Arg Ala Asp Trp Leu Ala Ala Ser Leu Ser
            100                 105                 110

Ser Gly Val Ser Tyr Thr Phe Leu Tyr Arg Val Thr Ala Gln His Arg
        115                 120                 125

Gly Phe Phe Glu Phe Tyr Val Thr Arg Asp Gly Tyr Glu Pro Thr Glu
    130                 135                 140

Pro Leu Lys Trp Ser Asp Leu Glu Glu Ser Pro Phe Ile Asn Val Thr
145                 150                 155                 160

Asp Pro Thr Ala Val Ser Gly Ser Tyr Gln Ile Pro Gly Thr Thr Pro
                165                 170                 175

Ala Gly Lys Ser Gly Arg His Leu Ile Tyr Val Ile Trp Gln Arg Ser
            180                 185                 190

Asp Ser Pro Glu Ala Phe Tyr Ser Cys Ser Asp Val Asp Phe Asp Val
        195                 200                 205

Glu Gly Ala Ala Val Ser Leu Arg Ser Thr Thr
    210                 215

<210> SEQ ID NO 214
<211> LENGTH: 215
<212> TYPE: PRT
<213> ORGANISM: Polystichum polyblepharum

<400> SEQUENCE: 214

Met Asn Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Asn Cys Arg Leu Glu Asn Pro Glu Ser Pro Thr Ser
        35                  40                  45

Ala Ala Cys Ile Ala Val Ala Leu Ser Gly Thr Gln Ala Phe Tyr
    50                  55                  60

Asp Trp Asn Glu Val Asn Leu Ala Asn Val Ala Gly Arg His Arg Glu
65                  70                  75                  80

```
Leu Ile Pro Asp Gly Lys Leu Cys Ser Ala Gly Arg Asp Lys Tyr Lys
                85                  90                  95

Gly Leu Asp Leu Ala Arg Ser Asp Trp Val Ala Thr Asn Leu Ser Ser
            100                 105                 110

Gly Val Ala Phe Thr Phe Leu Tyr Arg Val Thr Ala Gln His Arg Gly
        115                 120                 125

Phe Phe Glu Phe Tyr Val Thr Val Asp Asp Tyr Asp Pro Thr Glu Leu
    130                 135                 140

Leu Lys Trp Glu Asp Leu Glu Glu Thr Pro Phe Met Asn Val Thr Asp
145                 150                 155                 160

Pro Thr Leu Val Gly Leu Asn Tyr Glu Met Pro Gly Thr Thr Pro Ala
                165                 170                 175

Asn Lys Thr Gly Arg His Leu Ile Tyr Val Ile Trp Gln Arg Ser Asp
            180                 185                 190

Ser Pro Glu Ala Phe Tyr Ser Cys Ser Asp Val Asp Phe Val Asp Ala
        195                 200                 205

Val Ser Leu His Ser Ser Thr
    210                 215

<210> SEQ ID NO 215
<211> LENGTH: 218
<212> TYPE: PRT
<213> ORGANISM: Diplazium pycnocarpon

<400> SEQUENCE: 215

Met Gly Lys Ser Trp Gly Val Val Ala Ile Ile Leu Val Leu Cys Ala
1               5                   10                  15

Ser Gly Leu Leu Gly Val Ala Ser Gly His Gly Ser Met Ala Asp Pro
            20                  25                  30

Ile Ser Arg Ile Tyr Asn Cys Arg Gln Glu Asn Pro Glu Arg Pro Thr
        35                  40                  45

Ser Ala Ala Cys Gln Ala Ala Val Ala Leu Ser Gly Thr Gln Ala Phe
    50                  55                  60

Tyr Asp Trp Asn Glu Val Asn Gln Pro Asn Ala Ala Gly Arg His Arg
65                  70                  75                  80

Glu Ile Ile Pro Asp Gly Gln Leu Cys Ser Ala Gly Arg Tyr Lys Tyr
                85                  90                  95

Arg Gly Leu Asp Leu Ala Ser Ala Asp Trp Gln Trp Pro Ala Thr Ser
            100                 105                 110

Leu Ser Ser Gly Val Ser Phe Thr Tyr Arg Tyr Arg Ala Thr Ala Ala
        115                 120                 125

His Tyr Gly Tyr Phe Gln Phe Tyr Ile Thr Arg Asp Gly Tyr Gln Pro
    130                 135                 140

Thr Gln Pro Leu Lys Trp Ala Asp Leu Glu Gln Leu Pro Phe Leu Thr
145                 150                 155                 160

Val Tyr Asn Pro Thr Leu Val Asn Gly Phe Tyr Glu Met Gln Gly Thr
                165                 170                 175

Thr Pro Ala Gly Lys Thr Gly Arg His Leu Ile Tyr Val Ile Trp Gln
            180                 185                 190

Arg Ser Asp Ser Pro Glu Ala Phe Tyr Ser Cys Ser Asp Val Asp Phe
        195                 200                 205

Val Gly Ala Leu Ser Leu His Ser Thr Thr
    210                 215
```

```
<210> SEQ ID NO 216
<211> LENGTH: 216
<212> TYPE: PRT
<213> ORGANISM: Polystichum braunii

<400> SEQUENCE: 216

Met Gly Arg Ser Trp Gly Val Val Ala Ile Met Val Leu Cys Ala Ser
1               5                   10                  15

Gly Leu Leu Gly Ala Ala Ser Gly His Gly Thr Met Tyr Asp Pro Phe
            20                  25                  30

Ser Arg Val Tyr Asn Cys Arg Phe Arg Glu Asn Pro Glu Arg Pro Thr
        35                  40                  45

Ser Ala Ala Cys Ile Ala Ala Val Ala Leu Ser Gly Thr Gln Ala Phe
    50                  55                  60

Tyr Asp Trp Asn Glu Val Asn Leu Ala Asn Ala Ala Gly Arg His Arg
65                  70                  75                  80

Glu Leu Ile Pro Asp Gly Lys Leu Cys Ser Ala Gly Arg Asp Lys Tyr
                85                  90                  95

Lys Gly Leu Asp Leu Ala Arg Ser Asp Trp Val Ala Thr Asn Leu Ser
            100                 105                 110

Ser Gly Val Ala Phe Thr Phe Leu Tyr Arg Val Thr Ala Gln His Arg
        115                 120                 125

Gly Phe Phe Glu Phe Tyr Val Thr Val Asp Asp Tyr Asp Pro Thr Glu
    130                 135                 140

Ser Leu Lys Trp Glu Asp Leu Glu Glu Thr Pro Phe Leu Asn Val Thr
145                 150                 155                 160

Asp Pro Thr Val Val Gly Val Asn Tyr Gln Ile Ser Gly Thr Thr Pro
                165                 170                 175

Ala Ser Lys Thr Gly Arg His Leu Ile Tyr Val Ile Trp Gln Arg Ser
            180                 185                 190

Asp Ser Pro Glu Ala Phe Tyr Ser Cys Ser Asp Val Asp Phe Val Asp
        195                 200                 205

Ala Leu Ser Leu Gln Ser Thr Thr
    210                 215

<210> SEQ ID NO 217
<211> LENGTH: 215
<212> TYPE: PRT
<213> ORGANISM: Platycerium hillii

<400> SEQUENCE: 217

Met Gly Lys Pro Trp Arg Val Val Ala Ile Val Val Cys Ala
1               5                   10                  15

Ser Gly Leu Leu Gly Val Ala Ser Gly His Gly Ser Met Gly Glu Pro
            20                  25                  30

Ile Ser Arg Val Tyr Asn Cys Tyr Leu Glu Asn Pro Glu Arg Pro Thr
        35                  40                  45

Ser Ala Ala Cys Ile Ala Ala Val Ala Leu Ser Gly Thr Gln Ala Phe
    50                  55                  60

Tyr Asp Trp Asn Glu Val Asn Leu Pro Phe Ala Ala Gly Arg His Arg
65                  70                  75                  80

Glu Leu Ile Pro Asp Gly Gln Leu Cys Ser Ala Gly Arg Asp Lys Tyr
                85                  90                  95

Lys Gly Leu Asp Leu Ala Arg Ala Asp Trp Val Ala Thr Ser Leu Ser
            100                 105                 110

Ser Gly Val Ser Tyr Thr Phe Leu Tyr Arg Val Thr Ala Pro His Arg
```

-continued

```
                115                 120                 125
Gly Tyr Phe Glu Phe Tyr Val Thr Lys Asp Ser Tyr Asp Pro Thr Glu
    130                 135                 140

Pro Leu Ala Trp Ala Asp Leu Glu Asp Thr Pro Phe Ile Asn Ile Thr
145                 150                 155                 160

Asp Pro Thr Ile Val Ser Gly Ser Tyr Gln Ile Ser Ser Thr Thr Pro
                165                 170                 175

Ser Asp Lys Thr Gly Arg His Leu Ile Tyr Val Ile Trp Gln Arg Thr
                180                 185                 190

Asp Ser Pro Glu Ala Phe Tyr Ser Cys Ser Asp Ile Asp Phe Asp Asp
                195                 200                 205

Thr Leu Pro Leu His Ser Thr
    210                 215
```

<210> SEQ ID NO 218
<211> LENGTH: 227
<212> TYPE: PRT
<213> ORGANISM: Drynaria rigidula (whitei)

<400> SEQUENCE: 218

```
Met Gly Arg Thr Tyr Ser Trp Gly Ala Val Ala Val Met Val Val Leu
1               5                   10                  15

Cys Ala Ser Gly Leu Leu Gly Ile Ala Ser Gly His Gly Ser Met Asp
                20                  25                  30

Ser Pro Ile Ser Arg Val Tyr Arg Cys Tyr Leu Glu Asn Pro Glu Asn
                35                  40                  45

Pro Thr Ser Ala Ala Cys Gln Ala Val Ala Leu Ser Gly Thr Gln
    50                  55                  60

Ala Phe Tyr Asp Trp Asn Glu Val Asn Ile Ala Asp Ala Ala Gly Arg
65                  70                  75                  80

His Arg Glu Leu Ile Pro Asp Gly Gln Leu Cys Ser Ala Gly Arg Glu
                85                  90                  95

Lys Tyr Gln Gly Leu Asp Leu Ala Arg Ala Asp Trp Leu Ala Asp Ser
                100                 105                 110

Leu Ser Ser Gly Val Ser Phe Thr Phe Leu Tyr Lys Ala Thr Ala Ala
                115                 120                 125

His Leu Gly Phe Phe Glu Phe Tyr Val Thr Arg Asp Ala Tyr Asp Pro
    130                 135                 140

Thr Glu Pro Leu Lys Trp Ala Asp Leu Glu Asp Ser Pro Phe Leu Asn
145                 150                 155                 160

Val Thr Asp Pro Thr Leu Val Ser Gly Tyr Tyr Gln Ile Pro Gly Thr
                165                 170                 175

Thr Pro Ala Gly Lys Ser Gly Arg His Leu Leu Tyr Val Ile Trp Gln
                180                 185                 190

Arg Ser Asp Ser Pro Glu Ala Phe Tyr Ser Cys Ser Asp Val Asp Phe
                195                 200                 205

Asp Asp Asp Ala Ala Ala Gln His Met Ile Ile Ser Leu Arg His
    210                 215                 220

Ser Thr Thr
225
```

<210> SEQ ID NO 219
<211> LENGTH: 229
<212> TYPE: PRT
<213> ORGANISM: Adiantum monocolor

<400> SEQUENCE: 219

```
Met Gly Met Lys Met Ser Trp Glu Val Ala Leu Ala Glu Ile Val Ala
1               5                   10                  15
Leu Cys Leu Leu Gly Met Ala Ser Ser His Gly Thr Met Gln Asp Pro
            20                  25                  30
Ile Ser Arg Val Tyr Asn Cys Phe Leu Glu Asn Pro Glu Arg Pro Thr
        35                  40                  45
Ser Ala Ala Cys Gln Ala Ala Val Ala Leu Gly Gly Thr Gln Pro Leu
    50                  55                  60
Tyr Asp Trp Asn Glu Val Asn Ile His Asp Ala Ala Gly Asn His Arg
65                  70                  75                  80
Asp Leu Ile Pro Asp Gly Lys Leu Cys Ser Ala Gly Arg Gln Lys Phe
                85                  90                  95
Gln Gly Leu Asp Leu Ala Arg Ala Asp Trp Ile Ala Thr Ser Leu Ser
            100                 105                 110
Ser Gly Val Asp Tyr Thr Phe Leu Tyr Arg Ala Thr Ala Pro His Leu
        115                 120                 125
Gly Phe Phe Glu Phe Tyr Ile Thr Arg Asp Tyr Asp Pro Thr Gln
    130                 135                 140
Pro Leu Ala Trp Gly Asp Leu Glu Asp Ser Pro Phe Ile Asn Ile Thr
145                 150                 155                 160
Asn Pro Ser Ile Val Ser Thr Thr Leu Gly Pro Ala Tyr Ser Ile Pro
                165                 170                 175
Ser Thr Thr Pro Phe Ser Lys Ser Gly Arg His Leu Ile Tyr Val Ile
            180                 185                 190
Trp Gln Arg Thr Asp Ser Leu Glu Ala Phe Tyr Ser Cys Ser Asp Val
        195                 200                 205
Asp Phe Ser Thr Ser Ile Glu Asp Val Ile Val Ser Leu Arg
    210                 215                 220
Ser Ala Ala Leu Leu
225
```

<210> SEQ ID NO 220
<211> LENGTH: 223
<212> TYPE: PRT
<213> ORGANISM: Pellaea rotundifolia

<400> SEQUENCE: 220

```
Met Gln Arg Ser Cys Met Trp Gly Glu Ser Val Val Ala Ile Met Cys
1               5                   10                  15
Met Val Leu Gly Leu Leu Gly Asp Val Ala Ser Gly His Gly Ser Met
            20                  25                  30
Ala Ser Pro Ile Ser Arg Val Phe Asn Cys Tyr Leu Glu Asn Pro Glu
        35                  40                  45
Ser Pro Thr Ser Glu Ala Cys Lys Ala Ala Val Glu Glu Ser Gly Thr
    50                  55                  60
Gln Ala Phe Tyr Asp Trp Ala Glu Val Ser Leu Pro Asn Ala Ala Gly
65                  70                  75                  80
Arg His Arg Glu Leu Ile Pro Asp Gly Gln Leu Cys Ser Ala Gly Leu
                85                  90                  95
Ala Lys Tyr Ala Gly Leu Asp Leu Ala Arg Ala Asp Trp Thr Ala Thr
            100                 105                 110
Ser Leu Thr Ser Asn Ile Ser Tyr Thr Phe Ile Phe Glu Ala Thr Ala
        115                 120                 125
```

```
Gly Pro His Leu Gly Ser Phe Glu Phe Tyr Val Thr Asn Asp Asp Tyr
    130                 135                 140

Glu Pro Ala Glu Ala Leu Asn Trp Ala Asp Leu Glu Asp Thr Pro Phe
145                 150                 155                 160

Ile Ile Val Thr Asn Pro Thr Leu Val Ser Gly Ser Tyr Leu Ile Pro
                165                 170                 175

Gly Thr Thr Pro Ala Gly Lys Thr Gly Arg His Ile Ile Tyr Val Ile
            180                 185                 190

Trp Gln Arg Ser Asp Ser Pro Glu Ala Phe Tyr Ser Cys Ser Asp Ile
        195                 200                 205

Asp Phe Val Glu Glu Asp Pro Val Val Pro Leu His Ser Thr Thr
210                 215                 220
```

<210> SEQ ID NO 221
<211> LENGTH: 216
<212> TYPE: PRT
<213> ORGANISM: Microsorum punctatum

<400> SEQUENCE: 221

```
Met Arg Arg Ser Trp Gly Val Leu Ala Ile Val Val Ala Val Cys Ala
1               5                   10                  15

Ser Gly Leu Phe Gly Val Ala Ser Gly His Gly Ser Met Glu Asp Pro
            20                  25                  30

Ile Ser Arg Val Tyr Gln Cys Tyr Asp Glu Gly Pro Glu Asn Pro Lys
        35                  40                  45

Ser Pro Ala Cys Ile Ala Ala Val Gly Leu Ser Gly Ala Gln Ala Phe
    50                  55                  60

Tyr Asp Trp Asn Glu Val Asn Gln Pro Phe Ala Ala Gly Gln His Lys
65                  70                  75                  80

Glu Ile Ile His Asp Gly His Leu Cys Ser Gly Gly Arg Asp Lys Tyr
                85                  90                  95

Arg Gly Leu Asp Leu Pro Arg Ala Asp Trp Val Ala Thr Ser Leu Ser
            100                 105                 110

Ala Gly Ala Pro Tyr Thr Phe Leu Tyr Arg Ala Thr Ala His His Leu
        115                 120                 125

Gly Tyr Phe Glu Phe Tyr Val Thr Arg Asp Gly Tyr Asp Pro Thr Lys
    130                 135                 140

Pro Leu Ala Trp Ala Asp Leu Glu Asp Ser Pro Phe Ile Asn Val Thr
145                 150                 155                 160

Asn Pro Pro Leu Val Ser Gly Ser Tyr Arg Ile Pro Asp Thr Thr Pro
                165                 170                 175

Ala Leu Lys Thr Gly Arg His Leu Ile Tyr Val Ile Trp Gln Arg Thr
            180                 185                 190

Asp Ser Pro Glu Ala Phe Tyr Ser Cys Ser Asp Val Val Phe Ala Glu
        195                 200                 205

Ala Leu Ser Leu Ser Ser Thr Thr
    210                 215
```

<210> SEQ ID NO 222
<211> LENGTH: 217
<212> TYPE: PRT
<213> ORGANISM: Woodwardia fimbriata

<400> SEQUENCE: 222

```
Met Gly Arg Ser Ile Trp Gly Val Val Ala Met Met Val Leu Cys Ala
1               5                   10                  15
```

Ser Gly Leu Leu Arg Ile Ala Ser Gly His Gly Ser Met Glu Asn Pro
            20                  25                  30

Ile Ser Arg Val Tyr Asn Cys Tyr Leu Glu Gly Pro Glu Asn Pro Lys
            35                  40                  45

Ser Ala Ala Cys Lys Ala Ala Val Ala Ala Ser Gly Thr Gln Ala Phe
50                  55                  60

Tyr Asp Trp Asn Glu Val Asn Leu Ala Asn Ala Ala Gly Arg His Arg
65                  70                  75                  80

Glu Leu Ile Pro Asp Gly Gln Leu Cys Ser Ala Gly Arg Gln Lys Tyr
            85                  90                  95

Gln Gly Leu Asp Leu Val Arg Ser Asp Trp Pro Ala Thr Ser Leu Ser
            100                 105                 110

Ser Gly Val Pro Phe Thr Phe Leu Tyr Arg Ile Thr Ala Gln His Leu
            115                 120                 125

Gly Phe Phe Glu Phe Tyr Val Thr Arg Asp Gly Tyr Gln Pro Thr Ala
        130                 135                 140

Ala Leu Thr Trp Ala Asp Leu Glu Asp Ser Pro Phe Met Asn Val Thr
145                 150                 155                 160

Gly Asp Pro Thr Phe Ile Thr Gly Ser Trp Glu Ile Pro Gly Thr Ser
            165                 170                 175

Pro Ala Gly Lys Ser Gly Arg His Leu Ile Tyr Val Ile Trp Gln Arg
            180                 185                 190

Ser Asp Ser Pro Glu Ala Phe Tyr Ala Cys Cys Asp Val Asp Phe Val
            195                 200                 205

Asp Ala Leu Ser Leu His Ser Thr Thr
210                 215

<210> SEQ ID NO 223
<211> LENGTH: 213
<212> TYPE: PRT
<213> ORGANISM: Dryopteris celsa

<400> SEQUENCE: 223

Met Gly Arg Ser Ser Leu Gly Val Val Ala Ile Met Val Leu Cys Leu
1               5                   10                  15

Val Gly Val Ala Ser Gly His Gly Ser Met Gln Asp Pro Ile Ser Arg
            20                  25                  30

Val Tyr Asn Cys Tyr Leu Glu Asn Pro Glu Ser Pro Thr Ser Ala Ala
            35                  40                  45

Cys Gln Ala Ala Val Ala Leu Ser Gly Thr Gln Ala Phe Tyr Asp Trp
50                  55                  60

Asn Glu Val Asn Gln Pro Glu Ala Asp Gly Arg Ser Arg Glu Ile Ile
65                  70                  75                  80

Pro Asp Gly Gln Leu Cys Ser Gly Gly Arg Glu Lys Tyr Gln Gly Leu
            85                  90                  95

Asp Leu Ala Arg Ser Asp Trp Glu Ala Thr Thr Leu Ser Ser Ser Val
            100                 105                 110

Asn Tyr Thr Phe Leu Tyr Lys Ala Thr Ala Pro His Leu Gly Phe Phe
            115                 120                 125

Glu Phe Tyr Val Thr Gln Asp Gly Tyr Asp Pro Thr Glu Val Leu Lys
        130                 135                 140

Trp Ala Asp Leu Glu Asp Ser Pro Phe Leu Asn Val Thr Asp Pro Thr
145                 150                 155                 160

Leu Asp Ser Gly Ala Tyr Gln Ile Pro Gly Thr Thr Pro Ala Gly Lys
            165                 170                 175

```
Thr Gly Arg His Leu Ile Tyr Val Ile Trp Gln Arg Ser Asp Ser Pro
            180                 185                 190

Glu Ala Phe Tyr Ser Cys Ser Asp Val Asp Phe Pro Asp Ala Leu Ser
        195                 200                 205

Leu His Ser Thr Thr
    210

<210> SEQ ID NO 224
<211> LENGTH: 216
<212> TYPE: PRT
<213> ORGANISM: Campyloneurum angustifolium

<400> SEQUENCE: 224

Met Arg Arg Ser Trp Glu Val Val Gly Met Met Val Leu Cys Ala Cys
1               5                   10                  15

Gly Leu Leu Gly Val Ala Ser Gly His Gly Ser Met Glu Asp Pro Ile
            20                  25                  30

Ser Arg Val Tyr Arg Cys Arg Leu Glu Asn Pro Glu Arg Pro Thr Ser
        35                  40                  45

Pro Ala Cys Arg Ala Ala Val Ala Leu Ser Gly Thr Gln Ala Phe Tyr
    50                  55                  60

Asp Trp Asn Glu Val Asn Gln Pro Phe Ala Ala Gly Arg His Arg Glu
65                  70                  75                  80

Ile Ile Pro Asp Gly Gln Leu Cys Ser Ala Gly Arg Asp Lys Tyr Lys
                85                  90                  95

Gly Leu Asp Leu Ala Arg Ala Asp Trp Leu Ala Val Ser Leu Ser Ser
            100                 105                 110

Gly Ala Asp Tyr Thr Phe Leu Tyr Leu Ala Thr Ala Thr His Arg Gly
        115                 120                 125

Tyr Phe Glu Phe Tyr Val Thr Arg Asp Ser Tyr Asp Pro Thr Glu Pro
    130                 135                 140

Leu Lys Trp Ser Asp Leu Glu Asp Ser Pro Phe Ile Asn Val Thr Asp
145                 150                 155                 160

Pro Thr Glu Val Gly Pro Val Tyr Gln Ile Pro Gly Thr Thr Pro Ala
                165                 170                 175

Gly Lys Thr Gly Arg His Leu Ile Tyr Val Ile Trp Gln Arg Thr Asp
            180                 185                 190

Ser Pro Glu Ala Phe Tyr Ser Cys Ser Asp Val Asp Phe Gly Glu Ser
        195                 200                 205

Leu Ser Leu Tyr Ser Val Thr Glu
    210                 215

<210> SEQ ID NO 225
<211> LENGTH: 218
<212> TYPE: PRT
<213> ORGANISM: Onoclea sensibilis

<400> SEQUENCE: 225

Met Gly Arg Ser Trp Gly Val Val Gln Ala Ile Ile Met Val Leu Cys
1               5                   10                  15

Gly Ser Gly Leu Leu Gly Val Ala Ser Gly His Gly Ser Met Glu Asp
            20                  25                  30

Pro Ile Ser Arg Val Tyr Asn Cys Tyr Leu Glu Asn Pro Glu Ser Pro
        35                  40                  45

Thr Ser Ala Ala Cys Gln Ala Ala Val Ala Leu Ser Gly Ala Gln Ala
    50                  55                  60
```

```
Phe Tyr Asp Trp Asn Glu Val Asn Leu Ala Asp Ala Ala Gly Arg His
 65                  70                  75                  80

Arg Glu Leu Ile Pro Asp Gly Gln Leu Cys Ser Ala Gly Arg Glu Lys
                 85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
            115                 120                 125

Leu Gly Phe Phe Glu Phe Tyr Val Thr Lys Asp Gly Tyr Glu Pro Thr
        130                 135                 140

Glu Pro Leu Lys Trp Ala Asp Leu Glu Asp Ser Pro Leu Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
        195                 200                 205

Val Asp Ala Leu Ser Leu His Ser Thr Thr
    210                 215

<210> SEQ ID NO 226
<211> LENGTH: 235
<212> TYPE: PRT
<213> ORGANISM: Onoclea sensibilis

<400> SEQUENCE: 226

Met Gly Arg Ser Trp Gly Val Val Gln Ala Ile Ile Met Val Leu Cys
1               5                   10                  15

Gly Ser Gly Leu Leu Gly Val Ala Ser Gly His Gly Ser Met Glu Asp
            20                  25                  30

Pro Ile Ser Arg Val Tyr Asn Cys Tyr Leu Glu Asn Pro Glu Ser Pro
        35                  40                  45

Thr Ser Ala Ala Cys Gln Ala Ala Val Ala Leu Ser Gly Ala Gln Ala
    50                  55                  60

Phe Tyr Asp Trp Asn Glu Val Asn Leu Ala Asp Ala Ala Gly Arg His
 65                  70                  75                  80

Arg Glu Leu Ile Pro Asp Gly Gln Leu Cys Ser Ala Gly Arg Glu Lys
                 85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
            115                 120                 125

Leu Gly Phe Phe Glu Phe Tyr Val Thr Lys Asp Gly Tyr Glu Pro Thr
        130                 135                 140

Glu Pro Leu Lys Trp Ala Asp Leu Glu Asp Ser Pro Phe Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
        195                 200                 205

Val Asp Ala Leu Ser Leu His Ser Thr Pro Asn Leu Asp Leu Ser Ser
```

```
                        210                 215                 220
Ser Gly Leu Ala Asn Leu Ile Asn Val Cys Val
225                 230                 235

<210> SEQ ID NO 227
<211> LENGTH: 229
<212> TYPE: PRT
<213> ORGANISM: Onoclea sensibilis

<400> SEQUENCE: 227

Met Gly Arg Ser Trp Gly Val Val Gln Ala Ile Ile Met Val Leu Cys
1               5                   10                  15

Gly Ser Gly Leu Leu Gly Val Ala Ser Gly His Gly Ser Met Glu Asp
            20                  25                  30

Pro Ile Ser Arg Val Tyr Asn Cys Tyr Leu Glu Asn Pro Glu Ser Pro
        35                  40                  45

Thr Ser Ala Ala Cys Gln Ala Val Ala Leu Ser Gly Ala Gln Ala
    50                  55                  60

Phe Tyr Asp Trp Asn Glu Val Asn Leu Ala Asp Ala Ala Gly Arg His
65                  70                  75                  80

Arg Glu Leu Ile Pro Asp Gly Gln Leu Cys Ser Ala Gly Arg Glu Lys
                85                  90                  95

Tyr Gln Gly Leu Asp Leu Ala Arg Ser Asp Trp Thr Ala Thr Ser Leu
            100                 105                 110

Ser Ser Gly Val Ser Phe Thr Tyr Leu Tyr Lys Ala Thr Ala Pro His
        115                 120                 125

Leu Gly Phe Phe Glu Phe Tyr Val Thr Lys Asp Gly Tyr Glu Pro Thr
    130                 135                 140

Glu Pro Leu Lys Trp Ala Asp Leu Glu Asp Ser Pro Phe Ile Asn Val
145                 150                 155                 160

Thr Asp Pro Thr Leu Val Ser Gly Ser Tyr Gln Ile Pro Gly Thr Thr
                165                 170                 175

Pro Ser Gly Lys Ser Gly Arg His Leu Ile Tyr Val Ile Trp Gln Arg
            180                 185                 190

Ser Asp Ser Pro Glu Ala Phe Tyr Ser Cys Ser Asp Val Asp Phe Asp
        195                 200                 205

Val Asp Ala Leu Ser Leu His Ser Thr Pro Asn Leu Asp Leu Ser Ile
    210                 215                 220

Leu Asp Trp Pro Thr
225

<210> SEQ ID NO 228
<211> LENGTH: 215
<212> TYPE: PRT
<213> ORGANISM: Polystichum tripteron

<400> SEQUENCE: 228

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Ala Cys Arg Gln Glu Asn Pro Glu Pro Thr Thr
        35                  40                  45

Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
```

```
              65                  70                  75                  80
        Phe Ile Pro Asp Gly Lys Leu Cys Ser Ala Gly Arg Asn Lys Tyr Arg
                        85                  90                  95

Gly Leu Asp Leu Ala Arg Ser Asp Trp Thr Ala Thr Asn Leu Ser Ser
                        100                 105                 110

Gly Val Ala Tyr Thr Phe Leu Tyr Arg Val Thr Ala Gln His Arg Gly
                        115                 120                 125

Phe Phe Glu Phe Tyr Val Thr Val Asp Gly Tyr Asp Pro Thr Glu Pro
                        130                 135                 140

Leu Lys Trp Ala Asp Leu Glu Glu Thr Pro Phe Ile Asn Val Thr Asp
        145                 150                 155                 160

Pro Thr Val Val Gly Leu Asn Tyr Val Ile Pro Gly Thr Thr Pro Ala
                        165                 170                 175

Ser Lys Thr Gly Arg His Leu Ile Tyr Val Ile Trp Gln Arg Ser Asp
                        180                 185                 190

Ser Pro Glu Ala Phe Tyr Ser Cys Ser Asp Val Asn Phe Pro Asp Ala
                        195                 200                 205

Leu Ser Leu His Ser Ala Thr
                        210                 215

<210> SEQ ID NO 229
<211> LENGTH: 215
<212> TYPE: PRT
<213> ORGANISM: Polystichum tripteron

<400> SEQUENCE: 229

Met Gly Arg Ser Trp Gly Val Val Ala Ile Met Val Leu Cys Ala Ser
        1               5                   10                  15

Gly Leu Leu Gly Val Ala Ser Gly His Gly Thr Met Asn Asp Pro Ile
                        20                  25                  30

Ser Arg Val Tyr Ala Cys Arg Gln Glu Asn Pro Glu Arg Pro Thr Thr
                        35                  40                  45

Pro Ala Cys Ile Ala Ala Val Ala Leu Ser Gly Ala Gln Ala Phe Tyr
        50                  55                  60

Asp Trp Asn Glu Val Asn Leu Pro Phe Val Asn Gly Arg His Arg Gln
        65                  70                  75                  80

Phe Ile Pro Asp Gly Lys Leu Cys Ser Ala Gly Arg Asn Lys Tyr Arg
                        85                  90                  95

Gly Leu Asp Leu Ala Arg Ser Asp Trp Thr Ala Thr Asn Leu Ser Ser
                        100                 105                 110

Gly Val Ala Tyr Thr Phe Leu Tyr Arg Val Thr Ala Gln His Arg Gly
                        115                 120                 125

Phe Phe Glu Phe Tyr Val Thr Val Asp Gly Tyr Asp Pro Thr Glu Pro
                        130                 135                 140

Leu Lys Trp Ala Asp Leu Glu Glu Thr Pro Phe Ile Asn Val Thr Asp
        145                 150                 155                 160

Pro Thr Val Val Gly Leu Asn Tyr Val Ile Ser Gly Thr Thr Pro Ala
                        165                 170                 175

Ser Lys Thr Gly Arg His Leu Ile Tyr Val Ile Trp Gln Arg Thr Asp
                        180                 185                 190

Ser Pro Glu Ala Phe Tyr Ser Cys Ser Asp Val Asn Phe Pro Asp Ala
                        195                 200                 205

Leu Ser Leu His Ser Ala Thr
                        210                 215
```

```
<210> SEQ ID NO 230
<211> LENGTH: 215
<212> TYPE: PRT
<213> ORGANISM: Polystichum tripteron

<400> SEQUENCE: 230

Met Gly Arg Ser Trp Gly Val Val Ala Ile Met Met Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Ala Cys Arg Gln Glu Asn Pro Glu Arg Pro Thr Thr
        35                  40                  45

Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
            100                 105                 110

Gly Val Ala Tyr Thr Phe Leu Tyr Arg Val Thr Ala Gln His Arg Gly
        115                 120                 125

Phe Phe Glu Phe Tyr Val Thr Val Asp Gly Tyr Asp Pro Thr Glu Pro
    130                 135                 140

Leu Lys Trp Ala Asp Leu Glu Glu Thr Pro Phe Ile Asn Val Thr Asp
145                 150                 155                 160

Pro Thr Val Val Gly Leu Asn Tyr Val Ile Pro Gly Thr Thr Pro Ala
                165                 170                 175

Ser Lys Thr Gly Arg His Leu Ile Tyr Val Ile Trp Gln Arg Ser Asp
            180                 185                 190

Ser Pro Glu Ala Phe Tyr Ser Cys Ser Asp Val Asn Phe Pro Asp Ala
        195                 200                 205

Leu Ser Leu His Ser Ala Thr
    210                 215

<210> SEQ ID NO 231
<211> LENGTH: 215
<212> TYPE: PRT
<213> ORGANISM: Polystichum tripteron

<400> SEQUENCE: 231

Met Gly Arg Ser Trp Gly Val Val Ala Ile Met Val Leu Cys Ala Ser
1               5                   10                  15

Gly Leu Leu Gly Val Ala Ser Gly His Gly Thr Met Asn Asp Pro Ile
            20                  25                  30

Ser Arg Val Tyr Ala Cys Arg Gln Glu Asn Pro Glu Arg Pro Thr Thr
        35                  40                  45

Pro Ala Cys Ile Ala Ala Val Ala Leu Ser Gly Ala Gln Ala Phe Tyr
    50                  55                  60

Asp Trp Asn Glu Val Asn Leu Pro Phe Val Asn Gly Arg His Arg Gln
65                  70                  75                  80

Phe Ile Pro Asp Gly Lys Leu Cys Ser Ala Gly Arg Asn Lys Tyr Arg
                85                  90                  95

Gly Leu Asp Leu Ala Arg Ser Asp Trp Thr Ala Thr Asn Leu Ser Ser
            100                 105                 110
```

```
Gly Val Ala Tyr Thr Phe Leu Tyr Arg Val Thr Ala Gln His Arg Gly
            115                 120                 125

Phe Phe Glu Phe Tyr Val Thr Val Asp Gly Tyr Asp Pro Thr Glu Pro
130                 135                 140

Leu Lys Trp Ala Asp Leu Glu Glu Thr Pro Phe Ile Asn Val Ala Asn
145                 150                 155                 160

Pro Thr Val Val Gly Leu Asn Tyr Val Ile Ser Gly Thr Thr Pro Ala
                165                 170                 175

Ser Lys Thr Gly Arg His Leu Ile Tyr Val Ile Trp Gln Arg Thr Asp
            180                 185                 190

Ser Pro Glu Ala Phe Tyr Ser Cys Ser Asp Val Asn Phe Val Asp Ala
        195                 200                 205

Leu Ser Leu His Ser Ala Thr
    210                 215

<210> SEQ ID NO 232
<211> LENGTH: 217
<212> TYPE: PRT
<213> ORGANISM: Tectaria milnei

<400> SEQUENCE: 232

Met Gly Arg Ser Trp Gly Val Val Ala Val Met Val Val Cys Ala Ser
1               5                   10                  15

Gly Leu Leu Ser Val Val Arg Gly His Gly Ser Met Glu Asp Pro Ile
            20                  25                  30

Ser Arg Val Tyr Ala Cys Phe Leu Glu Asn Pro Glu Arg Pro Ile Ser
        35                  40                  45

Ala Ala Cys Gln Ala Ala Val Ala Met Gly Gly Thr Gln Ala Phe Tyr
    50                  55                  60

Asp Trp Asn Ala Val Ser Leu Pro Tyr Ala Ala Gly Arg His Arg Glu
65                  70                  75                  80

Leu Ile Pro Asp Gly Gln Leu Cys Ser Ala Gly Arg Ala Lys Tyr Arg
                85                  90                  95

Gly Leu Asp Leu Pro Arg Asp Asp Trp Pro Gly Thr Ser Asn Met Thr
            100                 105                 110

Ser Gly Val Ala Phe Thr Tyr Arg Tyr Lys Ala Thr Ala Pro His Leu
        115                 120                 125

Gly Ser Phe Gln Phe Tyr Val Thr Arg Asp Gly Tyr Asp Pro Thr Glu
    130                 135                 140

Pro Leu Lys Trp Ala Asp Leu Glu Asp Ser Pro Phe Met Asn Ala Thr
145                 150                 155                 160

Ser Thr Leu Ala Pro Asp Ser Tyr Leu Met Ser Gly Thr Thr Pro Ser
                165                 170                 175

Gly Lys Ala Gly His His Leu Ile Tyr Ala Ile Trp Gln Arg Ser Asp
            180                 185                 190

Ser Pro Glu Ala Phe Tyr Ser Cys Ser Asp Val Thr Phe Asp Val Ala
        195                 200                 205

Ala Val Ser Asp Leu His Ser Thr Thr
    210                 215

<210> SEQ ID NO 233
<211> LENGTH: 217
<212> TYPE: PRT
<213> ORGANISM: Tectaria milnei

<400> SEQUENCE: 233
```

```
Met Gly Arg Ser Trp Gly Val Val Ala Val Met Val Cys Ala Ser
1               5                   10                  15

Gly Leu Leu Ser Val Val Arg Gly His Gly Ser Met Glu Asp Pro Ile
            20                  25                  30

Ser Arg Val Tyr Ala Cys Phe Leu Glu Asn Pro Glu Arg Pro Ile Ser
        35                  40                  45

Ala Ala Cys Gln Ala Ala Val Ala Met Gly Gly Thr Gln Ala Phe Tyr
    50                  55                  60

Asp Trp Asn Ala Val Ser Leu Pro Tyr Ala Ala Gly Arg His Arg Glu
65                  70                  75                  80

Leu Ile Pro Asp Gly Gln Leu Cys Ser Ala Gly Arg Ala Lys Tyr Arg
                85                  90                  95

Gly Leu Asp Leu Pro Arg Asp Asp Trp Pro Gly Thr Ser Asn Met Thr
            100                 105                 110

Ser Gly Val Ala Phe Thr Tyr Arg Tyr Lys Ala Thr Ala Pro His Leu
        115                 120                 125

Gly Ser Phe Gln Phe His Val Thr Arg Asp Gly Tyr Asp Pro Thr Glu
    130                 135                 140

Pro Leu Lys Trp Ala Asp Leu Glu Asp Ser Pro Phe Met Asn Ala Thr
145                 150                 155                 160

Ser Thr Leu Ala Pro Asp Ser Tyr Leu Met Ser Gly Thr Thr Pro Ser
                165                 170                 175

Gly Lys Ala Gly His His Leu Ile Tyr Ala Ile Trp Gln Arg Ser Asp
            180                 185                 190

Ser Pro Glu Ala Phe Tyr Ser Cys Ser Asp Val Thr Phe Asp Val Ala
        195                 200                 205

Ala Val Ser Asp Leu His Ser Thr Thr
    210                 215

<210> SEQ ID NO 234
<211> LENGTH: 217
<212> TYPE: PRT
<213> ORGANISM: Tectaria milnei

<400> SEQUENCE: 234

Met Gly Arg Ser Trp Gly Val Val Ala Val Met Val Cys Ala Ser
1               5                   10                  15

Gly Leu Leu Ser Val Val Arg Gly His Gly Ser Met Glu Asp Pro Ile
            20                  25                  30

Ser Arg Val Tyr Ala Cys Phe Leu Glu Asn Pro Glu Arg Pro Ile Ser
        35                  40                  45

Ala Ala Cys Gln Ala Ala Val Ala Met Gly Gly Thr Gln Ala Phe Tyr
    50                  55                  60

Asp Trp Asn Ala Val Ser Leu Pro Tyr Ala Ala Gly Arg His Arg Glu
65                  70                  75                  80

Leu Ile Pro Asp Gly Gln Leu Cys Ser Ala Gly Arg Ala Lys Tyr Arg
                85                  90                  95

Gly Leu Asp Leu Pro Arg Asp Asp Trp Pro Gly Thr Ser Asn Met Thr
            100                 105                 110

Ser Gly Val Ala Phe Thr Tyr Arg Tyr Lys Ala Thr Ala Pro His Leu
        115                 120                 125

Gly Ser Phe Gln Phe Tyr Val Thr Arg Asp Gly Tyr Asp Pro Thr Glu
    130                 135                 140

Pro Leu Lys Trp Ala Asp Leu Glu Asp Ser Pro Leu Met Asn Ala Thr
145                 150                 155                 160
```

```
Ser Thr Leu Ala Pro Asp Ser Tyr Leu Met Ser Gly Thr Thr Pro Ser
                165                 170                 175

Gly Lys Ala Gly His His Leu Ile Tyr Ala Ile Trp Gln Arg Ser Asp
            180                 185                 190

Ser Pro Glu Ala Phe Tyr Ser Cys Ser Asp Val Thr Phe Asp Val Ala
        195                 200                 205

Ala Val Ser Asp Leu His Ser Thr Thr
        210                 215

<210> SEQ ID NO 235
<211> LENGTH: 51
<212> TYPE: DNA
<213> ORGANISM: Unknown
<220> FEATURE:
<223> OTHER INFORMATION: Synthetic sequence

<400> SEQUENCE: 235
gtttaacttt aagaaggaga tatacatatg ggcaggtcat ggggagttgt g          51

<210> SEQ ID NO 236
<211> LENGTH: 49
<212> TYPE: DNA
<213> ORGANISM: Unknown
<220> FEATURE:
<223> OTHER INFORMATION: Synthetic sequence

<400> SEQUENCE: 236
gtgatggtga tggtgatggt gggatccggt ggtggagtgg agagatagg              49

<210> SEQ ID NO 237
<211> LENGTH: 49
<212> TYPE: DNA
<213> ORGANISM: Unknown
<220> FEATURE:
<223> OTHER INFORMATION: Synthetic sequence

<400> SEQUENCE: 237
gtttaacttt aagaaggaga tatacatatg gggagatcat ggggagttg              49

<210> SEQ ID NO 238
<211> LENGTH: 49
<212> TYPE: DNA
<213> ORGANISM: Unknown
<220> FEATURE:
<223> OTHER INFORMATION: Synthetic sequence

<400> SEQUENCE: 238
gtgatggtga tggtgatggt gggatccggt ggtggagtgg agagagagg              49

<210> SEQ ID NO 239
<211> LENGTH: 49
<212> TYPE: DNA
<213> ORGANISM: Unknown
<220> FEATURE:
<223> OTHER INFORMATION: Synthetic sequence

<400> SEQUENCE: 239
gtttaacttt aagaaggaga tatacatatg gggaggtcat ggggagttg              49

<210> SEQ ID NO 240
<211> LENGTH: 50
<212> TYPE: DNA
<213> ORGANISM: Unknown
<220> FEATURE:
```

<223> OTHER INFORMATION: Synthetic sequence

<400> SEQUENCE: 240
gtgatggtga tggtgatggt gggatccggt ggtagagtgg agagagagag            50

<210> SEQ ID NO 241
<211> LENGTH: 51
<212> TYPE: DNA
<213> ORGANISM: Unknown
<220> FEATURE:
<223> OTHER INFORMATION: Synthetic sequence

<400> SEQUENCE: 241
gtttaacttt aagaaggaga tatacatatg gggaggccat ggggagttgt g          51

<210> SEQ ID NO 242
<211> LENGTH: 49
<212> TYPE: DNA
<213> ORGANISM: Unknown
<220> FEATURE:
<223> OTHER INFORMATION: Synthetic sequence

<400> SEQUENCE: 242
gtgatggtga tggtgatggt gggatccggt ggtggagtgg agagagagg             49

<210> SEQ ID NO 243
<211> LENGTH: 55
<212> TYPE: DNA
<213> ORGANISM: Unknown
<220> FEATURE:
<223> OTHER INFORMATION: Synthetic sequence

<400> SEQUENCE: 243
aatctctcat ctaagaggct ggatcctagg atggggaggt catggggagt ggtgc      55

<210> SEQ ID NO 244
<211> LENGTH: 55
<212> TYPE: DNA
<213> ORGANISM: Unknown
<220> FEATURE:
<223> OTHER INFORMATION: Synthetic sequence

<400> SEQUENCE: 244
tggccaatcc agaagatgga caagtctaga ttaggtggtg gagtggagag agagg      55

<210> SEQ ID NO 245
<211> LENGTH: 55
<212> TYPE: DNA
<213> ORGANISM: Unknown
<220> FEATURE:
<223> OTHER INFORMATION: Synthetic sequence

<400> SEQUENCE: 245
aatctctcat ctaagaggct ggatcctagg atggggaggt catggggagt ggtgg      55

<210> SEQ ID NO 246
<211> LENGTH: 55
<212> TYPE: DNA
<213> ORGANISM: Unknown
<220> FEATURE:
<223> OTHER INFORMATION: Synthetic sequence

<400> SEQUENCE: 246
tggccaatcc agaagatgga caagtctaga ttaggtggtg gagtggagat cagag      55

```
<210> SEQ ID NO 247
<211> LENGTH: 55
<212> TYPE: DNA
<213> ORGANISM: Unknown
<220> FEATURE:
<223> OTHER INFORMATION: Synthetic sequence

<400> SEQUENCE: 247
aatctctcat ctaagaggct ggatcctagg atgggcaggt catggggagt tgtgg          55

<210> SEQ ID NO 248
<211> LENGTH: 55
<212> TYPE: DNA
<213> ORGANISM: Unknown
<220> FEATURE:
<223> OTHER INFORMATION: Synthetic sequence

<400> SEQUENCE: 248
tggccaatcc agaagatgga caagtctaga ttaggtggcg gagtggagag acagg          55

<210> SEQ ID NO 249
<211> LENGTH: 5
<212> TYPE: PRT
<213> ORGANISM: Unknown
<220> FEATURE:
<223> OTHER INFORMATION: Synthetic sequence

<400> SEQUENCE: 249

Glu Glu Lys Lys Asn
1               5
```

INSECTICIDAL PROTEINS AND METHODS FOR THEIR USE

CROSS REFERENCE TO RELATED APPLICATIONS

This Application is a National Stage application of International Patent Application number PCT/US2018/031746, which claims the benefit of priority to U.S. Provisional Application No. 62/504,650 filed on May 11, 2017, the disclosures of each of which are incorporated herein by reference in their entireties.

REFERENCE TO SEQUENCE LISTING SUBMITTED ELECTRONICALLY

The official copy of the sequence listing is submitted electronically via EFS-Web as an ASCII formatted sequence listing with a file named "7440_WO_PCT_Sequence_Listing" created on May 2, 2018, and having a size of 334 kilobytes and is filed concurrently with the specification. The sequence listing contained in this ASCII formatted document is part of the specification and is herein incorporated by reference in its entirety.

FIELD

This disclosure relates to the field of molecular biology. Provided are novel genes that encode pesticidal proteins. These pesticidal proteins and the nucleic acid sequences that encode them are useful in preparing pesticidal formulations and in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants may provide resistance to only a narrow range of the economically important insect pests. In some cases, insects can develop resistance to different insecticidal compounds, which raises the need to identify alternative biological control agents for pest control.

Accordingly, there remains a need for new pesticidal proteins with different ranges of insecticidal activity against insect pests, e.g., insecticidal proteins which are active against a variety of insects in the order Lepidoptera and the order Coleoptera, including but not limited to insect pests that have developed resistance to existing insecticides.

SUMMARY

In one aspect compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect isolated or recombinant nucleic acid molecules are provided encoding IPD121 polypeptides including amino acid substitutions, deletions, insertions, and fragments thereof. Provided are isolated or recombinant nucleic acid molecules capable of encoding IPD121 polypeptides of SEQ ID NOS: 124-234, as well as amino acid substitutions, deletions, insertions, fragments thereof, and combinations thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant.

In another aspect IPD121 polypeptides are encompassed. Also provided are isolated or recombinant IPD121 polypeptides of SEQ ID NO: 124-234, as well as amino acid substitutions, deletions, insertions, fragments thereof and combinations thereof.

In another aspect, methods are provided for producing the polypeptides and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. It will be understood by one of skill in the art that the transgenic plant may comprise any gene imparting an agronomic trait of interest.

In another aspect, methods for detecting the nucleic acids and polypeptides of the embodiments in a sample are also included. A kit for detecting the presence of an IPD121 polypeptide or detecting the presence of a polynucleotide encoding an IPD121 polypeptide in a sample is provided. The kit may be provided along with all reagents and control samples necessary for carrying out a method for detecting the intended agent, as well as instructions for use.

In another aspect the compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of IPD121 polypeptides.

BRIEF DESCRIPTION OF THE FIGURES

Figure 1A:
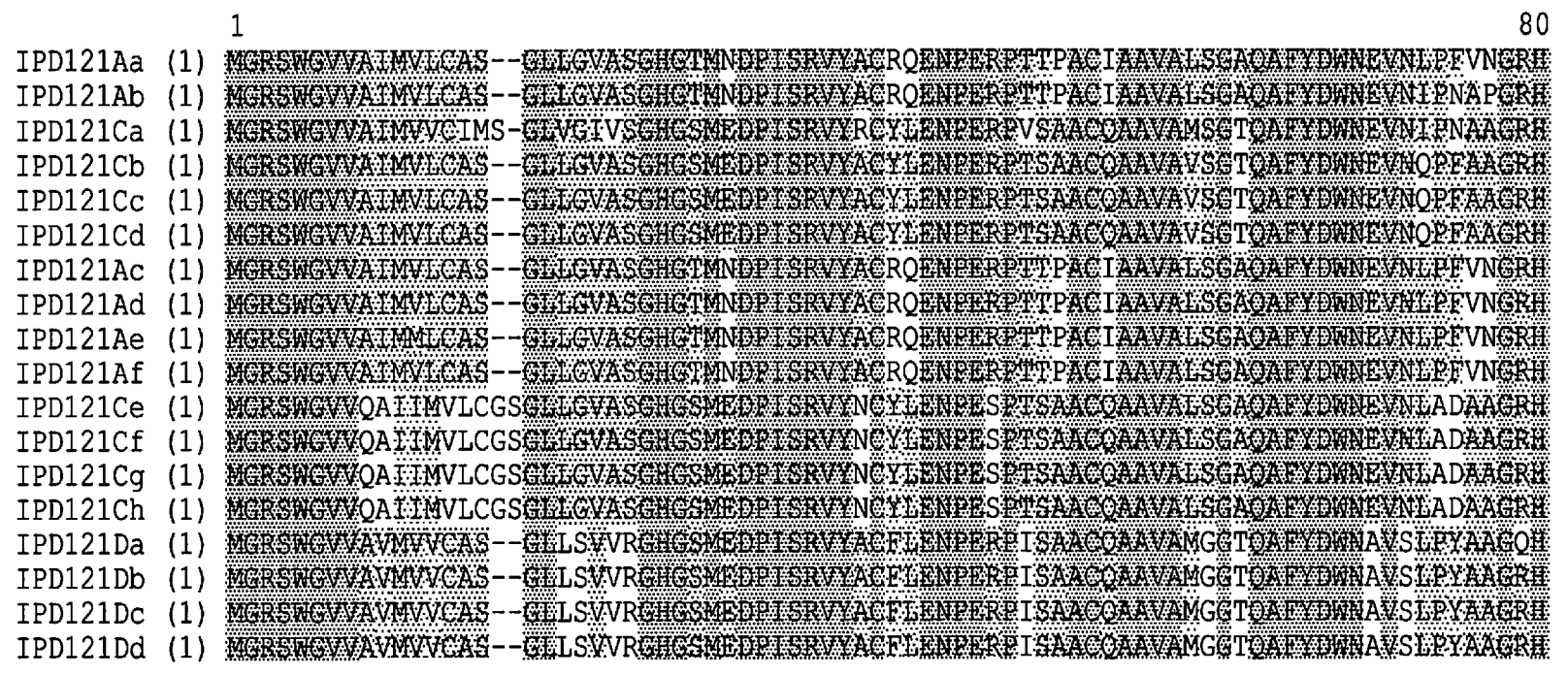
Figure 1B:
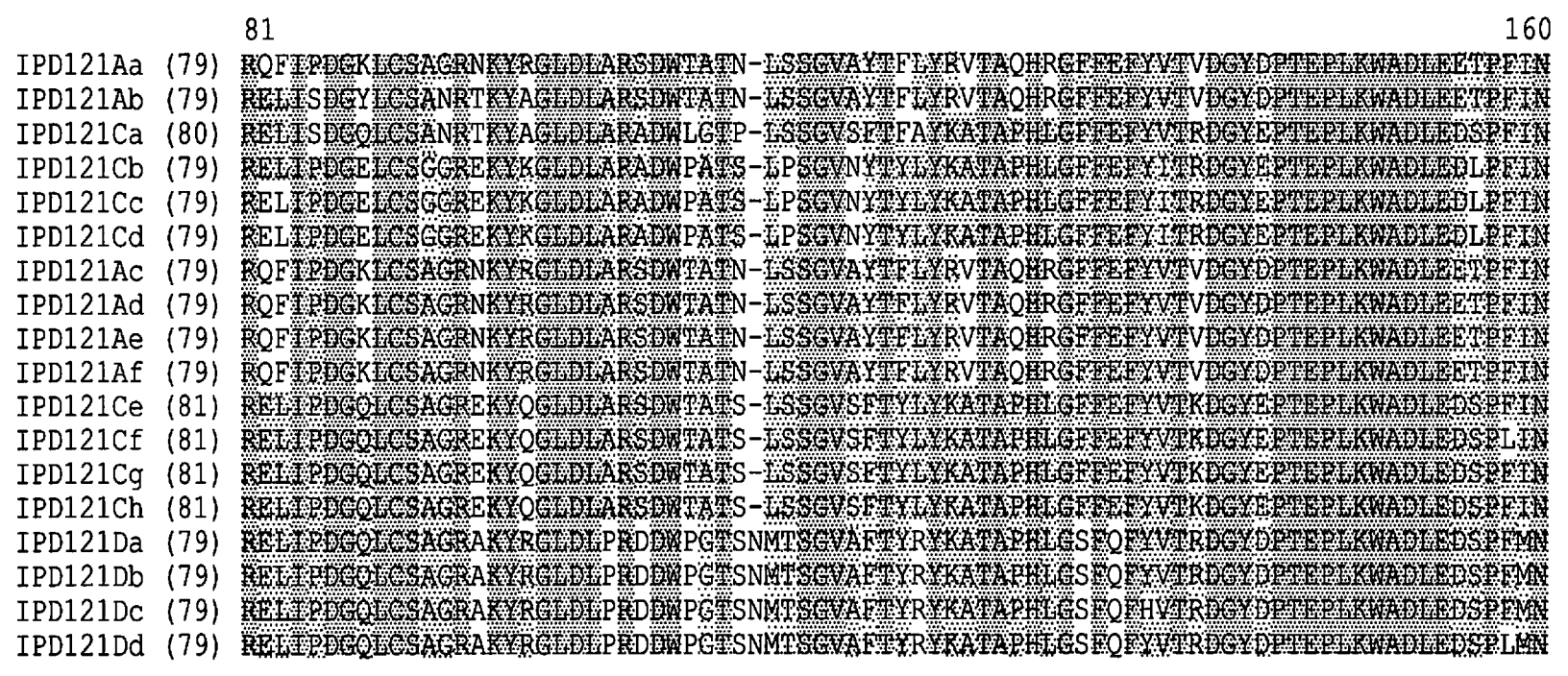

FIGS. 1A-C show an amino acid sequence alignment, using the ALIGNX® module of the Vector NTI® suite, of the IPD121Aa polypeptide (SEQ ID NO: 124), the IPD121Ab polypeptide (SEQ ID NO: 125), the IPD121Ac polypeptide (SEQ ID NO: 228), the IPD121Ad polypeptide (SEQ ID NO: 229), the IPD121Ae polypeptide (SEQ ID NO: 230), the IPD121Af polypeptide (SEQ ID NO: 231), the IPD121Ca polypeptide (SEQ ID NO: 126), the IPD121Cb polypeptide (SEQ ID NO: 127), the IPD121Cc polypeptide (SEQ ID NO: 128), the IPD121Cd polypeptide (SEQ ID NO: 129), the IPD121Ce polypeptide (SEQ ID NO: 139), the IPD121Cf polypeptide (SEQ ID NO: 225), the IPD121Cg polypeptide (SEQ ID NO: 226), the IPD121Ch polypeptide (SEQ ID NO: 227), the IPD121 Da polypeptide (SEQ ID NO: 142), the IPD121Db polypeptide (SEQ ID NO: 232), the IPD121Dc polypeptide (SEQ ID NO: 233), and the IPD121Dd polypeptide (SEQ ID NO: 234). The amino acid sequence diversity between the amino acid sequences is highlighted. Conservative amino acid differences are indicated by (▓) shading.

FIGS. 2A-D show activity of selected IPD121 polypeptides, transiently expressed in bush bean, against leaf feeding damage from a selection of Lepidoptera.

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The present disclosure is drawn to compositions and methods for controlling pests. The methods involve transforming organisms with nucleic acid sequences encoding IPD121 polypeptides. In particular, the nucleic acid sequences of the embodiments are useful for preparing plants and microorganisms that possess pesticidal activity. Thus, transformed bacteria, plants, plant cells, plant tissues and seeds are provided. The compositions include pesticidal nucleic acids and proteins of bacterial species. The nucleic acid sequences find use in the construction of expression vectors for subsequent transformation into organisms of interest, as probes for the isolation of other homologous (or partially homologous) genes, and for the generation of altered IPD121 polypeptides by methods known in the art, such as site directed mutagenesis, domain swapping or DNA shuffling. The IPD121 polypeptides find use in controlling or killing Lepidopteran, Coleopteran, Dipteran, fungal, Hemipteran and/or nematode pest populations and for producing compositions with pesticidal activity. Insect pests of interest include, but are not limited to, Lepidoptera species including but not limited to: Corn Earworm, (CEW) (*Helicoverpa zea*), European Corn Borer (ECB) (*Ostrinia nubialis*), Fall Armyworm (FAW), (*Spodoptera frugiperda*), soybean looper (SBL), e.g., *Pseudoplusia includens* Walker; and velvet bean caterpillar (VBC), e.g., *Anticarsia gemmatalis* Hübner.

By "pesticidal toxin" or "pesticidal protein" is used herein to refer to a toxin that has toxic activity against one or more pests. For example, pests may include members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*.

In some embodiments the IPD121 polypeptide includes an amino acid sequence deduced from the full-length nucleic acid sequence disclosed herein and amino acid sequences that are shorter than the full-length sequences, either due to the use of an alternate downstream start site or due to processing that produces a shorter protein having pesticidal activity. Processing may occur in the organism the protein is expressed in or in the pest after ingestion of the protein.

Thus, provided herein are isolated or recombinant nucleic acid sequences conferring pesticidal activity. Also provided are the amino acid sequences of IPD121 polypeptides. The polypeptides resulting from translation of these IPD121 genes allows cells to control or kill pests that ingest it.

IPD121 Proteins and Variants and Fragments Thereof

IPD121 polypeptides are encompassed by the disclosure. "IPD121 polypeptide", and "IPD121 protein" as used herein interchangeably refers to a polypeptide(s) having insecticidal activity including but not limited to insecticidal activity against one or more insect pests of the Lepidoptera and/or Coleoptera orders, and is sufficiently homologous to the IPD121Aa polypeptide of SEQ ID NO: 124. A variety of IPD121 polypeptides are contemplated. Sources of IPD121 polypeptides or related proteins include plant species selected from but not limited to *Polystichum, Davallia, Didymochlaena, Humata, Onoclea*, and *Tectaria* species. Alignment of the amino acid sequences of IPD121 polypeptide homologs (for example, see FIGS. 1A-1C), allows for the identification of residues that are highly conserved amongst the natural homologs of this family.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In one embodiment the IPD121 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOS: 124-234. In some embodiments the sequence identity is against the full length sequence of an IPD121 polypeptide. The term "about" when used herein in context with percent sequence identity means+/−1.0%.

A "recombinant protein" is used herein to refer to a protein that is no longer in its natural environment, for example in vitro or in a recombinant bacterial or plant host cell.

"Substantially free of cellular material" as used herein refers to a polypeptide including preparations of protein having less than about 30%, 20%, 10% or 5% (by dry weight) of non-pesticidal protein (also referred to herein as a "contaminating protein").

"Fragments" or "biologically active portions" include polypeptide fragments comprising amino acid sequences sufficiently identical to an IPD121 polypeptide and that exhibit insecticidal activity.

"Fragments" or "biologically active portions" of IPD121 polypeptides includes fragments comprising amino acid sequences sufficiently identical to the amino acid sequence set forth in any one of SEQ ID NOS: 124-234 wherein the IPD121 polypeptide has insecticidal activity. Such biologically active portions can be prepared by recombinant techniques and evaluated for insecticidal activity. In some embodiments, the IPD121 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus relative to any one of SEQ ID NOS: 124-234, e.g., by proteolysis, by insertion of a start codon, by deletion of the codons encoding the deleted amino acids and concomitant insertion of a start codon, and/or insertion of a stop codon. In some embodiments, the IPD121 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 amino acids from the N-terminus of any one of SEQ ID NOS: 124-234. In some embodiments, the IPD121 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to any one of SEQ ID NOS: 124-234.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments an IPD121 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the full length or a fragment of the amino acid sequence of any one of SEQ ID NOS: 124-234, wherein the IPD121 polypeptide has insecticidal activity.

In some embodiments an IPD121 polypeptide comprises an amino acid sequence of any one or more of SEQ ID NOS: 124-234 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or more amino acid substitutions compared to the amino acid at the corresponding position of any one or more of the respective SEQ ID NOS: 124-234.

Methods for such manipulations are generally known in the art. For example, amino acid sequence variants of an IPD121 polypeptide can be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess the desired pesticidal activity. However, it is understood that the ability of an IPD121 polypeptide to confer pesticidal activity may be improved by the use of such techniques upon the compositions of this disclosure.

Conservative amino acid substitutions may be made at one or more predicted nonessential amino acid residues. A "nonessential" amino acid residue is a residue that can be altered from the wild-type sequence of an IPD121 polypeptide without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues.

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

1.) Shuffling

Variant nucleotide and amino acid sequences of the disclosure also encompass sequences derived from mutagenic and recombinogenic procedures such as DNA shuffling. With such a procedure, one or more different IPD121 polypeptide coding regions can be used to create a new IPD121 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; and U.S. Pat. Nos. 5,605,793 and 5,837,458.

Domain swapping as shuffling is another mechanism for generating altered IPD121 polypeptides. Domains may be swapped between IPD121 polypeptides resulting in hybrid or chimeric toxins with improved insecticidal activity or target spectrum. Methods for generating recombinant proteins and testing them for pesticidal activity are well known in the art (see, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J Biol. Chem.* 266:17954-17958; Schnepf, et al., (1990) *J. Biol. Chem.* 265:20923-21010; Rang, et al., 91999) *Appl. Environ. Microbiol.* 65:2918-2925).

Phylogenetic, Sequence Motif, and Structural Analyses of Insecticidal Protein Families.

A sequence and structure analysis method can be employed, which is composed of four components: phylogenetic tree construction, protein sequence motifs finding, secondary structure prediction, and alignment of protein sequences and secondary structures. Details about each component are illustrated below.

1) Phylogenetic Tree Construction

The phylogenetic analysis can be performed using the software MEGA5. Protein sequences can be subjected to ClustalW version 2 analysis (Larkin M. A et al (2007) *Bioinformatics* 23(21): 2947-2948) for multiple sequence alignment. The evolutionary history is then inferred by the Maximum Likelihood method based on the JTT matrix-based model. The tree with the highest log likelihood is obtained, exported in Newick format, and further processed to extract the sequence IDs in the same order as they appeared in the tree. A few clades representing sub-families can be manually identified for each insecticidal protein family.

2) Protein Sequence Motifs Finding

Protein sequences are re-ordered according to the phylogenetic tree built previously, and fed to the MOTIF analysis tool MEME (Multiple EM for MOTIF Elicitation) (Bailey T. L., and Elkan C., *Proceedings of the Second International Conference on Intelligent Systems for Molecular Biology*, pp. 28-36, AAAI Press, Menlo Park, Calif., 1994.) for identification of key sequence motifs. MEME is setup as follows: Minimum number of sites 2, Minimum motif width 5, and Maximum number of motifs 30. Sequence motifs unique to each sub-family were identified by visual observation. The distribution of MOTIFs across the entire gene family could be visualized in HTML webpage. The MOTIFs are numbered relative to the ranking of the E-value for each MOTIF.

3) Secondary Structure Prediction

PSIPRED, top ranked secondary structure prediction method (Jones D T. (1999)*J Mol. Biol.* 292: 195-202), can be used for protein secondary structure prediction. The tool provides accurate structure prediction using two feed-forward neural networks based on the PSI-BLAST output. The PSI-BLAST database is created by removing low-complexity, transmembrane, and coiled-coil regions in Uniref100. The PSIPRED results contain the predicted secondary structures (Alpha helix: H, Beta strand: E, and Coil: C) and the corresponding confidence scores for each amino acid in a given protein sequence.

4) Alignment of Protein Sequences and Secondary Structures

A script can be developed to generate gapped secondary structure alignment according to the multiple protein sequence alignment from step 1 for all proteins. All aligned protein sequences and structures are concatenated into a single FASTA file, and then imported into MEGA for visualization and identification of conserved structures.

In some embodiments the IPD121 polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, IPD121 polypeptide having increased expression, increased solubility, decreased phytotoxicity, and digestibility of proteolytic fragments in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

In some embodiments variants include polypeptides that differ in amino acid sequence due to mutagenesis. Variant proteins encompassed by the disclosure are biologically active, that is they continue to possess the desired biological activity (i.e. pesticidal activity) of the native protein. In some embodiment the variant will have at least about 10%, at least about 30%, at least about 50%, at least about 70%, at least about 80% or more of the insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In some embodiments an IPD121 polypeptide comprises the amino acid sequence of any one or more of SEQ ID NOS: 124-234.

In some embodiments, chimeric polypeptides are provided comprising regions of at least two different IPD121 polypeptides of the disclosure.

In some embodiments, chimeric polypeptides are provided comprising regions of at least two different IPD121 polypeptides selected from any one or more of SEQ ID NOS: 124-234.

In some embodiments, chimeric IPD121 polypeptide(s) are provided comprising an N-terminal Region of a first IPD121 polypeptide of the disclosure operably fused to a C-terminal Region of a second IPD121 polypeptide of the disclosure.

In other embodiments the IPD121 polypeptide may be expressed as a precursor protein with an intervening sequence that catalyzes multi-step, post translational protein splicing. Protein splicing involves the excision of an intervening sequence from a polypeptide with the concomitant joining of the flanking sequences to yield a new polypeptide (Chong, et al., (1996) *J. Biol. Chem.*, 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterfication reaction between the two termini to form a branched ester or thioester intermediate and peptide bond cleavage coupled to cyclization of the intein C-terminal asparagine to free the intein (Evans, et al., (2000) *J. Biol. Chem.*, 275:9091-9094).

In another embodiment fusion proteins are provided that include within its amino acid sequence an amino acid sequence comprising an IPD121 polypeptide of the disclosure. Methods for design and construction of fusion proteins (and polynucleotides encoding same) are known to those of skill in the art. Polynucleotides encoding an IPD121 polypeptide may be fused to signal sequences which will direct the localization of the IPD121 polypeptide to particular compartments of a prokaryotic or eukaryotic cell and/or direct the secretion of the IPD121 polypeptide of the embodiments from a prokaryotic or eukaryotic cell. For example, in *E. coli*, one may wish to direct the expression of the protein to the periplasmic space. Examples of signal sequences or proteins (or fragments thereof) to which the IPD121 polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the IPD121 polypeptide may be fused to the pelB pectate lyase signal sequence to increase the efficiency of expression and purification of such polypeptides in Gram-negative bacteria (see, U.S. Pat. Nos. 5,576,195 and 5,846,818).

Plant plastid transit peptide/polypeptide fusions are well known in the art. Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the IPD121 polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. In some embodiments the IPD121 polypeptide is fused to a heterologous signal peptide or heterologous transit peptide.

In some embodiments fusion proteins are provide comprising an IPD121 polypeptide or chimeric IPD121 polypeptide of the disclosure represented by a formula selected from the group consisting of:

$$R^1\text{-L-}R^2, R^2\text{-L-}R^1, R^1\text{-}R^2 \text{ or } R^2\text{-}R^1$$

wherein $R^1$ is an IPD121 polypeptide or chimeric IPD121 polypeptide of the disclosure and $R^2$ is a protein of interest. In some embodiments $R^1$ and $R^2$ are an IPD121 polypeptide or chimeric IPD121 polypeptide of the disclosure. The $R^1$ polypeptide is fused either directly or through a linker (L) segment to the $R^2$ polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments the linkers comprise sequences selected from the group of formulas: $(Gly_3Ser)_n$, $(Gly_4Ser)_n$, $(Gly_5Ser)_n$, $(Gly_nSer)_n$, or $(AlaGlySer)_n$ where n is an integer. One example of a highly-flexible linker is the (GlySer)-rich spacer region present within the pIII protein of the filamentous bacteriophages, e.g. bacteriophages M13 or fd (Schaller, et al., 1975). This region provides a long, flexible spacer region between two domains of the pIII surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to, Plasmin, Enterokinase, Kallikerin, Urokinase, Tissue Plasminogen activator, clostripain, Chymosin, Collagenase, Russell's Viper Venom Protease, Postproline cleavage enzyme, V8 protease, Thrombin and factor Xa. In some embodiments the linker comprises the amino acids EEKKN (SEQ ID NO:249) from the multi-gene expression vehicle (MGEV), which is cleaved by vacuolar proteases as disclosed in US Patent Application Publication Number US 2007/0277263. In other embodiments, peptide linker segments from the hinge region of heavy chain immunoglobulins IgG, IgA, IgM, IgD or IgE provide an angular relationship between the attached polypeptides. Especially useful are those hinge regions where the cysteines are replaced with serines. Linkers of the present disclosure include sequences derived from murine IgG gamma 2b hinge region in which the cysteines have been changed to serines. The fusion proteins are not limited by the form, size or number of linker sequences employed and the only requirement of the linker is that functionally it does not interfere adversely with the folding and function of the individual molecules of the fusion.

Nucleic Acid Molecules, and Variants and Fragments Thereof

Isolated or recombinant nucleic acid molecules comprising nucleic acid sequences encoding IPD121 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding IPD121 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding IPD121 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an IPD121 polypeptide is a non-genomic sequence.

A variety of polynucleotides that encode IPD121 polypeptides or related proteins are contemplated. Such polynucleotides are useful for production of IPD121 polypeptides in host cells when operably linked to a suitable promoter, transcription termination and/or polyadenylation sequences. Such polynucleotides are also useful as probes for isolating homologous or substantially homologous polynucleotides that encode IPD121 polypeptides or related proteins.

Polynucleotides Encoding IPD121 Polypeptides

One source of polynucleotides that encode IPD121 polypeptides or related proteins is a *Polystichum*, *Davallia*, *Didymochlaena*, *Humata*, *Onoclea*, or *Tectaria* species which may contain an IPD121 polynucleotide of any one of SEQ ID NOs: 1-123, encoding an IPD121 polypeptide of SEQ ID NOs: 124-234. The polynucleotides of any one or more of SEQ ID NOS: 1-123, can be used to express IPD121 polypeptides in recombinant bacterial hosts that include but are not limited to *Agrobacterium*, *Bacillus*, *Escherichia*, *Salmonella*, *Lysinibacillus*, *Acetobacter*, *Pseudomonas* and *Rhizobium* bacterial host cells. The polynucleotides are also useful as probes for isolating homologous or substantially homologous polynucleotides encoding IPD121 polypeptides or related proteins. Such probes can be used to identify homologous or substantially homologous polynucleotides derived from *Polystichum*, *Davallia*, *Didymochlaena*, *Humata*, *Onoclea*, and *Tectaria* species.

Polynucleotides encoding IPD121 polypeptides can also be synthesized de novo from an IPD121 polypeptide sequence. The sequence of the polynucleotide gene can be deduced from an IPD121 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of IPD121 polypeptide sequences that can be used to obtain corresponding nucleotide encoding sequences include, but are not limited to the IPD121 polypeptides of SEQ ID NOS: 124-234. Furthermore, synthetic IPD121 polynucleotide sequences of the disclosure can be designed so that they will be expressed in plants.

In one embodiment, the polypeptide of SEQ ID NO: 124 is encoded by SEQ ID NO: 1; the polypeptide of SEQ ID NO: 125 is encoded by SEQ ID NO: 2; the polypeptide of SEQ ID NO: 126 is encoded by SEQ ID NO: 3; the polypeptide of SEQ ID NO: 127 is encoded by SEQ ID NO: 4; the polypeptide of SEQ ID NO: 128 in encoded by SEQ ID NO: 5; the polypeptide of SEQ ID NO: 129 is encoded by SEQ ID NO: 6; the polypeptide of SEQ ID NO: 130 is encoded by SEQ ID NO: 7; the polypeptide of SEQ ID NO: 131 is encoded by SEQ ID NO: 8; the polypeptide of SEQ ID NO: 132 is encoded by SEQ ID NO: 9 and SEQ ID NO: 81; the polypeptide of SEQ ID NO: 133 is encoded by SEQ ID NO: 10; the polypeptide of SEQ ID NO: 134 is encoded by SEQ ID NO: 11; the polypeptide of SEQ ID NO: 135 is encoded by SEQ ID NO: 12; the polypeptide of SEQ ID NO: 136 is encoded by SEQ ID NO: 13; the polypeptide of SEQ ID NO: 137 is encoded by SEQ ID NO: 14; the polypeptide of SEQ ID NO: 138 is encoded by SEQ ID NO: 15 and SEQ ID NO: 20; the polypeptide of SEQ ID NO: 139 is encoded by SEQ ID NO: 16; the polypeptide of SEQ ID NO: 140 is encoded by SEQ ID NO: 17; the polypeptide of SEQ ID NO: 141 is encoded by SEQ ID NO: 18; the polypeptide of SEQ ID NO: 142 is encoded by SEQ ID NO: 19; the polypeptide of SEQ ID NO: 143 is encoded by SEQ ID NO: 21; the polypeptide of SEQ ID NO: 144 is encoded by SEQ ID NO: 22; the polypeptide of SEQ ID NO: 145 is encoded by SEQ ID NO: 23; the polypeptide of SEQ ID NO: 146 is encoded by SEQ ID NO: 24 and SEQ ID NO: 78; the polypeptide of SEQ ID NO: 147 is encoded by SEQ ID NO: 25 and SEQ ID NO: 82; the polypeptide of SEQ ID NO: 148 is encoded by SEQ ID NO: 26; the polypeptide of SEQ ID NO: 149 is encoded by SEQ ID NO: 27; the polypeptide of SEQ ID NO: 150 is encoded by SEQ ID NO: 28; the polypeptide of SEQ ID NO: 151 is encoded by SEQ ID NO: 29; the polypeptide of SEQ ID NO: 152 is encoded by SEQ ID NO: 30; the polypeptide of SEQ ID NO: 153 is encoded by SEQ ID NO: 31 and SEQ ID NO: 37; the polypeptide of SEQ ID NO: 154 is encoded by SEQ ID NO: 32; the polypeptide of SEQ ID NO: 155 is encoded by SEQ ID NO: 33; the polypeptide of SEQ ID NO: 156 is encoded by SEQ ID NO: 34; the polypeptide of SEQ ID NO: 157 is encoded by SEQ ID NO: 35; the polypeptide of SEQ ID NO: 158 is encoded by SEQ ID NO: 36; the polypeptide of SEQ ID NO: 159 is encoded by SEQ ID NO: 38; the polypeptide of SEQ ID NO: 160 is encoded by SEQ ID NO: 39; the polypeptide of SEQ ID NO: 161 is encoded by SEQ ID NO: 40; the polypeptide of SEQ ID NO: 162 is encoded by SEQ ID NO: 41; the polypeptide of SEQ ID NO: 163 is encoded by SEQ ID NO: 42; the polypeptide of SEQ ID NO: 164 is encoded by SEQ ID NO: 43; the polypeptide of SEQ ID NO: 165 is encoded by SEQ ID NO: 44, SEQ ID NO: 47, SEQ ID NO: 49 and SEQ ID NO: 53; the polypeptide of SEQ ID NO: 166 is encoded by SEQ ID NO: 45; the polypeptide of SEQ ID NO: 167 is encoded by SEQ ID NO: 46; the polypeptide of SEQ ID NO: 168 is encoded by SEQ ID NO: 48; the polypeptide of SEQ ID NO: 169 is encoded by SEQ ID NO: 50; the polypeptide of SEQ ID NO: 170 is encoded by SEQ ID NO: 51; the polypeptide of SEQ ID NO: 171 is encoded by SEQ ID NO: 52; the polypeptide of SEQ ID NO: 172 is encoded by SEQ ID NO: 54; the polypeptide of SEQ ID NO: 173 is encoded by SEQ ID NO: 55; the polypeptide of SEQ ID NO: 174 is encoded by SEQ ID NO: 56 and SEQ ID NO: 109; the polypeptide of SEQ ID NO: 175 is encoded by SEQ ID NO: 57; the polypeptide of SEQ ID NO: 176 is encoded by SEQ ID NO: 58; the polypeptide of SEQ ID NO: 177 is encoded by SEQ ID NO: 59; the polypeptide of SEQ ID NO: 178 is encoded by SEQ ID NO: 60; the polypeptide of SEQ ID NO: 179 is encoded by SEQ ID NO: 61; the polypeptide of SEQ ID NO: 180 is encoded by SEQ ID NO: 62; the polypeptide of SEQ ID NO: 181 is encoded by SEQ ID NO: 63; the polypeptide of SEQ ID NO: 182 is encoded by SEQ ID NO: 64; the polypeptide of SEQ ID NO: 183 is encoded by SEQ ID NO: 65; the polypeptide of SEQ ID NO: 184 is encoded by SEQ ID NO: 66; the polypeptide of SEQ ID NO: 185 is encoded by SEQ ID NO: 67; the polypeptide of SEQ ID NO: 186 is encoded by SEQ ID NO: 68; the polypeptide of SEQ ID NO: 187 is encoded by SEQ ID NO: 69; the polypeptide of SEQ ID NO: 188 is encoded by SEQ ID NO: 70; the polypeptide of SEQ ID NO: 189 is encoded by SEQ ID NO: 71; the polypeptide of SEQ ID NO: 190 is encoded by SEQ ID NO: 72; the polypeptide of SEQ ID NO: 191 is encoded by SEQ ID NO: 73; the polypeptide of SEQ ID NO: 192 is encoded by SEQ ID NO: 74; the polypeptide of SEQ ID NO: 193 is encoded by SEQ ID NO: 75; the polypeptide of SEQ ID NO: 194 is encoded by SEQ ID NO: 76; the polypeptide of SEQ ID NO: 195 is encoded by SEQ ID NO: 77; the polypeptide of SEQ ID NO: 196 is encoded by SEQ ID NO: 79; the polypeptide of SEQ ID NO: 197 is encoded by SEQ ID NO: 80; the polypeptide of SEQ ID NO: 198 is encoded by SEQ ID NO: 83; the polypeptide of SEQ ID NO: 199 is encoded by SEQ ID NO: 84; the polypeptide of SEQ ID NO: 200 is encoded by SEQ ID NO: 85; the polypeptide of SEQ ID NO: 201 is encoded by SEQ ID NO: 88; the polypeptide of SEQ ID NO: 202 is encoded by SEQ ID NO: 89 and SEQ ID NO: 92; the polypeptide of SEQ ID NO: 203 is encoded by SEQ ID NO: 90; the polypeptide of SEQ ID NO: 204 is encoded by SEQ ID NO: 91; the polypeptide of SEQ ID NO: 205 is encoded by SEQ ID NO: 93; the polypeptide of SEQ ID NO: 206 is encoded by SEQ ID NO: 94; the polypeptide of SEQ ID NO: 207 is encoded by SEQ ID NO: 95; the polypeptide of SEQ ID NO: 208 is encoded by SEQ ID NO: 96; the polypeptide of SEQ ID NO: 209 is encoded by SEQ ID NO: 97; the polypeptide of SEQ ID NO: 210 is encoded by SEQ ID NO: 98; the polypeptide of SEQ ID NO: 211 is encoded by SEQ ID NO: 99; the polypeptide of SEQ ID NO: 212 is encoded by SEQ ID NO: 100; the polypeptide of SEQ ID NO: 213 is encoded by SEQ ID NO: 101; the polypeptide of SEQ ID NO: 214 is encoded by SEQ ID NO: 102; the polypeptide of SEQ ID NO: 215 is encoded by SEQ ID NO: 103; the polypeptide of SEQ ID NO: 216 is encoded by SEQ ID NO: 104; the polypeptide of SEQ ID NO: 217 is encoded by SEQ ID NO: 105; the polypeptide of SEQ ID NO: 218 is encoded by SEQ ID NO: 106; the polypeptide of SEQ ID NO: 219 is encoded by SEQ ID NO: 107; the polypeptide of SEQ ID NO: 220 is encoded by SEQ ID NO: 108; the polypeptide of SEQ ID NO: 221 is encoded by SEQ ID NO: 110; the polypeptide of SEQ ID NO: 222 is encoded by SEQ ID NO: 111; the polypeptide of SEQ ID NO: 223 is encoded by SEQ ID NO: 112; the polypeptide of SEQ ID NO: 224 is encoded by SEQ ID NO: 113; the polypeptide of SEQ ID NO: 225 is encoded by SEQ ID NO: 114; the polypeptide of SEQ ID NO: 226 is encoded by SEQ ID NO: 115; the polypeptide of SEQ ID NO: 227 is encoded by SEQ ID NO: 116; the polypeptide of SEQ ID NO: 228 is encoded by SEQ ID NO: 117; the polypeptide of SEQ ID NO: 229 is encoded by SEQ ID NO: 118; the polypeptide of SEQ ID NO: 230 is encoded by SEQ ID NO: 119; the polypeptide of SEQ ID NO: 231 is encoded by SEQ ID NO: 120; the polypeptide of SEQ ID NO: 232 is encoded by SEQ ID NO: 121; the polypeptide of SEQ ID NO: 233 is encoded by SEQ ID NO: 122; and the polypeptide of SEQ ID NO: 234 is encoded by SEQ ID NO: 123.

In some embodiments the nucleic acid molecule encoding an IPD121 polypeptide is a polynucleotide having the sequence set forth in any one of SEQ ID NOS: 1-123, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the IPD121 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an IPD121 polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of any one of SEQ ID NOS: 1-123, wherein the IPD121 polypeptide has insecticidal activity.

In some embodiments the nucleic acid molecule encodes an IPD121 polypeptide variant comprising one or more amino acid substitutions to the amino acid sequence of any one of SEQ ID NOS: 124-234.

Also provided are nucleic acid molecules that encode transcription and/or translation products that are subsequently spliced to ultimately produce functional IPD121 polypeptides. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an IPD121 polypeptide encoding sequence. An example of trans-splicing would be where a polynucleotide is encrypted by separating the coding sequence into two or more fragments that can be separately transcribed and then spliced to form the full-length pesticidal encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length IPD121 polypeptide, but rather encode a fragment or fragments of an IPD121 polypeptide. These polynucleotides can be used to express a functional IPD121 polypeptide through a mechanism involving splicing, where splicing can occur at the level of polynucleotide (e.g., intron/exon) and/or polypeptide (e.g., intein/extein). This can be useful, for example, in controlling expression of pesticidal activity, since a functional pesticidal polypeptide will only be expressed if all required fragments are expressed in an environment that permits splicing processes to generate functional product. In another example, introduction of one or more insertion sequences into a polynucleotide can facilitate recombination with a low homology polynucleotide; use of an intron or intein for the insertion sequence facilitates the removal of the intervening sequence, thereby restoring function of the encoded variant.

Nucleic acid molecules that are fragments of these nucleic acid sequences encoding IPD121 polypeptides are also encompassed by the embodiments. "Fragment" as used herein refers to a portion of the nucleic acid sequence encoding an IPD121 polypeptide. A fragment of a nucleic acid sequence may encode a biologically active portion of an IPD121 polypeptide or it may be a fragment that can be used as a hybridization probe or PCR primer using methods disclosed below. Nucleic acid molecules that are fragments of a nucleic acid sequence encoding an IPD121 polypeptide comprise at least about 150, 180, 210, 240, 270, 300, 330, 360, 400, 450, or 500 contiguous nucleotides or up to the number of nucleotides present in a full-length nucleic acid sequence encoding an IPD121 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD121 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of any one of the full-length IPD121 polypeptides set forth in SEQ ID NOS: 124-234. In some embodiments, the insecticidal activity is against a Lepidopteran species. In one embodiment, the insecticidal activity is against a Coleopteran species. In some embodiments, the insecticidal activity is against one or more insect pests of the corn rootworm complex: western corn rootworm, *Diabrotica virgifera*; northern corn rootworm, *D. barberi*: Southern corn rootworm or spotted cucumber beetle; *Diabrotica undecimpunctata howardi, Diabrotica speciosa*, and the Mexican corn rootworm, *D. virgifera zeae*. In one embodiment, the insecticidal activity is against a *Diabrotica* species.

In some embodiments the IPD121 polypeptide is encoded by a nucleic acid sequence sufficiently homologous to any one of the nucleic acid sequences of SEQ ID NOS: 1-123.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, FASTA, and various other implementations of Smith-Waterman or Needleman-Wunsch algorithms within these tools and in other tools. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments an IPD121 polynucleotide encodes an IPD121 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of SEQ ID NOS: 124-234.

In some embodiments polynucleotides are provided encoding chimeric polypeptides comprising regions of at least two different IPD121 polypeptides of the disclosure.

In some embodiments polynucleotides are provided encoding chimeric polypeptides comprising an N-terminal Region of a first IPD121 polypeptide of the disclosure operably fused to a C-terminal Region of a second IPD121 polypeptide of the disclosure.

The embodiments also encompass nucleic acid molecules encoding IPD121 polypeptide variants. "Variants" of the IPD121 polypeptide encoding nucleic acid sequences include those sequences that encode the IPD121 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the IPD121 polypeptides disclosed as discussed below.

The present disclosure provides isolated or recombinant polynucleotides that encode any of the IPD121 polypeptides disclosed herein. Those having ordinary skill in the art will readily appreciate that due to the degeneracy of the genetic code, a multitude of nucleotide sequences encoding IPD121 polypeptides of the present disclosure exist.

The skilled artisan will further appreciate that changes can be introduced by mutation of the nucleic acid sequences thereby leading to changes in the amino acid sequence of the encoded IPD121 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity or, such activity at a desired pH, etc. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having pesticidal activity or fragments thereof, are found in the following publications and the references cited therein: Soong, et al., (2000) *Nat Genet* 25(4):436-439; Stemmer, et al., (1999) *Tumor Targeting* 4:1-4; Ness, et al., (1999) *Nat Biotechnol* 17:893-896; Chang, et al., (1999) *Nat Biotechnol* 17:793-797; Minshull and Stemmer, (1999) *Curr Opin Chem Biol* 3:284-290; Christians, et al., (1999) *Nat Biotechnol* 17:259-264; Crameri, et al., (1998) *Nature* 391:288-291; Crameri, et al., (1997) *Nat Biotechnol* 15:436-438; Zhang, et al., (1997) *PNAS USA* 94:4504-4509; Patten, et al., (1997) *Curr Opin Biotechnol* 8:724-733; Crameri, et al., (1996) *Nat Med* 2:100-103; Crameri, et al., (1996) *Nat Biotechnol* 14:315-

319; Gates, et al., (1996) *J. Mol Biol* 255:373-386; Stemmer, (1996) "Sexual PCR and Assembly PCR" In: *The Encyclopedia of Molecular Biology*. VCH Publishers, New York. pp. 447-457; Crameri and Stemmer, (1995) *BioTechniques* 18:194-195; Stemmer, et al., (1995) *Gene*, 164:49-53; Stemmer, (1995) *Science* 270: 1510; Stemmer, (1995) *Bio/Technology* 13:549-553; Stemmer, (1994) *Nature* 370:389-391 and Stemmer, (1994) *PNAS USA* 91:10747-10751.

Mutational methods of generating diversity include, for example, site-directed mutagenesis (Ling, et al., (1997) *Anal Biochem* 254(2):157-178; Dale, et al., (1996) *Methods Mol Biol* 57:369-374; Smith, (1985) *Ann Rev Genet* 19:423-462; Botstein and Shortle, (1985) *Science* 229:1193-1201; Carter, (1986) *Biochem J* 237:1-7 and Kunkel, (1987) "The efficiency of oligonucleotide directed mutagenesis" in *Nucleic Acids & Molecular Biology* (Eckstein and Lilley, eds., Springer Verlag, Berlin)); mutagenesis using uracil containing templates (Kunkel, (1985) *PNAS USA* 82:488-492; Kunkel, et al., (1987) *Methods Enzymol* 154:367-382 and Bass, et al., (1988) *Science* 242:240-245); oligonucleotide-directed mutagenesis (Zoller and Smith, (1983) *Methods Enzymol* 100:468-500; Zoller and Smith, (1987) *Methods Enzymol* 154:329-350 (1987); Zoller and Smith, (1982) *Nucleic Acids Res* 10:6487-6500), phosphorothioate-modified DNA mutagenesis (Taylor, et al., (1985) *Nucl Acids Res* 13:8749-8764; Taylor, et al., (1985) *Nucl Acids Res* 13:8765-8787 (1985); Nakamaye and Eckstein, (1986) *Nucl Acids Res* 14:9679-9698; Sayers, et al., (1988) *Nucl Acids Res* 16:791-802 and Sayers, et al., (1988) *Nucl Acids Res* 16:803-814); mutagenesis using gapped duplex DNA (Kramer, et al., (1984) *Nucl Acids Res* 12:9441-9456; Kramer and Fritz, (1987) *Methods Enzymol* 154:350-367; Kramer, et al., (1988) *Nucl Acids Res* 16:7207 and Fritz, et al., (1988) *Nucl Acids Res* 16:6987-6999).

Additional suitable methods include point mismatch repair (Kramer, et al., (1984) *Cell* 38:879-887), mutagenesis using repair-deficient host strains (Carter, et al., (1985) *Nucl Acids Res* 13:4431-4443 and Carter, (1987) *Methods in Enzymol* 154:382-403), deletion mutagenesis (Eghtedarzadeh and Henikoff, (1986) *Nucl Acids Res* 14:5115), restriction-selection and restriction-purification (Wells, et al., (1986) *Phil Trans R Soc Lond A* 317:415-423), mutagenesis by total gene synthesis (Nambiar, et al., (1984) *Science* 223:1299-1301; Sakamar and Khorana, (1988) *Nucl Acids Res* 14:6361-6372; Wells, et al., (1985) *Gene* 34:315-323 and Grundström, et al., (1985) *Nucl Acids Res* 13:3305-3316), double-strand break repair (Mandecki, (1986) *PNAS USA*, 83:7177-7181 and Arnold, (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following US patents, PCT Publications and applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 1012670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, WO 2001/23401 and PCT/US01/06775.

The nucleotide sequences of the embodiments can also be used to isolate corresponding sequences from a plant source, including but not limited to a *Polystichum*, *Davallia*, *Didymochlaena*, *Humata*, *Onoclea*, and/or *Tectaria* species. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989)*Molecular Cloning: A Laboratory Manual* (2d ed., Cold Spring Harbor Laboratory Press, Plainview, N.Y.), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

To identify potential IPD121 polypeptides from plant collections, plant cell extracts can be screened with antibodies generated against IPD121 polypeptides using Western blotting and/or ELISA methods. This type of assay can be performed in a high throughput fashion. Positive samples can be further analyzed by various techniques such as antibody based protein purification and identification. Methods of generating antibodies are well known in the art as discussed infra.

Alternatively, mass spectrometry based protein identification method can be used to identify homologs of IPD121 polypeptides using protocols in the literatures (Scott Patterson, (1998), 10.22, 1-24, Current Protocol in Molecular Biology published by John Wiley & Son Inc). Specifically, LC-MS/MS based protein identification method is used to associate the MS data of given cell lysate or desired molecular weight enriched samples (excised from SDS-PAGE gel of relevant molecular weight bands to IPD121 polypeptides) with sequence information of an IPD121 polypeptide disclosed herein. Any match in peptide sequences indicates the potential of having the homologous proteins in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known IPD121 polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding IPD121 polypeptides of the disclosure or a fragment or variant thereof. Methods for the preparation of probes for hybridization and stringency conditions are generally known in the art and are disclosed in Sambrook and Russell, (2001), supra, herein incorporated by reference.

For example, an entire nucleic acid sequence, encoding an IPD121 polypeptide, disclosed herein or one or more portions thereof may be used as a probe capable of specifically hybridizing to corresponding nucleic acid sequences encoding IPD121 polypeptide-like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2d ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length Antibodies Antibodies to an IPD121 polypeptide of the embodiments or to variants or fragments thereof are also encompassed. The antibodies of the disclosure include polyclonal and monoclonal antibodies as well as fragments thereof which retain their ability to bind to an IPD121 polypeptide. An antibody, monoclonal antibody or fragment thereof is said to be capable of binding a molecule if it is capable of specifically reacting with the molecule to thereby bind the molecule to the antibody, monoclonal antibody or fragment thereof. The term "antibody" (Ab) or "monoclonal antibody" (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, "Monoclonal Antibody Technology," In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against IPD121 polypeptides or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an IPD121 polypeptide as antigens.

A kit for detecting the presence of an IPD121 polypeptide or detecting the presence of a nucleotide sequence encoding an IPD121 polypeptide in a sample is provided. In one embodiment, the kit provides antibody-based reagents for detecting the presence of an IPD121 polypeptide in a tissue sample. In another embodiment, the kit provides labeled nucleic acid probes useful for detecting the presence of one or more polynucleotides encoding an IPD121 polypeptide. The kit is provided along with appropriate reagents and controls for carrying out a detection method, as well as instructions for use of the kit.

Receptor Identification and Isolation

Receptors to the IPD121 polypeptides of the embodiments or to variants or fragments thereof are also encompassed. Methods for identifying receptors are well known in the art (see, Hofmann, et. al., (1988) *Eur. J. Biochem.* 173:85-91; Gill, et al., (1995) *J. Biol. Chem.* 27277-27282) can be employed to identify and isolate the receptor that recognizes the IPD121 polypeptide using the brush-border membrane vesicles from susceptible insects. In addition to the radioactive labeling method listed in the cited literatures, an IPD121 polypeptide can be labeled with fluorescent dye and other common labels such as streptavidin. Brush-border membrane vesicles (BBMV) of susceptible insects such as soybean looper and stink bugs can be prepared according to the protocols listed in the references of Hofmann and Gill above and separated on SDS-PAGE gel and blotted on suitable membrane. Labeled IPD121 polypeptide can be incubated with blotted membrane of BBMV and labeled IPD121 polypeptide can be identified with the labeled reporters. Identification of protein band(s) that interact with the IPD121 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the IPD121 polypeptide. Receptor function for insecticidal activity by the IPD121 polypeptide can be verified by RNAi type of gene knock out method (Rajagopal, et al., (2002) *J. Biol. Chem.* 277:46849-46851).

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD121 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an IPD121 polypeptide of the embodiments. In some embodiments the DNA construct comprises a polynucleotide encoding a fusion protein comprising an IPD121 polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991)*Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989)

*Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010, herein incorporated by reference. A *Zea* maize usage table can be also found at kazusa.or.jp//cgi-bin/show.cgi?species=4577, which can be accessed using the www prefix. A *Glycine max* usage table can be found at kazusa.or.jp//cgi-bin/show.cgi?species=3847&aa=1&style=N, which can be accessed using the www prefix.

In some embodiments the recombinant nucleic acid molecule encoding an IPD121 polypeptide has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987)*Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. Plant Cell 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research,* 78:249-264, 2003. In particular, Table 2 of this publication, which is incorporated into the description herewith by reference, discloses 85 proteins from the chloroplast lumen, identified by their accession number (see also US Patent Application Publication 2009/09044298).

Suitable chloroplast transit peptides (CTP) are well known to one skilled in the art also include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type (See US Patent Application Publication 2012/0304336).

The IPD121 polypeptide gene to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989)*Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156).

Tissue-preferred promoters can be utilized to target enhanced IPD121 polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7): 792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters are known in the art. See, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed rolC and rolD root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2): 343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and rolB promoter (Capana, et al., (1994) *Plant Mol.*

Biol. 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1101), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692., granted as U.S. Pat. No. 7,462,481); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad Sci. USA* 89:6314-6318; Yao, et al., (1992) *Cell* 71:63-72; Reznikoff, (1992)*Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad Sci. USA* 86:5400-5404; Fuerst, et al., (1989) *Proc. Natl. Acad Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baimn, et al., (1991) *Proc. Natl. Acad. Sci. USA* 88:5072-5076; Wyborski, et al., (1991)*Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants are known in the art including, but not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Bio/technology* 6:923-926) and Led transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P: 175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

In specific embodiments, the sequences of the embodiments can be provided to a plant using a variety of transient transformation methods. Such transient transformation methods include, but are not limited to, the introduction of the IPD121 polynucleotide or variants and fragments thereof directly into the plant or the introduction of the IPD121 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107: 775-784. Alternatively, the IPD121 polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired IPD121 polypeptide. It is also recognized that such a viral polyprotein, comprising at least a portion of the amino acid sequence of an IPD121 polypeptide of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, are known in the art. See, for example, U.S. Pat. Nos. 5,889,191; 5,889,190; 5,866,785; 5,589,367 and 5,316,931.

Methods for transformation of chloroplasts are known in the art. See, for example, Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), *macadamia* (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), *hydrangea* (*Macrophylla hydrangea*), *hibiscus* (*Hibiscus rosasanensis*), roses (*Rosa* spp.), tulips (*Tuhpa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*);

redtop (*Agrostis alba*); rough bluegrass (Poa trivial's); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); Zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore *paspalum* (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra). Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IPD121 polypeptide.

Methods to Introduce Genome Editing Technologies into Plants

In some embodiments, the disclosed IPD121 polynucleotide compositions can be introduced into the genome of a plant using genome editing technologies, or previously introduced IPD121 polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IPD121 polynucleotide has previously been introduced into a genome, genome editing technologies may be used to alter or modify the introduced polynucleotide sequence. Site specific modifications that can be introduced into the disclosed IPD121 polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed IPD121 polynucleotide compositions disclosed herein within the genome of a plant, in order to generate molecular stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, one or more of the polynucleotides encoding the IPD121 polypeptide(s) disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to: transgenes that confer resistance to a herbicide; transgenes that confer or contribute to an altered grain characteristic; genes that control male-sterility; genes that create a site for site specific dna integration; genes that affect abiotic stress resistance; genes that confer increased yield genes that confer plant digestibility; and transgenes that confer resistance to insects or disease.

Examples of transgenes that confer resistance to insects include genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas* protegees strain CHAO and Pf-5 (previously *fluorescens*) (Pechy-Tarr, (2008) *Environmental Microbiology* 10:2368-2386: GenBank Accession No. EU400157); from *Pseudomonas taiwanensis* (Liu, et al., (2010) 1 *Agric. Food Chem.* 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; an IPD079 polypeptide of U.S. Ser. No. 62/201,977; an IPD082 polypeptide of U.S. Ser. No. 62/269,482, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry72 classes of δ-endotoxin genes and the *B. thuringiensis* cytolytic Cyt1 and Cyt2 genes. Members of these classes of *B. thuringiensis* insecticidal proteins well known to one skilled in the art (see, Crickmore, et al., "*Bacillus thuringiensis* toxin nomenclature" (2011), atlifesci.sussex.ac.uk/home/Neil_Crickmore/Bt/which can be accessed on the world-wide web using the "www" prefix).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of US Patent Numbers 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AX-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of a WO11/103247; AXMI-11, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of U2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as Xenorhabdus, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

Further transgenes that confer resistance to insects may down-regulation of expression of target genes in insect pest species by interfering ribonucleic acid (RNA) molecules through RNA interference. RNA interference refers to the process of sequence-specific post-transcriptional gene silencing in animals mediated by short interfering RNAs (siRNAs) (Fire, et al., (1998) *Nature* 391:806). RNAi transgenes may include but are not limited to expression of dsRNA, siRNA, miRNA, iRNA, antisense RNA, or sense RNA molecules that down-regulate expression of target genes in insect pests. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus.

RNAi transgenes are provided for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describes polynucleotide silencing elements targeting RyanR and PAT3. PCT publications WO/2016/138106, WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents are known in the art.

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene(s) expressing one or more of the IPD121 polypeptides and desirably provide for improved protection of the pesticide from environmental degradation and inactivation.

Alternatively, the IPD121 polypeptide is produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated IPD121 polypeptides may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient or an agrochemical composition that contains at least one of the IPD121 polypeptide(s) produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus* thuriengiensis, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethonmethyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethy)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* J E Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (Xylomyges) *curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana inte-

*gerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *Colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *Phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *Phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus serous* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (*Bagrada* Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *Cereus, Firmus, Megaterium, Pumilis, Sphaericus, Subtilis* and/or *Thuringiensis* species), *Bradyrhizobium* spp. (including one or more of *Betae, Canariense, Elkanii, Iriomotense, Japonicum, Liaonigense, Pachyrhizi* and/or *Yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *Penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *Trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant IPD121 polypeptide of the disclosure. In some embodiments methods are provided for killing an insect pest, comprising contacting the insect pest with an insecticidally-effective amount of one or more of a recombinant pesticidal protein of SEQ ID NOS: 124-234, or a variant or insecticidally active fragment thereof.

In some embodiments methods are provided for controlling an insect pest population, comprising contacting the insect pest population, either simultaneously or sequentially, with an insecticidally-effective amount of one or more of a recombinant IPD121 polypeptide of the disclosure. In some embodiments, methods are provided for controlling an insect pest population, comprising contacting the insect pest population with an insecticidally-effective amount of one or more of a recombinant IPD121 polypeptide of SEQ ID NOS: 124-234, or a variant or insecticidally active fragment thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of one or more of a recombinant IPD121 polypeptide of the disclosure. In some embodiments, methods are provided for controlling an insect pest population resistant to a pesticidal protein, comprising contacting the insect pest population with an insecticidally-effective amount of one or more of a recombinant IPD121 polypeptide of SEQ ID NOS: 124-234, or a variant or insecticidally active fragment thereof.

In some embodiments methods are provided for protecting a plant from an insect pest, comprising expressing in the plant or cell thereof at least one recombinant polynucleotide encoding an IPD121 polypeptide of the disclosure. In some embodiments methods are provided for protecting a plant from an insect pest, comprising expressing in the plant or cell thereof a recombinant polynucleotide encoding one or more IPD121 polypeptides of SEQ ID NOS: 124-234, or variants or insecticidally active fragments thereof.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, in certain instances insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way of increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt-_corn_refuge_2006. htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the IPD121 polypeptides of the disclosure are useful as an insect resistance management strategy in combination (i.e., pyramided) with other pesticidal proteins or other transgenes (i.e., an RNAi trait) including but not limited to Bt toxins, *Xenorhabdus* sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management comprises the presentation of at least one of the IPD121 polypeptide insecticidal proteins to insects in the order Lepidoptera and/or Coleoptera.

In some embodiments the methods of controlling Lepidoptera and/or Coleoptera insect infestation in a transgenic plant and promoting insect resistance management comprises the presentation of at least one of the IPD121 polypeptides of SEQ ID NOS: 124-234, or variants or insecticidally active fragments thereof, insecticidal to insects in the order Lepidoptera and/or Coleoptera.

In some embodiments the methods of controlling Lepidoptera and/or Coleoptera insect infestation in a transgenic plant and promoting insect resistance management comprise expressing in the transgenic plant an IPD121 polypeptide and a Cry protein or other insecticidal protein to insects in the order Lepidoptera and/or Coleoptera having different modes of action.

In some embodiments the methods of controlling Lepidoptera and/or Coleoptera insect infestation in a transgenic plant and promoting insect resistance management comprise expression in the transgenic plant of at least one of an IPD121 polypeptide of SEQ ID NOS: 124-234, or variants or insecticidally active fragments thereof and a Cry protein or other insecticidal protein to insects in the order Lepidoptera and/or Coleoptera, where the IPD121 polypeptide and Cry protein have different modes of action.

Also provided are methods of reducing likelihood of emergence of Lepidoptera and/or Coleoptera insect resistance to transgenic plants expressing in the plants insecticidal proteins to control the insect species, comprising expression of at least one of an IPD121 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins or other insecticidal transgenes (e.g., an RNAi trait) toxic to Lepidoptera and/or Coleoptera insects but each exhibiting a different mode of effectuating its killing activity, wherein two or more of the insecticidal proteins or other insecticidal transgenes comprise an IPD121 polypeptide and a Cry protein. Also provided are means for effective Lepidoptera and/or Coleoptera insect resistance management of transgenic plants, comprising co-expressing at high levels in the plants two or more insecticidal proteins or other insecticidal transgenes (e.g., an RNAi trait) toxic to Lepidoptera and/or Coleoptera insects but each exhibiting a different mode of effectuating its killing activity, wherein two or more insecticidal proteins or other insecticidal transgenes comprise at least one of an IPD121 polypeptide of SEQ ID NOS: 124-234, or variants or insecticidally active fragments thereof and a Cry protein or other insecticidally active protein.

In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD121 polypeptide does not compete with binding sites for Cry proteins in such insects. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that one or more of the IPD121 polypeptides of SEQ ID NOS: 124-234, or variant or insecticidally active fragment thereof does not compete with binding sites for Cry proteins in such insects.

An embodiment of the invention contemplates a recombinant polynucleotide encoding an insecticidal polypeptide having at least 76% sequence identity to a polypeptide selected from SEQ ID NOS: 124-234. In an embodiment, the recombinant polynucleotide encodes a polypeptide having at least 90% sequence identity to a polypeptide selected from SEQ ID NOS: 124-234. In an embodiment, the insecticidal polypeptide is joined to a heterologous signal sequence or a transit sequence. In an embodiment, the recombinant polynucleotide has at least 80% or at least 90% sequence identity to a polynucleotide selected from any one of SEQ ID NOS: 1-123, wherein the polynucleotide is operably linked to a heterologous regulatory element. In an embodiment, the recombinant polynucleotide has codons optimized for expression in an agriculturally important crop. A DNA construct comprising these recombinant polynucleotides is contemplated, as are transgenic plants comprising the recombinant polynucleotides or DNA constructs.

Some embodiments of the invention relate to a method of inhibiting growth or killing an insect pest or pest population, comprising contacting the insect pest with an insecticidal polypeptide having at least 76% sequence identity to a polypeptide selected from SEQ ID NOS: 124-234. An embodiment relates to a method of inhibiting growth or killing an insect pest or pest population comprising expressing in a plant a recombinant polynucleotide encoding an insecticidal polypeptide having at least 76% sequence identity to a polypeptide selected from SEQ ID NOS: 124-234. A method for controlling pest infestation comprising providing in the diet of the pest the transgenic plant expressing a recombinant polynucleotide encoding an insecticidal polypeptide having at least 76% sequence identity to a polypeptide selected from SEQ ID NOS: 124-234 is also contemplated.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing at least one IPD121 polypeptide disclosed herein. Expression of the IPD121 polypeptide(s) results in a reduced ability of a pest to infest or feed on the plant, thus improving plant yield.

Methods of Processing

Further provided are methods of processing a plant, plant part or seed to obtain a food or feed product from a plant, plant part or seed comprising at least one IPD121 polynucleotide. The plants, plant parts or seeds provided herein, can be processed to yield oil, protein products and/or by-products that are derivatives obtained by processing that have commercial value. Non-limiting examples include transgenic seeds comprising a nucleic acid molecule encoding one or more IPD121 polypeptides which can be processed to yield soy oil, soy products and/or soy by-products.

"Processing" refers to any physical and chemical methods used to obtain any soy product and includes, but is not limited to, heat conditioning, flaking and grinding, extrusion, solvent extraction or aqueous soaking and extraction of whole or partial seeds The following examples are offered by way of illustration and not by way of limitation.

EXAMPLES

Example 1—Transcriptome Sequencing of Plants

Transcriptomes for various plant samples were prepared as follows. Total RNA was isolated from frozen tissues with an RNeasy® kit (Qiagen®). Sequencing libraries from the resulting total RNAs were prepared using the TruSeq™ mRNA-Seq kit and protocol from Illumina®, Inc. (San Diego, Calif.). Briefly, mRNAs were isolated via attachment to oligo(dT) beads, fragmented to a mean size of 180 nt, reverse transcribed into cDNA by random hexamer primers, end repaired, 3' A-tailed, and ligated with Illumina® indexed TruSeq™ adapters. Ligated cDNA fragments were PCR amplified using Illumina® TruSeq™ primers and purified PCR products were checked for quality and quantity on the Agilent Bioanalyzer® DNA 7500 chip. Post quality and quantity assessment, 100 ng of the transcript library was normalized by treatment with Duplex Specific Nuclease (DSN) (Evrogen®, Moscow, Russia). Normalization was accomplished by addition of 200 mM Hepes buffer, followed by heat denaturation and five hour anneal at 68° C. Annealed library was treated with 2 µL of DSN enzyme for 25 minutes, purified by Qiagen® MinElute® columns according to manufacturer protocols, and amplified twelve cycles using Illumina® adapter specific primers. Final products were purified with Ampure® XP beads (Beckman Genomics, Danvers, Mass.) and checked for quality and quantity on the Agilent Bioanalyzer® DNA 7500 chip.

Normalized transcript libraries were sequenced according to manufacturer protocols on the Illumina® HiSeq® 2500. Libraries were pooled, hybridized and sequenced three per flowcell lane using onboard clustering methods followed by sequencing to a target depth of sixty million 75 bp paired end reads per normalized library.

Example 2—Identification of IPD121Aa and Homologs

Candidate transcriptome DNA assembly sequences harboring the predicted coding sequences for IPD121Aa, IPD121Ab, IPD121Ca, IPD121Cb, IPD121Cc, and IPD121Cd were identified in proprietary sequence databases. The corresponding predicted coding sequences (SEQ ID NOS 1, 2, 3, 4, 5, and 6, respectively) were used to design the primers listed in Table 1. These were used for cloning by polymerase chain reaction using the Kappa HiFi™ polymerase (Kapa Bioscience, Wilmington, Mass.) and the cDNA prepared from the total RNA from the plants using the SuperScript® II kit (Thermo Fischer Scientific, Waltham, Mass.) as the template. PCR products were gel purified, digested with NdeI and XhoI restriction enzymes (New England Biolabs) and ligated into pET14b (Novagen®) also digested with the same enzymes. Colonies were sequenced to confirm the clones. The SEQ ID numbers of cloned polynucleotide sequences and their corresponding polypeptide sequences are listed in Table 2.

TABLE 1

| Source | Source species | Forward PCR primer | Reverse PCR primer |
|---|---|---|---|
| PS12415 | Polystichum tripteron | SEQ ID NO: 235 | SEQ ID NO: 236 |
| PS9179 | Davallia fejeensis | SEQ ID NO: 241 | SEQ ID NO: 242 |
| NY006 | Didymochlaena truncatula | SEQ ID NO: 237 | SEQ ID NO: 238 |
| NY008 | Humata tyermanii | SEQ ID NO: 239 | SEQ ID NO: 240 |
| PS12275 | Onoclea sensibilis | SEQ ID NO: 243 | SEQ ID NO: 244 |
| PS9539 | Tectaria milnei | SEQ ID NO: 245 | SEQ ID NO: 246 |

TABLE 2

| Gene Name | Source | Organism | DNA Seq | AA Seq |
|---|---|---|---|---|
| IPD121Aa | PS12415 | Polystichum tripteron | SEQ ID NO: 1 | SEQ ID NO: 124 |
| IPD121Ab | PS12415 | Polystichum tripteron | SEQ ID NO: 2 | SEQ ID NO: 125 |
| IPD121Ac | PS12415 | Polystichum tripteron | SEQ ID NO: 117 | SEQ ID NO: 228 |
| IPD121Ad | PS12415 | Polystichum tripteron | SEQ ID NO: 118 | SEQ ID NO: 229 |
| IPD121Ae | PS12415 | Polystichum tripteron | SEQ ID NO: 119 | SEQ ID NO: 230 |
| IPD121Af | PS12415 | Polystichum tripteron | SEQ ID NO: 120 | SEQ ID NO: 231 |
| IPD121Ca | PS9179 | Davallia fejeensis | SEQ ID NO: 3 | SEQ ID NO: 126 |
| IPD121Cb | NY006 | Didymochlaena truncatula | SEQ ID NO: 4 | SEQ ID NO: 127 |
| IPD121Cc | NY006 | Didymochlaena truncatula | SEQ ID NO: 5 | SEQ ID NO: 128 |
| IPD121Cd | NY008 | Humata tyermanii | SEQ ID NO: 6 | SEQ ID NO: 129 |
| IPD121Ce | PS12275 | Onoclea sensibilis | SEQ ID NO: 16 | SEQ ID NO: 139 |
| IPD121Cf | PS12275 | Onoclea sensibilis | SEQ ID NO: 114 | SEQ ID NO: 225 |
| IPD121Cg | PS12275 | Onoclea sensibilis | SEQ ID NO: 115 | SEQ ID NO: 226 |
| IPD121Ch | PS12275 | Onoclea sensibilis | SEQ ID NO: 116 | SEQ ID NO: 227 |
| IPD121Da | PS9539 | Tectaria milnei | SEQ ID NO: 19 | SEQ ID NO: 142 |
| IPD121Db | PS9539 | Tectaria milnei | SEQ ID NO: 121 | SEQ ID NO: 232 |
| IPD121Dc | PS9539 | Tectaria milnei | SEQ ID NO: 122 | SEQ ID NO: 233 |
| IPD121Dd | PS9539 | Tectaria milnei | SEQ ID NO: 123 | SEQ ID NO: 234 |

Example 3—Identification of Homologs

Gene identities were determined by conducting BLAST™ (Basic Local Alignment Search Tool; Altschul, et al., (1993) *J. Mol. Biol.* 215:403-410; see also ncbi.nlm.nih.gov/BLAST/, which can be accessed using the www prefix) searches under default parameters for similarity to sequences. The polynucleotide sequence for IPD121Aa (SEQ ID NO: 1) was analyzed. Gene identities conducted by BLAST™ in a DUPONT PIONEER internal proprietary database identified multiple homologs of the IPD121Aa protein, as represented by the polynucleotide sequences of SEQ ID NOs 2-123 and the corresponding polypeptide sequences of SEQ ID NOs 125-234.

Example 4—Expression and Insect Bioassay on Transient Leaf Tissues

To confirm activity of IPD121Aa (SEQ ID NO: 124) and the homologs IPD121Ab, IPD121Ac, IPD121Ad, IPD121Ae, IPD121Af, IPD121Ca, IPD121Cb, IPD121Cc, IPD121Cd, IPD121Ce, IPD121Cf, IPD121Cg, IPD121Ch, IPD121 Da, IPD121Db, IPD121Dc, and IPD121Dd, the corresponding genes were cloned into a transient expression system under control of the viral promoter dMMV promoter (Dey, et. al., (1999) *Plant Mol. Biol.* 40:771-782; PCT Patent Publication WO2011133387). The expression plasmids were transformed into *Agrobacterium tumefaciens* AGL1, and the resulting strains were used for transient expression in bush bean (common bean, *Phaseolus vulgaris*). The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, the unifoliate stage of bush bean (common bean, *Phaseolus vulgaris*) were agro-infiltrated with normalized bacterial cell suspensions of test and control strains. Leaf discs were excised from each plantlet and infested with neonates of Soy Bean Looper (SBL) (*Pseudoplusia includens*), Corn Earworm, (CEW) (*Helicoverpa zea*), (FAW), Velvet Bean Caterpillar (VBC) (*Anticarsia gemmatalis*) or European Corn Borer (ECB) (*Ostrinia nubialis*). Leaf discs from a control were generated with *Agrobacterium* containing only empty expression vector. Leaf discs from a non-infiltrated plant were used as a second control. The consumption of green leaf tissue was scored three days after infestation and given scores of 0 to 9 as indicated by Table 3. The transiently expressed IPD121Aa (SEQ ID NO: 124) and several homologs protected bush bean leaf discs from consumption by the infested insects while total green tissue consumption was observed for the negative control and untreated tissue. Transient protein expression of IPD121Aa (SEQ ID NO: 124) and IPD121Ab (SEQ ID NO: 125) was confirmed by a mass spectrometry-based protein identification method using extracted protein lysates from infiltrated leave tissues (Patterson, (1998) 10(22):1-24, Current Protocol in Molecular Biology published by John Wiley & Son Inc). As shown in FIGS. 2A-2D, transient protein expression of IPD121Aa (SEQ ID NO: 124), IPD121Ca (SEQ ID NO: 126), IPD121Cb (SEQ ID NO: 127), IPD121Cc (SEQ ID NO:128), IPD121Cd (SEQ ID NO:129), and IPD121Ce (SEQ ID NO: 139) resulted in protection of bush bean against leaf feeding damage from a diversity of Lepidoptera.

TABLE 3

| Leaf Feeding Score | % Consumed |
| --- | --- |
| 1 | 86-100 |
| 2 | 71-85 |
| 3 | 61-70 |
| 4 | 51-60 |
| 5 | 36-50 |
| 6 | 11-35 |
| 7 | 7-10 |
| 8 | 1-3 |
| 9 | 0 |

Activity of selected IPD121 polypeptides, transiently expressed in bush bean, against leaf feeding damage from a selection of Lepidoptera is shown in FIGS. 2A-2D. The average score and standard error (SE) for 6 replicate measurements are shown. Samples with Average Leaf Damage Scores which were greater than one Standard Error different from the negative control were considered to be active under test conditions. Accordingly, samples which were not considered active under test conditions are shaded grey.

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed is:

1. A DNA construct comprising a heterologous regulatory element and a recombinant polynucleotide encoding an insecticidal polypeptide comprising an amino acid sequence having at least 95% sequence identity to SEQ ID NO: 124 or a fragment thereof having insecticidal activity.

2. The recombinant polynucleotide of claim 1, wherein the polynucleotide has codons optimized for expression in an agriculturally important crop.

3. A transgenic plant comprising the polynucleotide of claim 1.

4. A method of inhibiting growth or killing an insect pest or pest population, comprising contacting the insect pest with an insecticidal polypeptide comprising an amino acid sequence having at least 95% sequence identity to SEQ ID NO: 124 or a fragment thereof having insecticidal activity.

5. A method of inhibiting growth or killing an insect pest or pest population comprising expressing in a plant the polynucleotide of claim 1.

6. A method of controlling insect pest damage to plants comprising providing the insecticidal polypeptide of claim 1 an insect pest or pest population for ingestion, wherein said insecticidal polypeptide is produced by a transgenic plant and is present in at least one of said plants.

7. A method for controlling pest infestation comprising providing in the diet of the pest the transgenic plant of claim 3, or a part thereof.

8. A method for improving the yield of a crop comprising growing the transgenic plant of claim 3, wherein the yield of the crop is increased in the presence of the insect pest relative to the crop not comprising said transgenic plant.

9. The method of claim 4, wherein the insect pest or pest population is resistant to at least one Cry insecticidal protein.

10. The method of claim 6, wherein the transgenic plant is selected from corn, soybean, wheat, rice, sorghum, sunflower, canola, barley, sugarcane, potatoes, tomatoes, cotton, rape seed, peanut, and alfalfa.

11. The method of claim 4, wherein the insect pest or insect pest population is an agriculturally important species in the Order Lepidoptera.

12. The method of claim 11, wherein the insect pest or insect pest population is selected from corn earworm, European corn borer, fall armyworm, soybean looper, velvet bean caterpillar, and diamondback moth.

* * * * *